US012584919B2

(12) United States Patent
Mulé et al.

(10) Patent No.: US 12,584,919 B2
(45) Date of Patent: Mar. 24, 2026

(54) ENHANCING ANTI-TUMOR RESPONSE IN MELANOMA CELLS WITH DEFECTIVE STING SIGNALING

(71) Applicants: H. Lee Moffitt Cancer Center and Research Institute, Inc., Tampa, FL (US); University of Miami, Miami, FL (US)

(72) Inventors: James Mulé, Odessa, FL (US); Rana Falahat, Tampa, FL (US); Glen Barber, Miami, FL (US)

(73) Assignees: H. Lee Moffitt Cancer Center, Tampa, FL (US); Research Institute, Inc., Miami, FL (US)

( * ) Notice: Subject to any disclaimer, the term of this patent is extended or adjusted under 35 U.S.C. 154(b) by 768 days.

(21) Appl. No.: 17/932,857

(22) Filed: Sep. 16, 2022

(65) Prior Publication Data

US 2023/0288422 A1     Sep. 14, 2023

Related U.S. Application Data

(63) Continuation-in-part of application No. 17/154,192, filed on Jan. 21, 2021, which is a continuation of
(Continued)

(51) Int. Cl.
| | |
|---|---|
| *G01N 33/574* | (2006.01) |
| *A61K 35/17* | (2025.01) |
| *C12N 5/0783* | (2010.01) |

(52) U.S. Cl.
CPC ......... *G01N 33/5743* (2013.01); *A61K 35/17* (2013.01); *C12N 5/0636* (2013.01);
(Continued)

(58) Field of Classification Search
CPC ........... G01N 33/5743; G01N 2800/52; A61K 35/17; C12N 5/0636; C12N 2501/01; C12N 2501/998; C12N 2502/30; C12N 2501/24
See application file for complete search history.

(56) References Cited

PUBLICATIONS

Corrales, Leticia et al. "Direct Activation of STING in the Tumor Microenvironment Leads to Potent and Systemic Tumor Regression and Immunity." Cell reports vol. 11,7 (2015): 1018-30. (Year: 2015).*

(Continued)

*Primary Examiner* — Tracy Vivlemore
*Assistant Examiner* — Thomas R. Amick
(74) *Attorney, Agent, or Firm* — Pabst Patent Group LLP

(57)     ABSTRACT

Disclosed herein is a method for enhancing antitumor T cell responses in subjects. The method involves administering to the subject in need thereof a composition comprising a demethylating agent in an amount effective to demethylate STING proteins in the tumor cells. This method is particularly useful in subjects with deficient STING expression in the tumor cells. Therefore, also disclosed is a method for treating a tumor in a subject that involves detecting in a biopsy sample from the subject reduced STING expression, reduced cGAS expression, or a combination thereof; and then administering to the subject a demethylating agent in an amount effective to demethylate STING proteins in the tumor cells. The method can further involve administering to the subject a therapeutically effective amount of a STING agonist. The method can further involve administering to the subject tumor infiltrating lymphocytes (TILs), such as HLA-matched TILs.

17 Claims, 151 Drawing Sheets

Related U.S. Application Data application No. PCT/US2019/042788, filed on Jul. 22, 2019.

(60) Provisional application No. 62/712,561, filed on Jul. 31, 2018, provisional application No. 62/702,195, filed on Jul. 23, 2018.

(52) U.S. Cl.
CPC .... *C12N 2501/01* (2013.01); *C12N 2501/998* (2013.01); *C12N 2502/30* (2013.01); *G01N 2800/52* (2013.01)

(56) References Cited

PUBLICATIONS

Andersen, R., et al. "T cells isolated from patients with checkpoint inhibitor-resistant melanoma are functional and can mediate tumor regression." Annals of Oncology 29.7 (2018): 1575-1581. (Year: 2018).*

Hulen, Thomas Morgan, et al. "ACT up TIL now: the evolution of tumor-infiltrating lymphocytes in adoptive cell therapy for the treatment of solid tumors." Immuno 1.3 (2021): 194-211. (Year: 2021).*

* cited by examiner

40019

| MART-1 pulsed WM39 | + | + | + | + | + | + | - | - |
| 2' 3' cGAMP | - | + | - | - | + | + | - | + |
| 40019 TIL | - | - | + | + | + | + | + | + |
| w6/32 | - | - | - | + | - | + | - | - |
| α-CD3 | - | - | - | - | - | - | + | - |

V40195

| MART-1 pulsed WM39 | + | + | + | + | + | + | - | - |
| 2' 3' cGAMP | - | + | - | - | + | + | - | + |
| V40195 TIL | - | - | + | + | + | + | + | + |
| w6/32 | - | - | - | + | - | + | - | - |
| α-CD3 | - | - | - | - | - | - | + | - |

V40195

| MART-1 pulsed WM39 | + | + | + | + | + | + | - | - |
| 2' 3' cGAMP | - | + | - | - | + | + | - | + |
| V40195 TIL | - | - | + | + | + | + | + | + |
| w6/32 | - | - | - | + | - | + | - | - |
| α-CD3 | - | - | - | - | - | - | + | - |

I40123

| | | | | | | | | |
|---|---|---|---|---|---|---|---|---|
| MART-1 pulsed WM39 | + | + | + | + | + | + | – | – |
| 2' 3' cGAMP | – | + | – | – | + | + | – | + |
| I40132 TIL | – | – | + | + | + | + | + | + |
| w6/32 | – | – | – | + | – | + | – | – |
| α-CD3 | – | – | – | – | – | – | + | – |

40019

| MART-1 pulsed WM39 | + | + | + | + | + | + | - | - |
| 2' 3' cGAMP | - | + | - | - | + | + | - | + |
| 40019 TIL | - | - | + | + | + | + | + | + |
| w6/32 | - | - | - | + | - | + | - | - |
| α-CD3 | - | - | - | - | - | - | + | - |

V40195

| MART-1 pulsed WM39 | + | + | + | + | + | + | - | - |
| 2' 3' cGAMP | - | + | - | - | + | + | - | + |
| V40195 TIL | - | - | + | + | + | + | + | + |
| w6/32 | - | - | - | + | - | + | - | - |
| α-CD3 | - | - | - | - | - | - | + | - |

WM3629

WM3629

| WM3629 | + | + | + | + | + | + | − | − |
|---|---|---|---|---|---|---|---|---|
| 2' 3' cGAMP | − | + | − | − | + | + | − | + |
| V40195 TIL | − | − | + | + | + | + | + | + |
| w6/32 | − | − | − | + | − | + | − | − |
| α-CD3 | − | − | − | − | − | − | + | − |

MART-1 pulsed WM39

| MART-1 pulsed WM39 | + | + | + | + | + | + | - | - |
|---|---|---|---|---|---|---|---|---|
| 2' 3' cGAMP | - | + | - | - | + | + | - | + |
| V40195 TIL | - | - | + | + | + | + | + | + |
| w6/32 | - | - | - | + | - | + | - | - |
| α-CD3 | - | - | - | - | - | - | + | - |

WM3629

| WM3629 | + | + | + | + | + | + | - | - |
| 2' 3' cGAMP | - | + | - | - | + | + | - | + |
| V40195 TIL | - | - | + | + | + | + | + | + |
| w6/32 | - | - | - | + | - | + | - | - |
| α-CD3 | - | - | - | - | - | - | + | - |

Defective STING Signaling

1205Lu     WM266-4     WM2032     526-MEL

HLA-A.B.C ⟶

Intact STING Signaling

WM9     WM3629     A375     WM39

HLA-A.B.C ⟶ untreated     + 2'3' cGAMP

WM39

WM39 + α-IFNAR

HLA-A,B,C.

■ + 2'3'-cGAMP
▨ + 2'3'-cGAMP - FMO
□ - 2'3'-cGAMP
▨ - 2'3'-cGAMP - FMO 6 cell lines:
- 888-MEL
- SK-MEL-28
- WM1361A
- WM2032
- WM239A
- WM266-4

ENHANCING ANTI-TUMOR RESPONSE IN MELANOMA CELLS WITH DEFECTIVE STING SIGNALING

CROSS-REFERENCE TO RELATED APPLICATIONS

This application is a continuation-in-part of copending application Ser. No. 17/154,192, filed Jan. 21, 2021, which is a continuation of copending International Application No. PCT/US2019/042788, filed Jul. 22, 2019, which claims benefit of U.S. Provisional Application No. 62/702,195, filed Jul. 23, 2018, and application Ser. No. 62/712,561, filed Jul. 31, 2018, which are hereby incorporated herein by reference in their entireties.

BACKGROUND

Stimulator of interferon genes (STING) is an endoplasmic reticulum-resident signaling molecule. It is responsible for controlling the transcription of several host defense genes, including type I IFNs and pro-inflammatory cytokines, in response to recognition of cytosolic DNA species or cyclic dinucleotides. Recent studies have indicated that STING signaling is the major innate immune pathway involved in the generation of a spontaneous antitumor T cell response. Mice lacking STING cannot generate efficient antitumor T cell responses and reject melanoma tumor growth. Based on this finding, many STING agonists have been developed to utilize STING activation as a cancer therapy. Such agonists have been found to be experimentally useful in inducing robust tumor control through the host immune cell activation. While STING activation has been extensively investigated in antigen presenting cells (in particular dendritic cells), little is known regarding its activation in tumor cells

SUMMARY

Disclosed herein is a method for enhancing antitumor T cell responses in subjects, such as those receiving adoptive cell transfer (ACT) of tumor infiltrating lymphocytes (TIL). The method involves administering to the subject in need thereof a composition comprising a demethylating agent in an amount effective to demethylate STING proteins in the tumor cells, such as melanoma cells. This method is particularly useful in subjects with deficient STING expression in the tumor cells. Therefore, also disclosed is a method for treating a tumor in a subject that involves detecting in a biopsy sample from the subject reduced STING expression, reduced cGAS expression, or a combination thereof; and then administering to the subject a demethylating agent in an amount effective to demethylate STING proteins in the tumor cells. The method can further involve administering to the subject a therapeutically effective amount of a STING agonist. The method can further involve administering to the subject tumor infiltrating lymphocytes (TILs), such as HLA-matched TILs.

Also disclosed is a method for enhancing TIL function that involves culturing a tumor sample from a subject in the presence of i) a demethylating agent in an amount effective to demethylate STING proteins in the tumor cells and ii) a STING agonist in an amount effective to increase the antigenicity of the tumor cells and/or upregulating expression of MHC molecules, and then exposing TILs to these modified tumor cells to enhance their function (i.e. killing and cytokine production) and further expansion for subsequent adoptive transfer to the cancer patient. In preferred embodiments, the TILs are HLA matched to the tumor sample from the subject.

Also disclosed is a method for enhancing TIL function that involves treating a subject with an effective amount of a demethylating agent to increase STING expression in tumor cells of the subject; isolating tumor cells from the subject; culturing the tumor cells in the presence of a STING agonist in an amount effective to increase the antigenicity of the tumor cells; and co-culturing TILs with these treated tumor cells and further expanding the TILs after their exposure. In some embodiments, this method further involves comprises culturing the tumor cells in the presence of a demethylating agent in an amount effective to demethylate STING proteins in the tumor cells. In some embodiments, the method involves detecting in a biopsy sample from the subject reduced STING expression, reduced cGAS expression, or a combination thereof prior to treating them with the demethylating agent. In some embodiments, the method involves detecting in a biopsy sample from the subject DNA methylation within regulatory regions of STING and/or cGAS genes prior to treating them with the demethylating agent.

Also disclosed is a method of treating a subject that involves producing TILs according to the disclosed methods and then adoptively transferring the TILs to the subject. Also disclosed is a method of treating a cancer in a subject that involves detecting in a tumor sample from the subject reduced STING expression, reduced cGAS expression, or a combination thereof, and then administering to the subject a therapeutically effective amount of TILs produced according to the disclosed methods. For example, in some embodiments of the disclosed methods, the subject has a cancer, and the method treats the cancer.

Downstream induction of CXCR3-binding chemokines such as CXCL10 and CXCL9 in melanoma cell lines following their stimulation with the STING agonist has at least three important implications. First, it could be used to recruit higher numbers of T cells into the tumors that lack T cell infiltration and therefore increase the likelihood of patients responding to current immune checkpoint antibody therapies. Second, a same strategy could be used in TIL-based therapies prior to tumor resection and TIL expansion to attract higher numbers of tumor-specific T cells into the tumors with the aim of increasing the probability of successful expansion of tumor-reactive TIL ex vivo. A third implication would also be in adoptive T cell therapy where STING agonist-mediated CXCL10 induction in tumor cells could be used to improve TIL trafficking into the tumor sites.

In some embodiments, the tumor of the disclosed compositions and methods is a solid tumor. In some cases, the tumor is a melanoma, ovarian cancer, breast cancer, or colorectal cancer. The cancer can be metastatic, recurrent, or a combination thereof. In some embodiments, these TILs are administered back to the subject. In some of these embodiments, the subject is treated with a demethylating agent and a STING agonist.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7A is a bar graph showing cGAS relative expression level in SK-MEL-23, A375, and SK-MEL-5 cells with and without 5AZADC treatment. FIG. 7B is an example blot showing STING, cGAS and β-actin expression in A375, G361, MeWO, and SK-MEL-5 cells with and without 5AZADC treatment. FIG. 7C are example images of STING and cGAS in A375, G361, MeWO, and SK-MEL-5 cells with and without 5AZADC treatment. FIGS. 7D and 7E are bar graphs showing IFN-β (FIG. 7D) and CXCL10 (FIG. 7E) fold changes in SK-MEL-24, A375, G361, MeWo, and SK-MEL-5 cells with and without 5AZADC treatment, with Lipo or dsDNA90.

FIG. 8A is an example blot of STING and β-actin expression in 2032, 266-4, and 1361 A cells with and without 5AZADC treatment. FIGS. 8B to 8D are bar graphs showing CXCL-10 expression in 2032 (FIG. 8B), 266-4 (FIG. 8C), and 1361 A (FIG. 8D) cells with and without 5AZADC treatment.

FIG. 15A shows immu-noblot analysis of STING and cGAS expression in a series of human melanoma cell lines. NK-92 was used as a positive control for the expression of STING and cGAS. Twenty µg of whole-cell lysate was used and β-actin was analyzed as a loading control. FIGS. 15B and 15C show ratio of total STING relative to β-actin (FIG. 15B), and ratio of total cGAS relative to β-actin (FIG. 15C) for each cell line were quantified using ImageJ software. FIG. 15D shows immu-noblot analysis of p-IRF3 and total IRF3 in five STING-positive (WM164, WM9, WM39, A375 and WM1366) and one STING-negative (WM2032) human melanoma cell lines after 4 h stimulation with 2'3'-cGAMP or lipo-fectamine. Twenty µg of whole-cell lysate was used and β-actin was analyzed as loading control. FIG. 15E shows ratio of p-IRF3 relative to IRF-3 for 2'3'-cGAMP stimulated cell lines were quantified using ImageJ software. FIG. 15F shows induction of CXCL10 and FIG. 15G shows IFN-β in cell culture supernatants of indicated human melanoma cells after.

FIG. 16A shows immunoblot analysis of p-IRF3 and total IRF3 in 526-MEL and WM39 melanoma cells after stimu-lation with 2'3'-cGAMP. FIGS. 16B and 16C show induction of CXCL10 (FIG. 16B) and IFN-β (FIG. 15C) in 526-MEL and WM39 cells after 24 h stimulation with 2'3'-cGAMP measured using ELISA. FIGS. 16D and 16E show 526-MEL and WM39 cells were co-cultured with TIL 19 (FIG. 16D) and TIL 195 (FIG. 16E) for 24 h with or without 2'3'-cGAMP. IFN-γ levels in supernatants were measured using ELISA.

FIGS. 17A to 17E show 61Cr cytotox-icity assays using WM39 (FIG. 17A), MART-1 pulsed WM39 (FIG. 17B), WM39+w6/32 (FIG. 17C), WM3629 (FIG. 17D), and 526-MEL (FIG. 17E) cells as target cells and TIL 195 as effector cells at the indicated effector/target (E/T) ratios with or without 2'3'-cGAMP. Data represent the mean±SEM of quadruplicate wells. FIG. 17F show lytic activity of TIL 195 against different agonist-treated and untreated melanoma targets was measured in lytic units ($10^6$ divided by the number of effector cells required to cause 20% lysis of $5×10^3$ tumor cells).

FIG. 18A shows representative histograms of HLA-A.B.C expression on four STING-defective (1205Lu, WM266-4, WM2032 and 526-MEL) and four STING-intact (WM9, WM3629, A375 and WM39) human melanoma cell lines with or without 2'3'-cGAMP stimulation. FIG. 18B shows mean fluorescence intensity (MFI) of HLA-A.B.C on indicated human melanoma cells.

FIG. 19A shows immunoblot analysis of STING expression in WM39, sh-control, and sh-STING cells. Twenty µg of whole-cell lysate was used and β-actin was analyzed as a loading control. FIG. 19B shows immu-noblot analysis of p-IRF3 and total IRF3 in WM39, sh-control and sh-STING cells after stimulation with 2'3'- cGAMP or lipofectamine. FIGS. 19C and 19D show induction of CXCL10 (FIG. 19C) and IFN-β (FIG. 19D) in WM39, sh-control and sh-STING cells after stimulation with 2'3'-cGAMP or lipofectamine. FIG. 19E shows representative histograms of HLA-A.B.C expression on indicated cells with or without 2'3'-cGAMP stimulation. FIG. 19F shows mean fluorescence intensity (MFI) of HLA-A.B.C on indicated cells. Data are represented as mean±SEM. p<0.01; **p<0.0001 (Student's t test).

FIG. 20A shows WM39, sh-control and sh-STING cells were co-cultured with TIL 195 for 24 h in the presence or absence of 2'3-cGAMP. IFN-γ levels in supernatants were measured using ELISA. FIG. 20B shows $^{51}$Cr cytotoxicity assay using WM39, sh-control and sh-STING cells as target cells and TIL 195 as effector cells at the indicated effector/target (E/T) ratios with or without 2'3'-cGAMP. Data represent the mean±SEM of quadruplicate wells. FIG. 20C shows lytic activity of TIL 195 against indicated targets with or without 2'3'-cGAMP stimulation was measured in lytic units.

FIG. 36B shows that these four cell lines have no expression of STING protein. Only cell lines with no methylation express STING but there are also cell lines with no methylation and no protein expression.

DETAILED DESCRIPTION

Figures 1A, 1B:
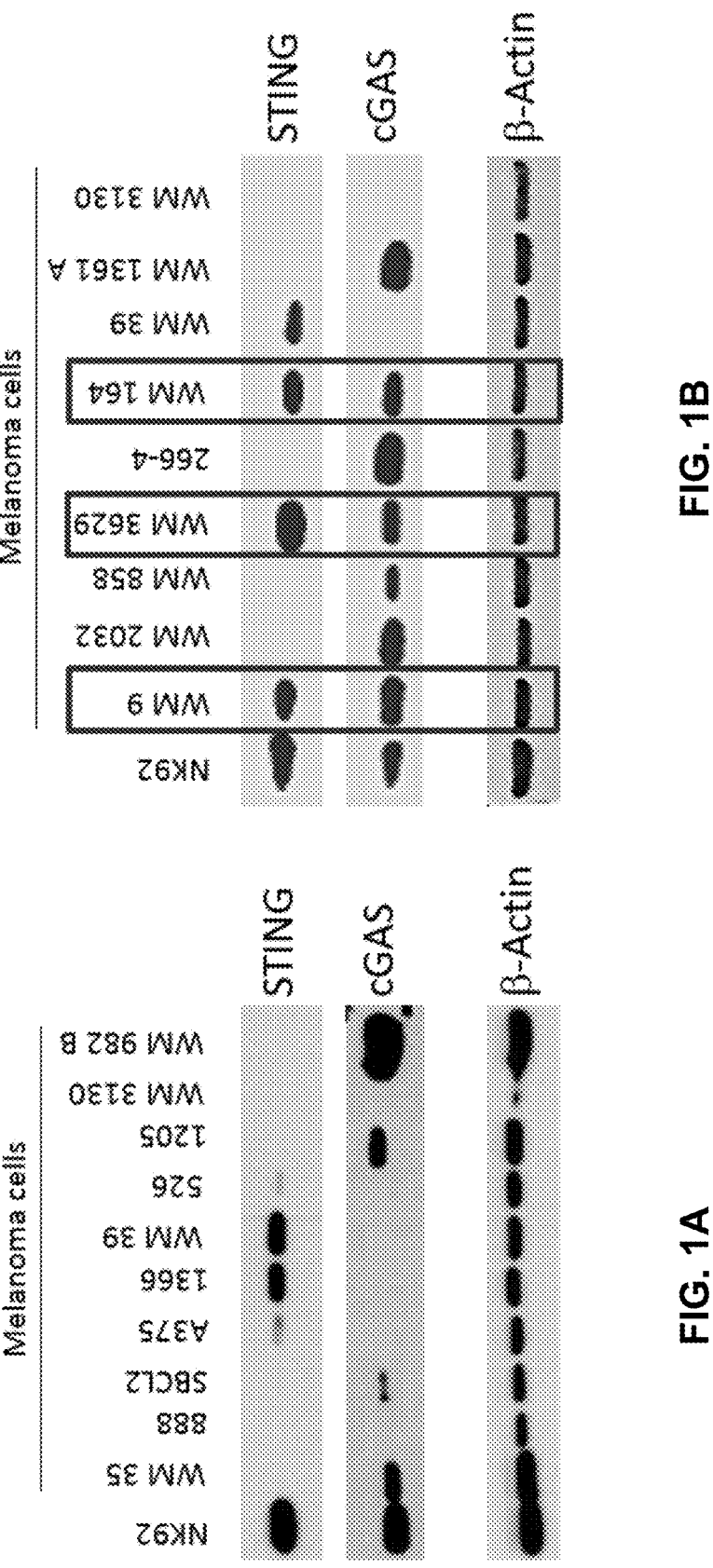
FIGS. 1A and 1B are example blots showing STING and cGAS expression in melanoma cell lines.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "tumor infiltrating lymphocyte" or "TIL" refers to white blood cells that have left the bloodstream and migrated into a tumor.

10

Method

Disclosed herein is a method for enhancing antitumor T cell responses in subjects, such as those receiving adoptive cell transfer (ACT) of tumor infiltrating lymphocytes (TIL).

Patient Screening

In some embodiments, the disclosed methods involve assaying a biopsy sample from the subject for STING expression, cGAS expression, or a combination thereof. In some embodiments, the disclosed methods involve assaying a biopsy sample from the subject for DNA methylation within the regulatory regions of STING and/or cGAS genes.

In some aspects, the method is an immunoassay. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

Demethylating Agents

In some embodiments, the disclosed methods involve treating the subject with a demethylating agent. Cytidine analogs with demethylating activity are known. Examples of cytidine analogs with demethylating activity include, but are not limited to, 5-Azacytidine, 5,6-dihydro-5-azacytidine, 1-β-D-arabinofuranosyl-5-azacytidine, 5-Aza-2'-deoxycytidine (decitabine) or 1-(beta-D-ribofuranosyl)-1,2dihydropropyrimindin-2-one (zebularine). Additional examples of demethylating agents include 5-aza-cytidine (5-aza-C), 5-aza-2'-deoxycytidine (5-aza-dC or decitabine), 5-fluoro-2'-deoxycytidine (5-F-dC), Pseudoisocytidine, 2-H pyrimidinone-1-b-D (2'-deoxyriboside) (Zebularine), Guadecitabine (SGI-110), and Disulfiram.

STING Agonists

In some aspects, the disclosed methods involve treating the subject with a cyclic GMP-AMP Synthase (cGAS)/Stimulator of Interferon Genes (STING) pathway agonist. In some aspects, the cGAS/STING pathway agonist is 2'3'-cyclic-GMP-AMP (2'3'-cGAMP). Additional STING agonists are known in the art, including those disclosed in U.S. Patent Publication No. 2016/0287623 and U.S. Patent Publication No. 2017/0044206, which are incorporated by reference herein for these agonists. In some aspects, the STING agonist is a natural cyclic dinucleotide (CDN), such as 2'3'-cGAMP, 3'3'-cGAMP, c-di-AMP, or c-di-GMP. In some aspects, the STING agonist is a cAIM-derived CDN, such as cAIMP, cAIMP Difluor, or cAIM(PS)2 Difluor (Rp/Sp). In some aspects, the STING agonist is a cGAMP-derived CDN, such as 2'2'-cGAMP, 2'3'-cGAM(PS)2 (Rp/Sp), or 3'3'-cGAMP Fluorinated. In some aspects, the STING agonist is a c-di-AMP-derived CDN, such as c-di-AMP Fluorinated, 2'3'-c-di-AMP, or 2'3'-c-di-AM(PS)2 (Rp,Rp). In some aspects, the STING agonist is a c-di-GMP-derived CDN, such as c-di-GMP Fluorinated or 2'3'-c-di-GMP. In some aspects, the STING agonist is a c-di-IMP-derived CDN, such as c-di-IMP. In some aspects, the STING agonist is a xanthenone analog, such as DMXAA. In some aspects, the STING agonist is ADU-S100 (MIW815, Aduro Biotech). In some aspects, the STING agonist is MK-1454 (Merck).

Adoptive Cell Transfer

In some aspects, the disclosed methods involve treating the subject with Adoptive Cell Transfer (ACT) of lymphocytes, such as tumor-infiltrating lymphocytes (TILs), such as HLA-matched TILs.

Tumor-infiltrating lymphocyte (TIL) production is a 2-step process: 1) the pre-REP (Rapid Expansion) stage where you the grow the cells in standard lab media such as RPMI and treat the TILs w/reagents such as irradiated feeder cells, and anti-CD3 antibodies to achieve the desired effect; and 2) the REP stage where you expand the TILs in a large enough culture amount for treating the patients. The REP stage requires cGMP grade reagents and 30-40 L of culture medium. However, the pre-REP stage can utilize lab grade reagents (under the assumption that the lab grade reagents get diluted out during the REP stage), making it easier to incorporate alternative strategies for improving TIL production. Therefore, in some embodiments, the disclosed TLR agonist and/or peptide or peptidomimetics can be included in the culture medium during the pre-REP stage.

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILS). They can also be derived or from blood if they are genetically engineered to express antitumor T cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. US 2011/0052530 relates to a method for performing adoptive cell therapy to promote cancer regression, primarily for treatment of patients suffering from metastatic melanoma, which is incorporated by reference in its entirety for these methods.

ACT may be performed by (i) obtaining autologous lymphocytes from a mammal, (ii) culturing the autologous lymphocytes to produce expanded lymphocytes, and (ii) administering the expanded lymphocytes to the mammal. Preferably, the lymphocytes are tumor-derived, i.e. they are TILs, and are isolated from the mammal to be treated, i.e. autologous transfer.

Autologous ACT as described herein may also be performed by (i) culturing autologous lymphocytes to produce expanded lymphocytes; (ii) administering nonmyeloablative lymphodepleting chemotherapy to the mammal; and (iii) after administering nonmyeloablative lymphodepleting chemotherapy, administering the expanded lymphocytes to the mammal.

Autologous TILs may be obtained from the stroma of resected tumors. Tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase).

Expansion of lymphocytes, including tumor-infiltrating lymphocytes, such as T cells can be accomplished by any of a number of methods as are known in the art. For example, T cells can be rapidly expanded using non-specific T-cell receptor stimulation in the presence of feeder lymphocytes and interleukin-2 (IL-2), IL-7, IL-15, IL-21, or combinations thereof. The non-specific T-cell receptor stimulus can e.g. include around 30 ng/ml of OKT3, a mouse monoclonal anti-CD3 antibody (available from Ortho-McNeil®, Raritan, N.J. or Miltenyi Biotec, Bergisch Gladbach, Germany). Alternatively, T cells can be rapidly expanded by stimulation of peripheral blood mononuclear cells (PBMC) in vitro with one or more antigens (including antigenic portions thereof, such as epitope(s), or a cell of the cancer, which can be optionally expressed from a vector, such as an human leukocyte antigen A2 (HLA-A2) binding peptide, e.g., approximately 0.3 μM MART-1: 26-35 (27 L) or gp100: 209-217 (210M)), in the presence of a T-cell growth factor, such as around 200-400 III/ml, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

In some embodiments, nonmyeloablative lymphodepleting chemotherapy is administered to the mammal prior to administering to the mammal the expanded tumor-infiltrating lymphocytes. The purpose of lymphodepletion is to make room for the infused lymphocytes, in particular by eliminating regulatory T cells and other non-specific T cells which compete for homeostatic cytokines Nonmyeloablative lymphodepleting chemotherapy can be any suitable such therapy, which can be administered by any suitable route known to a person of skill. The nonmyeloablative lymphodepleting chemotherapy can comprise, for example, the administration of cyclophosphamide and fludarabine, particularly if the cancer is melanoma, which can be metastatic. A preferred route of administering cyclophosphamide and fludarabine is intravenously. Likewise, any suitable dose of cyclophosphamide and fludarabine can be administered. Preferably, around 40-80 mg/kg, such as around 60 mg/kg of cyclophosphamide is administered for approximately two days after which around 15-35 mg/m2, such as around 25 mg/m2 fludarabine is administered for around five days, particularly if the cancer is melanoma.

Specific tumor reactivity of the expanded TILs can be tested by any method known in the art, e.g., by measuring cytokine release (e.g., interferon-gamma) following co-culture with tumor cells. In one embodiment, the autologous ACT method comprises enriching cultured TILs for CD8+ T cells prior to rapid expansion of the cells. Following culture of the TILs in IL-2, the T cells are depleted of CD4+ cells and enriched for CD8+ cells using, for example, a CD8 microbead separation (e.g., using a CliniMACS<plus>CD8 microbead system (Miltenyi Biotec)). In an embodiment of the method, a T-cell growth factor that promotes the growth and activation of the autologous T cells is administered to the mammal either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, IL-12 and IL-21, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

Preferably, expanded lymphocytes produced by these methods are administered as an intra-arterial or intravenous infusion, which preferably lasts about 30 to about 60 minutes. Other examples of routes of administration include intraperitoneal, intrathecal and intralymphatic. Likewise, any suitable dose of lymphocytes can be administered. In one embodiment, about 1×1010 lymphocytes to about 15×1010 lymphocytes are administered.

The cancer treated by the disclosed compositions and methods can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the vulva, chronic lymphocytic leukemia, chronic myeloid cancer, cervical cancer, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, peritoneum, omentum, and mesentery cancer, pharynx cancer, prostate cancer, rectal cancer, renal cancer, skin cancer, soft tissue cancer, testicular cancer, thyroid cancer, ureter cancer, urinary bladder cancer, and digestive tract cancer such as, e.g., esophageal cancer, gastric cancer, pancreatic cancer, stomach cancer, small intestine cancer, gastrointestinal carcinoid tumor, cancer of the oral cavity, colorectal cancer, and hepatobiliary cancer.

The cancer can be a recurrent cancer. Preferably, the cancer is a solid cancer. Preferably, the cancer is melanoma, ovarian, breast and colorectal cancer, even more preferred is melanoma, in particular metastatic melanoma.

Combination Therapy

The disclosed compositions and methods can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy. The disclosed compositions and methods can be used in combination with immunotherapy. For example, in some embodiment, the disclosed compositions and methods are used in combination with CAR-T therapy.

The disclosed compositions and methods can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed compositions and methods can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and *vinca* alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbB1 (EGFR) (such as an EGFR antibody, e.g. zalutumumab, cetuximab, panitumumab or nimo-tuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, dara-tumumab, ranibizumab, nimotuzumab, panitumumab, hu806, daclizumab (Zenapax), basiliximab (Simulect), inf-liximab (Remicade), adalimumab (Humira), natalizumab (Tysabri), omalizumab (Xolair), efalizumab (Raptiva), and/or rituximab.

In some embodiments, a therapeutic agent for use in combination with disclosed compositions and methods for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C—C chemokine families. Suitable cytokines include cytokine derivatives, cytokine variants, cytokine fragments, and cytokine fusion proteins.

In some embodiments, a therapeutic agent for use in combination with disclosed compositions and methods for treating the disorders as described above may be a cell cycle control/apoptosis regulator (or "regulating agent"). A cell cycle control/apoptosis regulator may include molecules that target and modulate cell cycle control/apoptosis regu-lators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with disclosed compositions and methods for treating the disorders as described above may be a hormonal regulating agent, such as agents useful for anti-androgen and anti-estrogen therapy. Examples of such hormonal regulat-ing agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, predni-sone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with disclosed compositions and methods for treating the disorders as described above may be an anti-cancer nucleic acid or an anti-cancer inhibitory RNA mol-ecule.

Combined administration, as described above, may be simultaneous, separate, or sequential. For simultaneous administration the agents may be administered as one com-position or as separate compositions, as appropriate.

In some embodiments, the disclosed compositions and methods is administered in combination with radiotherapy. Radiotherapy may comprise radiation or associated admin-istration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed compositions and methods is administered in combination with surgery.

Therapeutic Methods

The disclosed therapeutic compositions may be adminis-tered either alone, or as a pharmaceutical composition in combination with diluents and/or with other components such as IL-2, IL-15, or other cytokines or cell populations. Briefly, pharmaceutical compositions may comprise agents or cell populations as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypep-tides or amino acids such as glycine; antioxidants; chelating agents such as EDTA or glutathione; adjuvants (e.g., alumi-num hydroxide); and preservatives. Compositions for use in the disclosed methods are in some embodiments formulated for intravenous administration. Pharmaceutical composi-tions may be administered in any manner appropriate treat the cancer. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with con-sideration of individual differences in age, weight, tumor size, extent of infection or metastasis, and condition of the patient (subject). It can generally be stated that a pharma-ceutical composition comprising the CAR-TIL cells described herein may be administered at a dosage of $10^4$ to $10^9$ cells/kg body weight, such as $10^5$ to $10^6$ cells/kg body weight, including all integer values within those ranges.

CAR-TIL cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed compositions are administered to a patient in conjunction with (e.g., before, simultaneously or following) any number of relevant treatment modalities, including but not limited to thalidomide, dexamethasone, bortezomib, and lenalidomide. In further embodiments, the compositions may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-TILs are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The disclosed compositions can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed compositions can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed compositions can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 TIL responses may also require T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and *vinca* alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with compositions for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C—C chemokine families. Suitable cytokines include cytokine derivatives, cytokine variants, cytokine fragments, and cytokine fusion proteins.

In some embodiments, a therapeutic agent for use in combination with a composition for treating cancers as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with compositions for treating cancers as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with compositions for treating the cancers as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed compositions are administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed compositions are administered in combination with surgery.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Background

Stimulator of interferon genes (STING) is an endoplasmic reticulum-resident signaling molecule. It is responsible for controlling the transcription of several host defense genes, including type I IFNs and pro-inflammatory cytokines, in response to recognition of cytosolic DNA species or cyclic dinucleotides. Recent studies have indicated that STING signaling is the major innate immune pathway involved in the generation of a spontaneous antitumor T cell response. Mice lacking STING cannot generate efficient antitumor T cell responses and reject melanoma tumor growth. Based on this finding, many STING agonists have been developed to utilize STING activation as a cancer therapy. Such agonists have been found to be experimentally useful in inducing robust tumor control through the host immune cell activation. While STING activation has been extensively investigated in antigen presenting cells (in particular dendritic cells), little is known regarding its activation in tumor cells.

Methods

To gain more insights into the role of STING signaling in melanoma, first we have explored the expression of STING and cGAS (cyclic GMP-AMP synthase) in a panel of human melanoma cell lines by immunoblot. Next, we have studied the functional STING signaling activation in STING positive melanoma cells following their stimulation with a known STING agonist 2'3'-cGAMP by measuring the induction of CXCL-10 and IFN-□ using ELISA.

To determine if epigenetic processes such as hypermethylation are involved in the suppression of STING expression and its functional signaling, we have treated melanoma cells lacking STING expression with the demethylating agent 5-aza-2'-deoxycytidine (5AZADC) and evaluated induction of STING expression by immunoblot.

To study the role of STING signaling in immunogenicity of melanoma, we have set up co-cultures of expanded human melanoma tumor infiltrating lymphocytes (TILs) with their HLA-matched melanoma cell lines in the presence of the STING agonist 2'3'-cGAMP. We have assessed the subsequent immunogenicity by IFN-γ release and 51Cr release cytotoxicity assays.

Results

Examining STING and cGAS expression by immunoblot showed that there is a diverse STING/cGAS expression status among human melanoma cell lines. STING expression was not detectable in 11 of 18 human melanoma cell lines. Also, STING activation in majority of human melanoma cell lines was found to be defective.

Partial induction of STING expression in 5AZADC-treated melanoma cell lines lacking STING and induction of CXCL-10 following their stimulation with the STING agonist suggested DNA hypermethylation may be involved in the suppression of STING signaling.

Activation of STING pathway in human melanoma cell lines when cultured with their HLA-matched TILs resulted in increased IFN-□ secretion suggesting the presence of a STING-induced immunogenicity. 51Cr release cytotoxicity assay further confirmed that STING activation in human melanoma cells augments their cytotoxic T lymphocyte-mediated lysis. Accordingly, we have found that STING activation in melanoma cells induces increased surface expression of MHC class I which could allow them to be more effectively recognized by cytotoxic T cells.

There is a diverse STING/cGAS expression status among melanoma cell lines.

STING expression is suppressed and dsDNA-induced innate immune activation is impaired in majority of human melanoma cell lines. FIGS. 1A, 1B, and Table 1 show STING and cGAS expression in melanoma cell lines.

TABLE 1

| STING and cGAS expression in human melanoma cell lines | | | |
|---|---|---|---|
| Cell Line | STING | cGAS | BRAF |
| WM 35 | – | + | V600E |
| 888 | – | – | V600E |
| SBCL2 | – | Low | V600E |

TABLE 1-continued

| STING and cGAS expression in human melanoma cell lines | | | |
|---|---|---|---|
| Cell Line | STING | cGAS | BRAF |
| A375 | Low | – | V600E |
| 1366 | + | – | V600E |
| WM 39 | + | – | V600E |
| 526 | Low | – | V600E |
| 1205 | – | + | V600E |
| WM 3130 | – | – | ? |
| WM 982 B | – | + | ? |
| 239 | – | – | V600D |
| WM 9 | + | + | V600D |
| WM 2032 | – | + | –V600E |
| WM 858 | – | + | V600D |
| WM 3629 | + | + | D549G het |
| 266-4 | – | + | V600D |
| WM 164 | + | + | V600E |
| WM 1361 A | – | + | WT |

STING signaling pathway is defective in majority of human melanoma cell lines.

Figure 2:
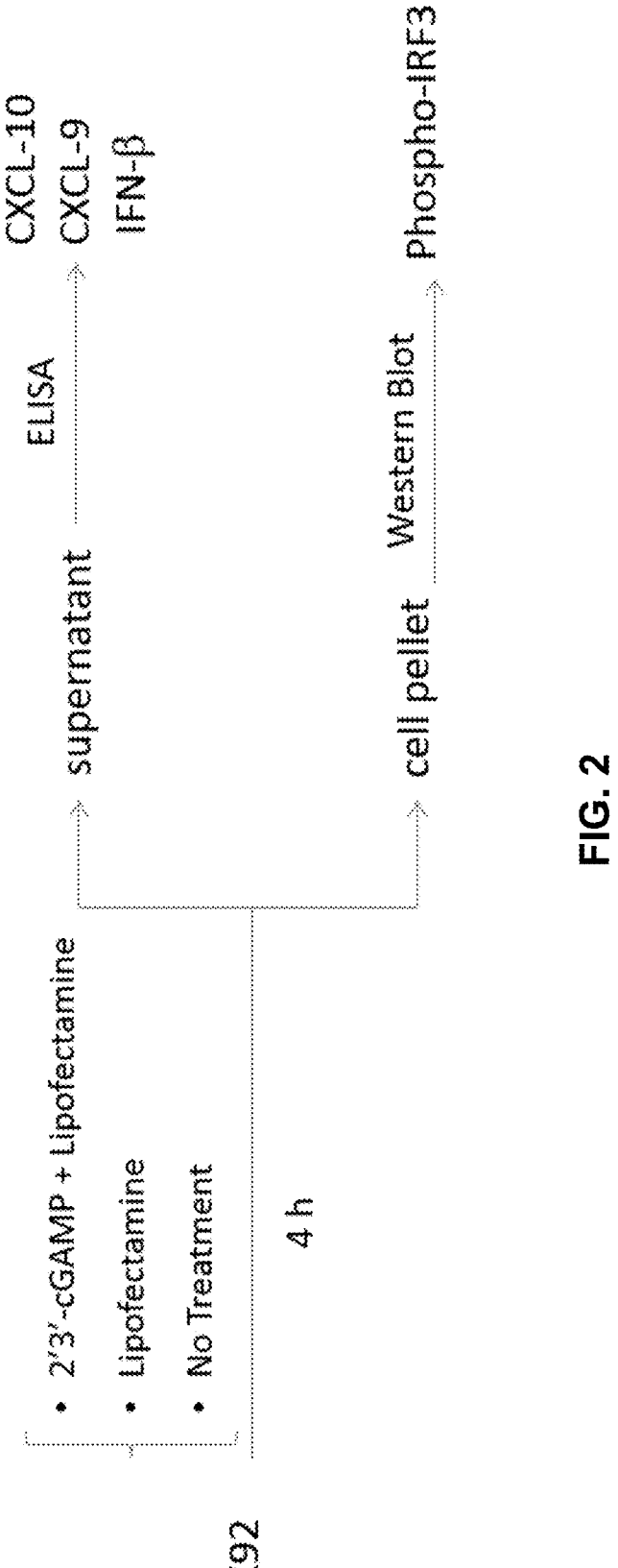
FIG. 2 illustrates the activation of STING pathway in NK92 cells (positive control) with 2'3'-cGAMP.

FIG. 2 illustrates the activation of STING pathway in NK92 cells (positive control) with 2'3'-cGAMP.

Figure 3:
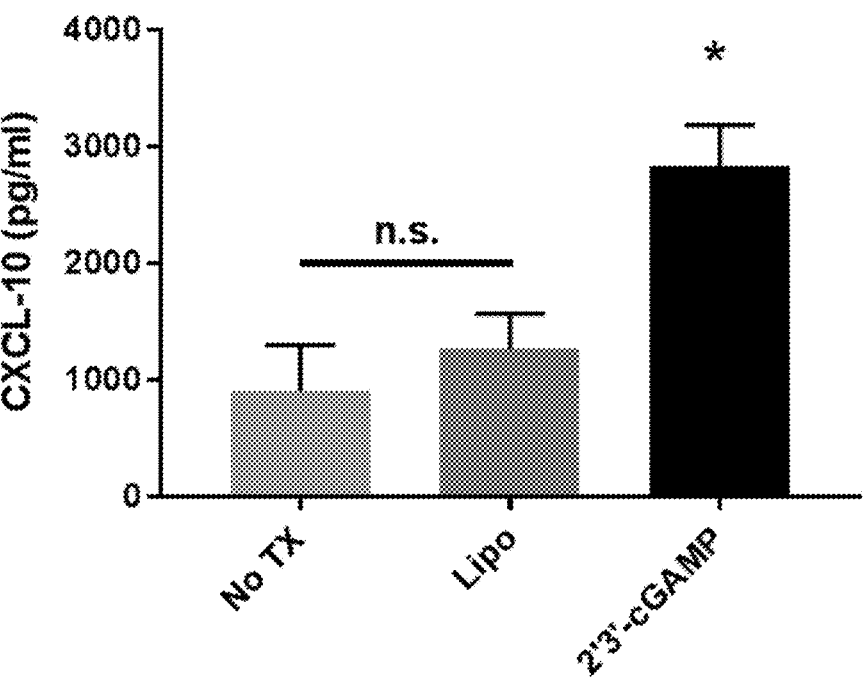
FIG. 3 is a bar graph showing induction of CXCL-10 expression in NK92 cells after 4 h treatment with 2'3-cGAMP.

FIG. 3 is a bar graph showing induction of CXCL-10 expression in NK92 cells after 4 h treatment with 2'3-cGAMP.

Table 2 shows the activation of STING pathway in NK92 cells (positive control) with 2'3'-cGAMP.

TABLE 2

| Activation of STING pathway in human melanoma cell lines with 2'3'-cGAMP | | |
|---|---|---|
| Cell Line | STING | cGAS |
| WM 164 | + | + |
| WM 9 | + | + |
| WM 39 | + | – |
| A375 | low | – |
| 1366 | + | – |
| 2032 | – | + |

Figure 4A:
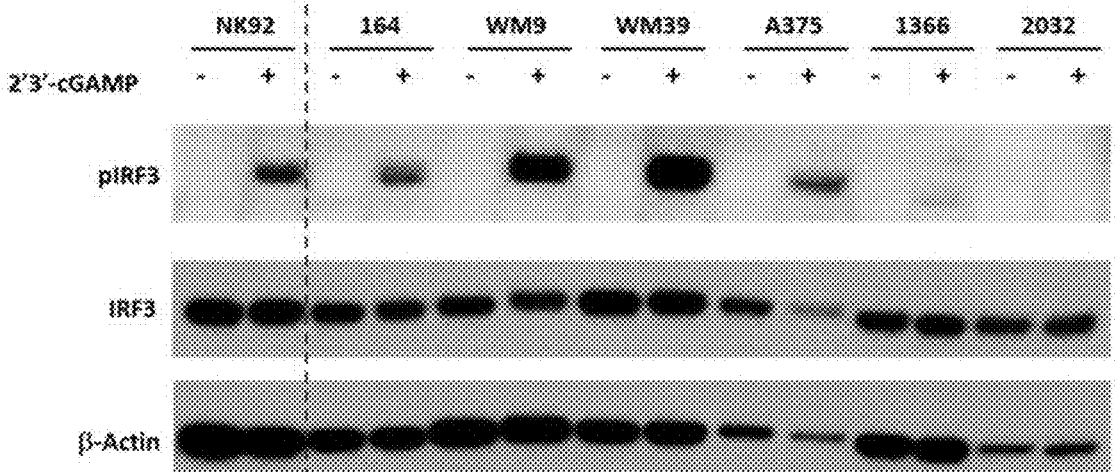
FIG. 4A is an example blot showing pIRF3, IRF3, and β-actin expression in NK92 and human melanoma cell lines 164, WM9, WM39, A375, 1366, and 2032 with and without treatment with 2'3'-cGAMP.
Figure 4B:
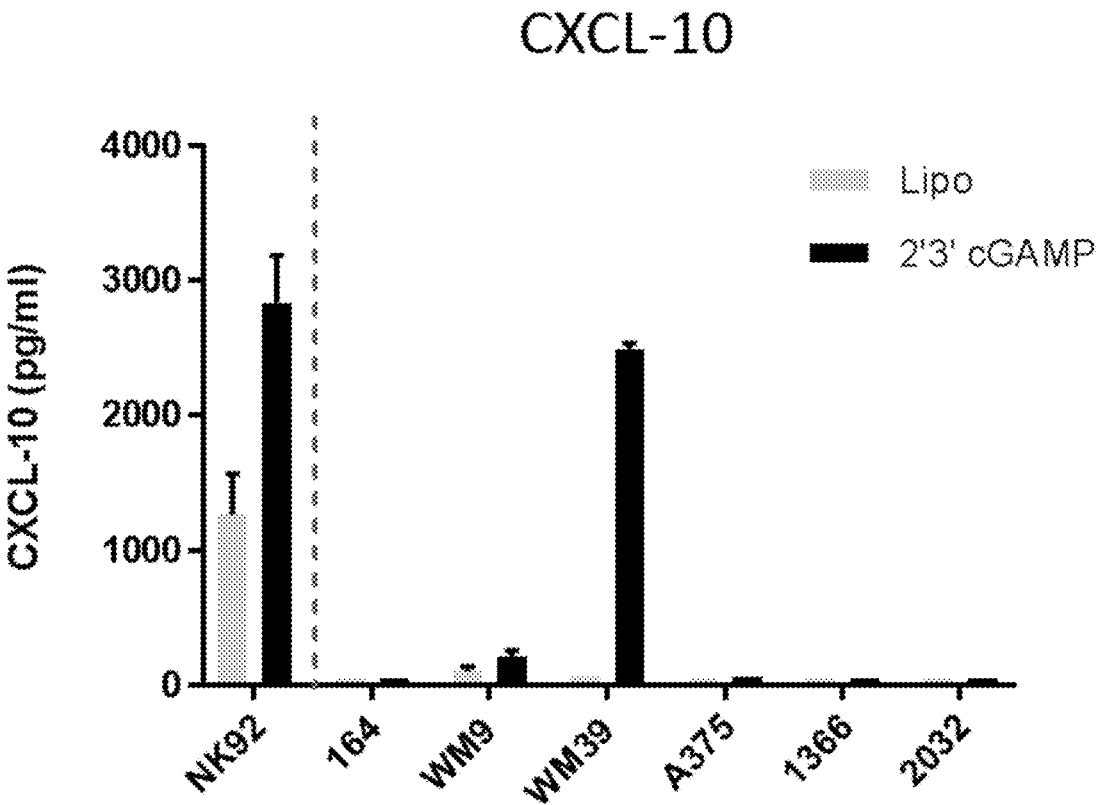
FIGS. 4B and 4C are bar graphs showing CXCL-10 (FIG. 4B) and IFN-β expression in NK92 and human melanoma cell lines 164, WM9, WM39, A375, 1366, and 2032 with and without treatment with 2'3'-cGAMP.
Figure 4C:
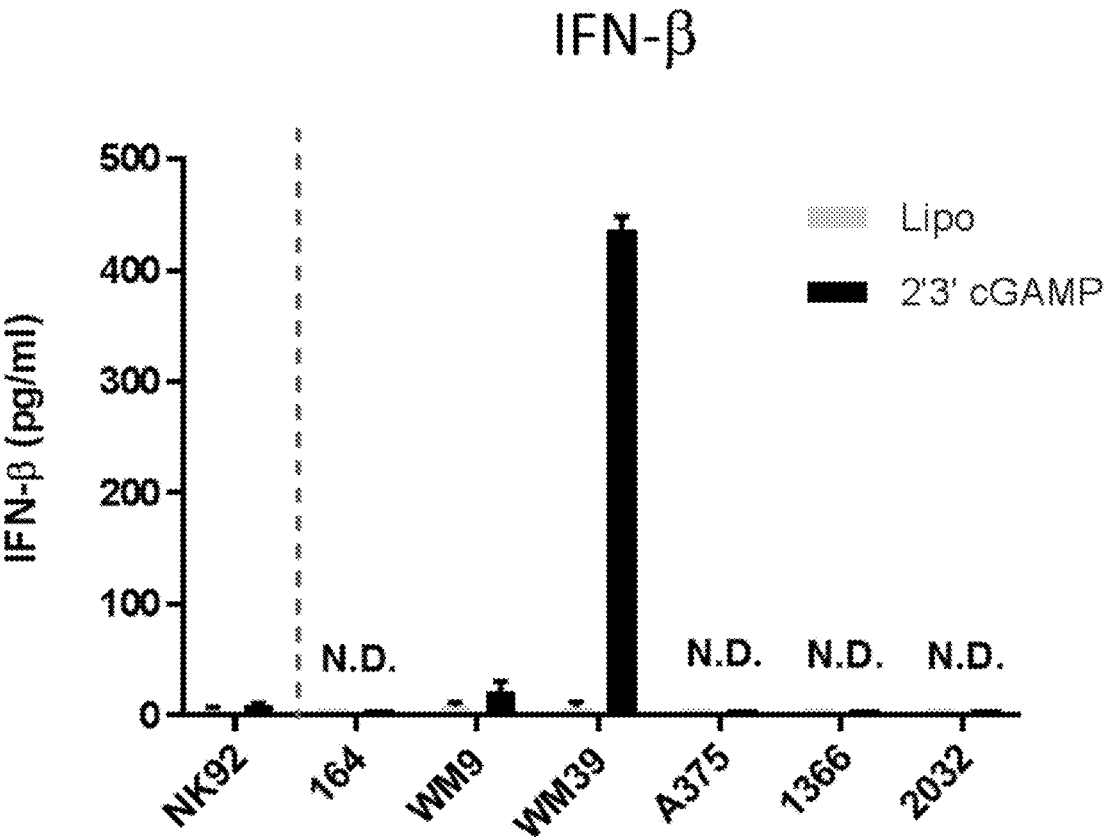

FIGS. 4A to 4C show analysis of STING signaling activation in human melanoma cell lines.

Figure 5A:
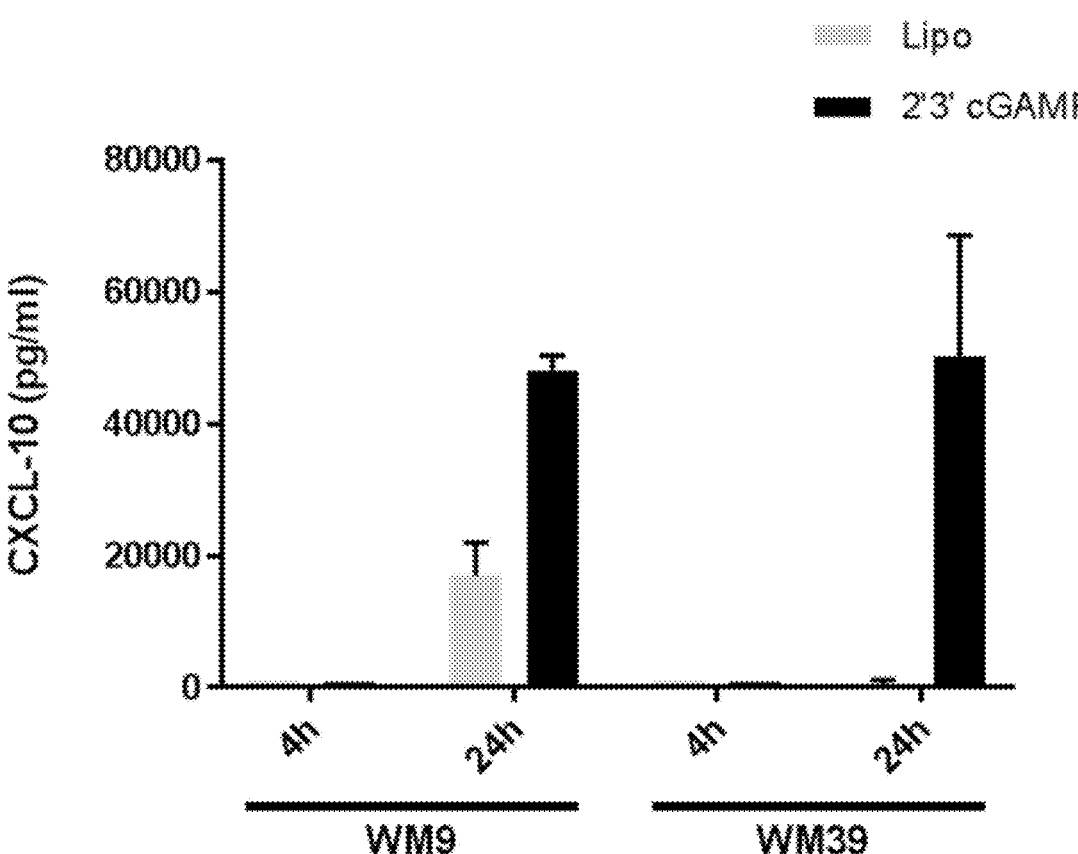
FIGS. 5A and 5B are bar graphs showing expression of CXCL-10 (FIG. 5A) and IFN-β (FIG. 5B) in WM9 and WM39 cell lines after 4 h & 24 h treatment with 2'3'-cGAMP.
Figure 5B:
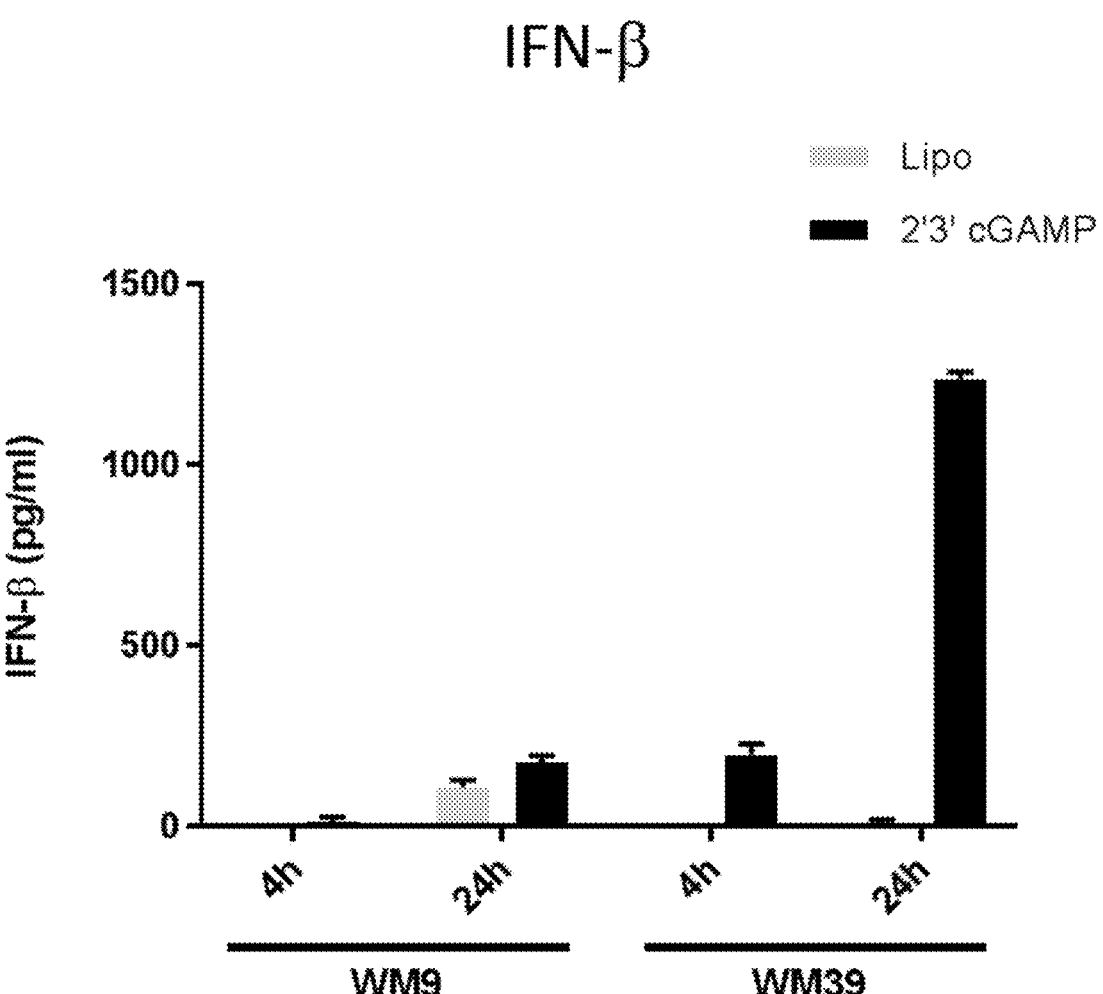

FIGS. 5A and 5B show expression of CXCL-10 and IFN-b in WM9 and WM39 cell lines after 4 h & 24 h treatment with 2'3' cGAMP.

Figure 6:
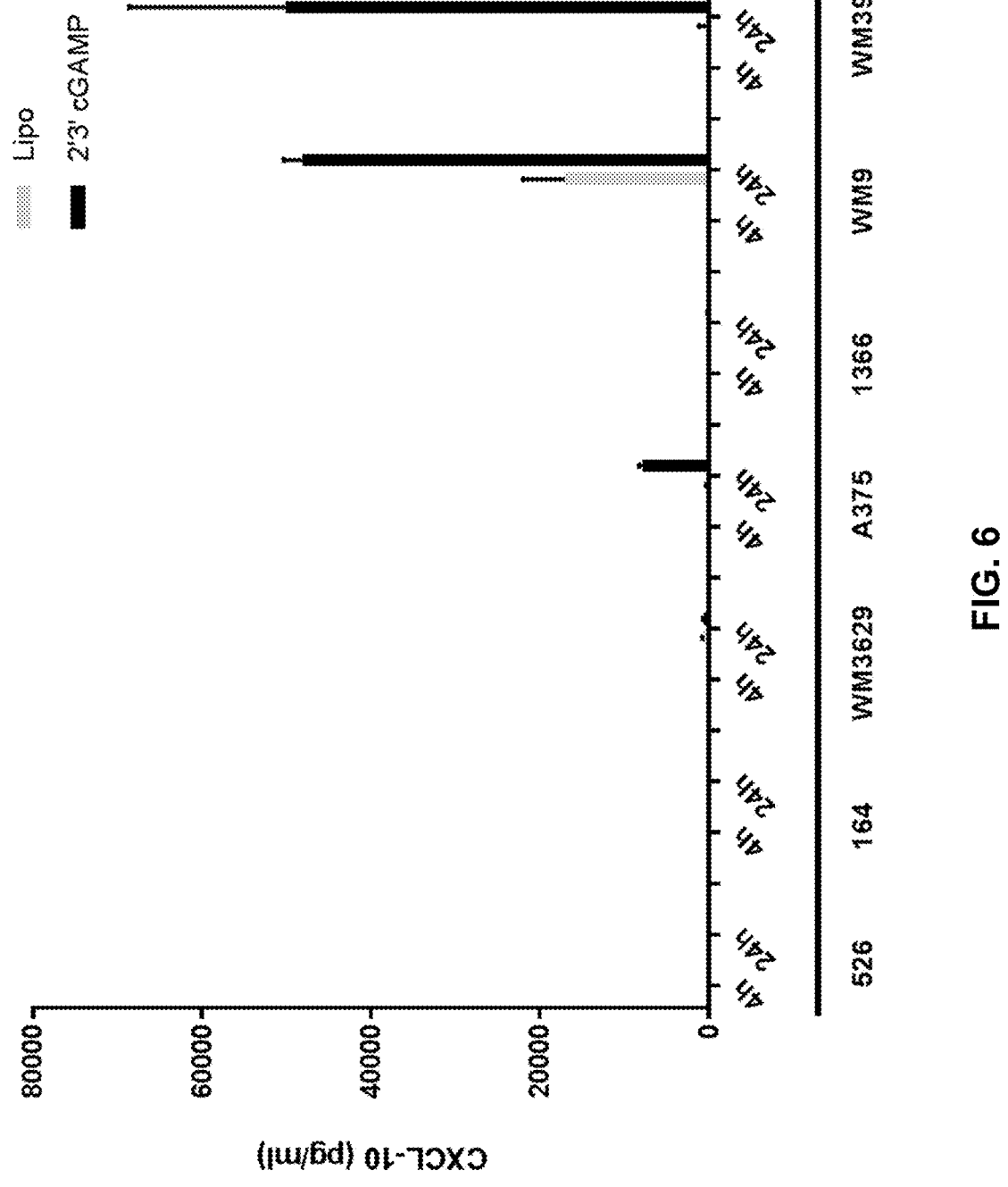
FIG. 6 is a bar graph showing expression of CXCL-10 in STING positive melanoma cell lines after 4 h & 24 h treatment with 2'3-cGAMP.

FIG. 6 is a bar graph showing expression of CXCL-10 in STING positive melanoma cell lines after 4 h & 24 h treatment with 2'3-cGAMP.

DNA Hypermethylation May be Involved in the Suppression of STING Signaling in Melanoma FIGS. 7A to 7E show DNA demethylation partially recapitulated STING and cGAS expression in human melanoma cell lines.

FIGS. 8A to 8D show reconstitution of STING expression in 5AZADC-treated melanoma cells and STING-dependent CXCL-10 induction following 2'3'-cGAMP stimulation.

FIGS. 9A to 9F show CXCL-10 induction in 5AZADC-treated melanoma cells following 2'3'-cGAMP stimulation.

In summary, CXCL-10 induction in 5AZADC-treated melanoma cell lines following stimulation with the STING agonist suggests DNA hypermethylation may be involved in suppressing STING signaling.

STING Signaling Impact in Immunogenicity of Melanoma

A co-culture assay was performed that involved melanoma cells treated with or without 2'3' cGAMP (WM39 (HLA A01/02)) with melanoma TILs (V40195 (A2), 40019 (A2)). Specifically, WM39 cells were plated at 2×10⁶ cells/ ml and 50 μl/well (1×10⁶ cells/well) with W6/32 Ab (HLA-ABC antibody). Next, 2'3'-cGAMP was added to WM39 cells at 50 μl/well. This was incubated for 1 hour. The TILs were then added and incubated for another hour. The co-culture supernatants were then collected and evaluated for IFN-γ by ELISA.

Figure 10:
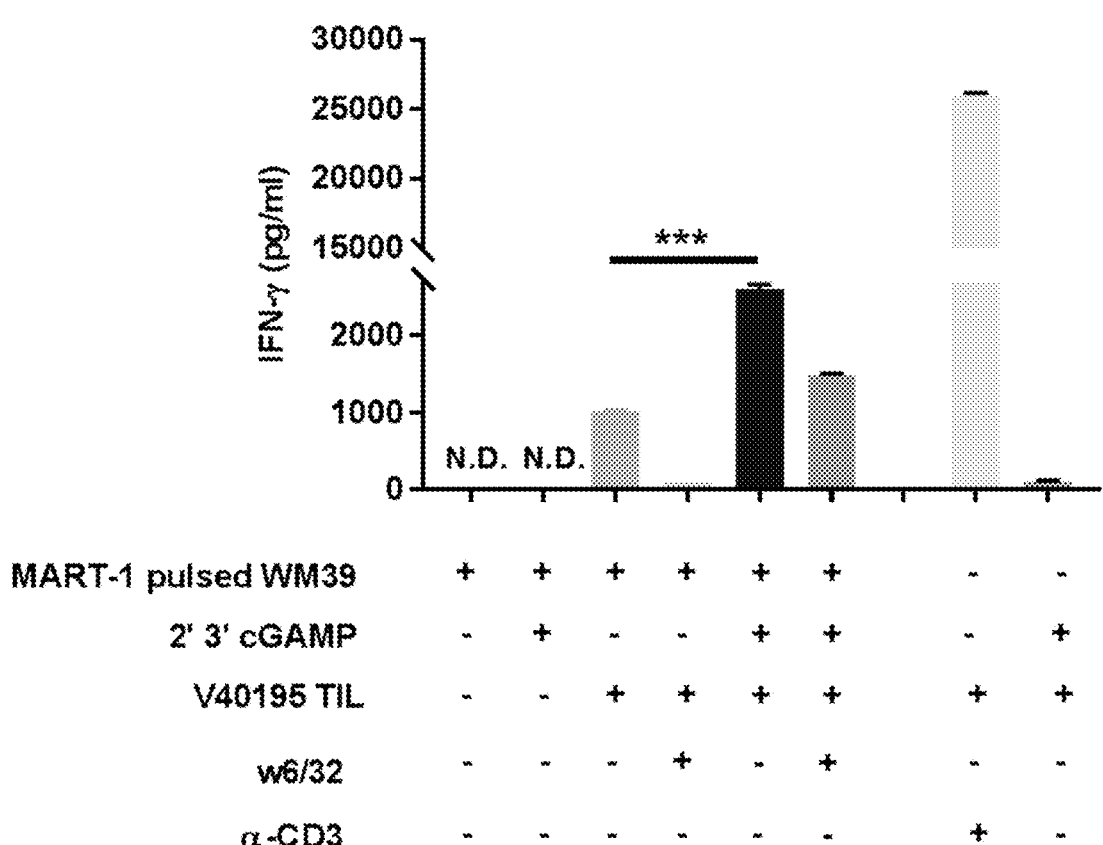
FIG. 10 is a bar graph showing activation of STING signaling in MART-1 pulsed WM39 melanoma cells results in increased IFN-γ secretion when cultured with V40195 TIL.
Figure 11A:
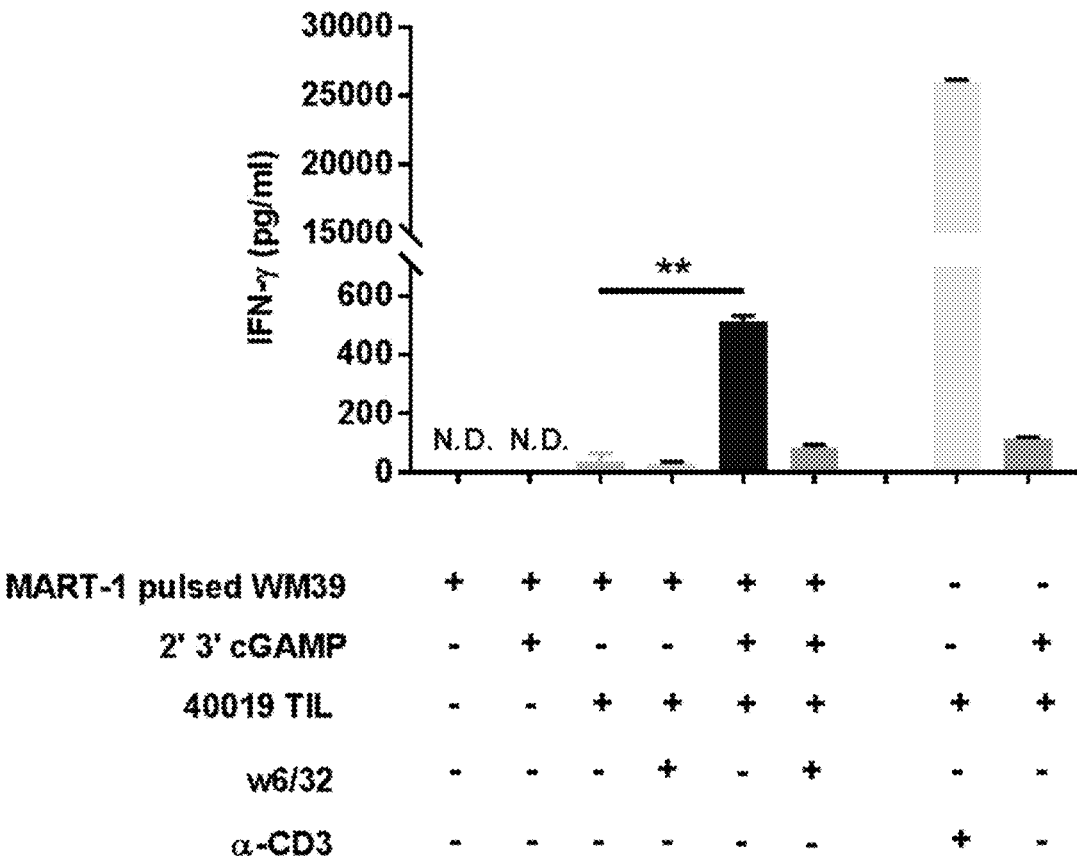
FIGS. 11A to 11I are bar graph showing IFN-γ (FIGS. 11A-11C), CXCL-10 (FIGS. 11D-11F), and IFN-β (FIGS. 11G-11I) expression in co-cultures of MART-1 pulsed WM39 with HLA-matched TILs.
Figure 11B:
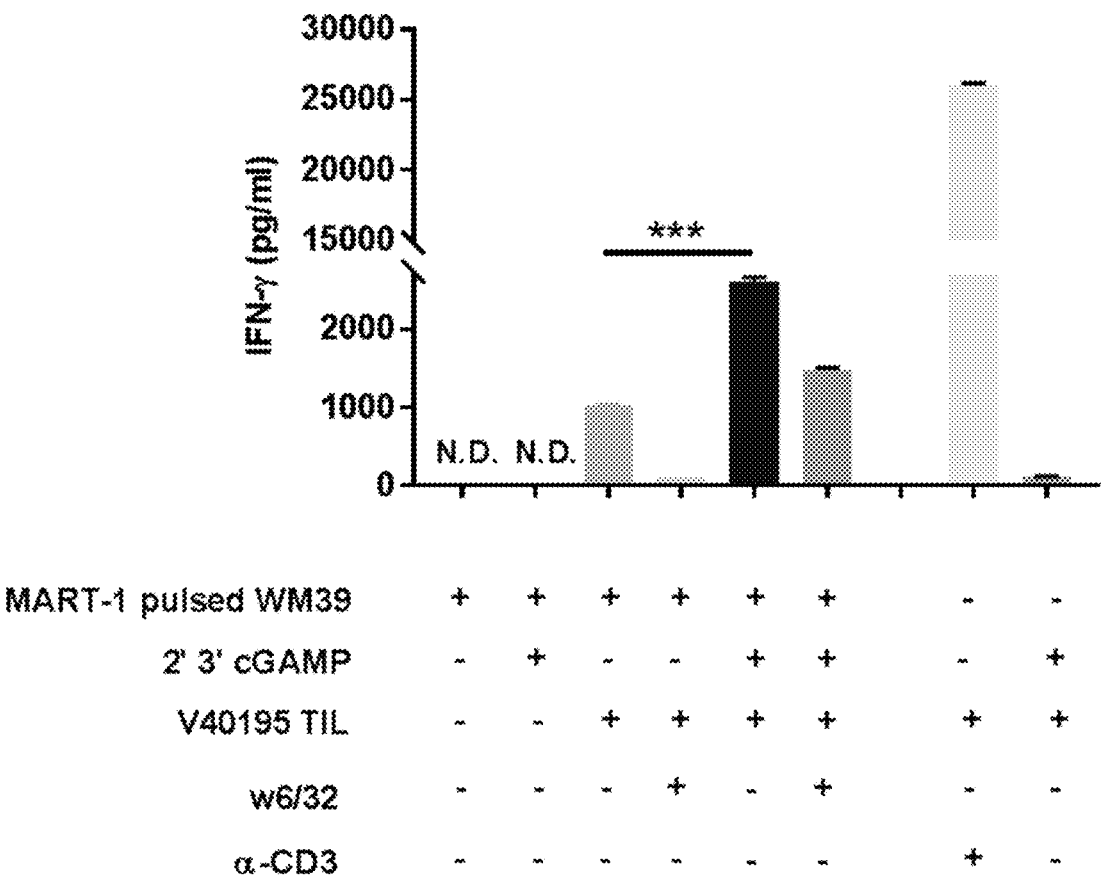
Figure 11C:
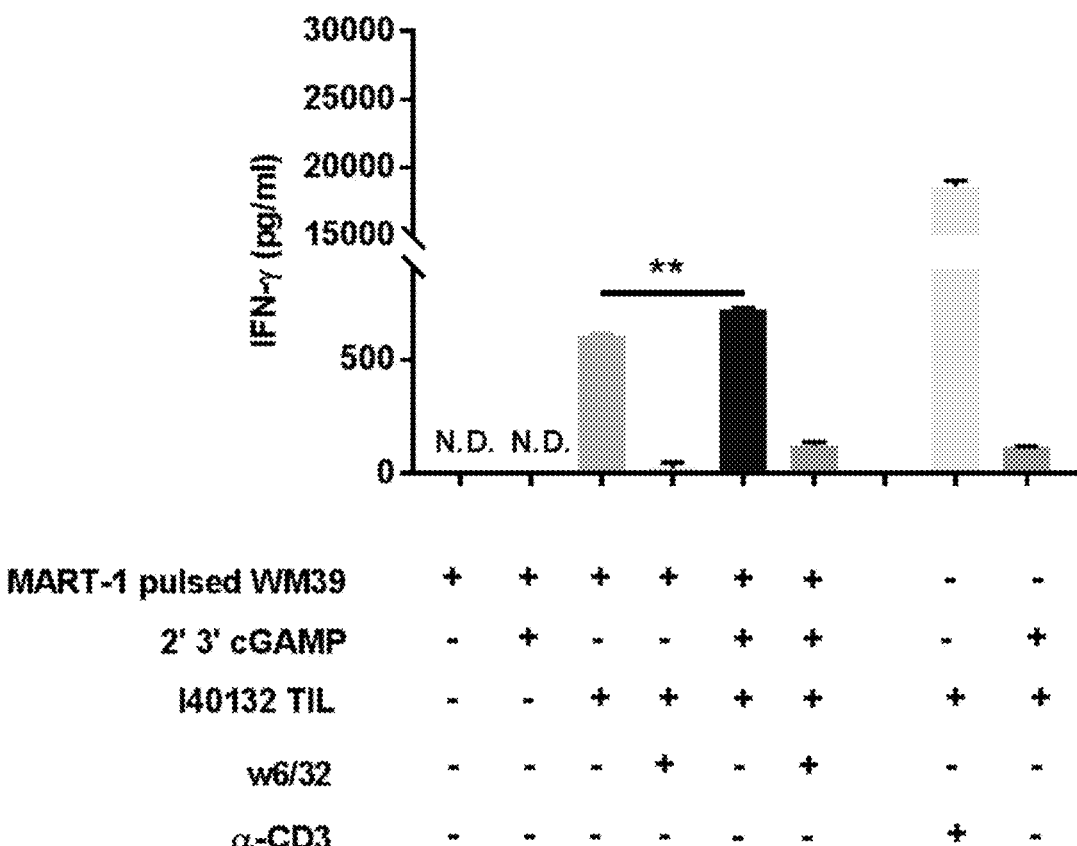
Figure 11D:
Figure 11D:
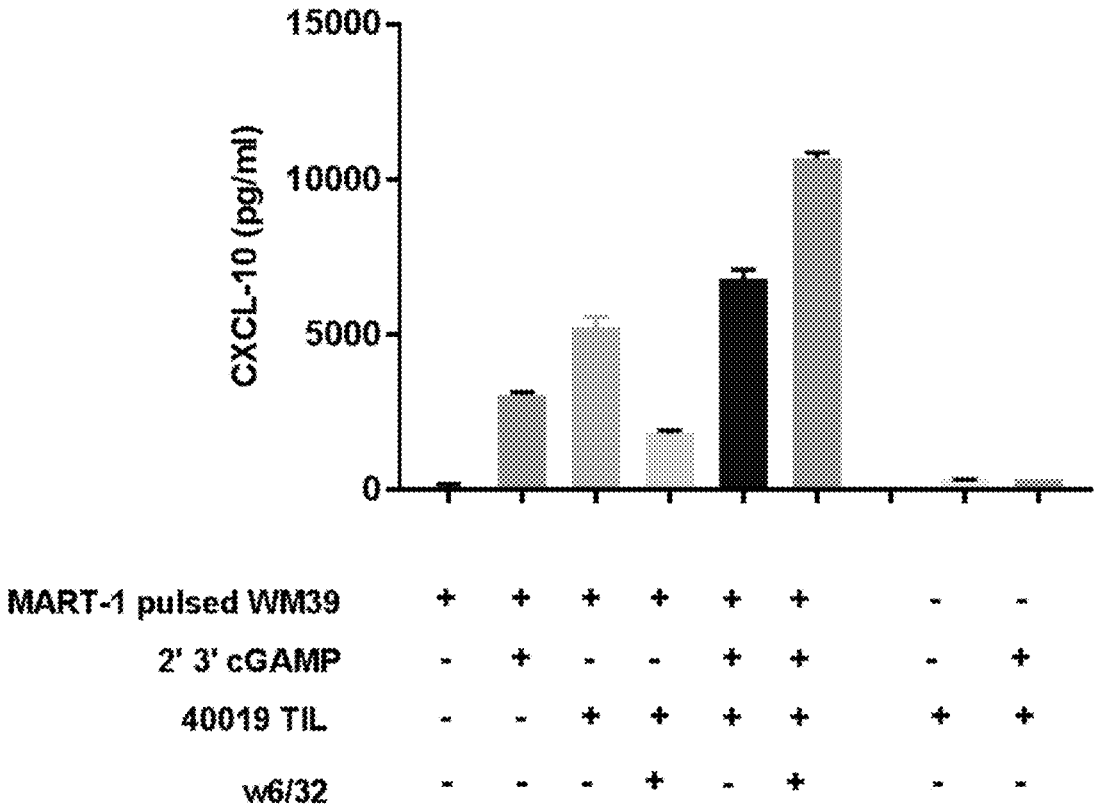
Figure 11E:
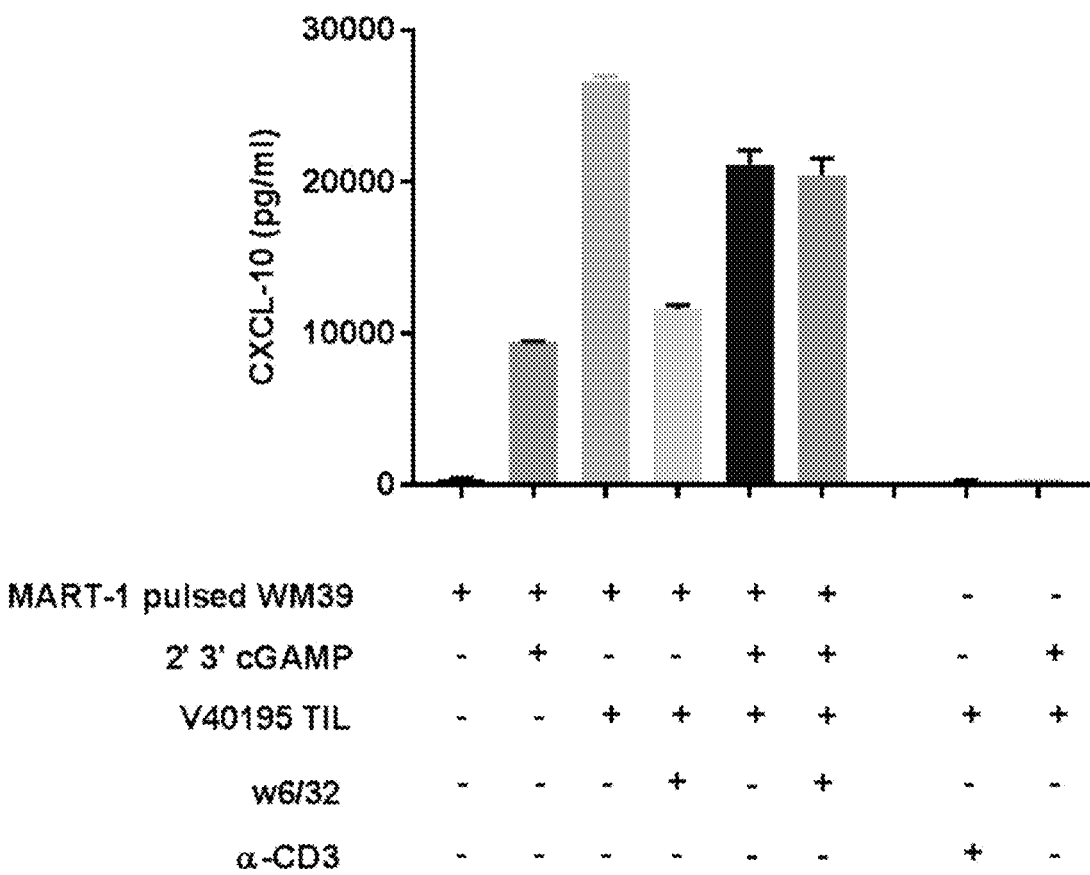
Figure 11F:
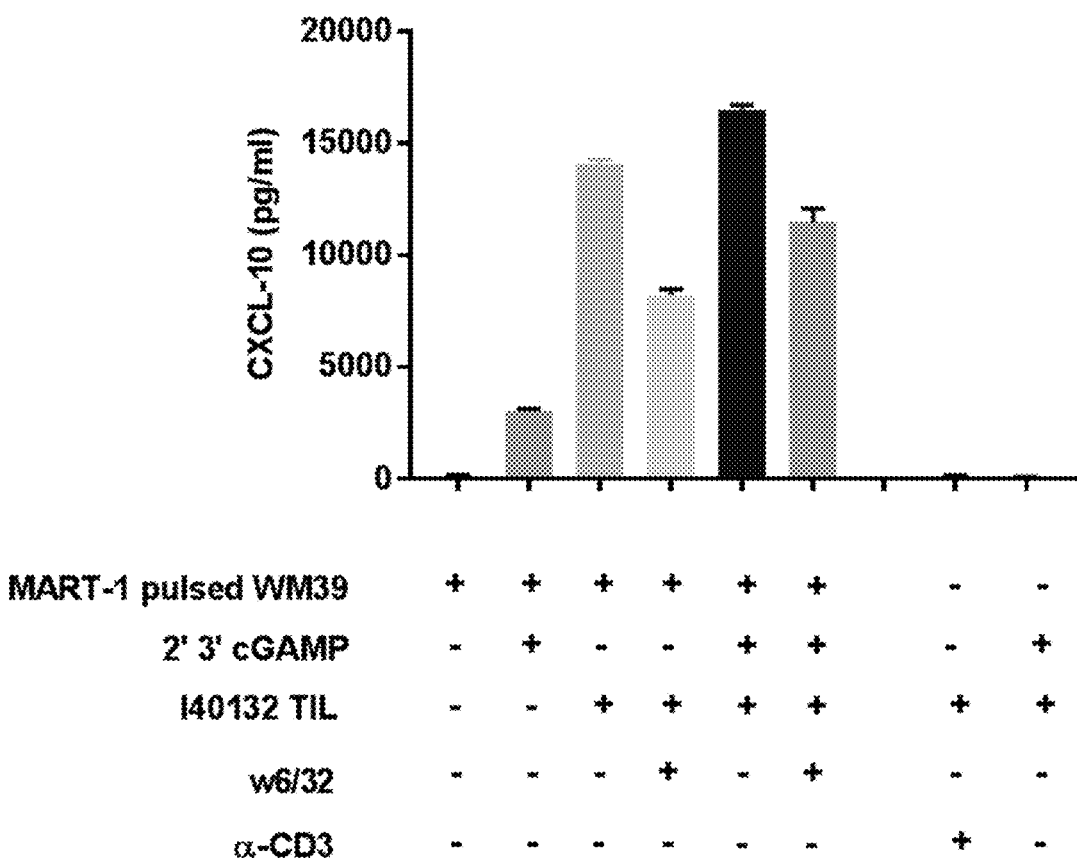
Figure 11G:
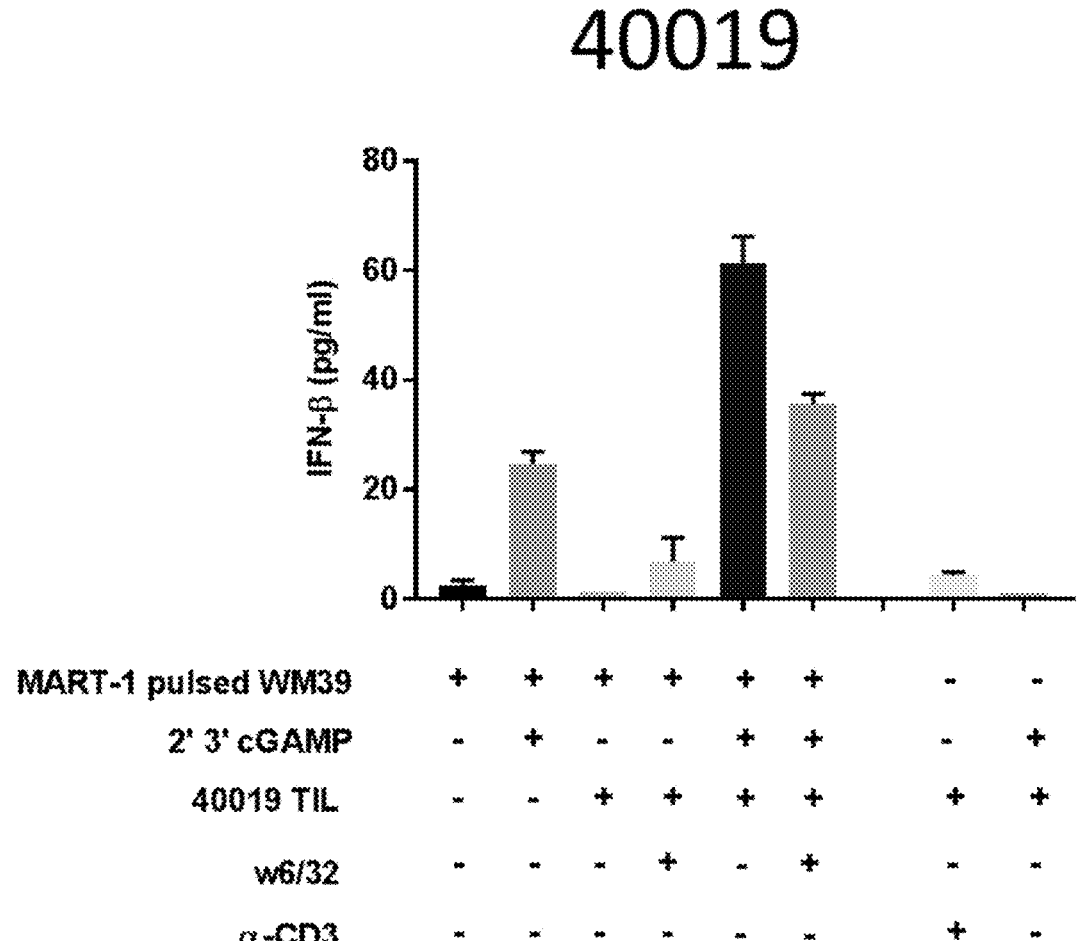
Figure 11H:
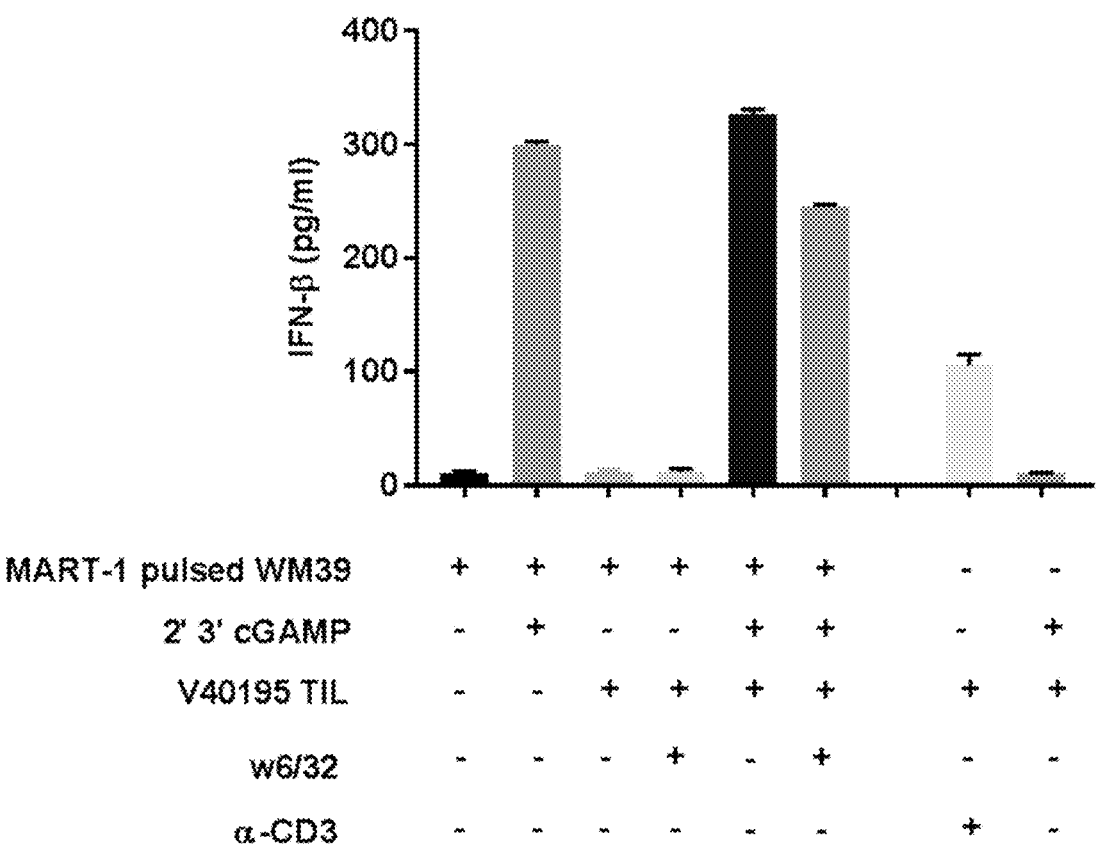
Figure 11I:
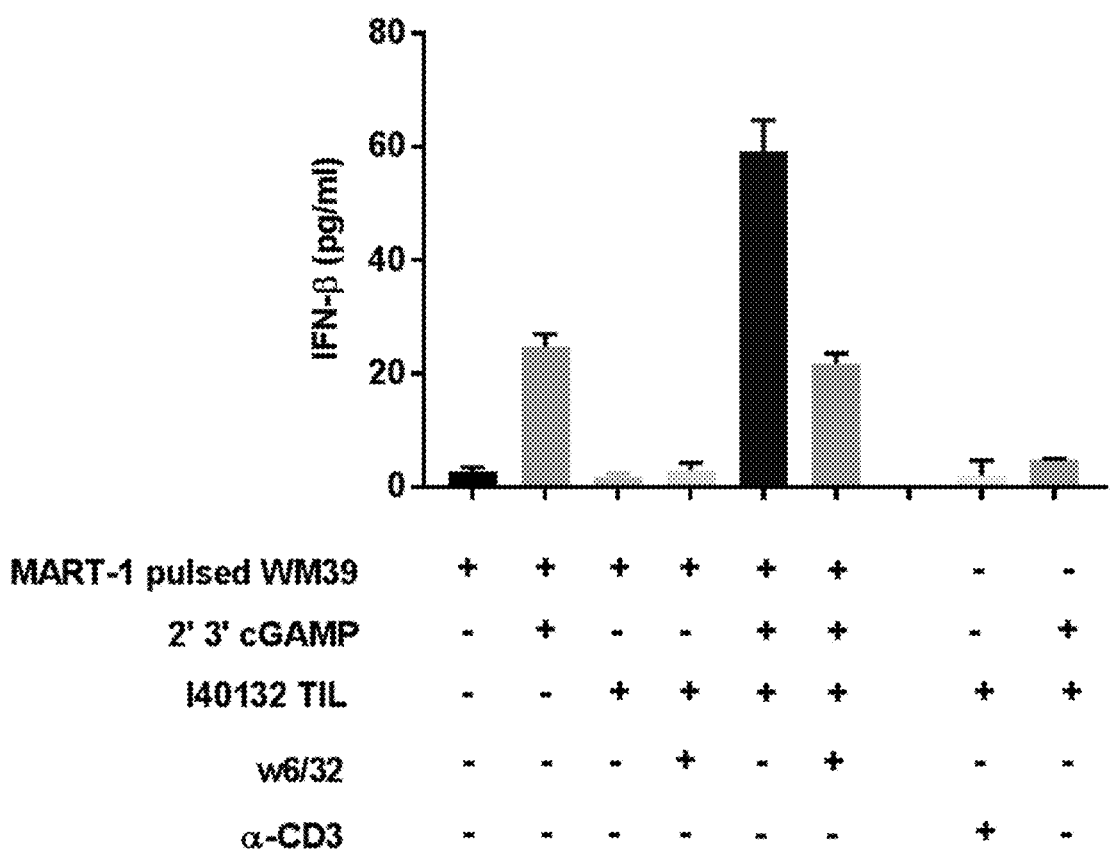
Figure 12A:
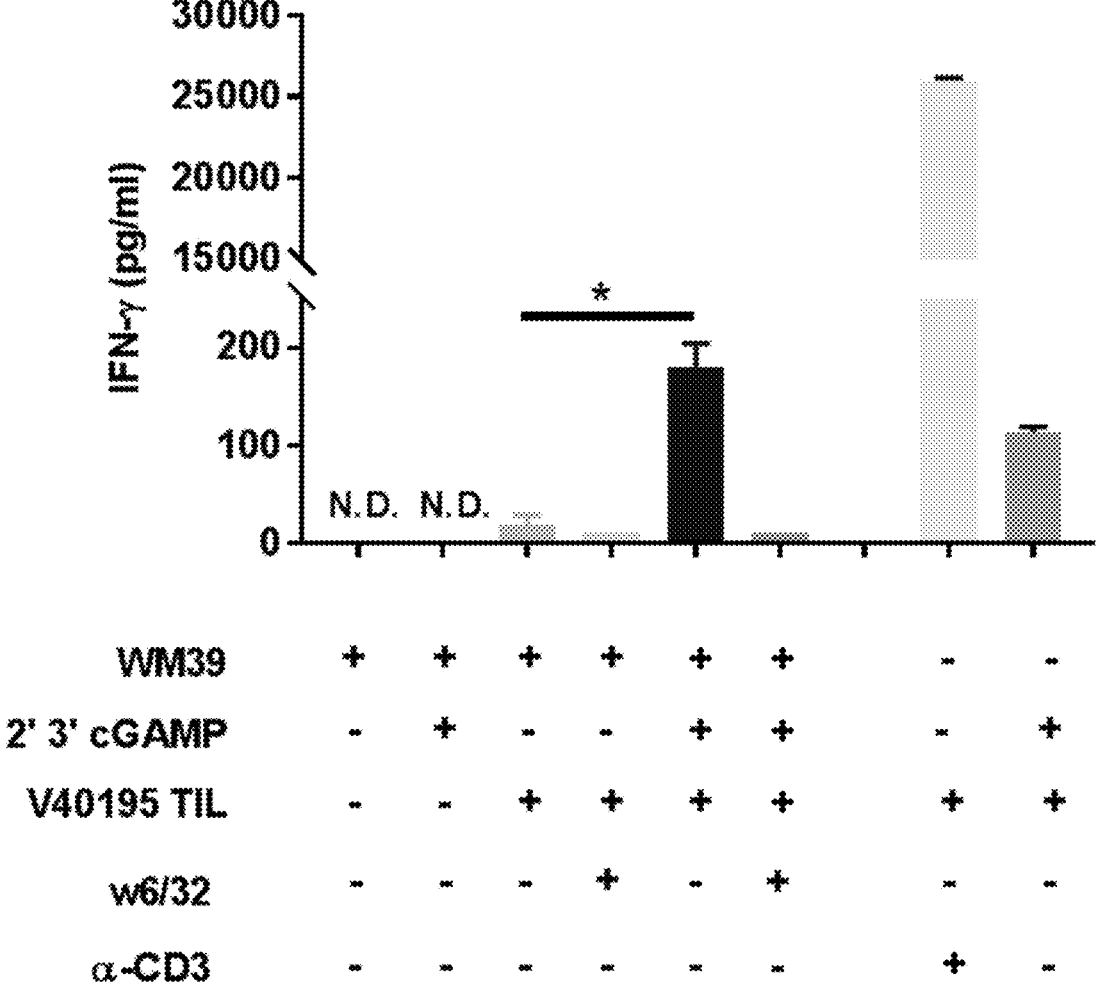
FIGS. 12A to 12I are bar graph showing IFN-γ (FIGS. 12A-12C), CXCL-10 (FIGS. 12D-12F), and IFN-β (FIGS. 12G-12I) expression in co-cultures of WM39, MART-1 pulsed WM39 or WM3629 with V40195 TIL.
Figure 12B:
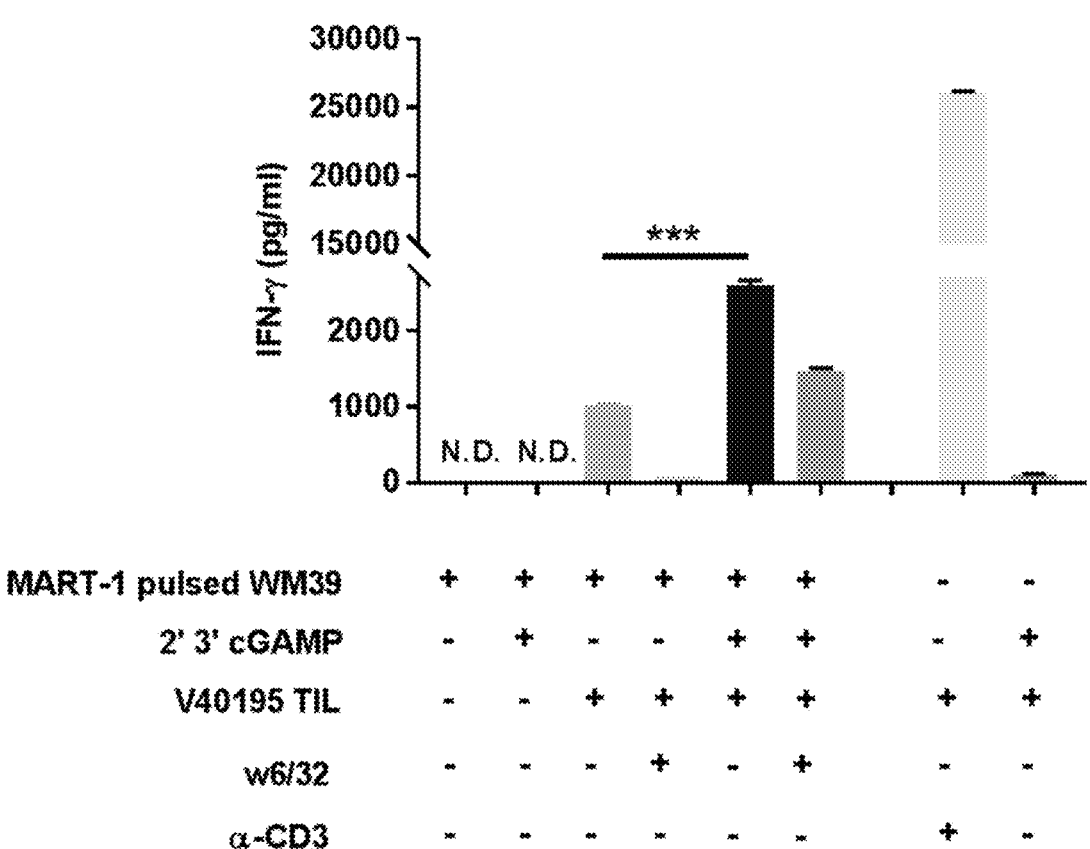
Figure 12C:
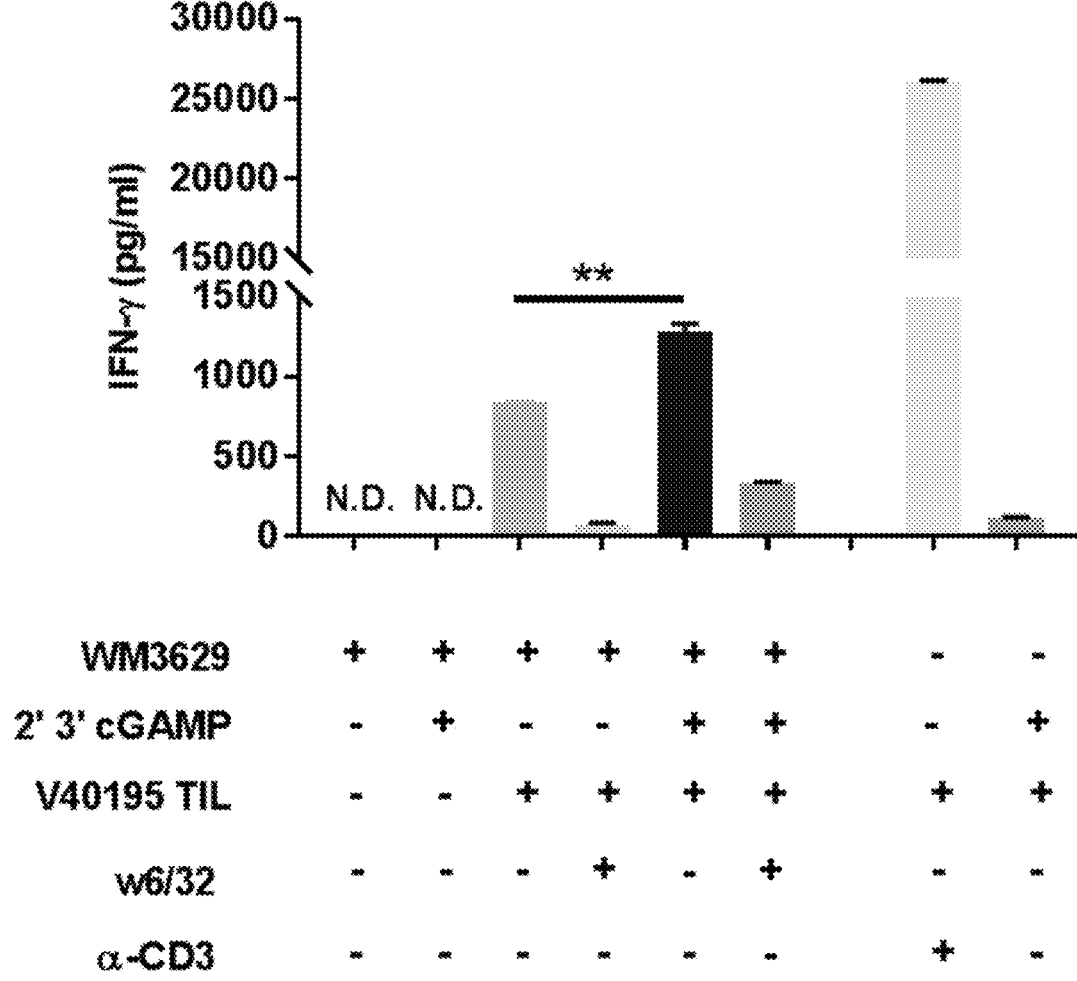
Figure 12D:
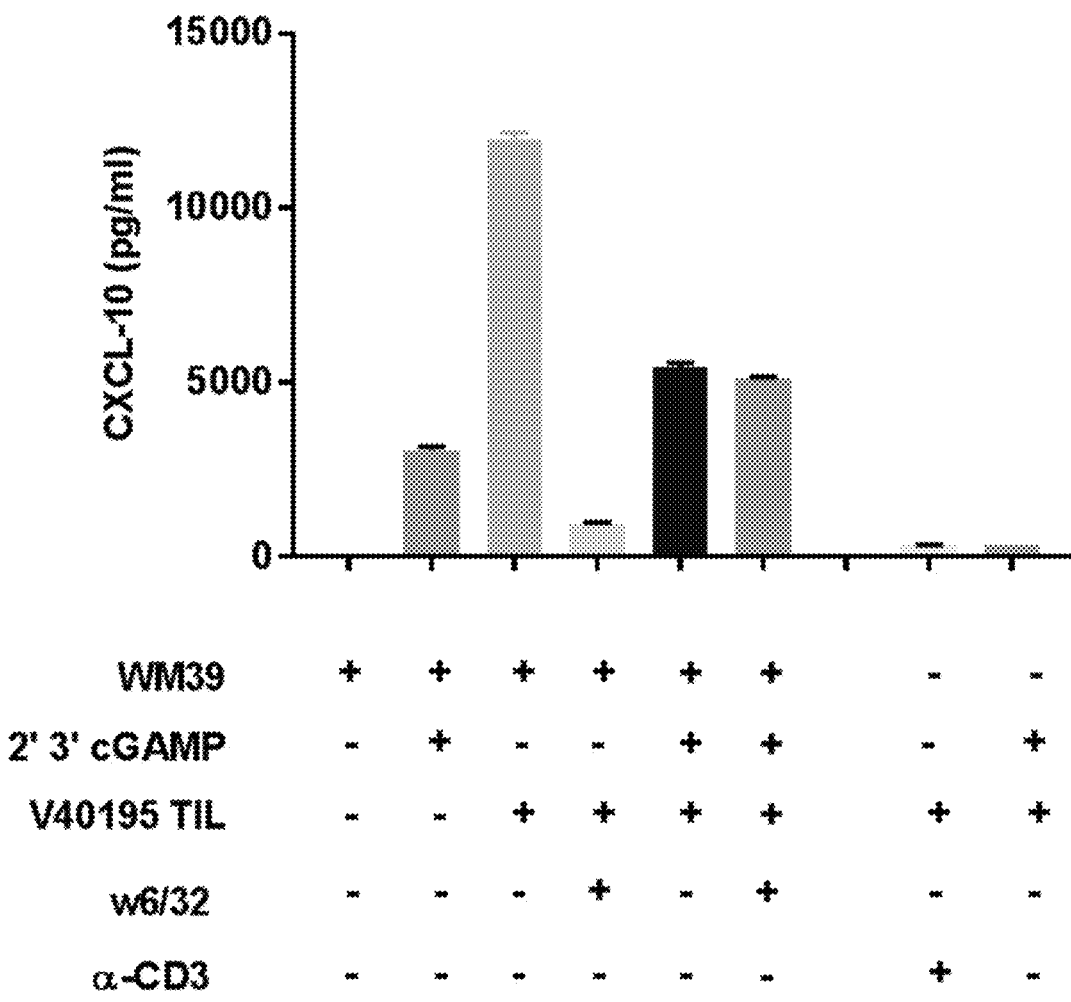
Figure 12E:
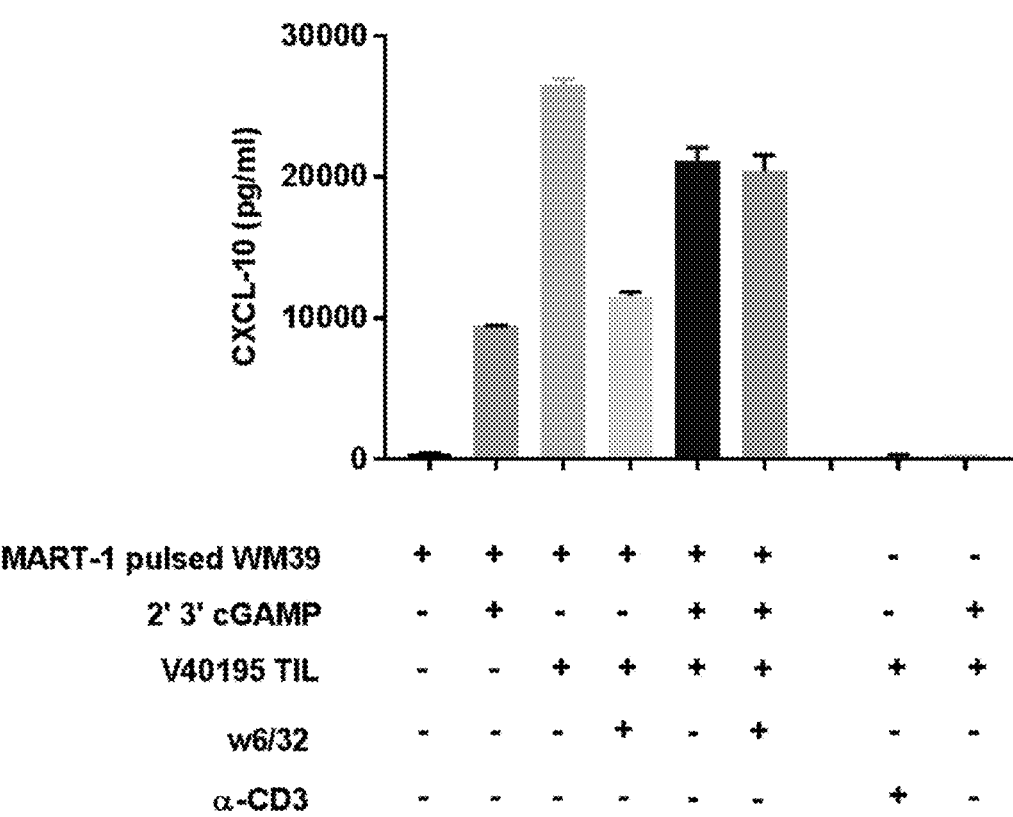
Figure 12F:
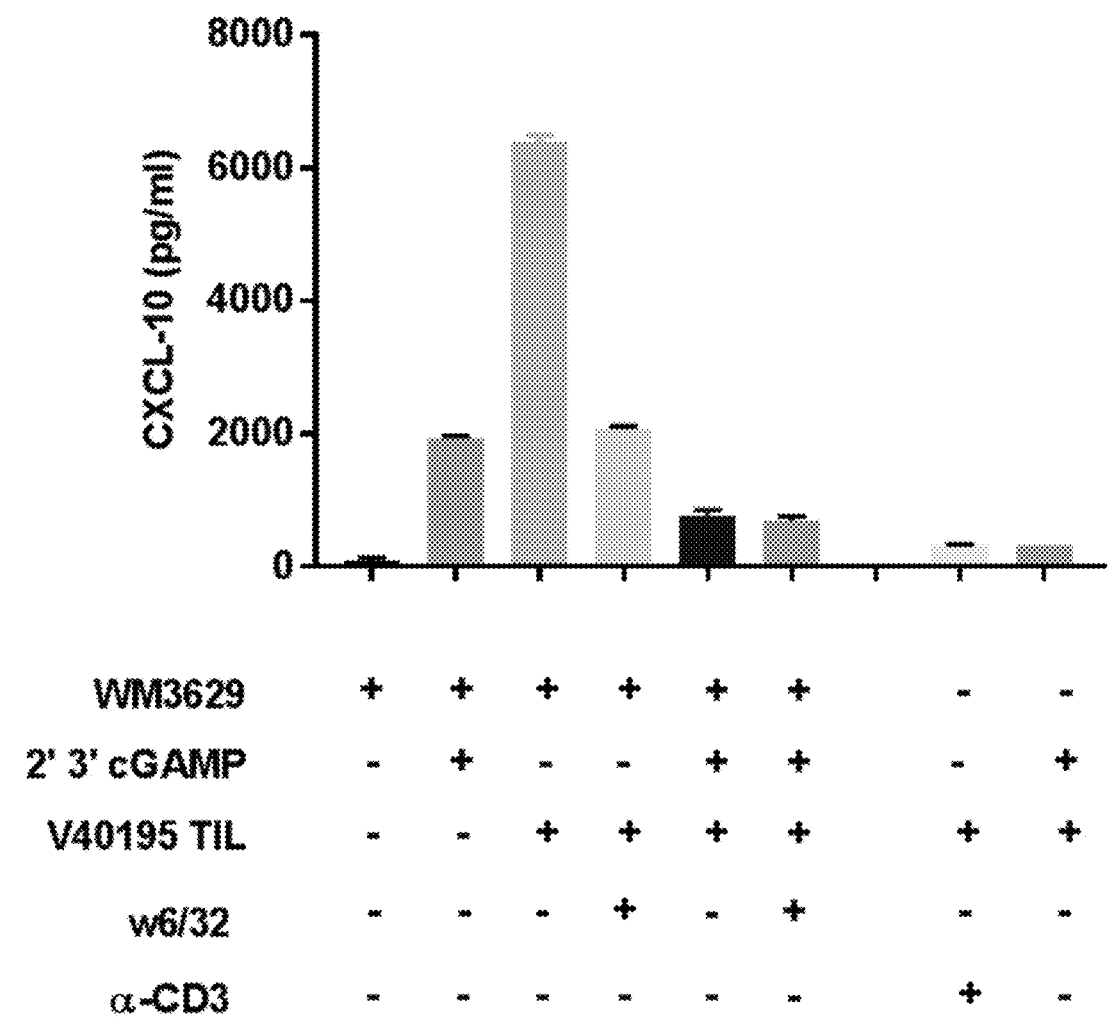
Figure 12G:
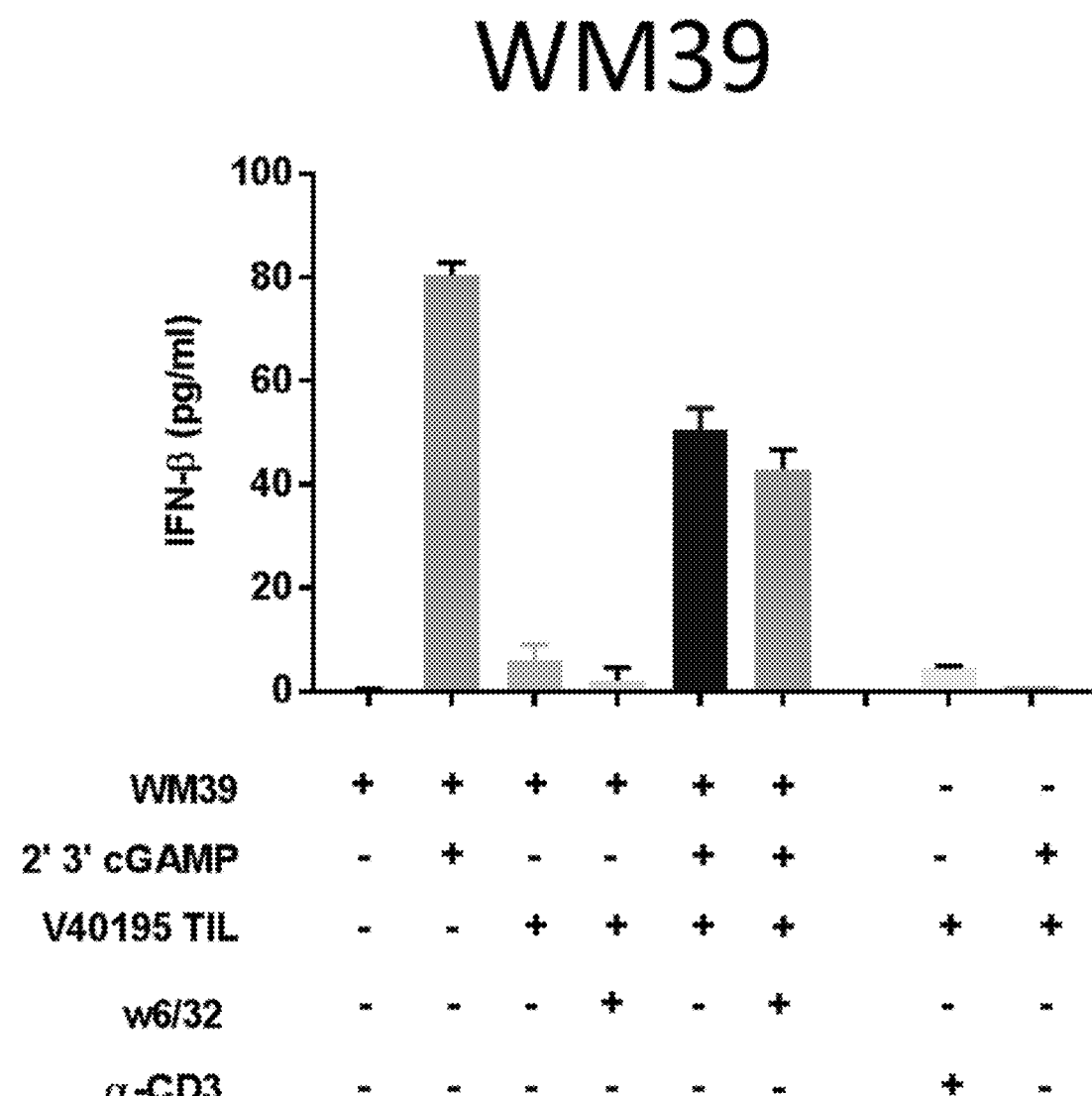
Figure 12H:
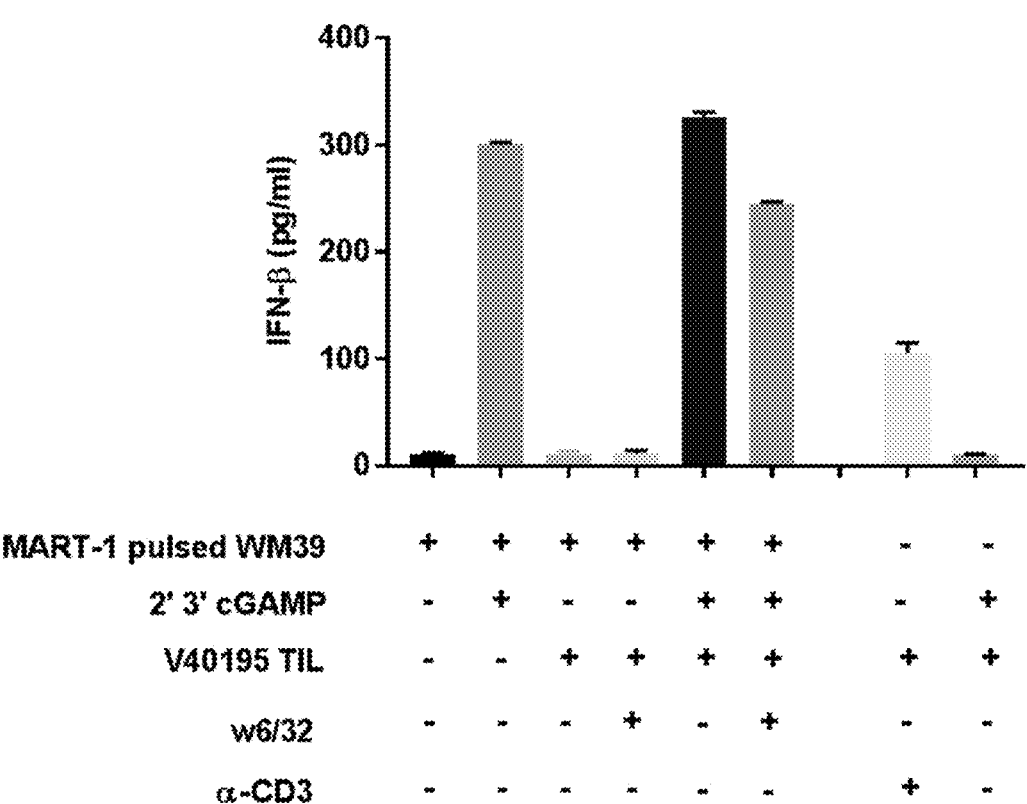
Figure 12I:
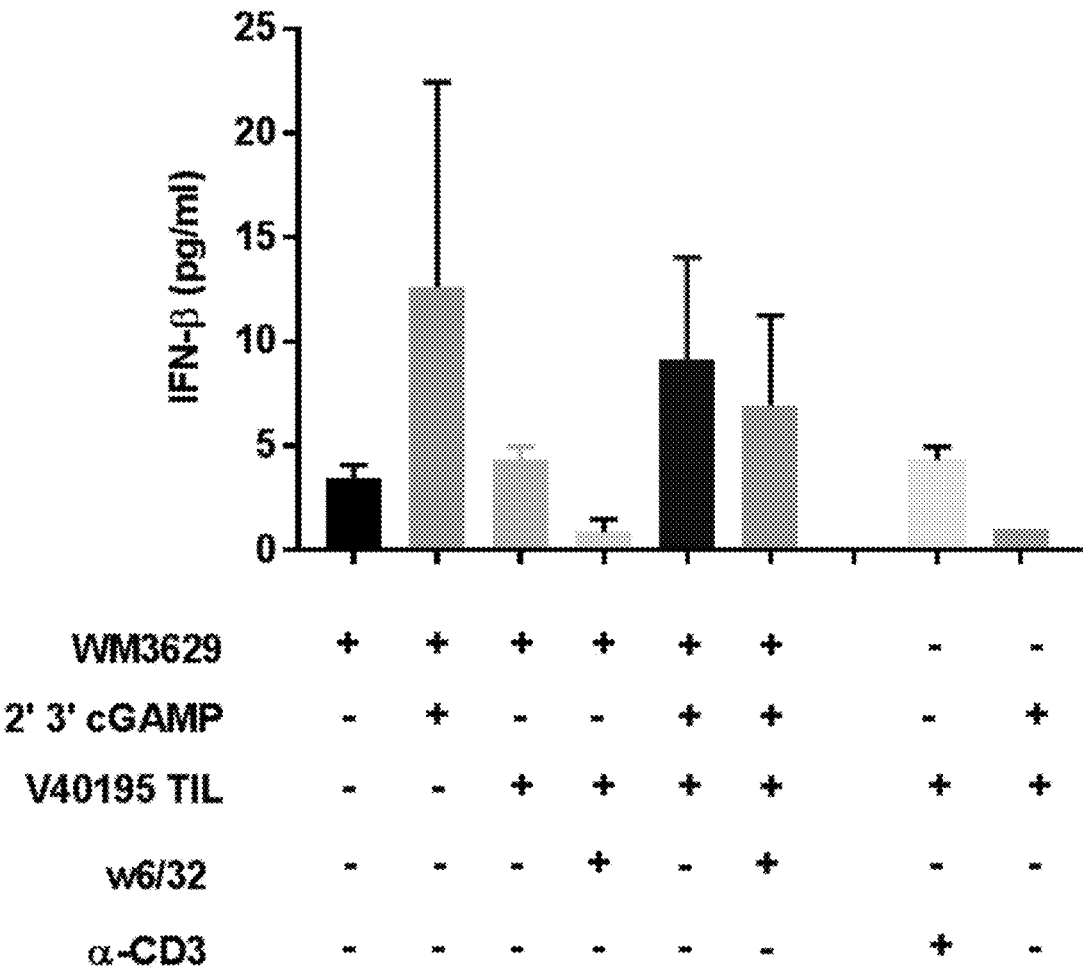

FIG. 10 is a bar graph showing activation of STING signaling in MART-1 pulsed WM39 melanoma cells results in increased IFN-γ secretion when cultured with V40195 TIL.

FIGS. 11A to 11I are bar graph showing IFN-γ, CXCL-10 &IFN-β expression in co-cultures of MART-1 pulsed WM39 with HLA-matched TILs.

FIGS. 12A to 12I are bar graph showing IFN-g, CXCL-10 & IFN-b expression in co-cultures of WM39, MART-1 pulsed WM39 or WM3629 with V40195 TIL.

Figure 13A:
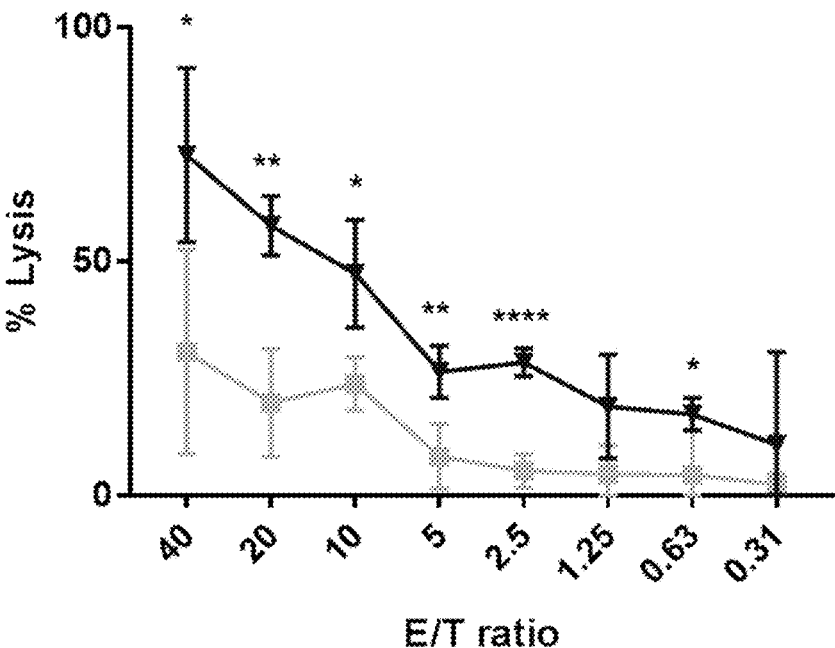
FIGS. 13A and 13B show activation of STING pathway in human melanomas improves their cytotoxic T lympho-cyte-mediated lysis.
Figure 13B:
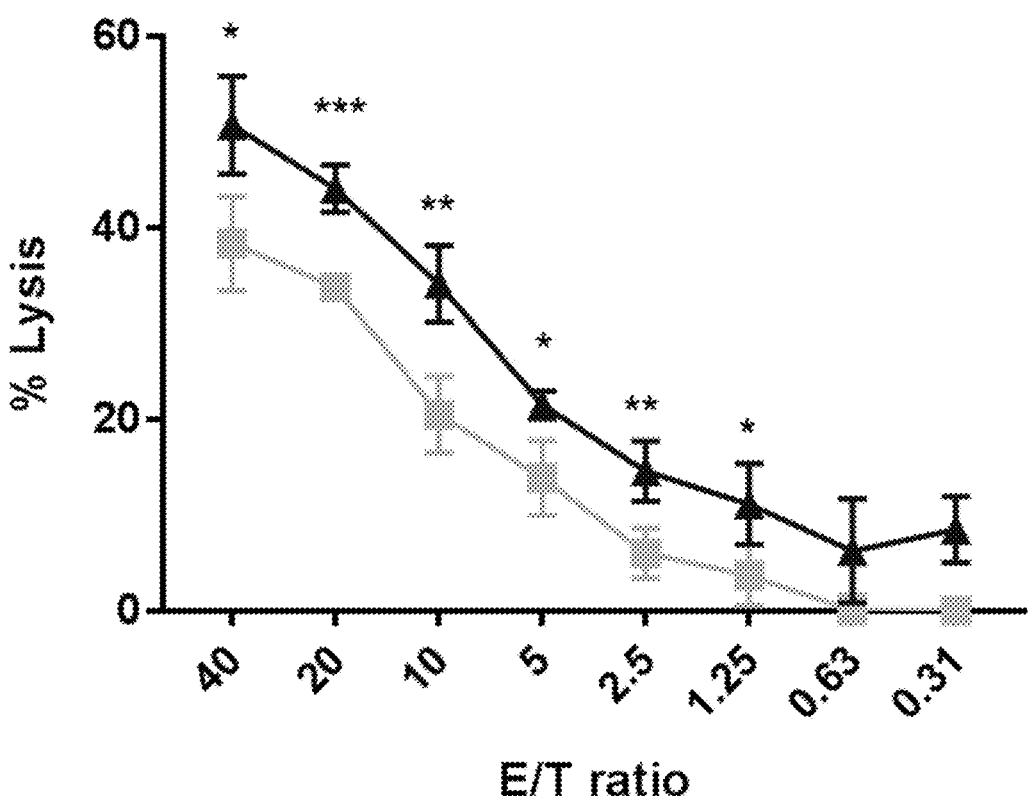

FIGS. 13A and 13B show activation of STING pathway in human melanomas improves their cytotoxic T lymphocyte-mediated lysis.

Figure 14:
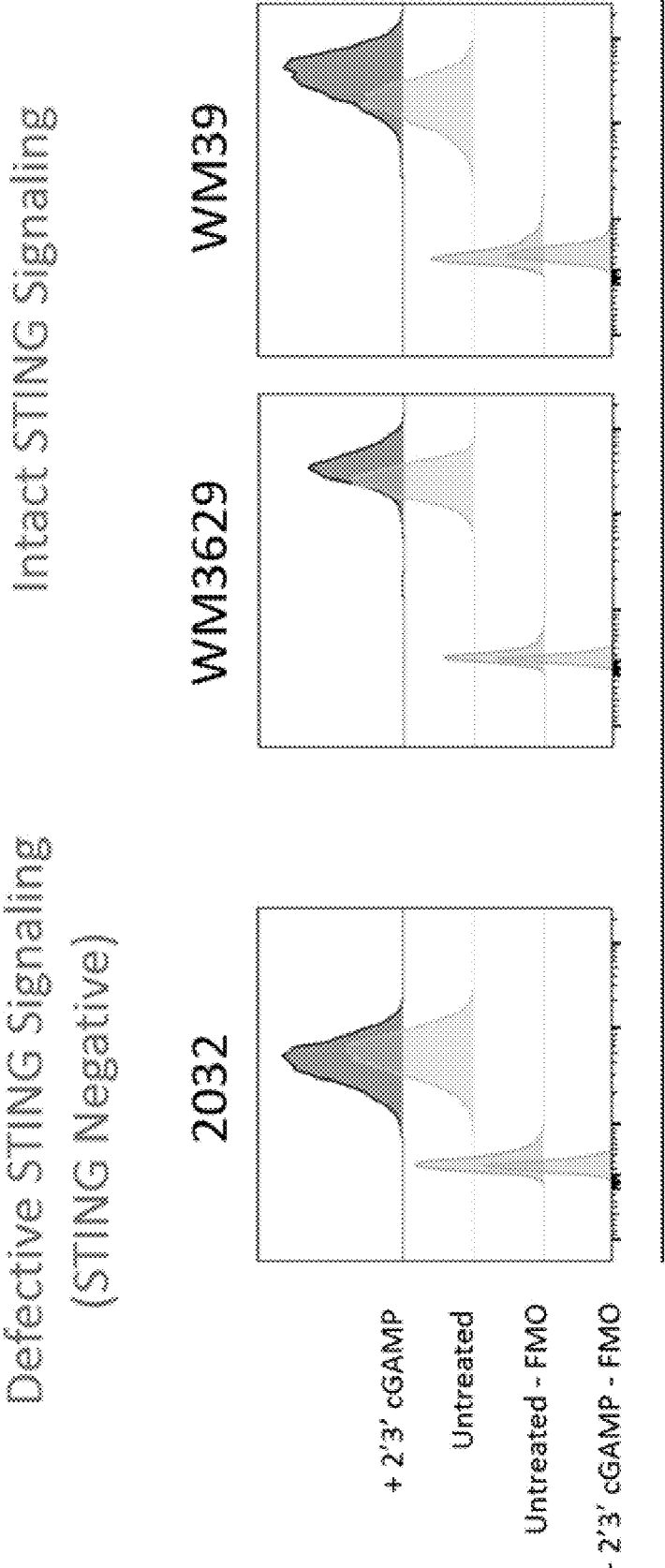
FIG. 14 shows MHC-I/HLA-A.B.C expression in mela-noma cell lines after treatment with 2'3' cGAMP. STING activation in human melanoma cell lines induces upregula-tion of MHC I (HLA-A.B.C).

FIG. 14 shows MHC-I/HLA-A.B.C expression in melanoma cell lines after treatment with 2'3' cGAMP. STING activation in human melanoma cell lines induces upregulation of MHC I (HLA-A.B.C).

In summary, activation of STING pathway in human melanoma cell lines improves their immunogenicity when cultured with HLA-matched TILs; improves their cytotoxic T lymphocyte-mediated lysis; and induces upregulation of MHC I (HLA-A.B.C).

Example 2: STING Signaling can Enhance Melanoma Antigenicity

Methods

STING and cGAS expression were examined in a panel of human melanoma cell lines by immunoblot. Functional STING signaling activation was examined in STING-positive melanoma cell lines upon stimulation with the agonist 2'3'-cGAMP by measuring the induction of CXCL-10 and IFN-β. To determine if hypermethylation was involved in the suppression of STING expression and signaling where gene mutations were absent, melanoma cells lacking STING expression were treated with 5-aza-2'-deoxycytidine (5AZADC). To study the role of STING signaling on antigenicity of melanoma, expanded human tumor infiltrating lymphocytes (TIL) were co-cultured with their HLA-matched melanoma cell lines in the presence or absence of 2'3'-cGAMP agonist. TIL production of IFN-γ and ⁵¹Cr release was assessed for cytotoxicity.

Results

Immunoblot analysis revealed a diverse STING/cGAS expression status in human melanoma cell lines. STING expression was not detected in 11 of 18 of them. Induction of STING expression in 5AZADC-treated melanoma cell lines lacking STING and production of CXCL-10 following their stimulation with the STING agonist suggested DNA hypermethylation involvement in cases where STING gene mutations were absent. Among STING-positive cell lines, two responded strongly to STING signaling activation with 2'3'-cGAMP. Activation of the STING pathway in these cell lines when cultured with their HLA-matched TILs resulted in up to a 15-fold increase in IFN-γ secretion (p<0.01) as well augmentation of TIL cytotoxicity by >2-fold (p<0.05). In addition, STING activation could induce enhanced surface expression of MHC class I in human melanoma cell lines leading to more effective tumor antigen recognition by TIL.

CONCLUSIONS

Direct activation of the STING pathway in human melanoma cell lines can result in improved antigenicity.

Example 3: Tumor Cell-Intrinsic STING Signaling Impacts Antigenicity of Melanoma and can Promote Antitumor T-Cell Activity Methods

Preparation of TIL

Melanoma TIL were established as described previously (Pilon-Thomas S, et al. J Immunother. 2012 35:615-20). Briefly, melanomas were minced into 1-2 mm³ fragments and plated in 24-well plates with 2 mL TIL culture medium (TIL-CM) containing 6000 IU/mL IL-2 (Proleukin) per well. The TIL-CM consisted of RPMI 1640, 2.05 mM L—glutamine (HyClone, Thermo Fisher Scientific), 10% heat-inactivated human AB serum (Omega Scientific), 55 μM 2-mercaptoethanol (Invitrogen), 50 μg/mL gentamicin (Invitogen), 100 IU/mL penicillin, 100 μg/mL streptomycin, and 10 mM HEPES Buffer (Mediatech). Half of the medium was replaced every 2 to 3 days or wells were split when 90% confluent. TIL were expanded for 3-5 weeks. HLA typing of TIL was performed by the HLA Laboratory (American Red Cross, Dedham, MA). TIL 195, TIL 19 and TIL 123 were HLA-A typed as A02, A02/26 and A02/11, respectively.

Melanoma Cell Lines

Human melanoma cell lines 1205Lu, A375, SBCL2, WM9, WM35, WM39, WM164, WM858, WM1361A, WM1366, WM2032, WM3130, WM3629, 526-MEL and 888-MEL were maintained as monolayers in complete medium consisting of RPMI 1640 supplemented with 10% heat-inactivated FBS and antibiotics. HLA typing of melanoma cell lines was performed by the HLA Laboratory (American Red Cross, Dedham, MA). WM39, WM3629 and 526-MEL were HLA-A typed as A01/02, A02/30 and A02/03, respectively.

Knockdown of STING in WM39 cells was achieved using lentiviral particles carrying a target gene sequence for human STING (TMEM173) or scrambled control (Origene Technologies). Transduced cells were selected by addition of puromycin (0.5 μg/ml) to the medium 24 h after infection.

STING Agonist Stimulation

Human melanoma cell lines (4×10⁵ cells/well in 24-well plates) were stimulated with 2'3'-cGAMP (10 μg/ml) in the presence of Lipofectamine 2000 (Invitrogen) according to the manufacturer's instructions. After 4 or 24 hours of incubation at 37° C. in a humidified CO₂ incubator, the supernatants were collected for detection of CXCL10 and IFN-β release using enzyme-linked immunosorbent assays (Quantikine ELISA Kit, R&D Systems), and cells were scraped, washed and lysed for assessment of IRF3 phosphorylation by immunoblot.

Immunoblot Analysis

Proteins were extracted with RIPA buffer (ThermoFisher Scientific) containing protease inhibitors (Thermo Scientific). Protein extracts from NK92, a natural killer cell line, was used as a positive control for the expression of STING and cGAS (Souza-Fonseca-Guimaraes F, et al. J Biol Chem. 2013 288:10715-21). Equal amounts of proteins were resolved on SDS-PAGE gels (Bio-Rad) and transferred to polyvinylidene fluoride (PVDF) membranes (Bio-Rad). After blocking with 5% non-fat dry milk, membranes were incubated with antibodies specific for STING, cGAS, p-IRF3, IRF3 (all from Cell Signaling) and β-actin (Sigma Aldrich). Following incubation with appropriate secondary antibodies, bands were visualized using an enhanced chemi-luminescence detection system.

Co-Culture Assay $1\times10^5$ of melanoma cells were cultured with TIL at a 1:1 ratio with or without 2'3'-cGAMP (10 μg/ml) in 96-well round-bottom plates. After 24 hours of incubation at 37° C. in a humidified $CO_2$ incubator, the supernatant was harvested for detection of IFN-γ release using enzyme-linked immunosorbent assay (Human IFN-γ Quantikine ELISA Kit, R&D Systems). For the MHC class I blocking assay, melanoma cells were incubated with W6/32 (anti-HLA-A, B,C monoclonal antibody, Biolegend) at a final concentration of 50 μg/mL for 1 hour at 37° C. prior to the addition of TIL.

$^{51}Cr$ Release Assay

Lysis of melanoma cell targets by their HLA-matched TIL cultures was measured in a standard $^{51}Cr$ release assay, as described previously (Zhu G, et al. Front Immunol. 2018 9:1609). Briefly, $1\times10^6$ melanoma cells were labeled with 100 μCi of $^{51}Cr$ (Amersham Corp) for 2 h at 37° C. Following three washes with HBSS, labeled target cells were resuspended in TIL CM with or without 2'3'-cGAMP (10 μg/ml) at a concentration of $5\times10^4$ tumor cells/ml and added to the effector cells at different effector-to-target cell ratios in a 96-well plate and incubated at 37° C. In addition, two control conditions were included in this assay: a minimum release control containing just the target cells and a maximum release control in which target cells were lysed by TritonX-100. After 4 hours, supernatant was harvested and measured in Trilux (PerkinElmer). Each point represented the average of quadruplicate wells and percentage of specific lysis was calculated by: (experimental release—minimum release)/(maximum release-minimum release)×100. Lytic units were calculated as the number of effector cells required to produce 20% lysis of $5\times10^3$ target cells expressed as the inverse and normalized to $1\times10^6$ cells (Bryant J, et al. J Immunol Methods. 1992 146:91-103).

Flow Cytometry

Flow cytometry was performed using HLA-A.B.C-PE antibody (1:100, Biolegend, clone W6/32). DAPI (Sigma-Aldrich) was used as a viability dye. Sample acquisition was performed on an LSR II flow cytometer (BD Biosciences), and the data were analyzed using FlowJo software (Tree Star).

Statistical Methods

Statistical analyses were performed using GraphPad Prism7 software. All data are presented as mean±SEM. Means for all data were compared by unpaired Student's t-test or one-way ANOVA. P-values of <0.05 were considered statistically significant. *p<0.05, p<0.01, *p<0.001, ****p<0.0001.

Results

Identification of Melanoma Cell Lines with Intact STING Signaling

Figure 15A:
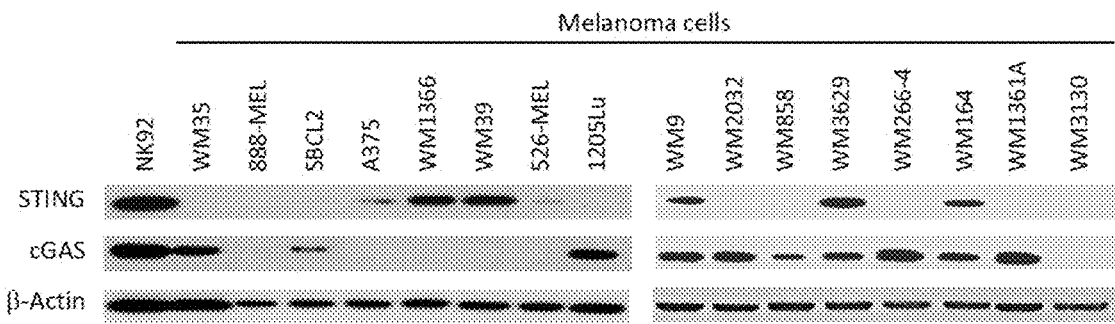
FIGS. 15A to 15F show identification of melanoma cell lines with intact STING signaling.
Figure 15B:
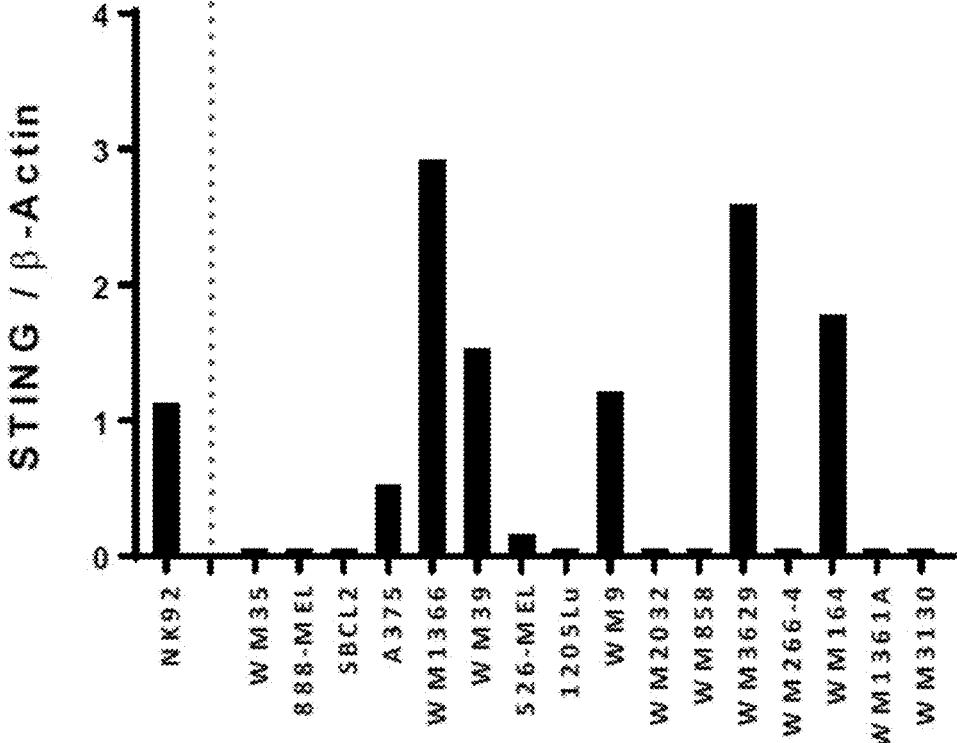
Figure 15C:
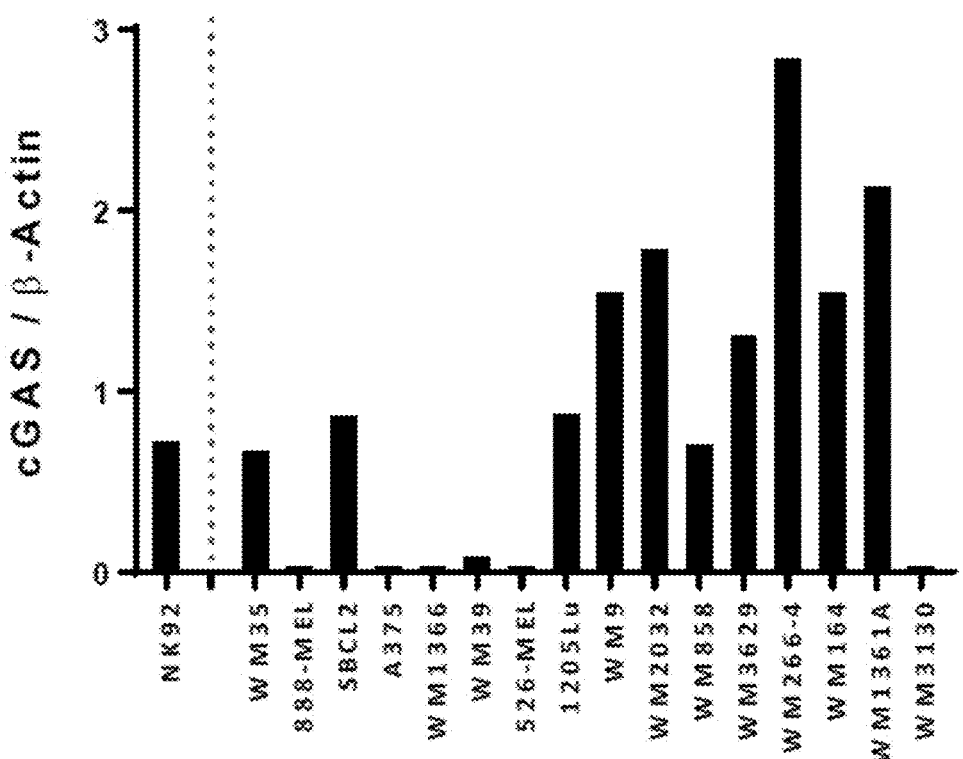

To identify melanoma cell lines with intact STING signaling, expression of STING and cGAS was first evaluated in a panel of human melanoma cell lines by immunoblot (FIG. 15A). There were varying expression levels of STING and cGAS among these cell lines consistent with a previous report (Xia T, et al. Cancer research. 2016 76:6747-59). STING was not detectable in 9 of 16 melanoma cell lines (WM35, 888-MEL, SBCL2, 1205Lu, WM2032, WM858, WM266-4, WM1361A and WM3130). We identified A375, WM1366, WM39, WM9, WM3629 and WM164 as STING-positive cell lines (FIG. 15B). cGAS was detected in 10 of 16 cell lines (FIG. 15C), and only 3 cell lines (WM9, WM3629 and WM164) expressed both cGAS and STING.

Figure 15D:
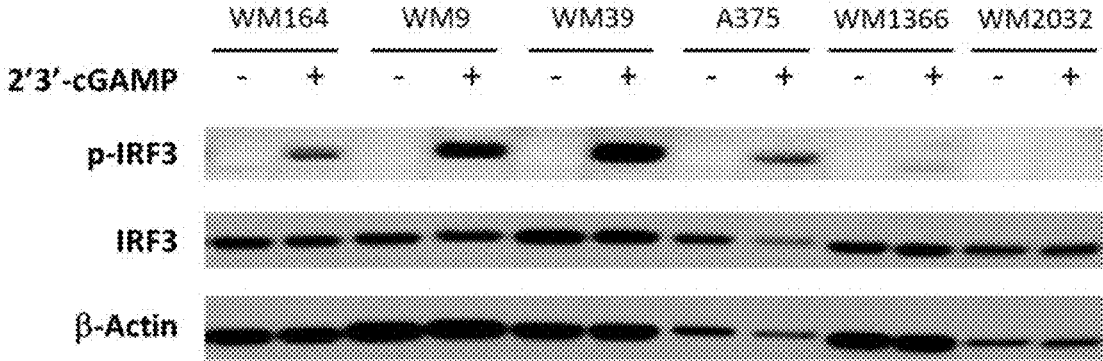
Figure 15E:
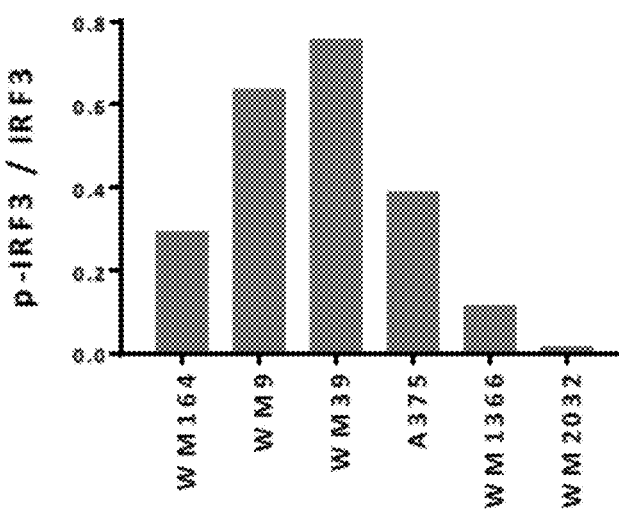
Figure 15F:
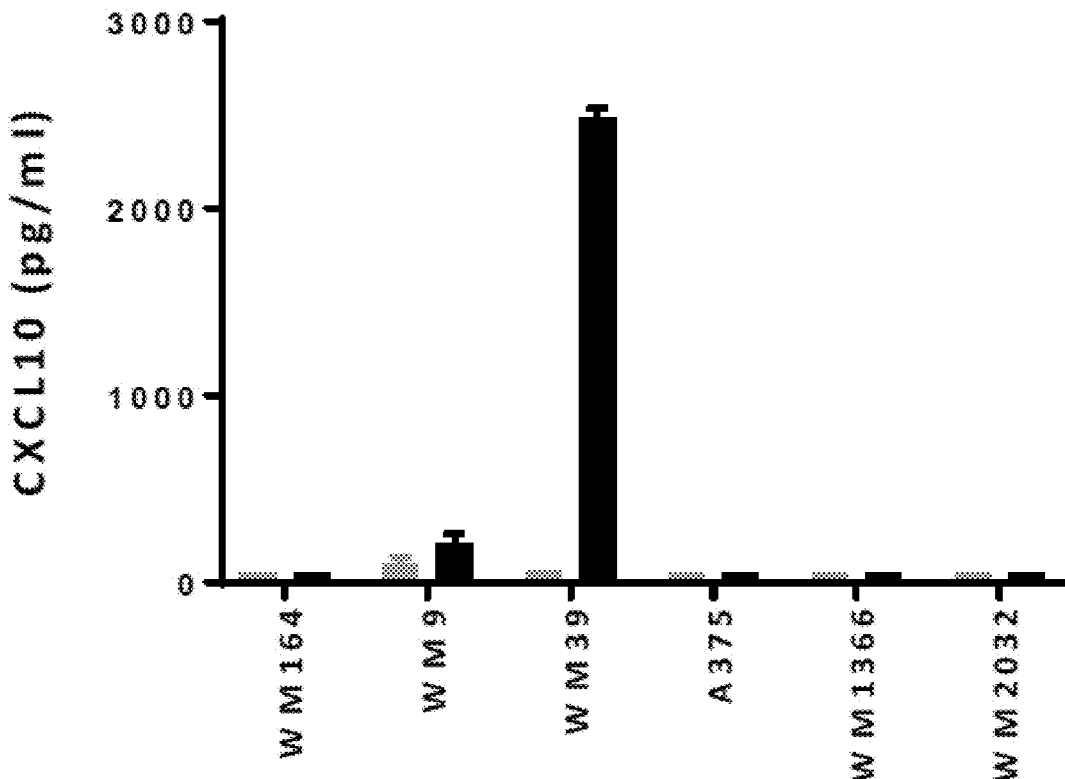
Figure 15G:
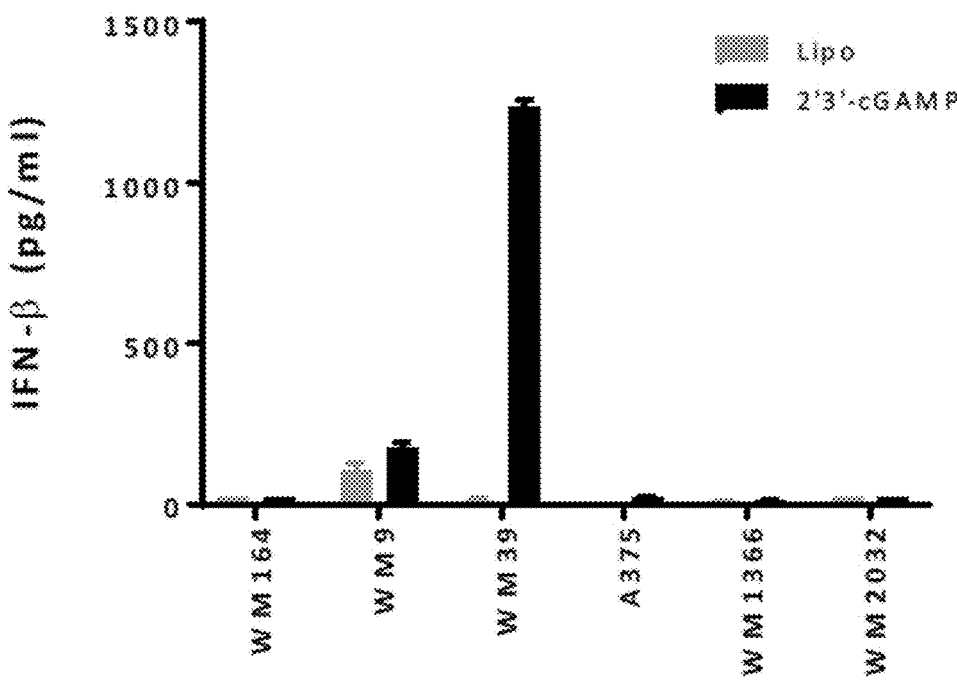

Next investigated was the functional STING signaling activation by stimulating melanoma cell lines with the STING agonist 2'3'-cGAMP. As this agonist activates STING signaling in a cGAS-independent manner, 5 STING-positive cell lines (WM164, WM9, WM39, A375 and WM1366) and 1 STING-negative cell line (WM2032) were. Immunoblot analysis was performed on cell extracts after stimulation with 2'3'-cGAMP to assess phosphorylation of the transcription factor IRF3, which is a critical downstream regulatory element for STING-dependent type I IFN induction (Tanaka Y, et al. Science signaling. 2012 5:ra20). phosphorylation of IRF3 in 4 of 5 STING-positive cell lines was observed following their stimulation with 2'3'-cGAMP (FIGS. 15D and 15E). As expected, phosphorylation of IRF3 was not detected for the 2'3'-cGAMP stimulated WM2032 (STING-negative) cell line. STING-dependent CXCL10 and IFN-β induction was also determined in cell culture supernatants of the indicated melanoma cell lines following stimulation with 2'3'-cGAMP (FIGS. 15F and 15G). Among these cell lines, WM9 and WM39 induced detectable levels of CXCL10 and IFN-β in response to stimulation with 2'3'-cGAMP.

Activation of STING Signaling Results in Enhanced Antigenicity of Human Melanoma Cell Lines To study the role of STING signaling in antigenicity of melanoma, WM39 (HLA-A2) was initially selected, as this cell line responded strongly to STING signaling activation with 2'3'-cGAMP, and it was used in co-cultures of HLA-A2-restricted human melanoma TIL (TIL 195) in the presence or absence of the STING agonist. Experimental conditions in which WM39 cells were pre-incubated with an MHC class I blocking Ab (w6/32) were also included to determine whether IFN-γ release was mediated by CD8+ TIL TCR engagement with peptide/MHC class I.

The antigenicity by IFN-γ release was assessed, demonstrating that when co-cultures were performed with 2'3'-cGAMP-treatment, there was significantly enhanced IFN-γ secretion by HLA-matched TIL 195 (FIG. 2A). Blockade of IFN-γ release was also observed in the presence of the MHC class I blocking Ab (w6/32), which confirmed MHC class I—mediated CD8+ reactivity.

CXCL10 and IFN-β (FIG. 12) levels were also measured in co-culture supernatants to confirm 2'3'-cGAMP-triggered activation of STING signaling. Although there was CXCL10 induction in the co-culture group without 2'3'-cGAMP, this effect was related to STING-independent and IFN-γ-mediated induction of CXCL10 in WM39 cells (Peng W, et al. Cancer research. 2012 72:5209-18). Induction of IFN-β in co-culture groups with 2'3'-cGAMP confirmed activation of STING signaling. IFN-β induction was not observed for the control group containing TIL with 2'3'-cGAMP which suggests tumor cells are the main source of IFN-β expression in the co-culture group in response to stimulation with the agonist. Taken together, these data indicate that activation of STING signaling plays a notable role in enhancing antigenicity of WM39 cells.

To further investigate the impact of STING activation on antigen-presentation and immune T cell activity, WM39 cells were pulsed with MART-1 (a known melanoma specific peptide recognized by HLA-A2-restricted TIL (Kawakami Y, et al. J Exp Med. 1994 180:347-52)), and co-cultured them with TIL 195 in the presence or absence of the STING agonist 2'3'-cGAMP (FIG. 12). Similarly, there was a significantly increased (p<0.001) secretion of IFN-γ by TIL 195 in the 2'3'-cGAMP-treated co-culture group.

Consistent with the WM39 co-cultures, there were similar patterns of CXCL10 and IFN-β (FIG. 12) induction for MART-1-pulsed WM39 co-cultures, which confirmed activation of STING signaling in 2'3'-cGAMP-treated groups.

MART-1 pulsed WM39 cells were also co-cultured with two additional HLA-A2 TIL. Similarly, there were higher levels of IFN-γ production (p<0.01) by both TIL samples in 2'3'-cGAMP-treated co-cultures compared to the untreated co-cultures. Furthermore, WM3629 (HLA-A2) melanoma cell line was tested that in earlier experiments responded to 2'3'-cGAMP stimulation but to a lesser extent than WM39, and used it in co-cultures with TIL 195 in the presence or absence of the STING agonist (FIG. 12). Stimulation with 2'3'-cGAMP similarly resulted in increased (p<0.01) IFN-γ release in WM3629/TIL 195 co-cultures, indicating that the enhancing effect of 2'3'-cGAMP was not restricted to the WM39 melanoma cell line.

Figure 16A:
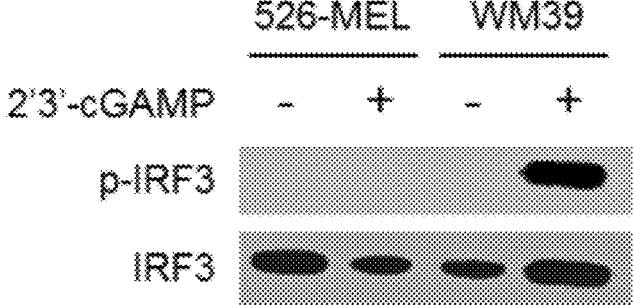
FIGS. 16A to 16E show STING signaling is required in melanoma cells for agonist-induced improved antigenicity.
Figure 16B:
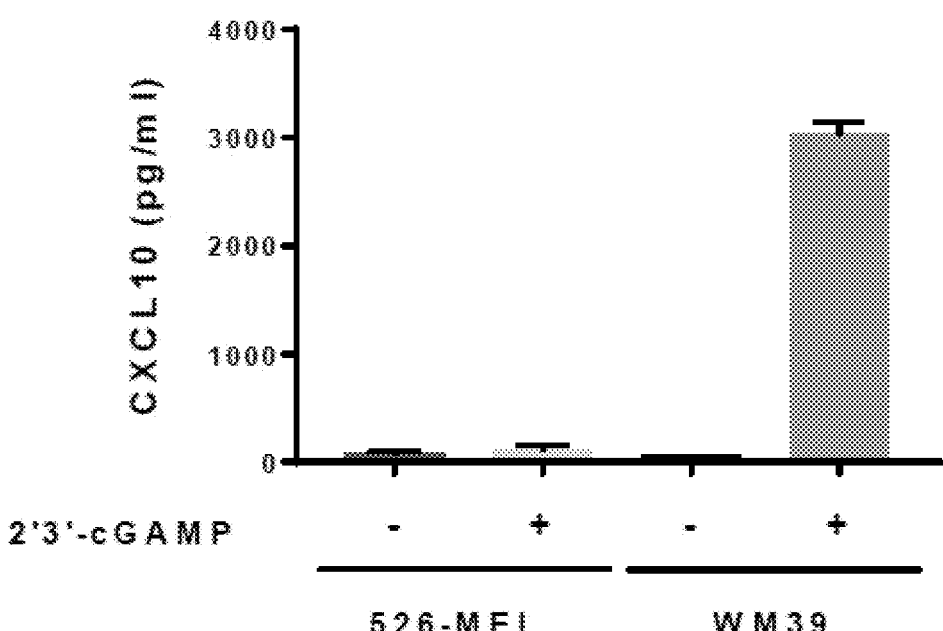
Figure 16C:
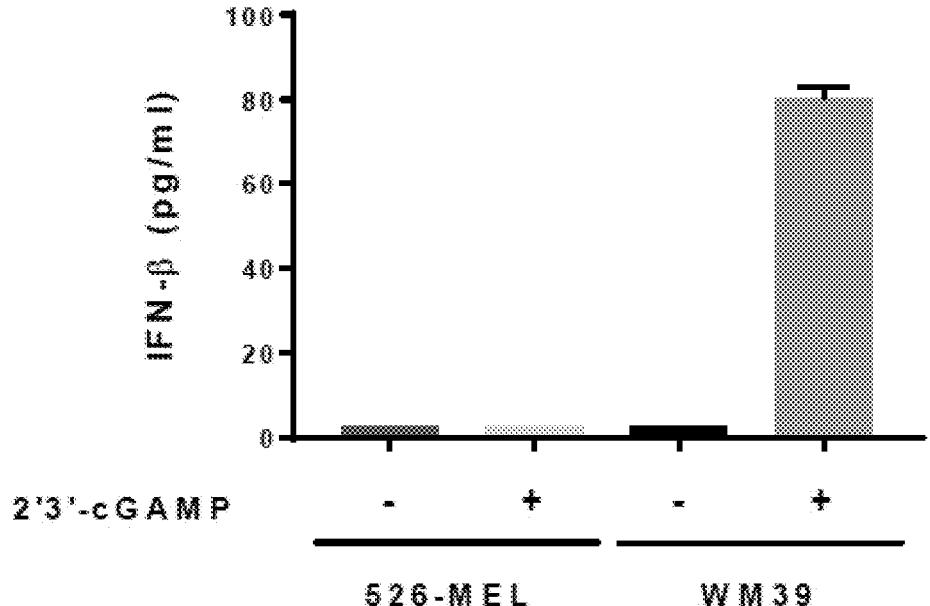
Figure 16D:
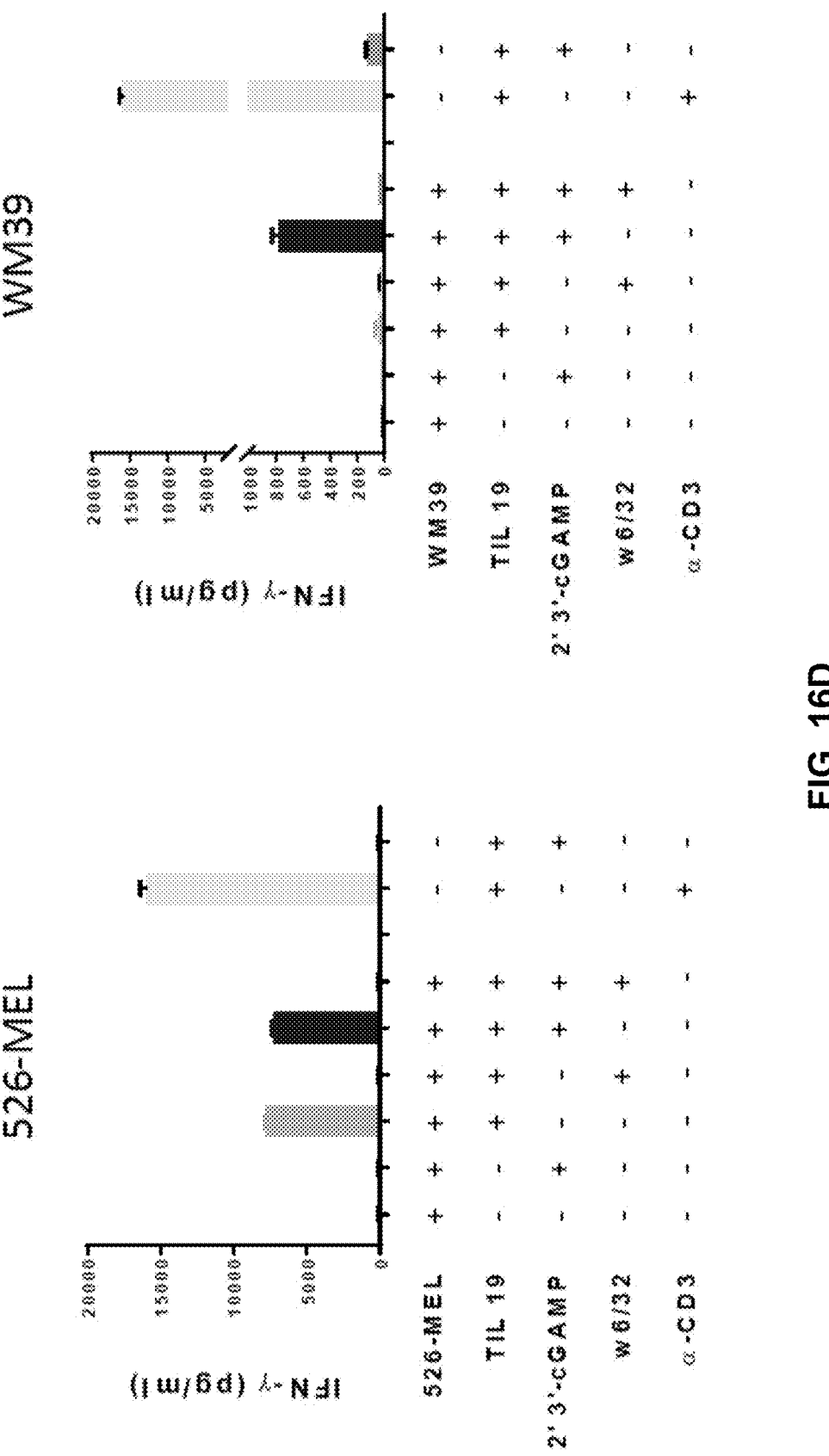
Figure 16E:
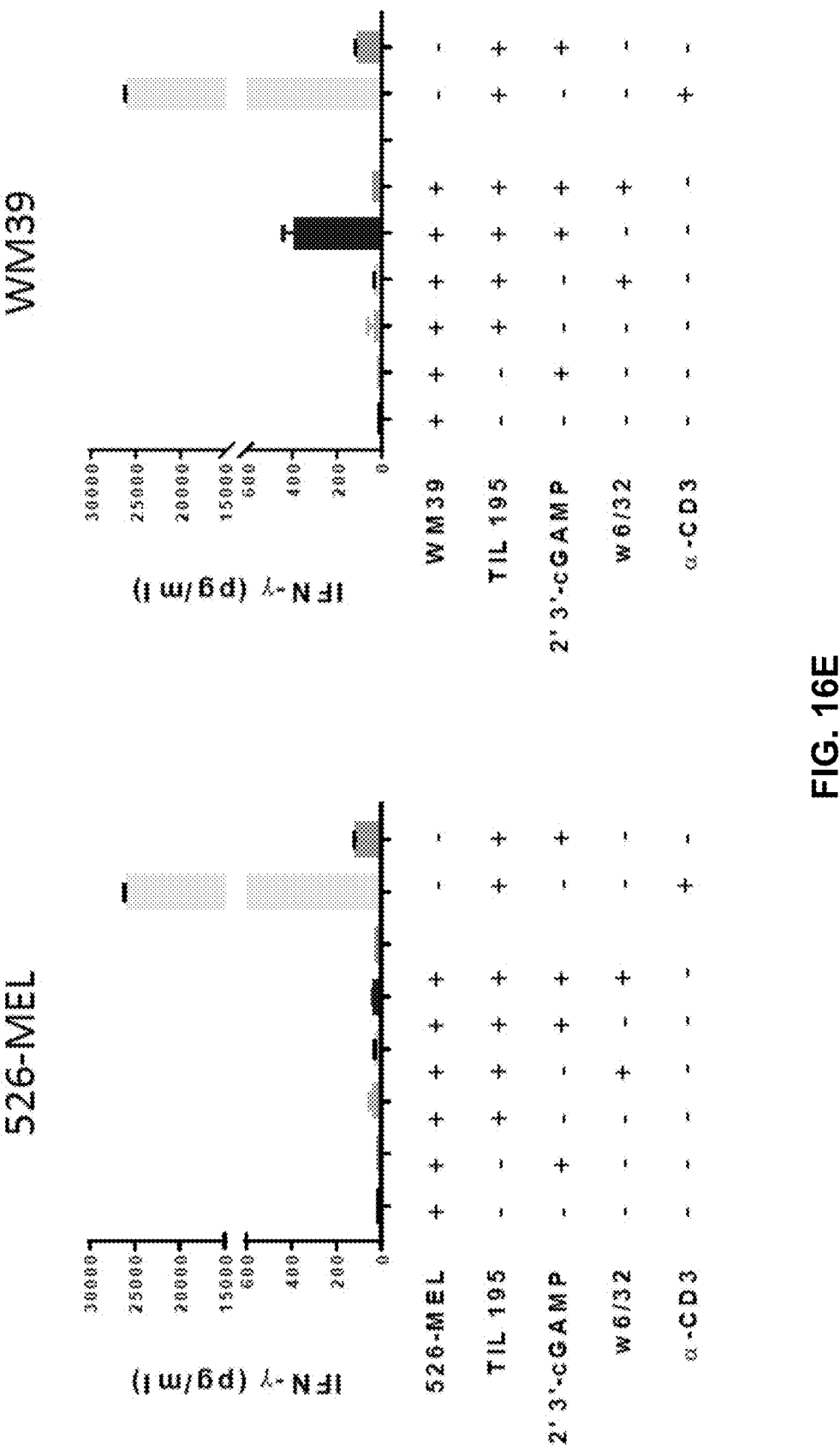

There was a notable decrease in the expression of CXCL10 in the agonist-treated co-cultures compared to the untreated co-cultures (FIGS. 12A-12I). As tumor cells are the primary source of CXCL10 expression, this is likely an indication that more tumor cells were lysed by TIL in the agonist-treated groups compared to the untreated controls.
STING Signaling is Required in Melanoma Cells for Agonist-Induced Improved Antigenicity Given the pronounced impact of the STING agonist on IFN-γ release in melanoma/TIL cocultures, the next goal was to determine whether this was due to the direct activation of STING signaling in melanoma cells. To address this possibility, the 526-MEL (HLA-A2) melanoma cell line that did not respond to 2'3'-cGAMP stimulation (FIG. 16A-16C) was co-cultured with two HLAA2-restricted TIL (TIL 19 and TIL 195) in the presence or absence of the STING agonist and in parallel co-cultures we used WM39 cells with the same TIL samples (FIGS. 16D and 16E). 526-MEL stimulated much higher amounts of IFN-γ release from TIL 19 compared to WM39 cells. However, in contrast to WM39/TIL 19 co-cultures for which stimulation with 2'3'-cGAMP resulted in 24-fold higher (p<0.001) IFN-γ release than the untreated group, agonist treatment did not induce any increased IFN-γ secretion for 526-MEL/TIL 19 co-culture (FIG. 16D). Similarly, no increase in IFN-γ release was observed for the 526-MEL/TIL 195 co-cultures in the presence of the agonist (FIG. 16E), supporting that STING agonist-mediated enhanced antigenicity is driven by activation of STING signaling in melanoma cells.
Activation of STING Pathway in Human Melanoma Cell Lines Improves Cytotoxic T Lymphocyte-Mediated Lysis

Figure 7A:
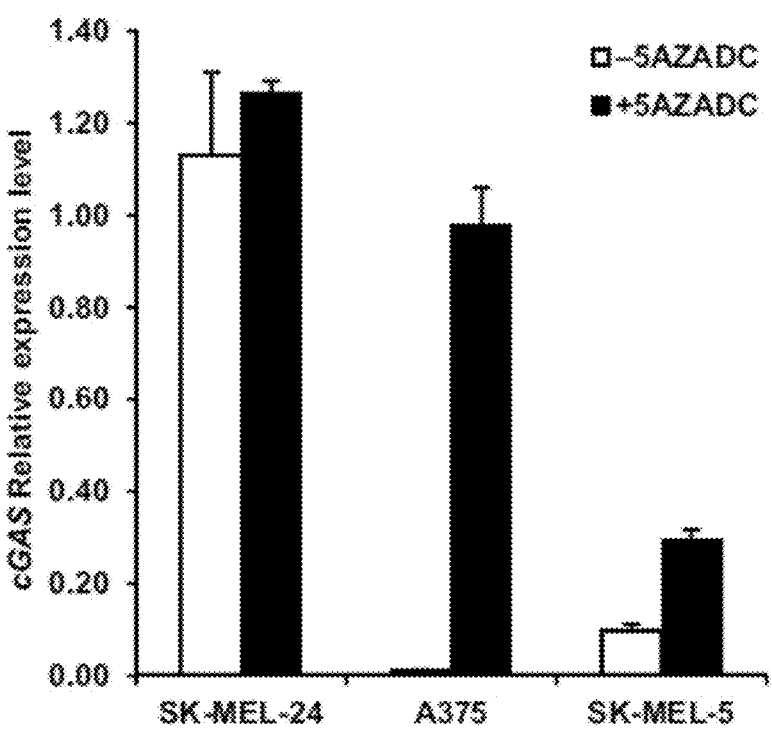
FIGS. 7A to 7E show DNA demethylation partially reca-pitulated STING and cGAS expression in human melanoma cell lines.
Figure 7B:
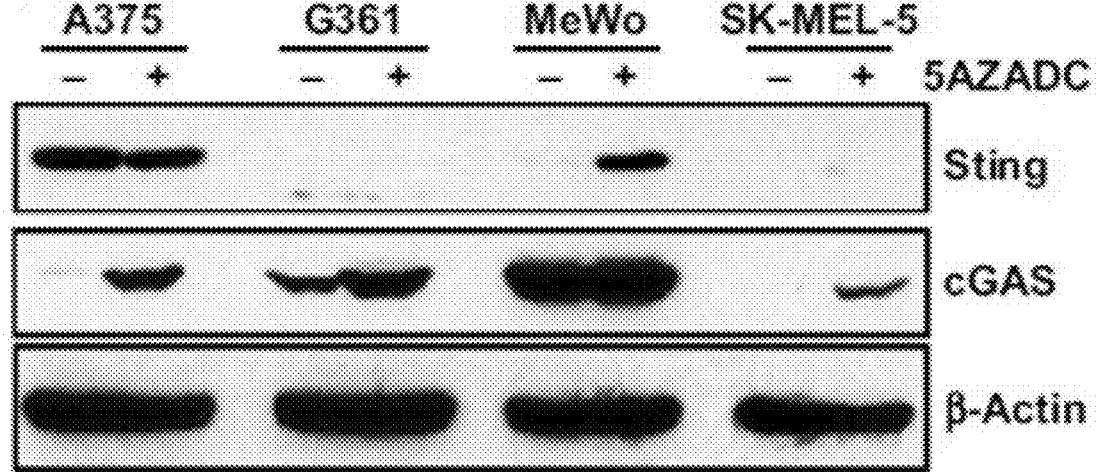
Figure 7C:
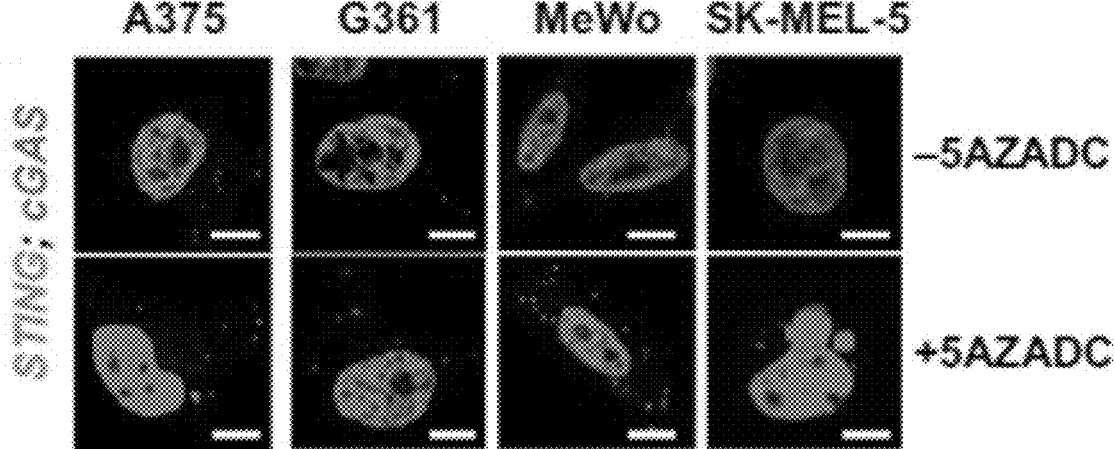
Figure 7D:
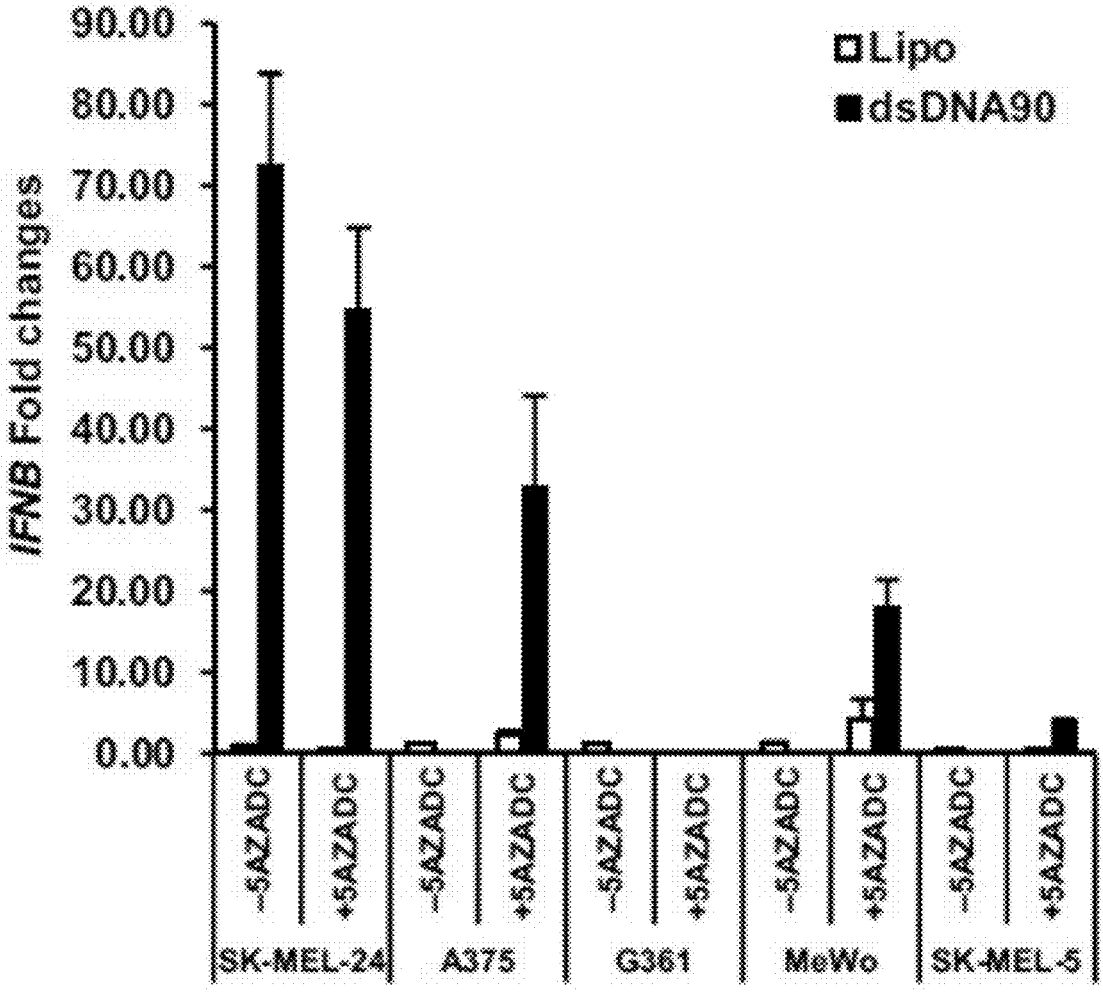
Figure 7E:
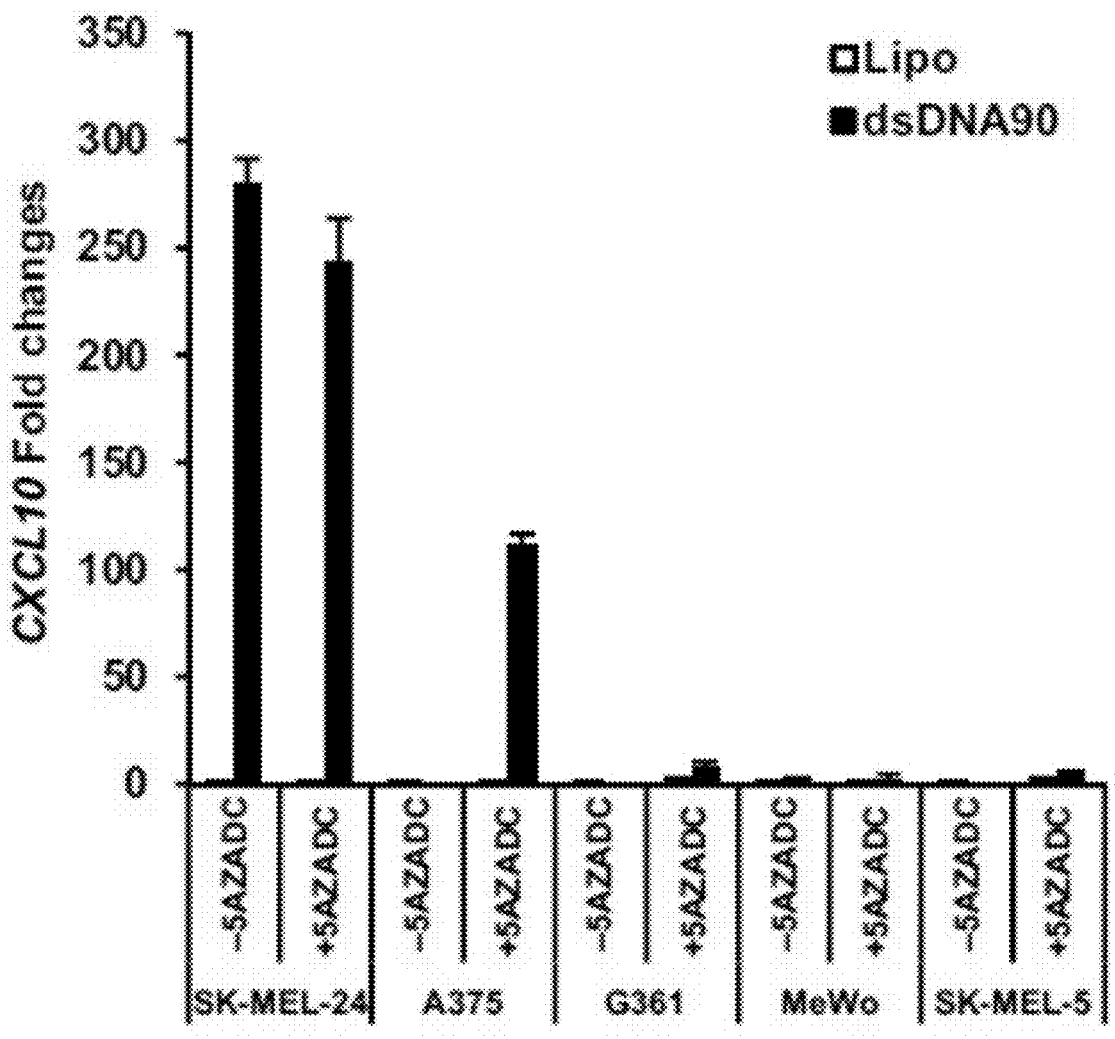
Figure 8A:
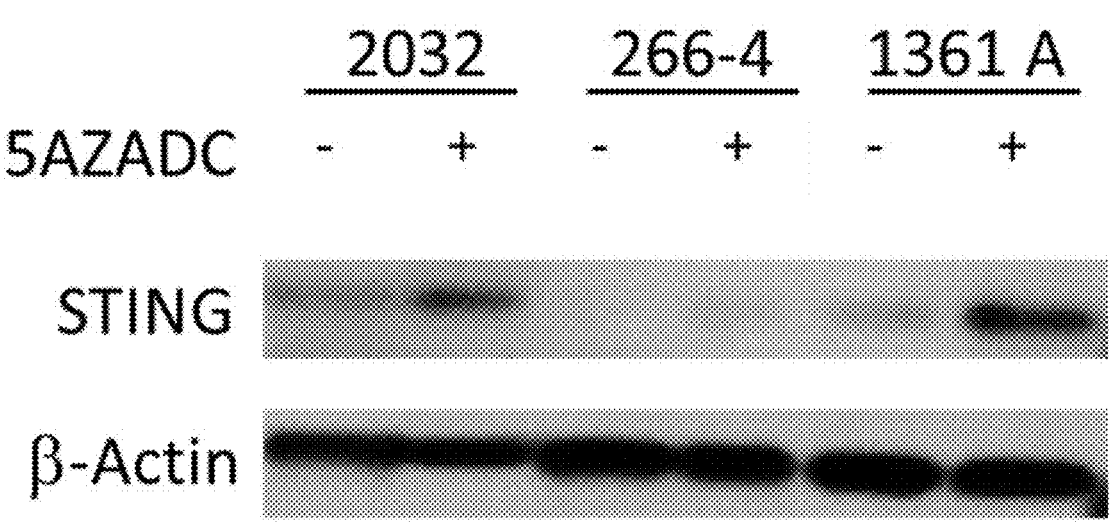
FIGS. 8A to 8D show reconstitution of STING expression in 5AZADC-treated melanoma cells and STING-dependent CXCL-10 induction following 2'3'-cGAMP stimulation.
Figure 8B:
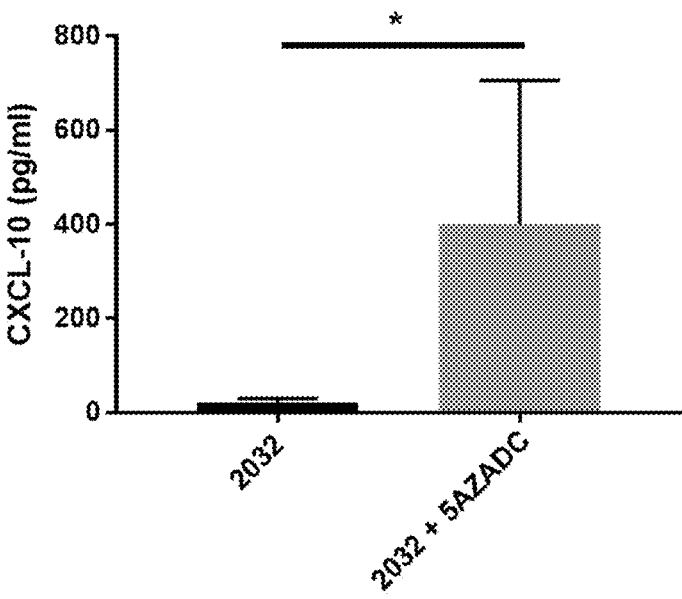
Figure 8C:
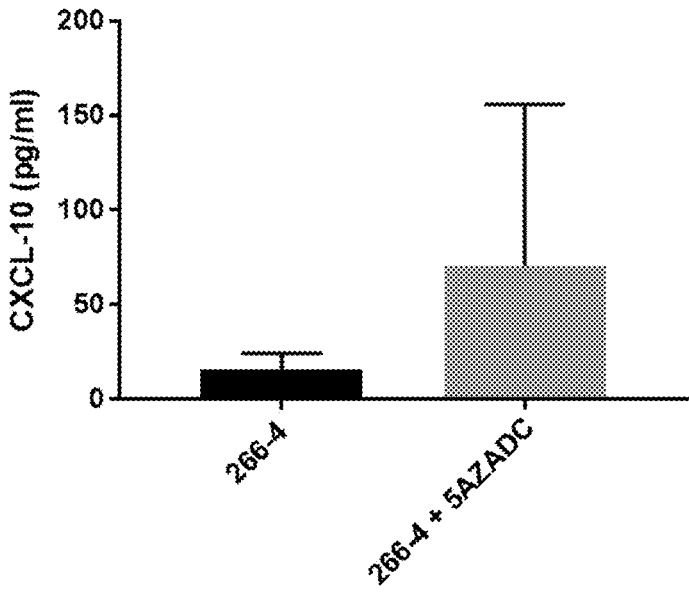
Figure 8D:
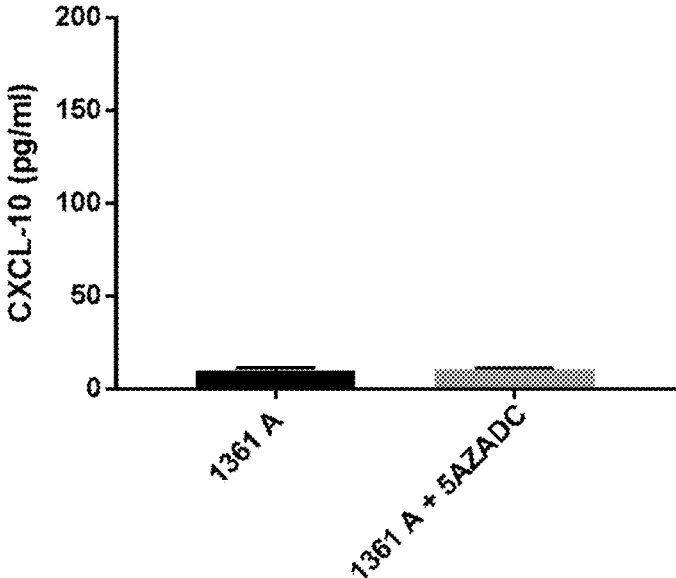
Figure 9A:
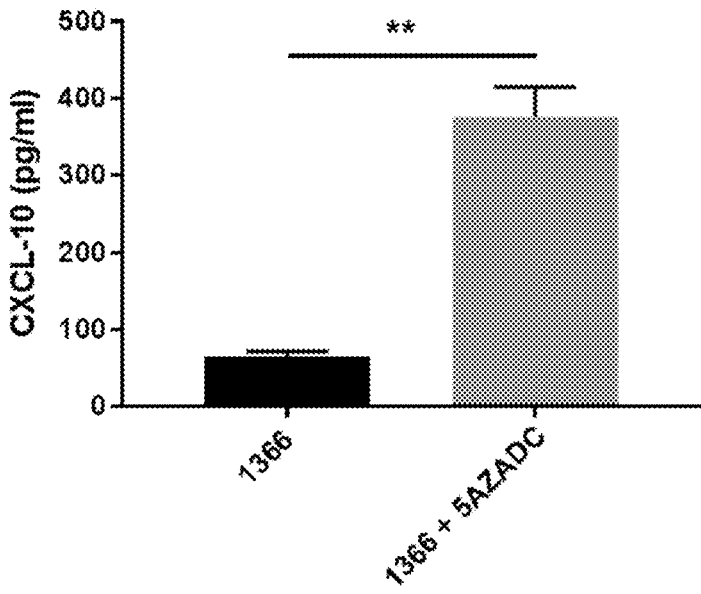
FIGS. 9A to 9F are bar graphs showing CXCL-10 induc-tion in 1366 (FIG. 9A), 526 (FIG. 9B), 164 (FIG. 9C), A375 (FIG. 9D), WM3629 (FIG. 9E), and WM9 (FIG. 9F) mela-noma cells with and without 5AZADC treatment.
Figure 9B:
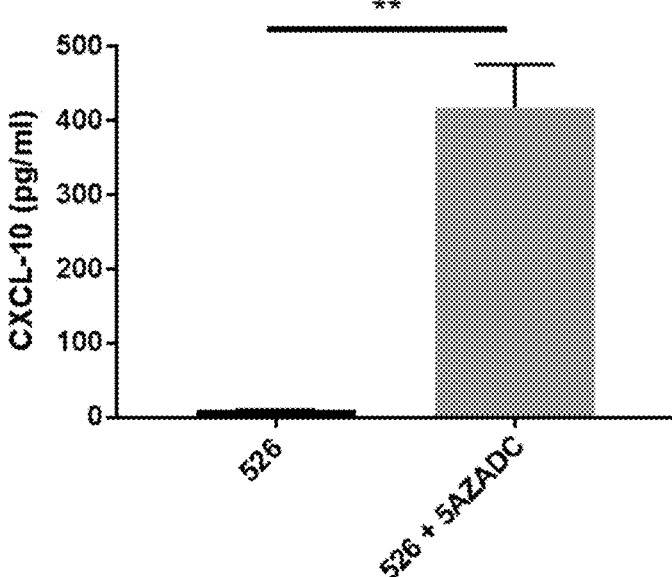
Figure 9C:
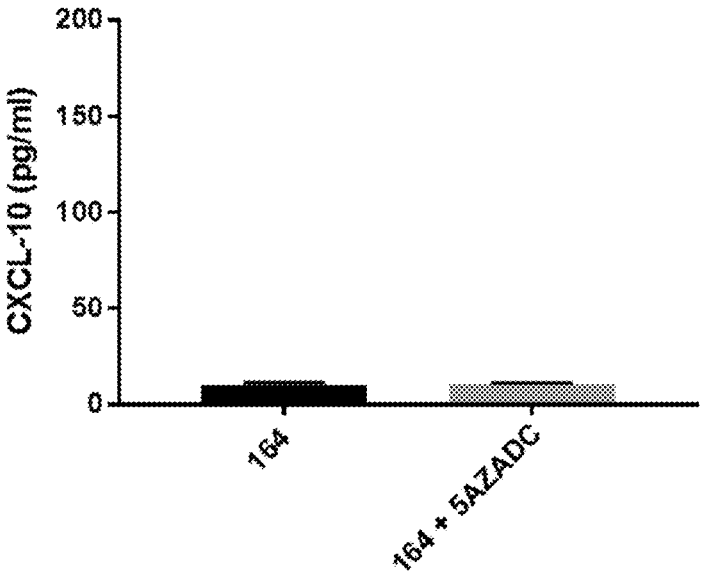
Figure 9D:
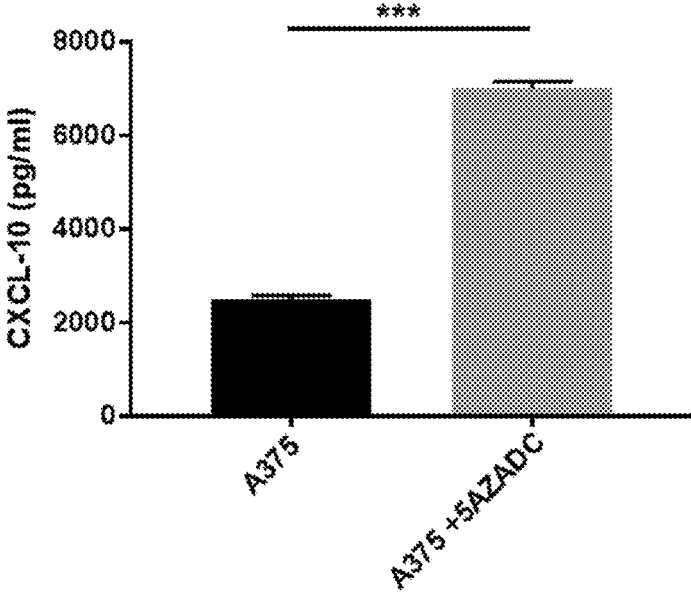
Figure 9E:
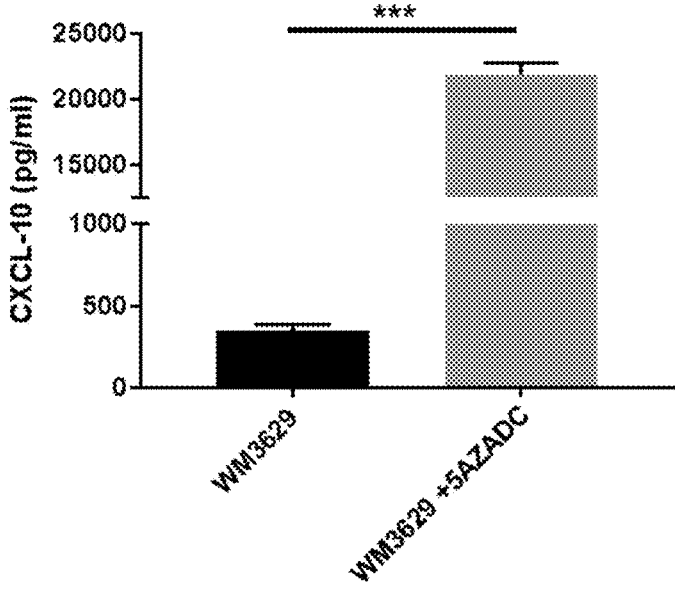
Figure 9F:
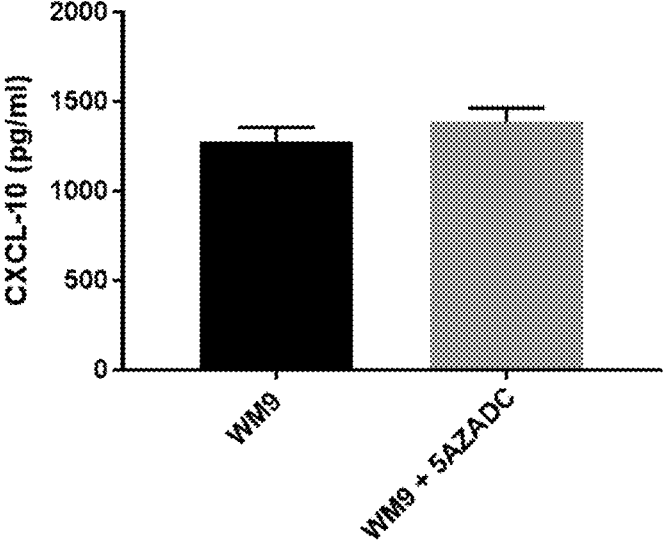
Figures 17A, 17B:
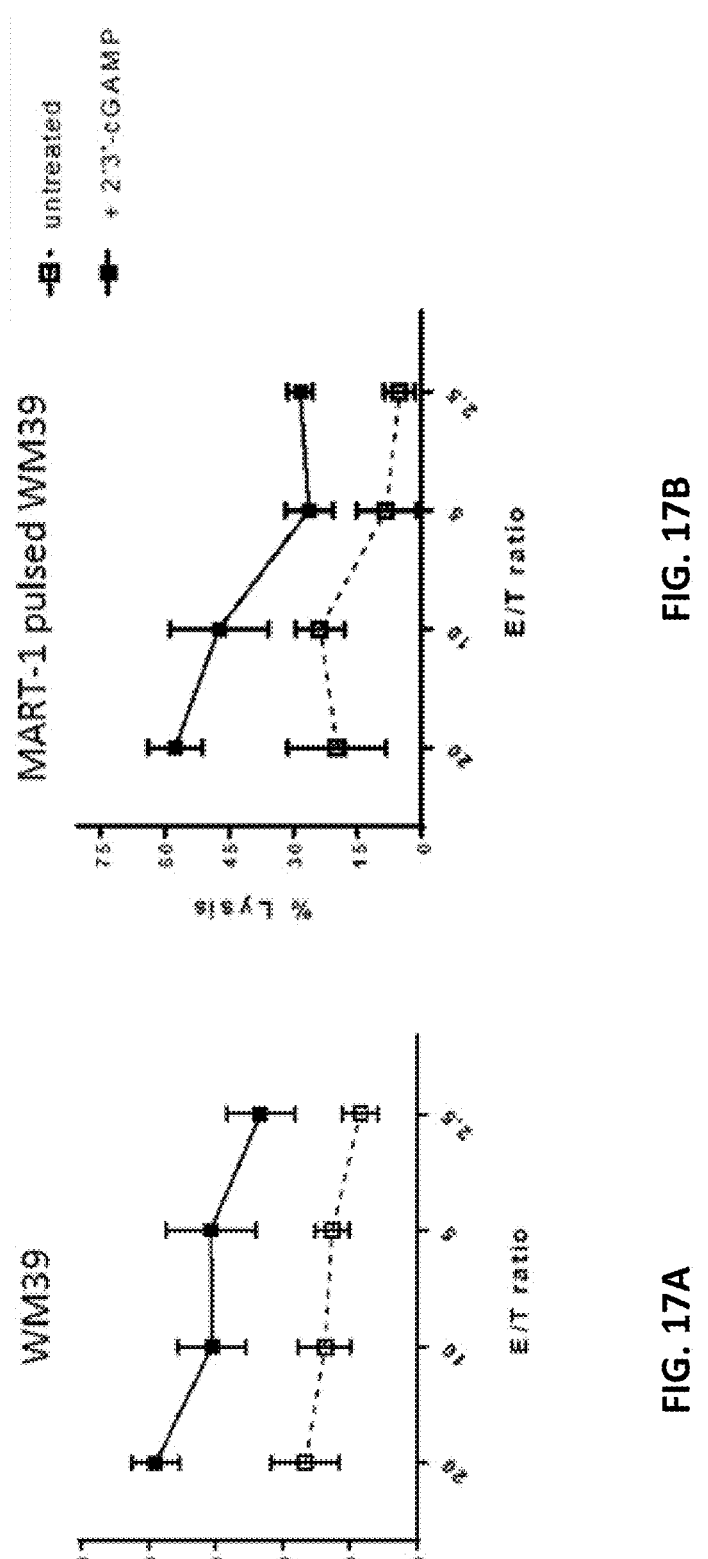
FIGS. 17A to 17F show activation of STING pathway in human melanoma cell lines improves cytotoxic T lympho-cyte-mediated lysis.
Figures 17C, 17D:
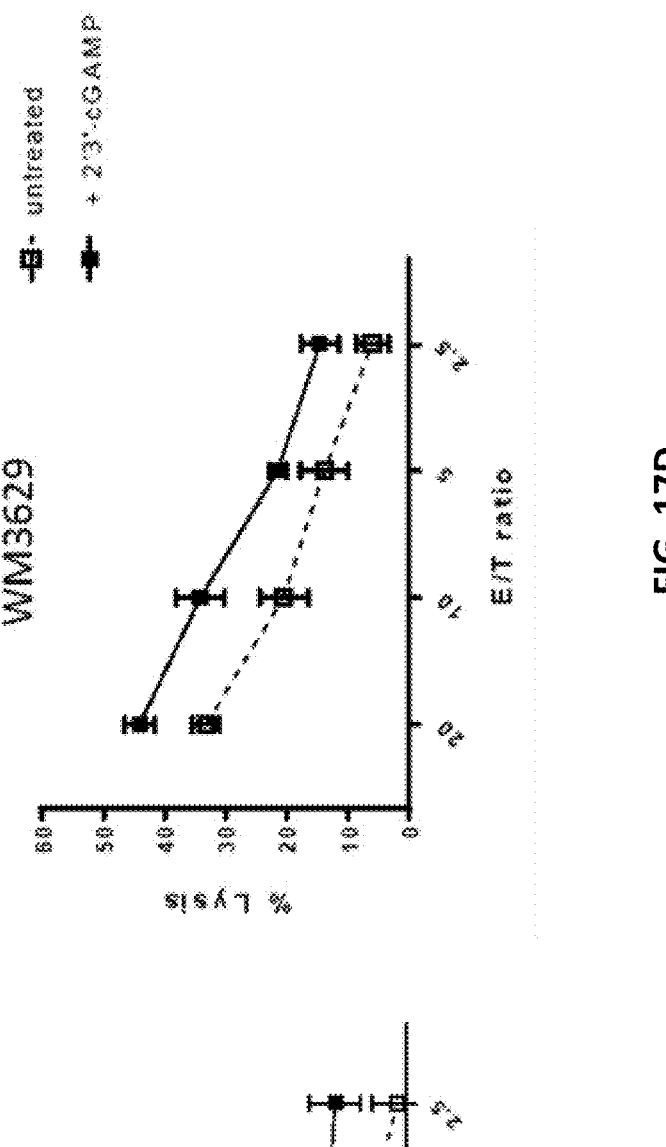
Figure 17E:
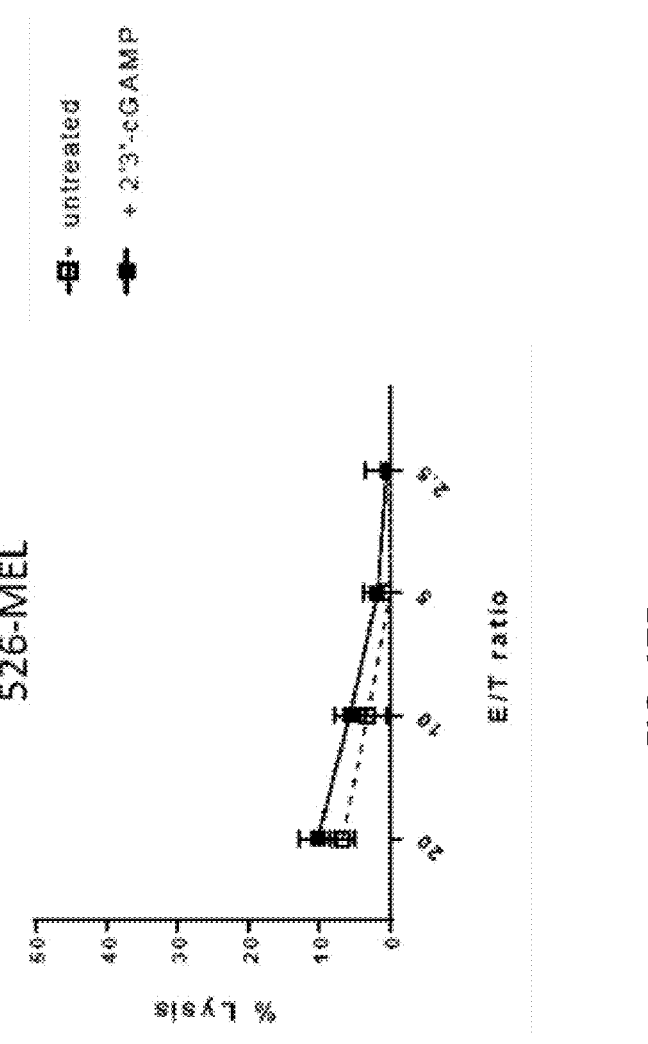
Figure 17F:
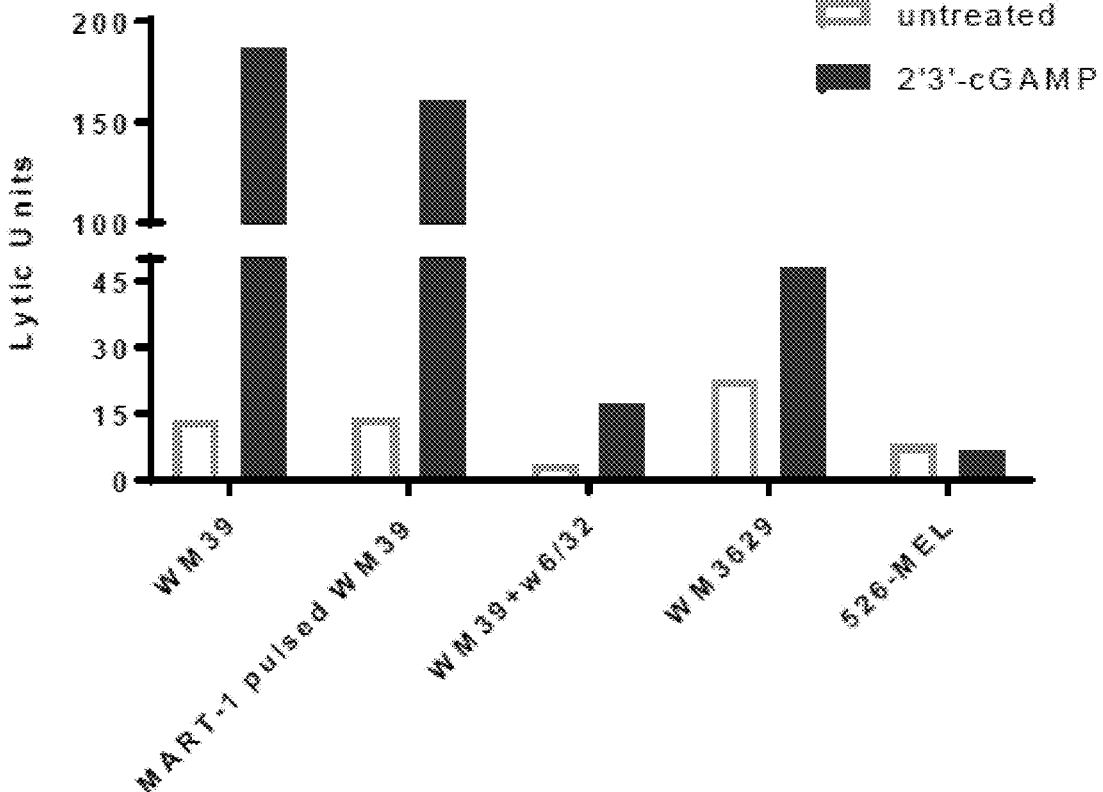
Figure 18A:
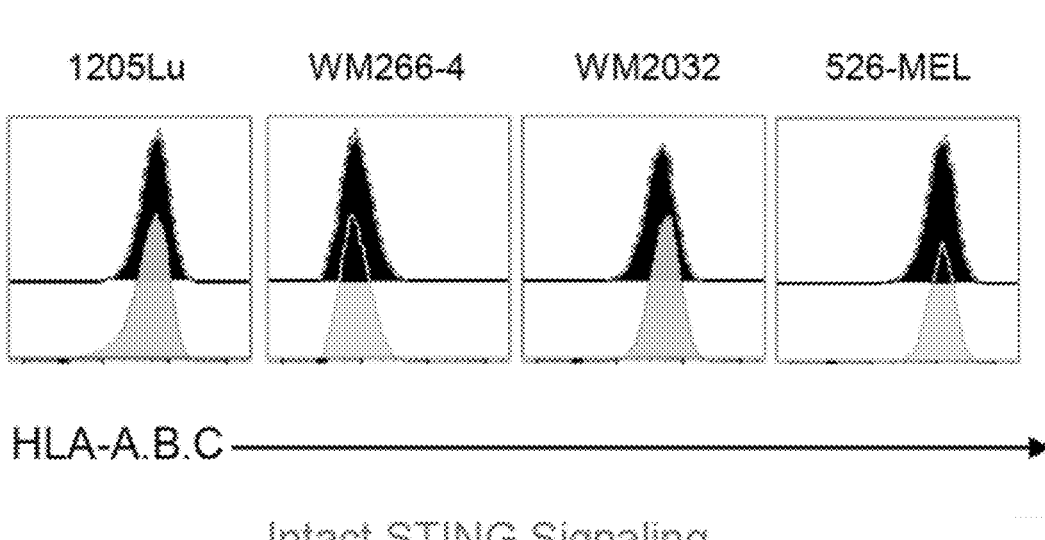
FIGS. 18A and 18B show STING activation in human melanoma cell lines induces up-regulation of MHC class I (HLA-A.B.C).
Figure 18A:
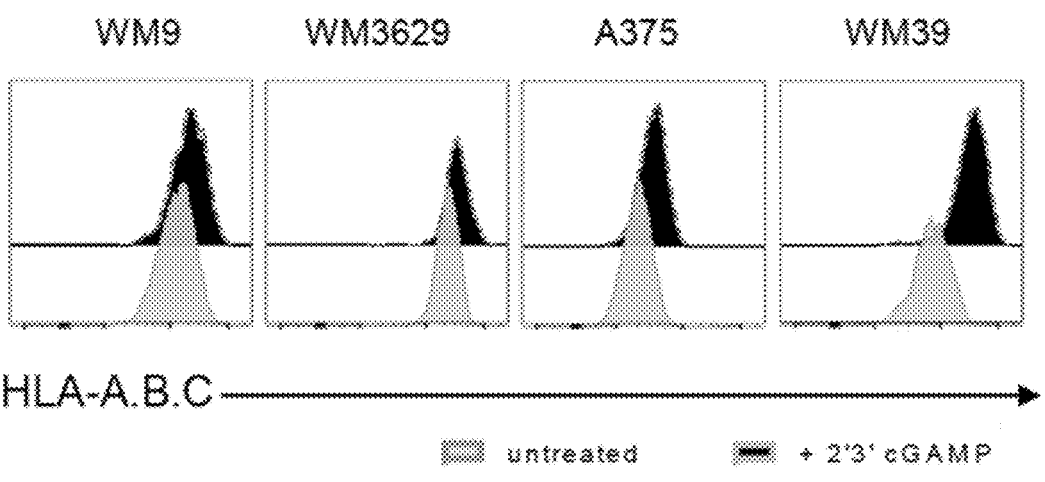
Figure 18B:
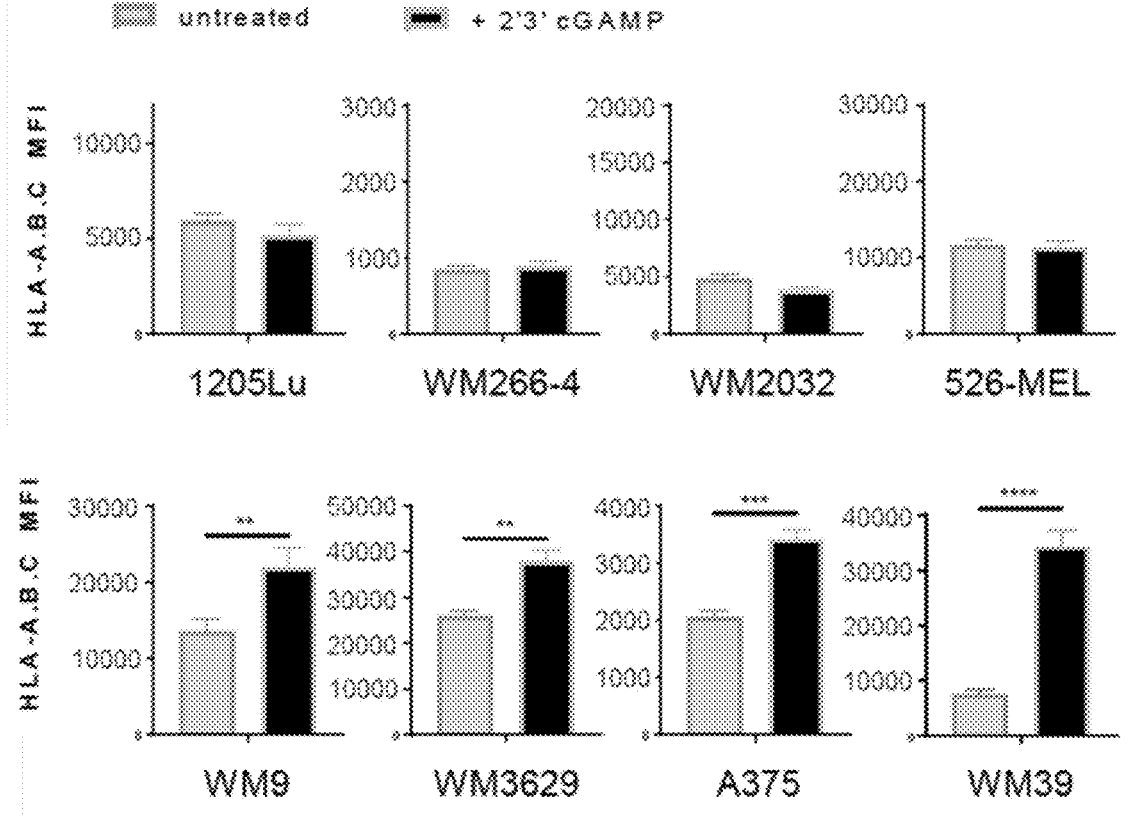
Figure 19B:
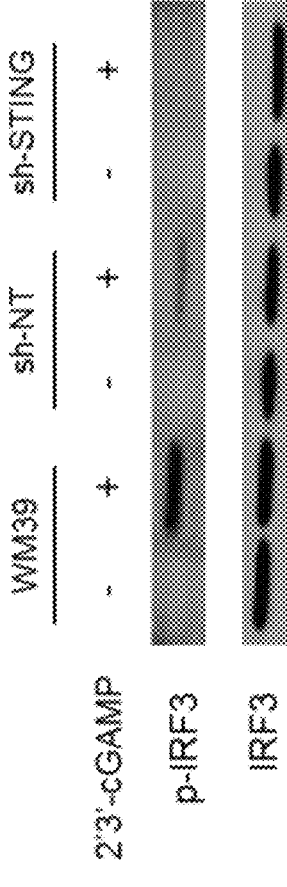
FIGS. 19A to 19F shows knockdown of STING blocks agonist-induced upregulation of MHC class I in melanoma cells. WM39 cells were stably transduced with a lentiviral shRNA specific for STING (sh-STING) or non-target shRNA (sh-control).
Figure 19A:
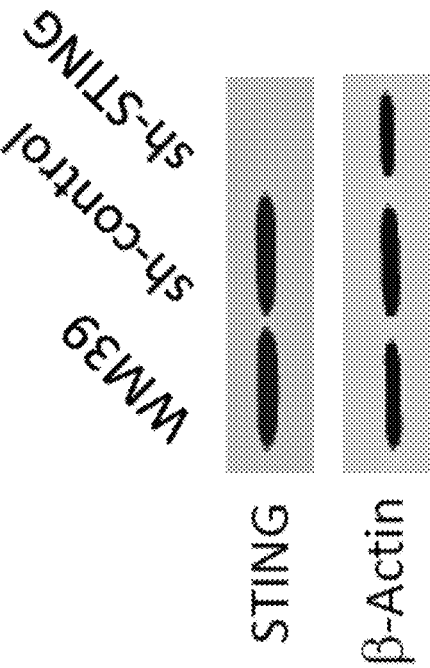
Figure 19D:
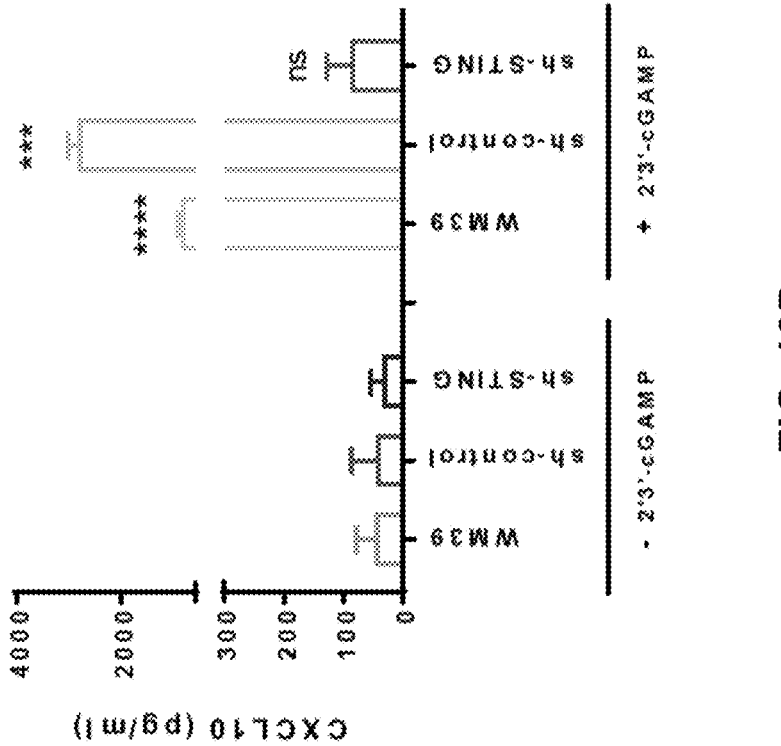
Figure 19C:
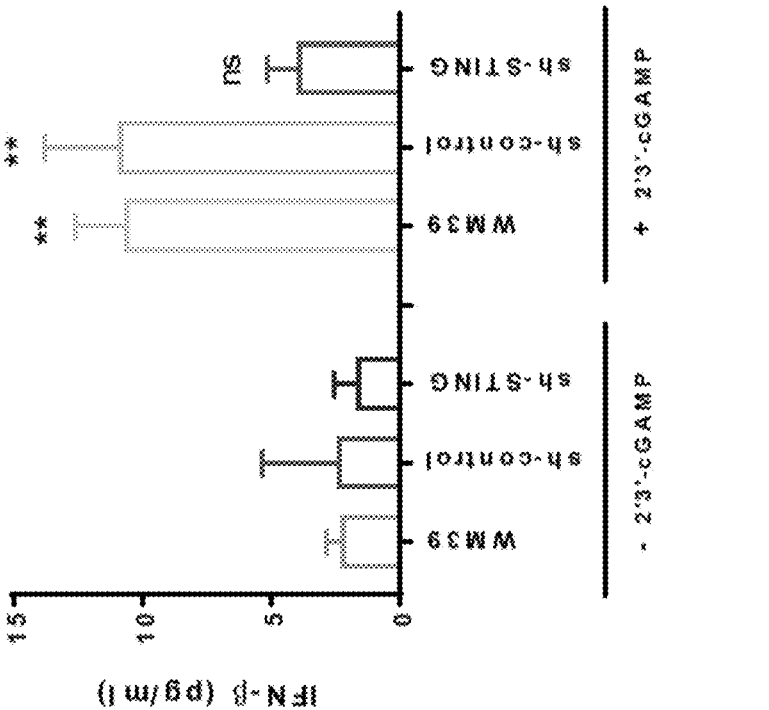
Figure 19E:
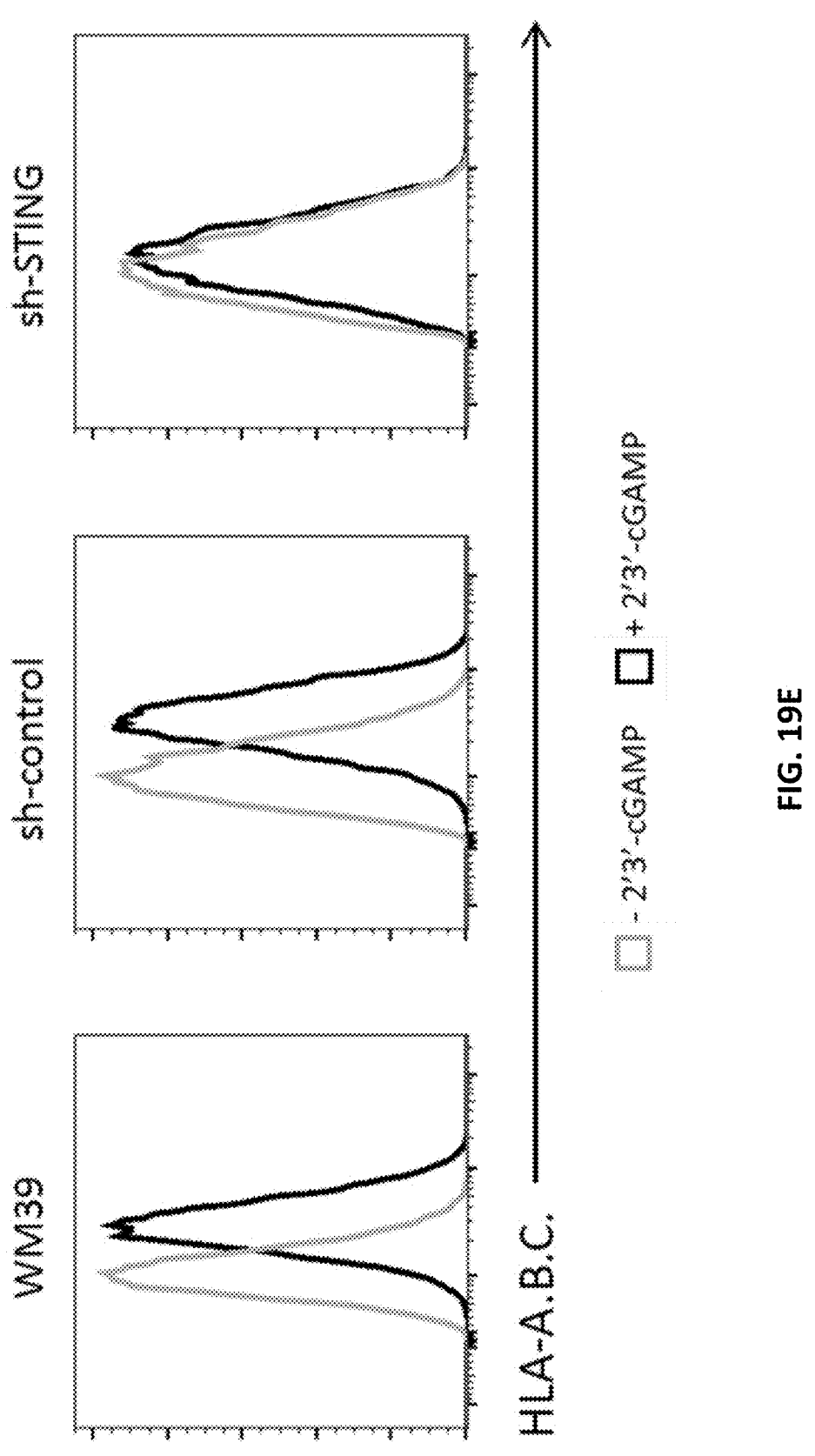
Figure 19F:
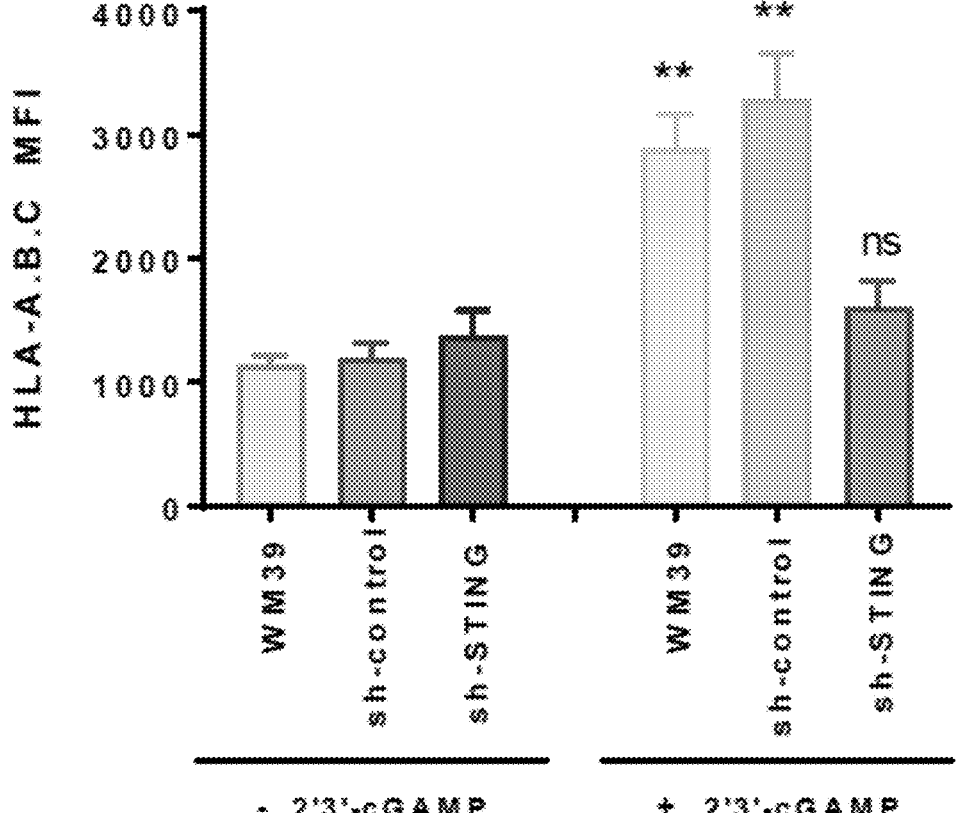
Figure 20A:
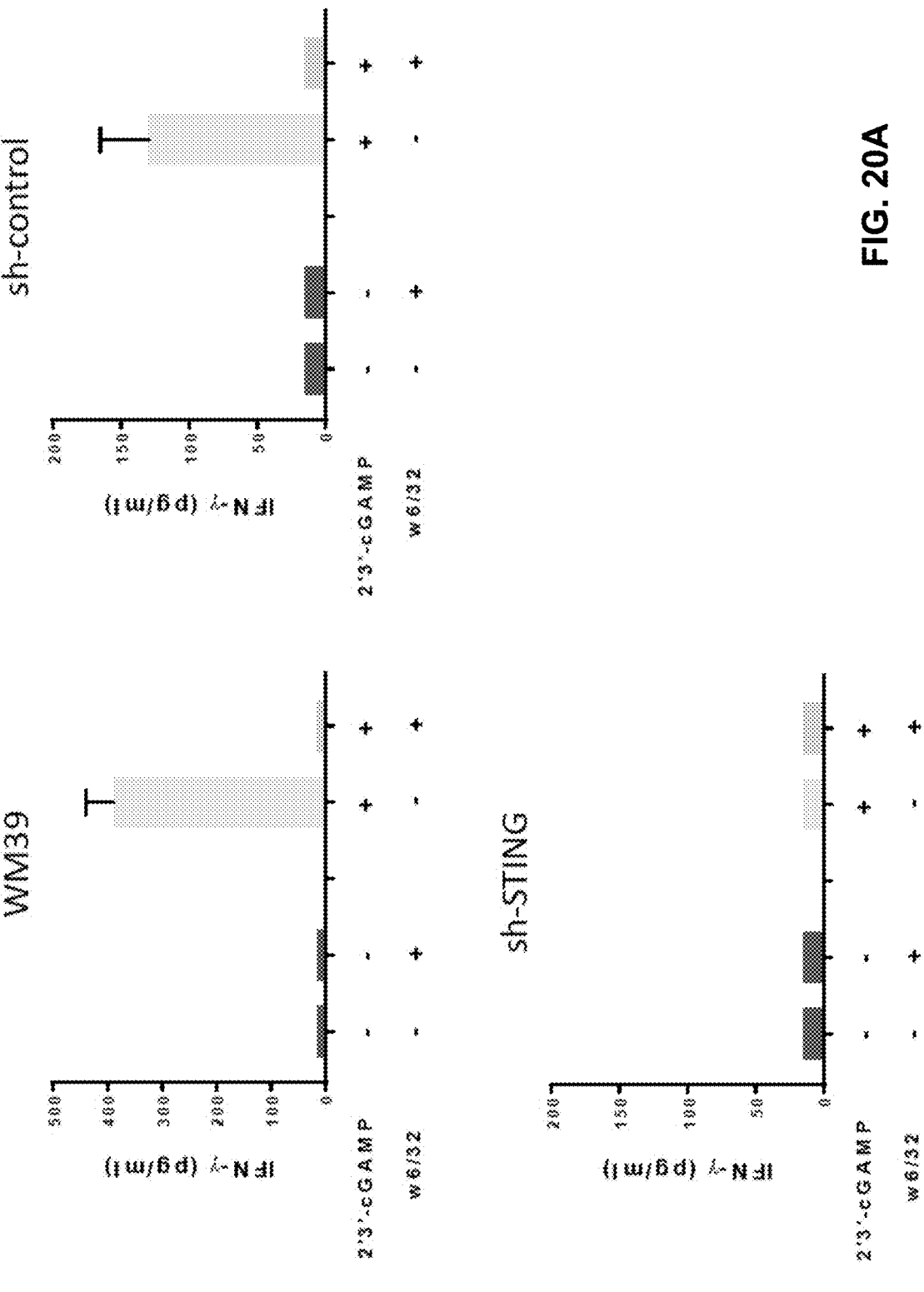
FIGS. 20A to 20C show STING is essential for agonist-induced enhanced antigenicity in melanoma cells.
Figure 20B:
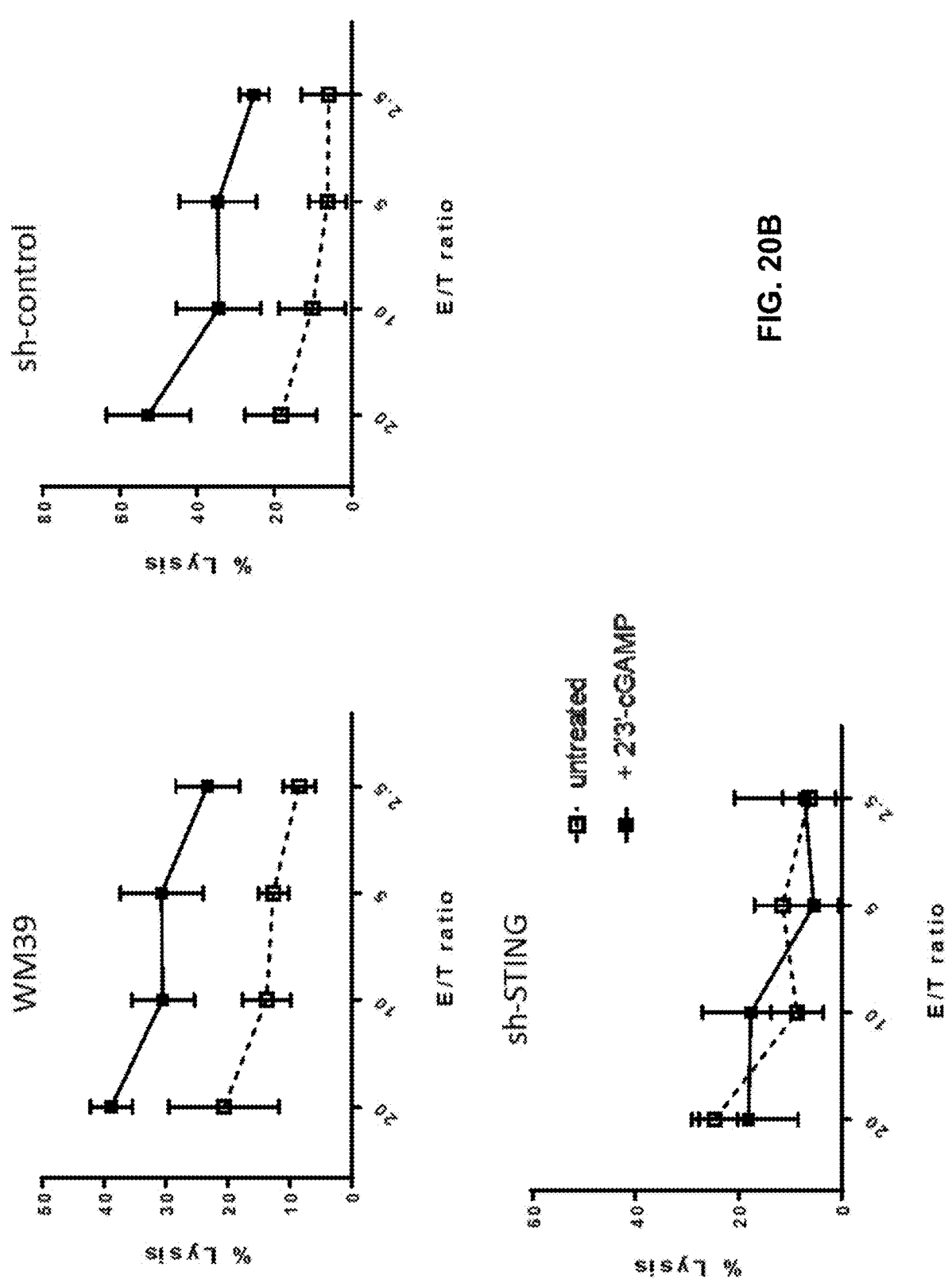
Figure 20C:
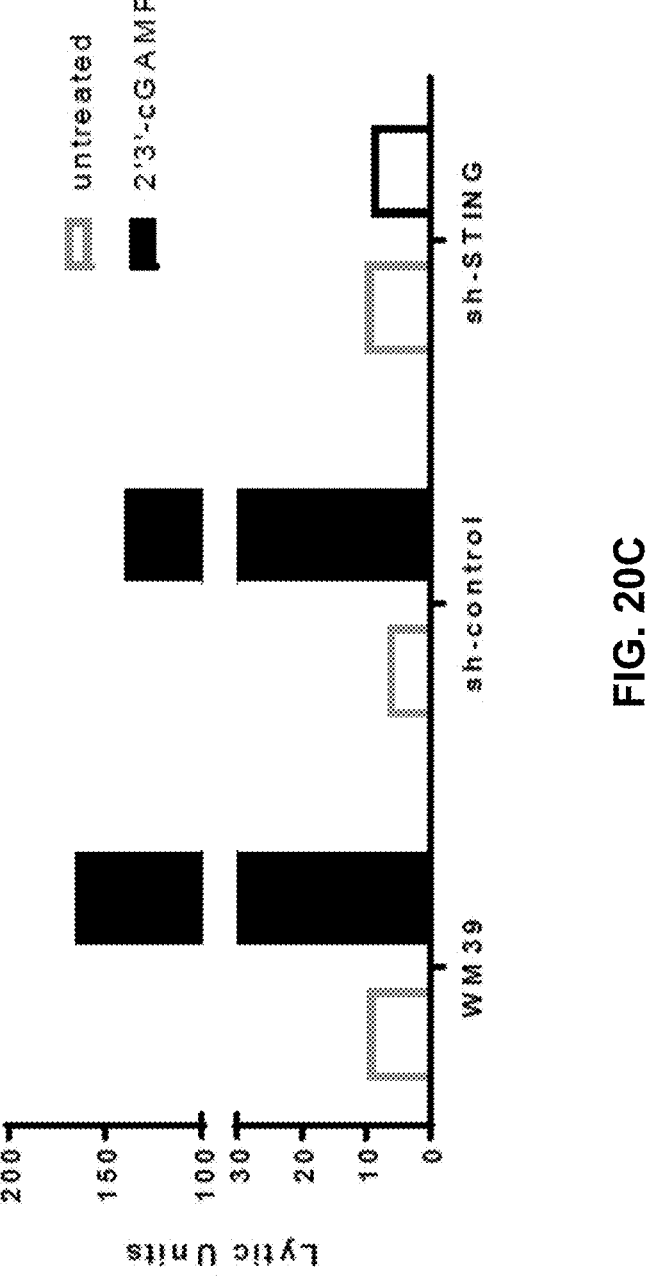
Figure 21:
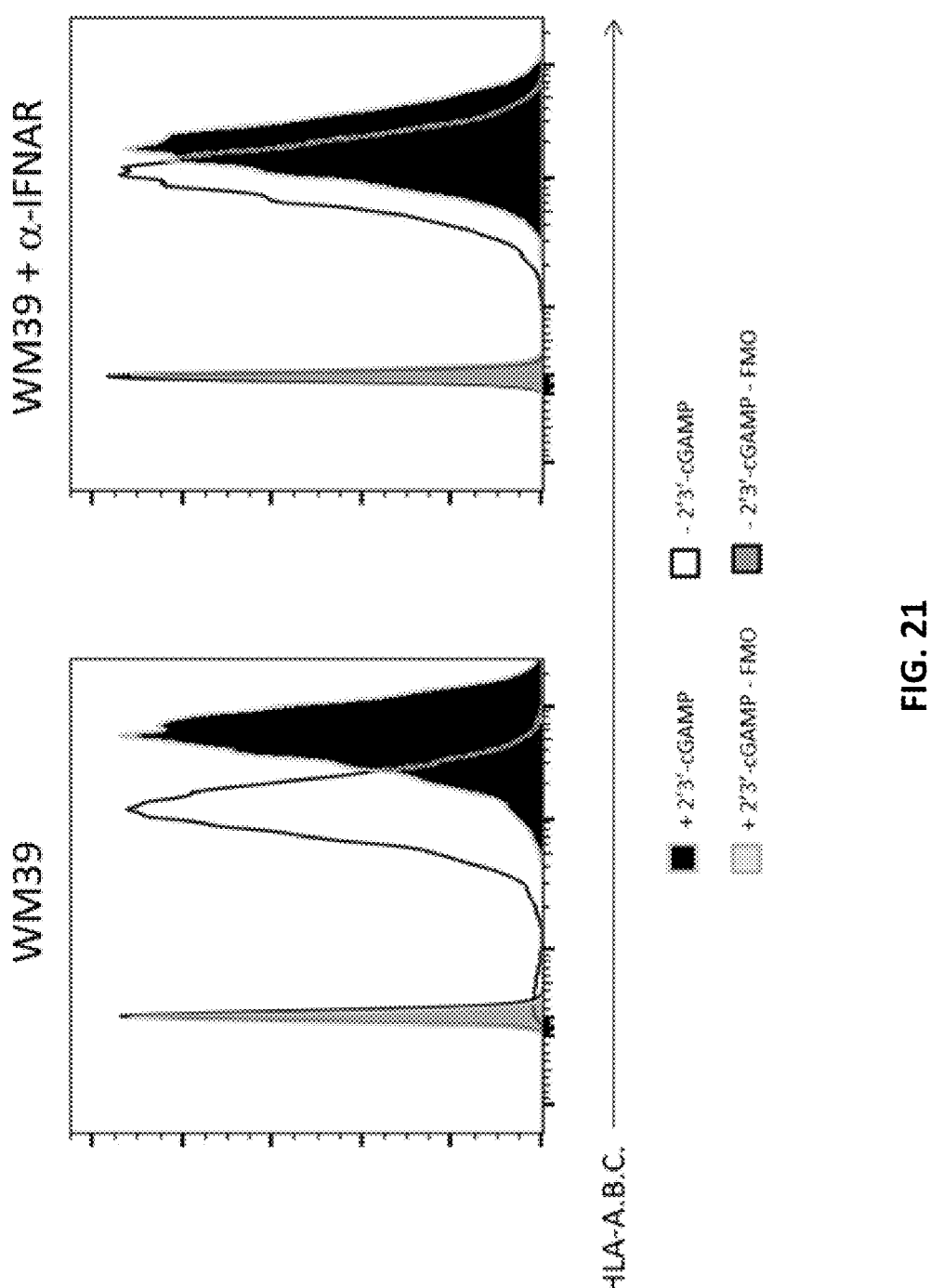
FIG. 21 shows blockade of IFNAR inhibits agonist-induced upregulation of MHC class I.
Figures 22A, 22B:
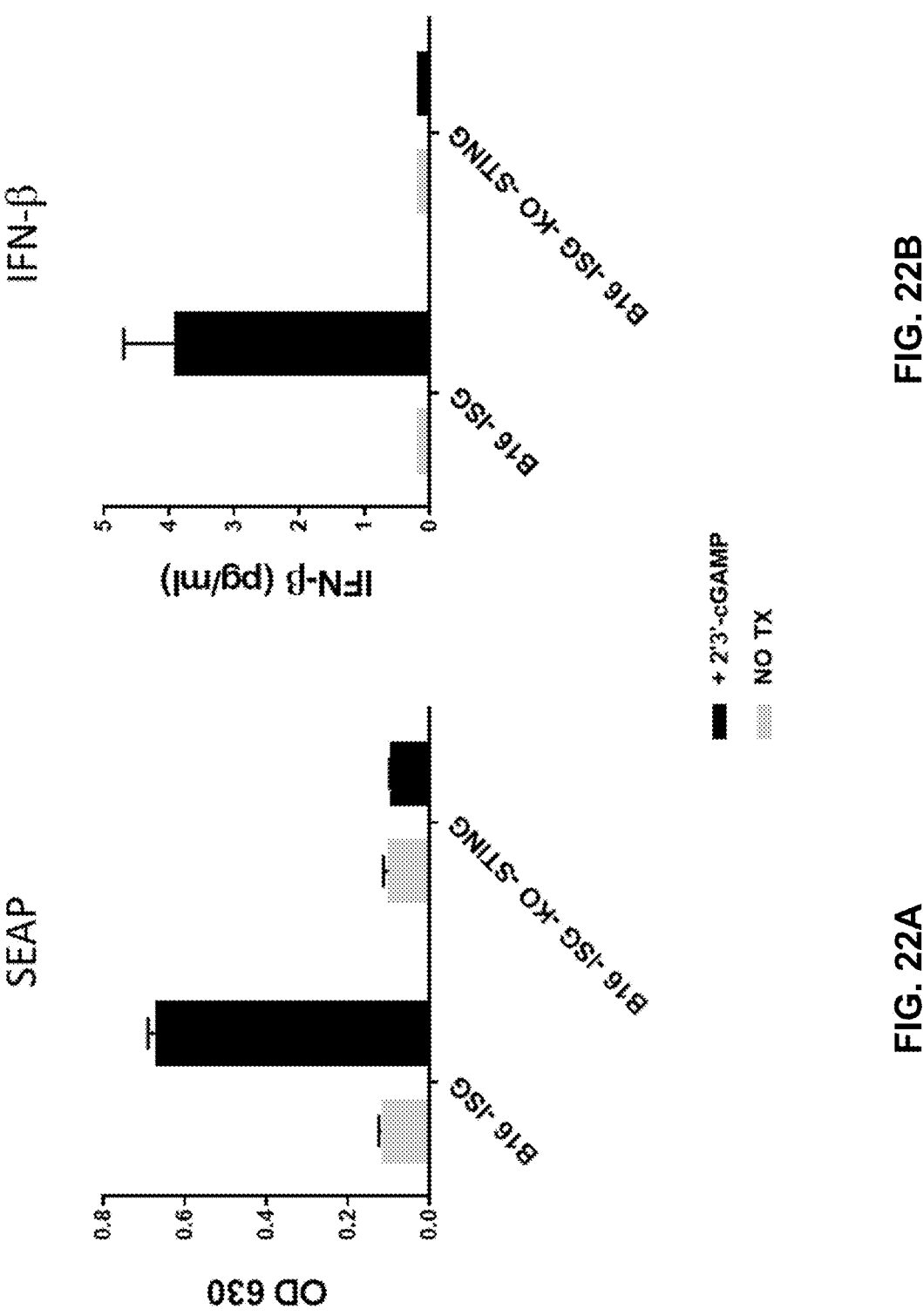
FIGS. 22A and 22B shows in vitro stimulation of SEAP (FIG. 22A) and IFN-β (FIG. 22B) with 2'3'-cGAMP.
Figure 23:
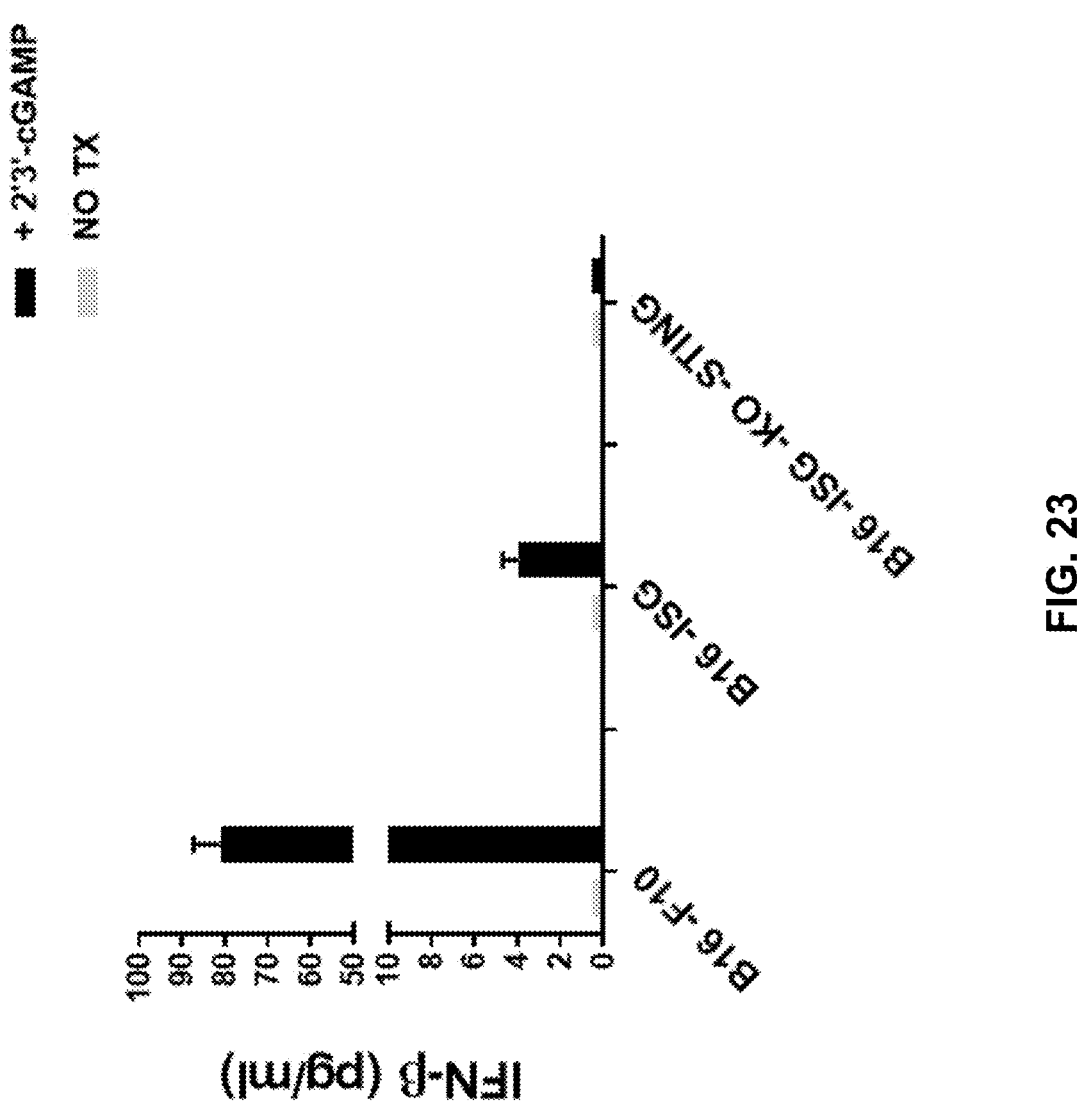
FIG. 23 shows in vitro stimulation of IFN-β with 2'3'-cGAMP.
Figure 24:
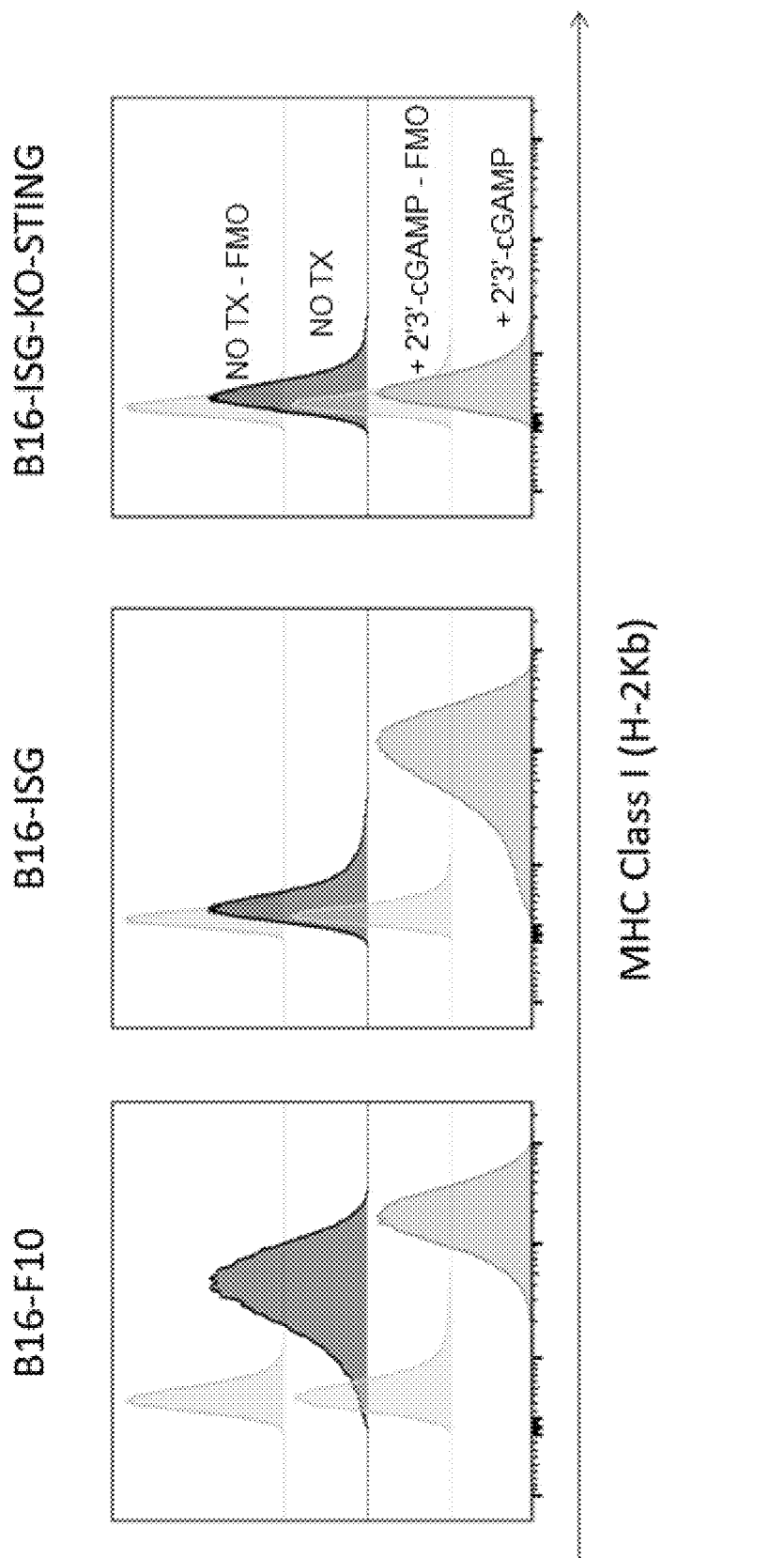
FIG. 24 shows Activation of STING in B16 melanoma cell lines induces up-regulation of MHC class I.
Figures 25A, 25B, 25C:
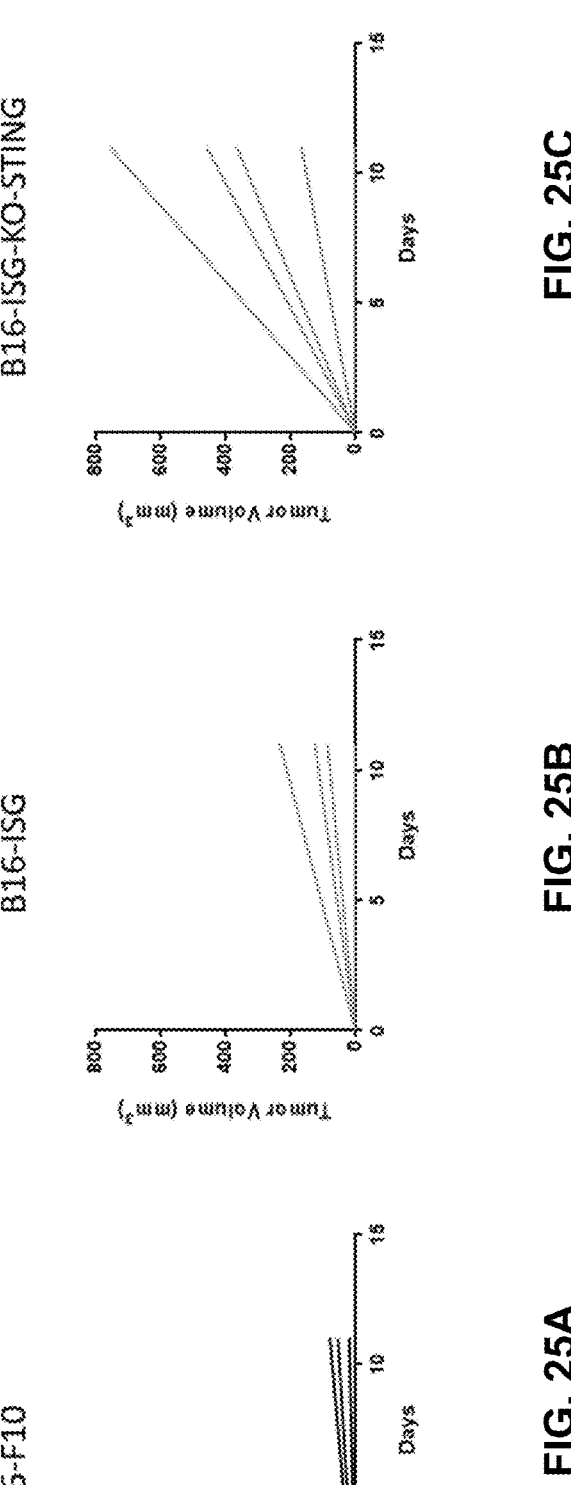
FIGS. 25A to 25E show loss of STING in B16-ISG accelerates tumor growth at early time points.
Figure 25E:
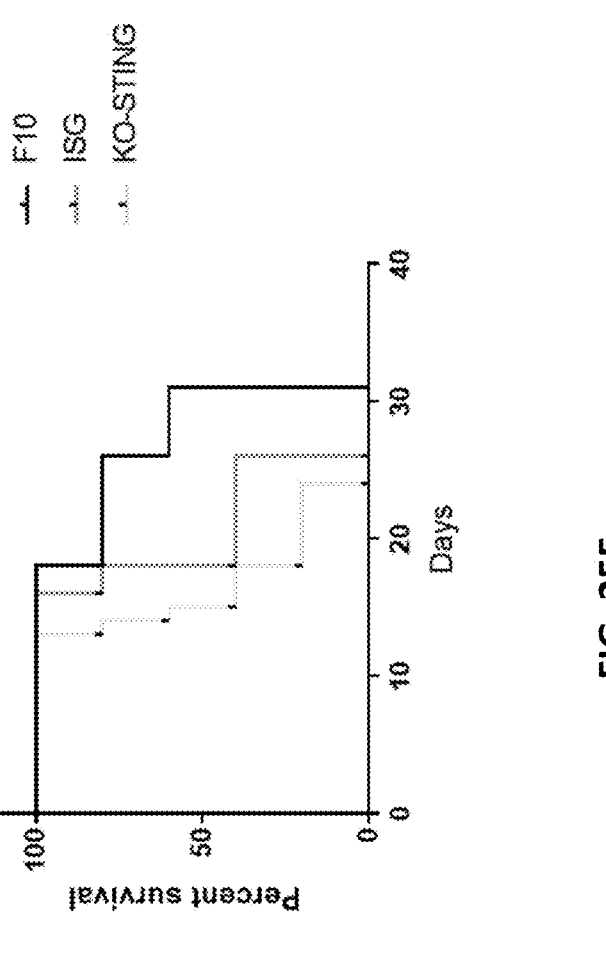
Figure 25D:
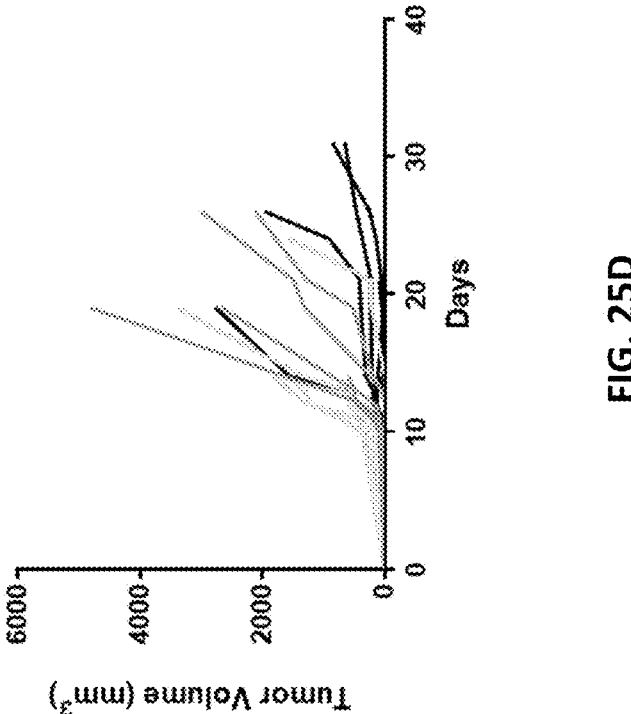
Figure 26A:
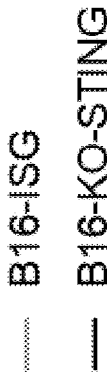
FIGS. 26A and 26B show loss of STING in B16-ISG cells does not affect their proliferation in vitro.
Figure 26A:
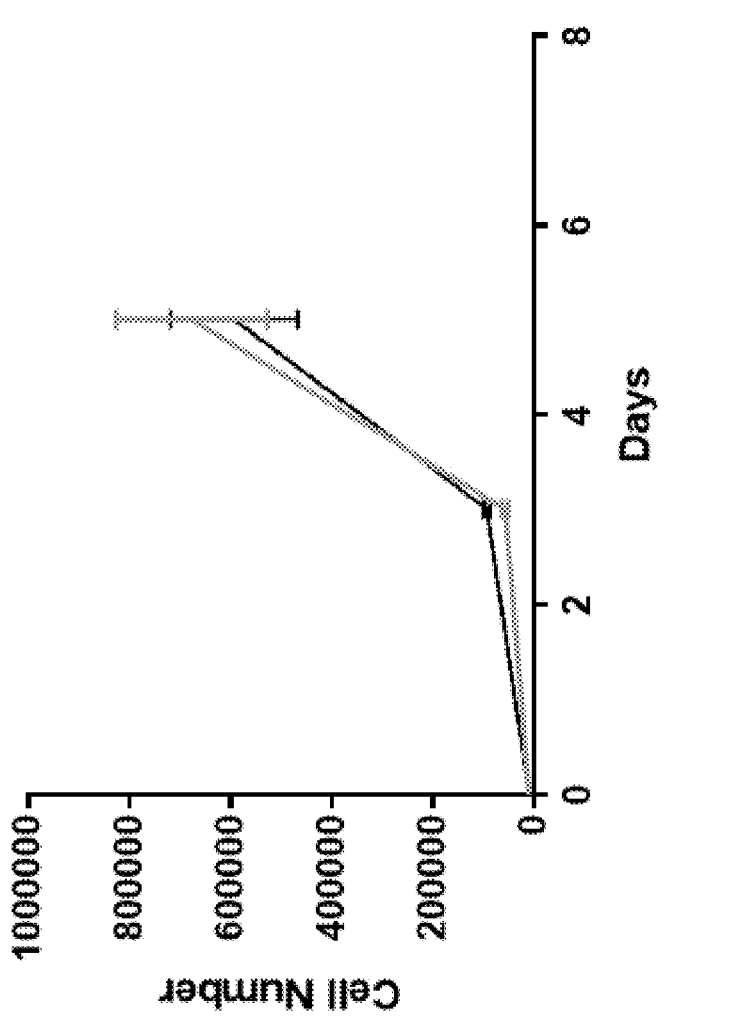
Figure 26B:
Figure 26B:
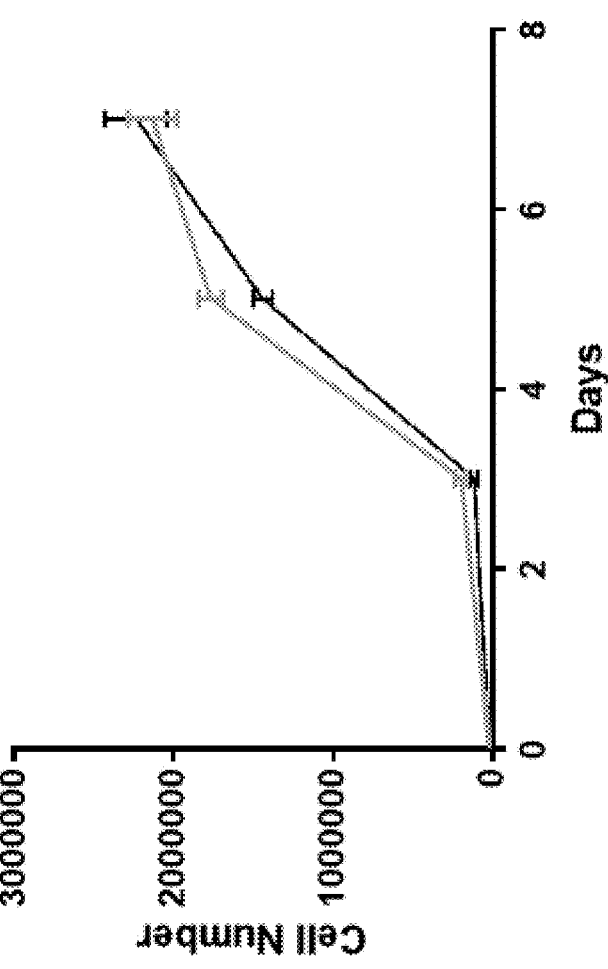
Figures 27A, 27B, 27C:
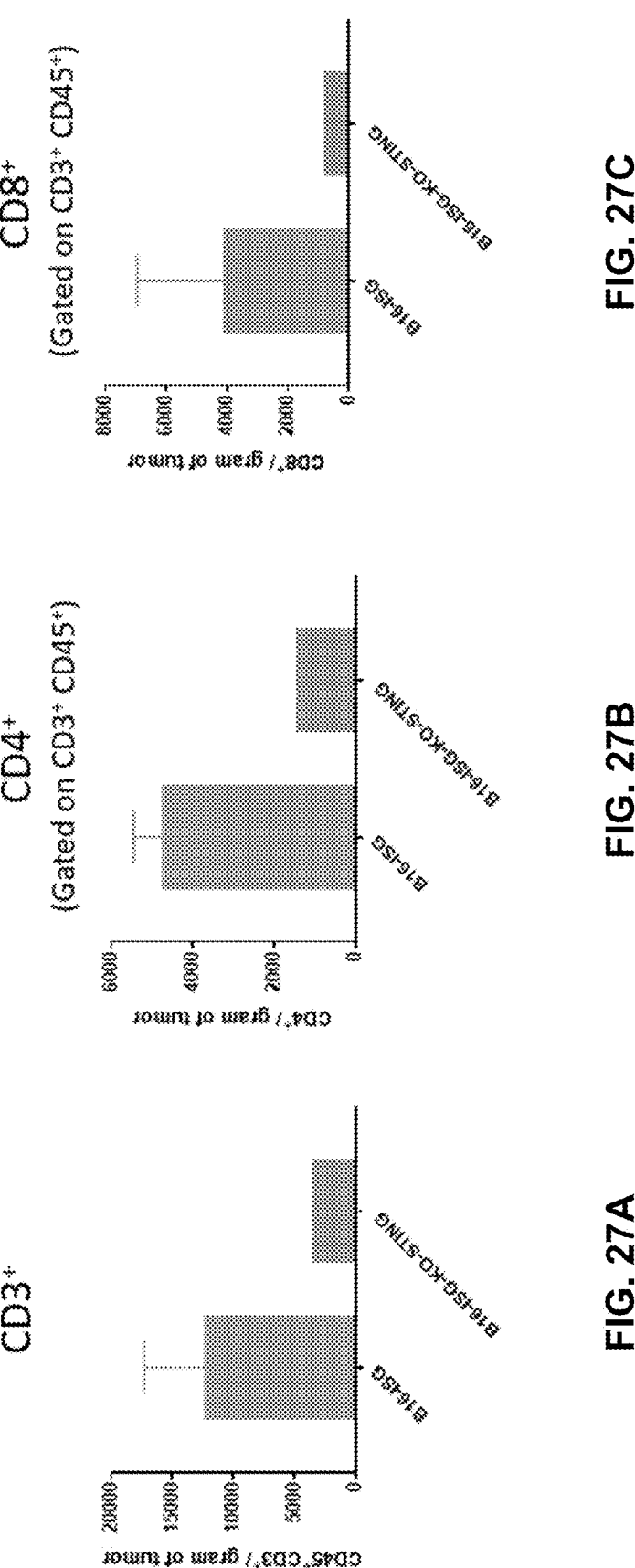
FIGS. 27A to 27E show loss of STING in B16-ISG cells alters numbers and phenotype of TIL in vivo.
Figure 27E:
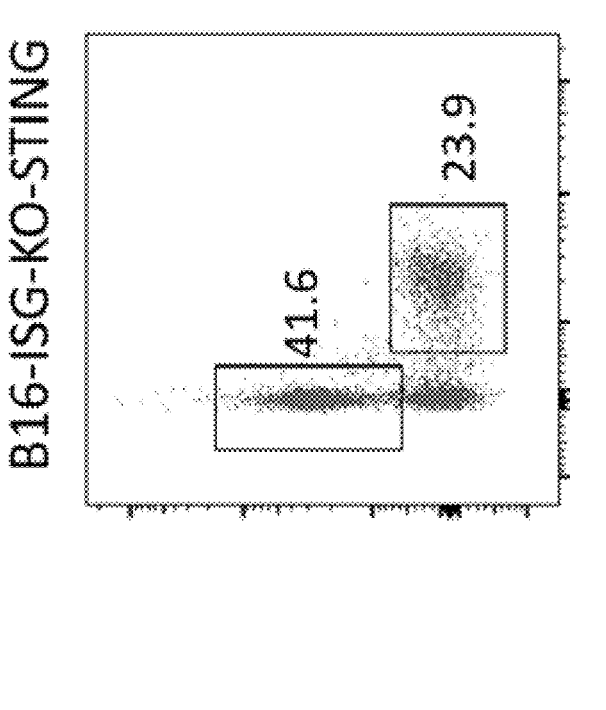
Figure 27D:
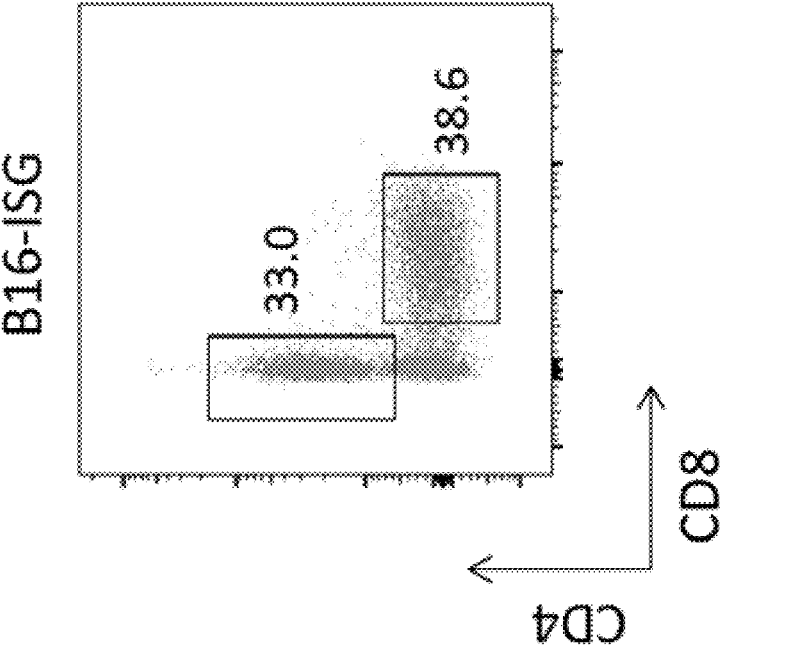
Figure 28B:
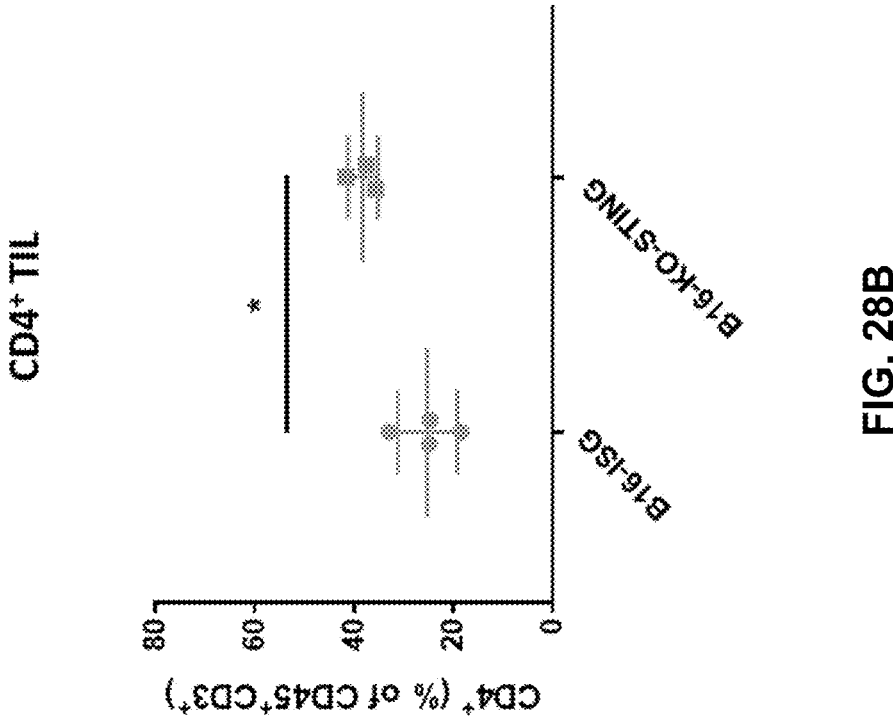
FIGS. 28A and 28B show loss of STING in B16-ISG cells alters numbers and phenotype of TIL in vivo.
Figure 28A:
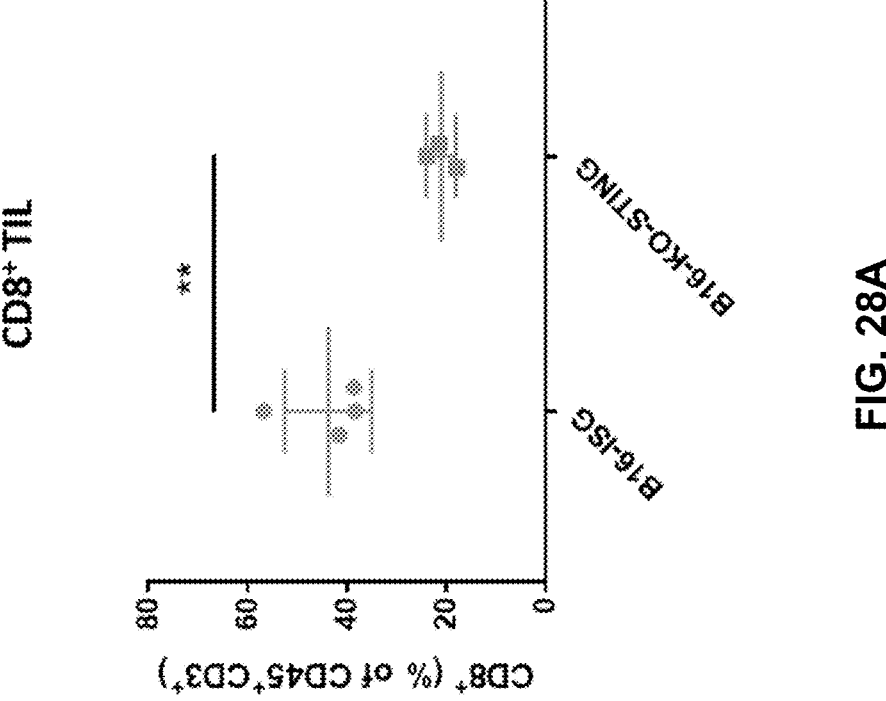
Figure 29B:
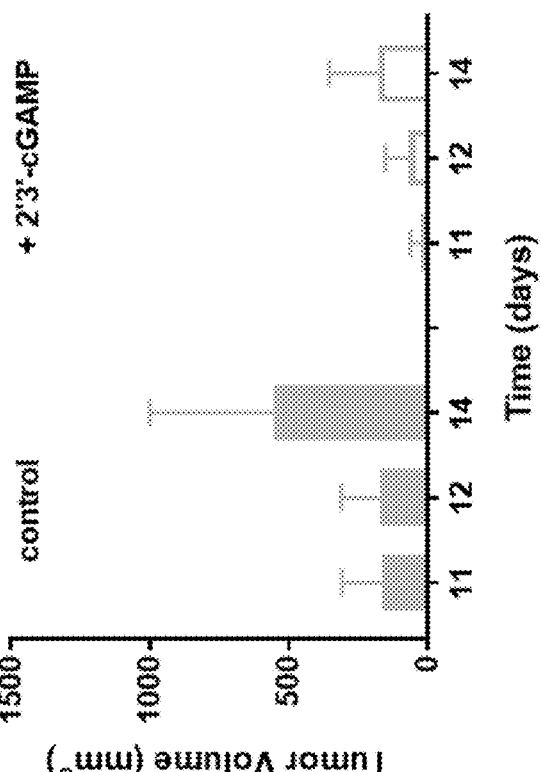
FIGS. 29A and 29B show intratumoral 2'3'-cGAMP delays tumor growth of B16 tumors in wild-type C57BL/6 mice.
Figure 29A:
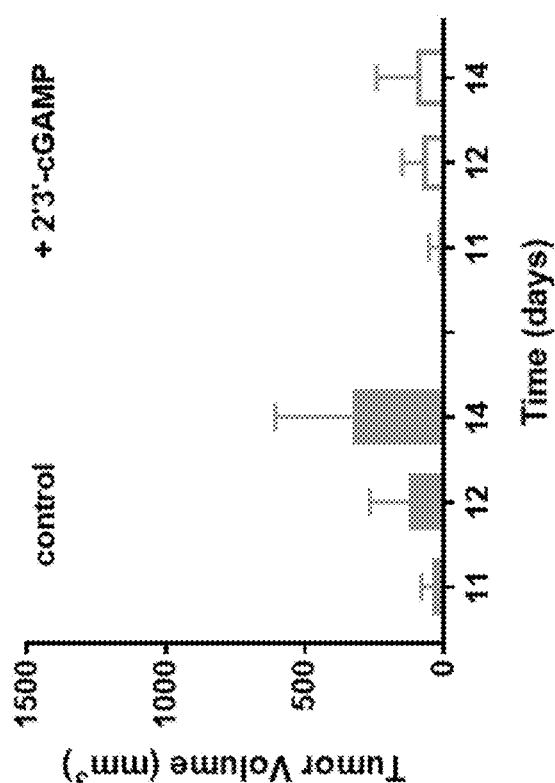
Figure 30:
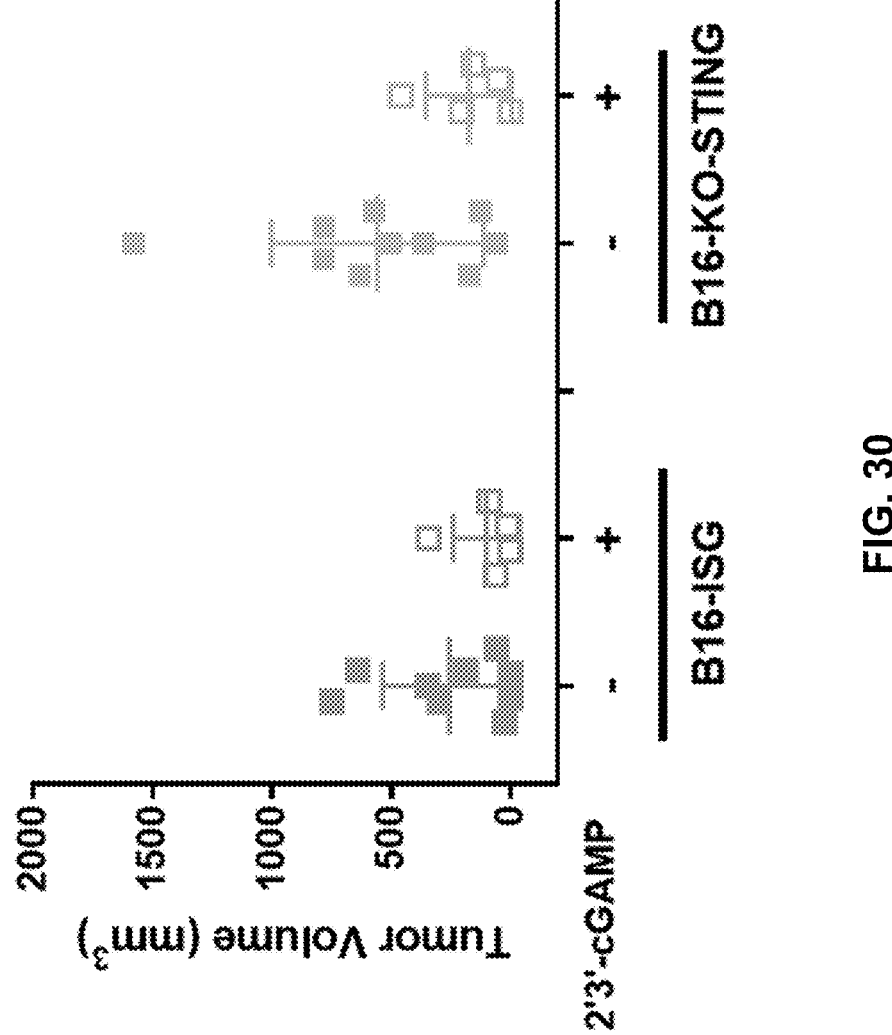
FIG. 30 shows intratumoral 2'3'-cGAMP delays tumor growth of B16 tumors in wild-type C57BL/6 mice.
Figure 31B:
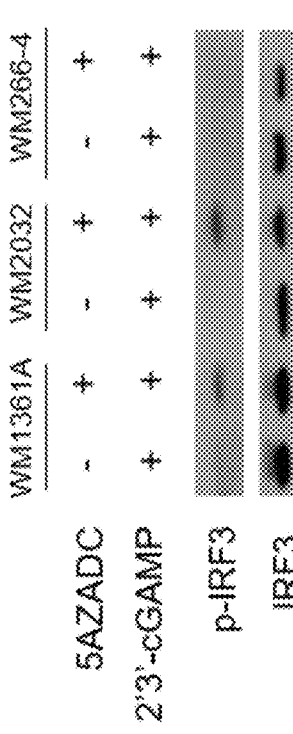
FIGS. 31A to 31D show reconstitution of STING expression through DNA demethylation can rescue agonist-induced STING signaling in melanoma cell lines.
Figure 31A:
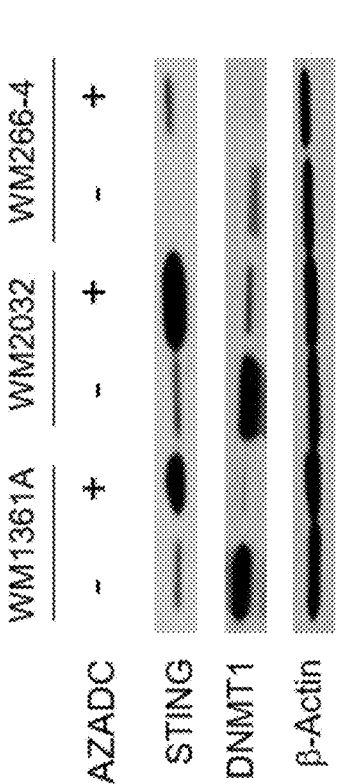
Figure 31C:
Figure 31D:
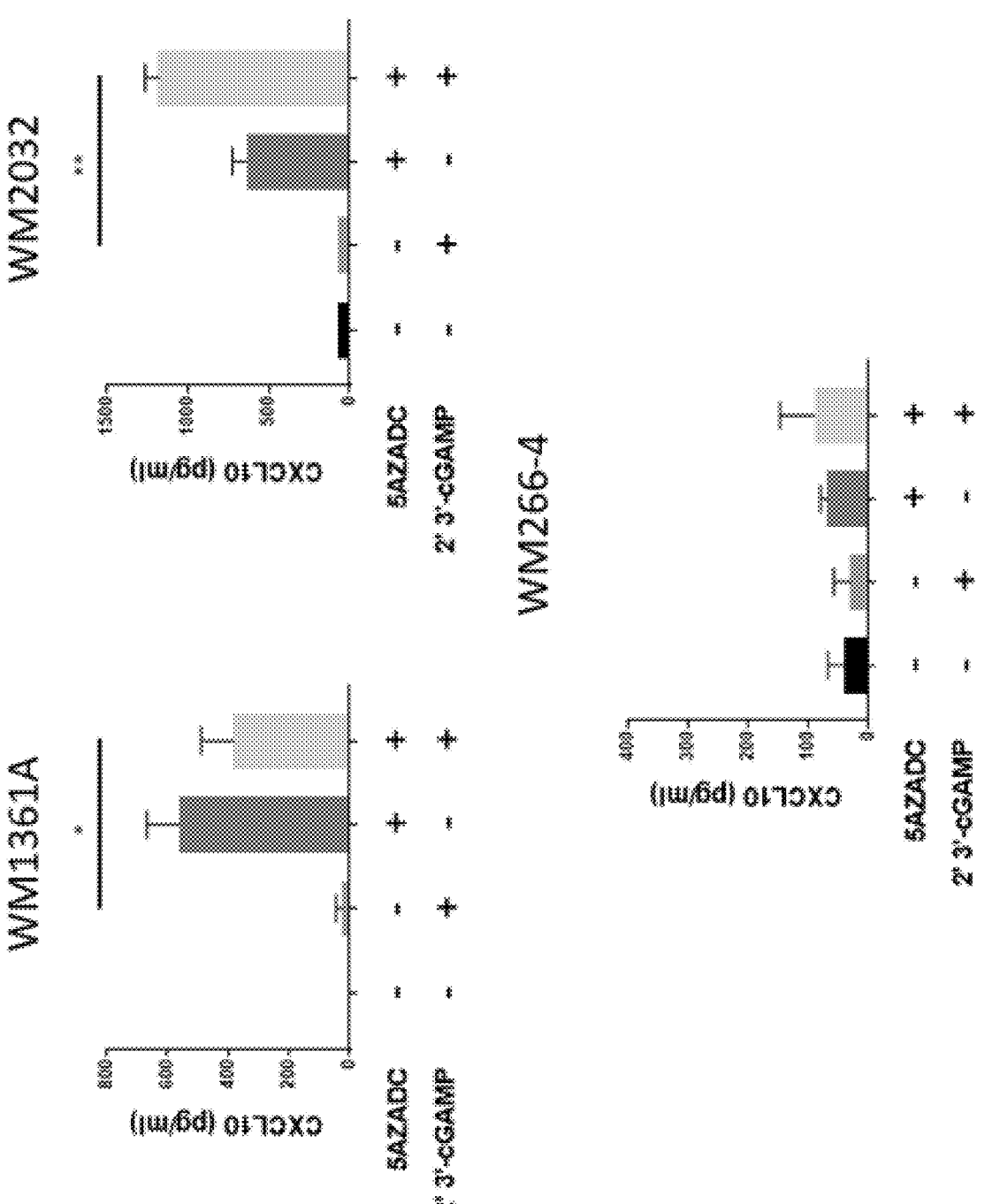
Figure 32:
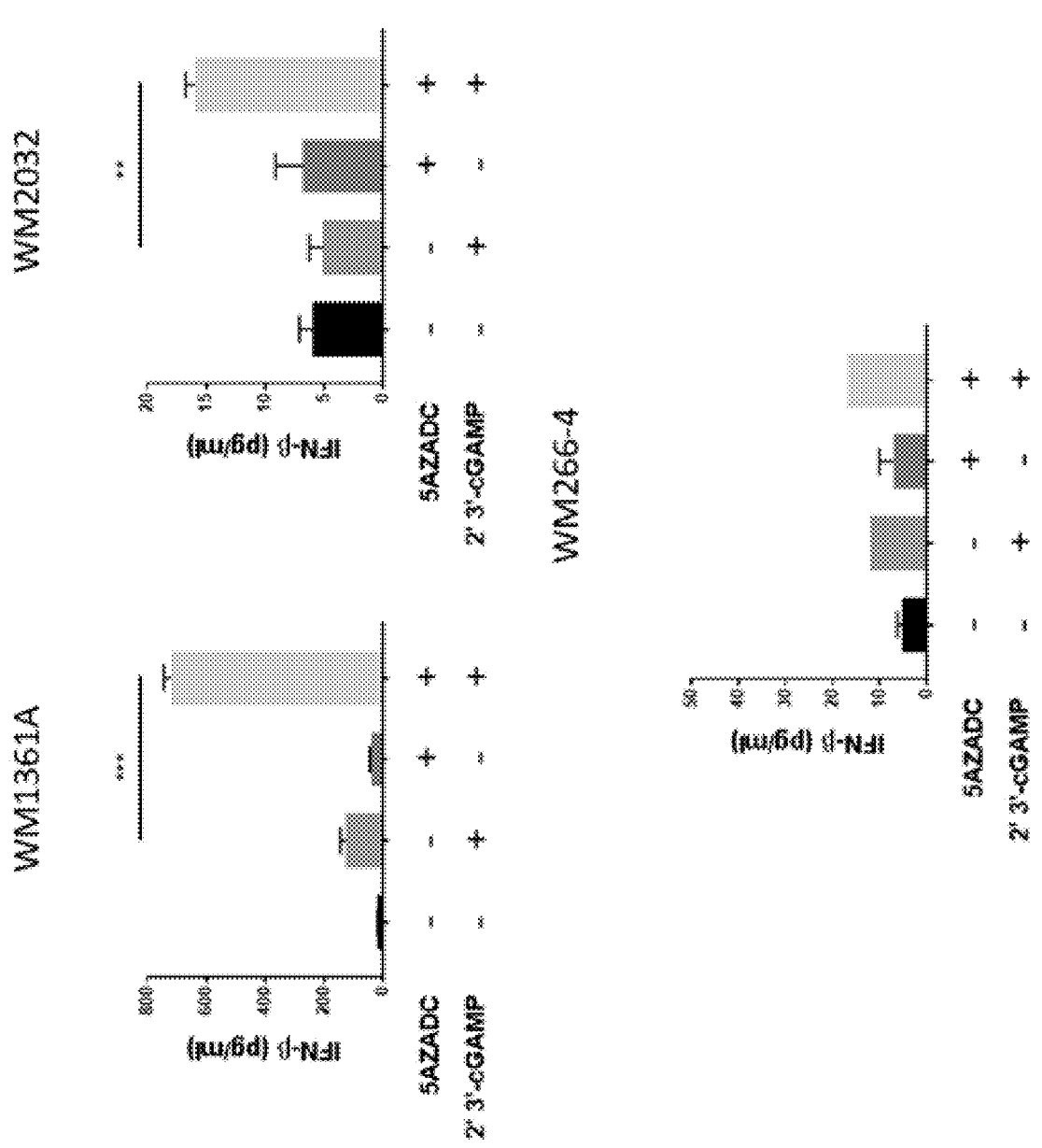
FIG. 32 shows IFN-β induction in 5AZADC treated melanoma cell lines in response to stimulation with 2'3'-cGAMP.
Figure 33:
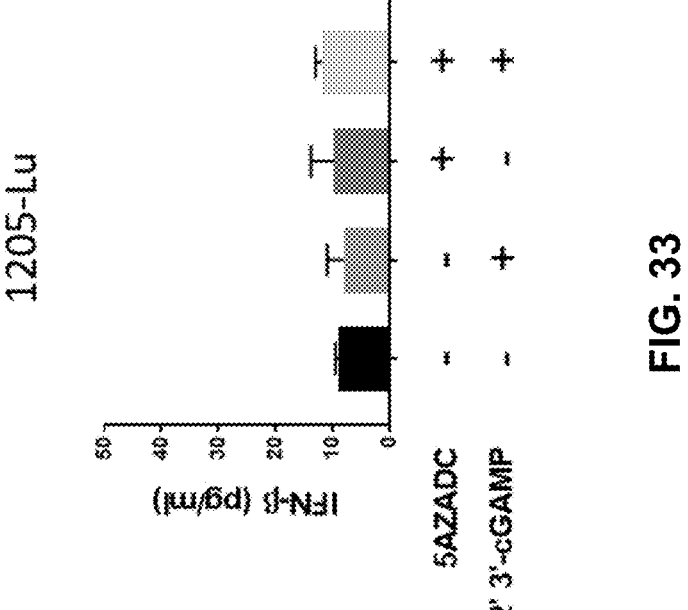
FIG. 33 shows IFN-β levels in 5AZADC treated 1205-Lu cell line in response to stimulation with 2'3'-cGAMP.
Figure 34A:
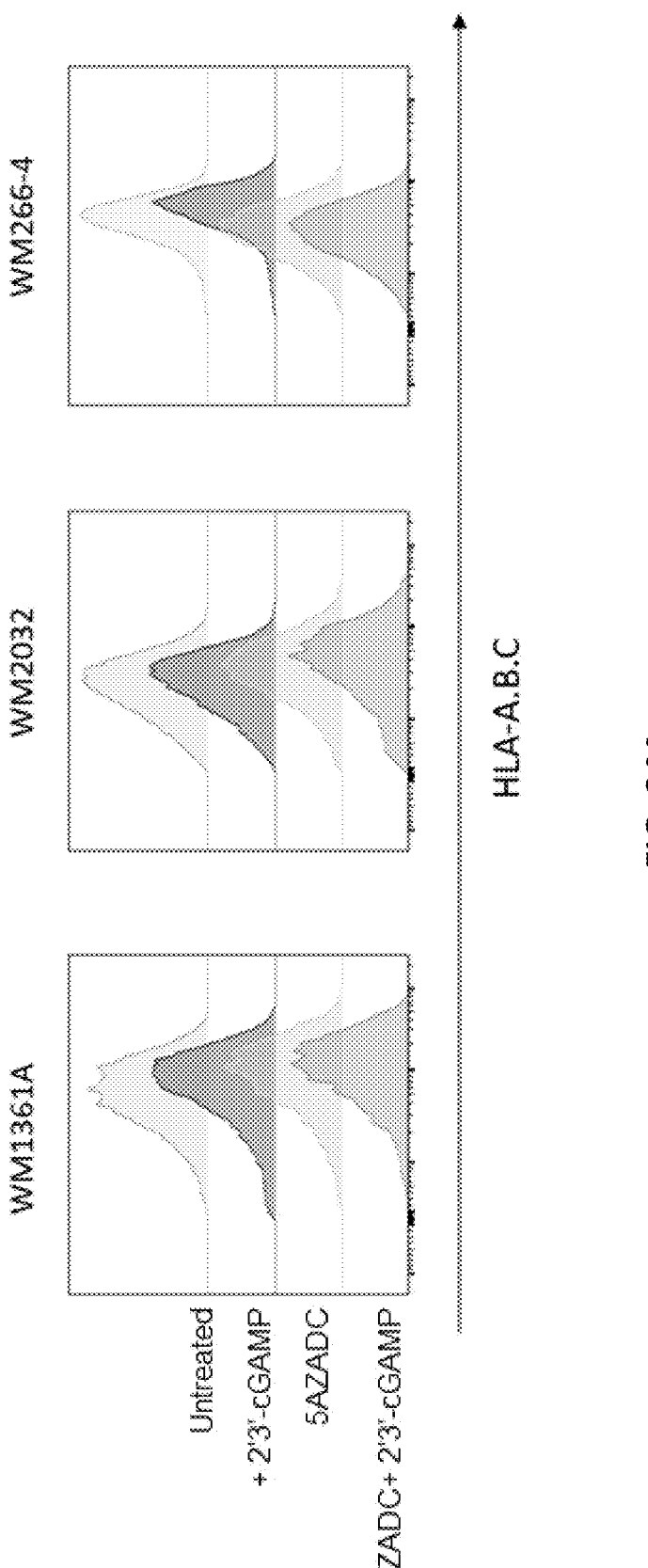
FIG. 34A to 34D show MHC class I surface expression in 5AZADC treated melanoma cell lines in response to stimulation with 2'3'-cGAMP.
Figure 34D:
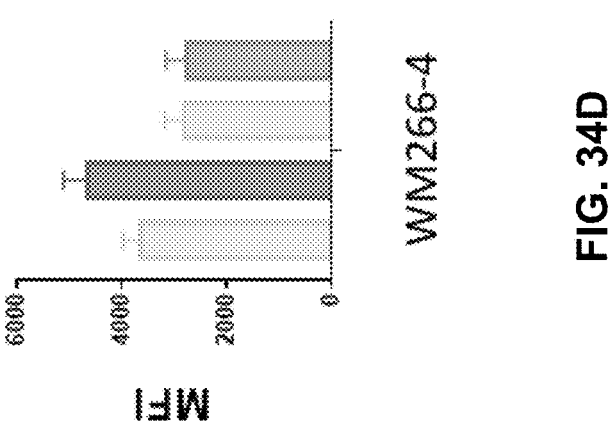
Figure 34C:
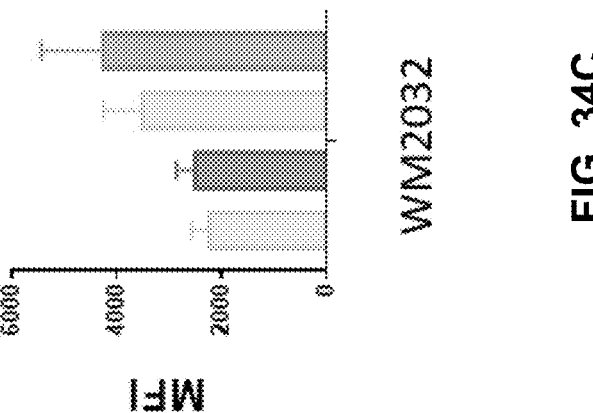
Figure 34B:
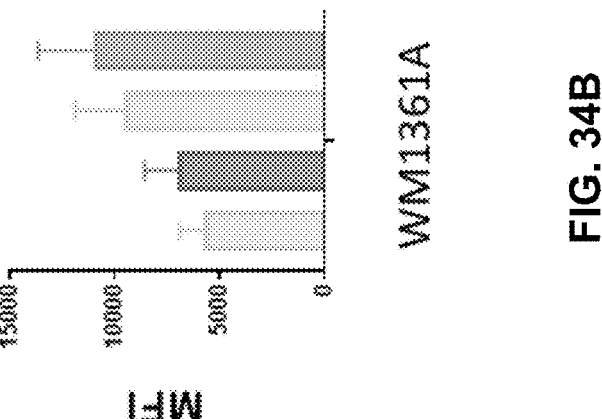
Figure 35A:
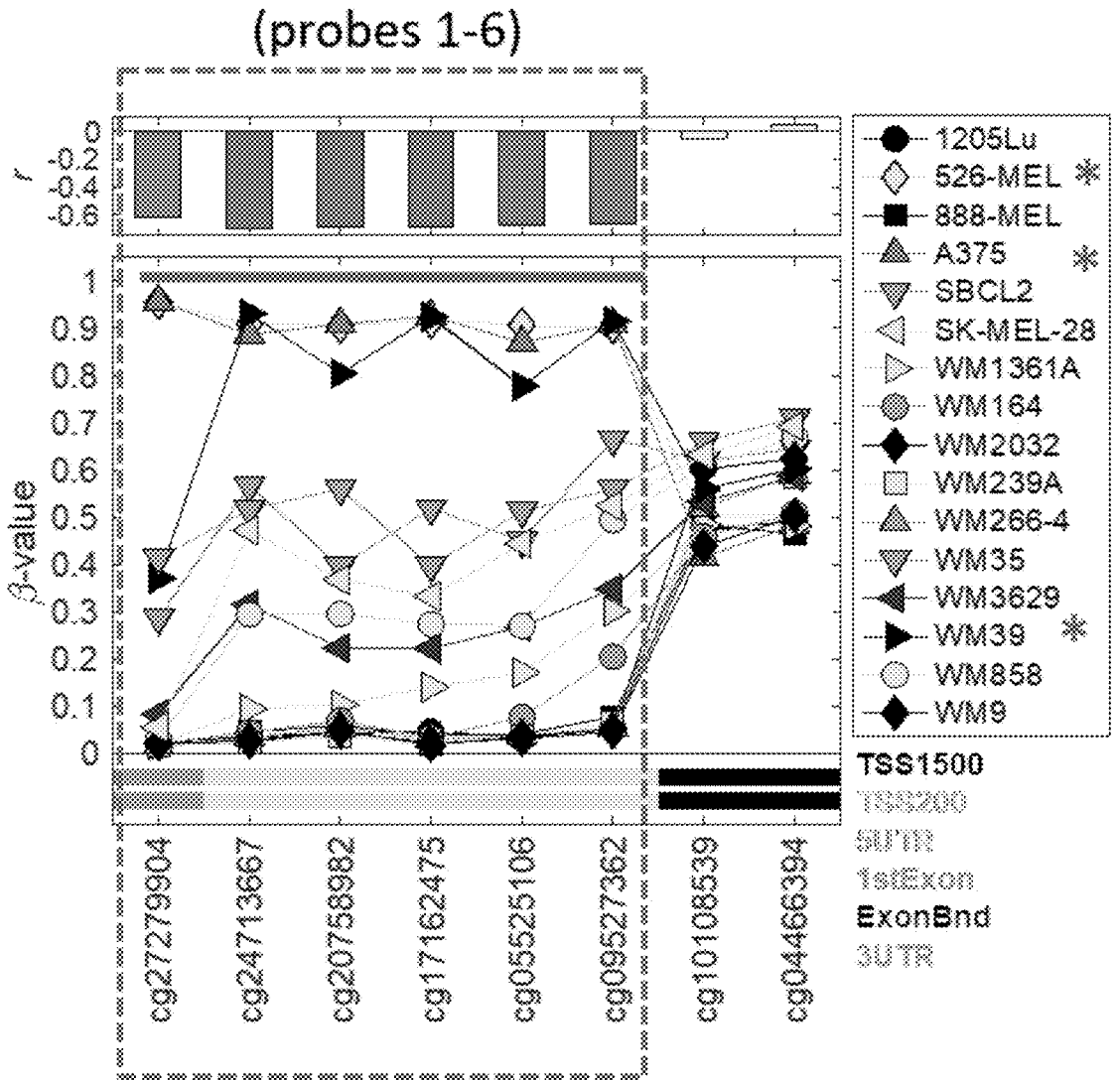
FIG. 35A shows cGAS has 8 probes on the EPIC chip. The 6 first probes all show a similar methylation pattern across the 16 melanoma cell lines. The bar plot on top shows that the first 6 probes are negatively correlated to the protein level of cGAS. 526-MEL, A375 and WM39 show a high degree of methylation. WM35, SBCL2, SK-MREL-28, WM858 and WM3629 show some degree of methylation while the rest are show little methylation.
Figure 35B:
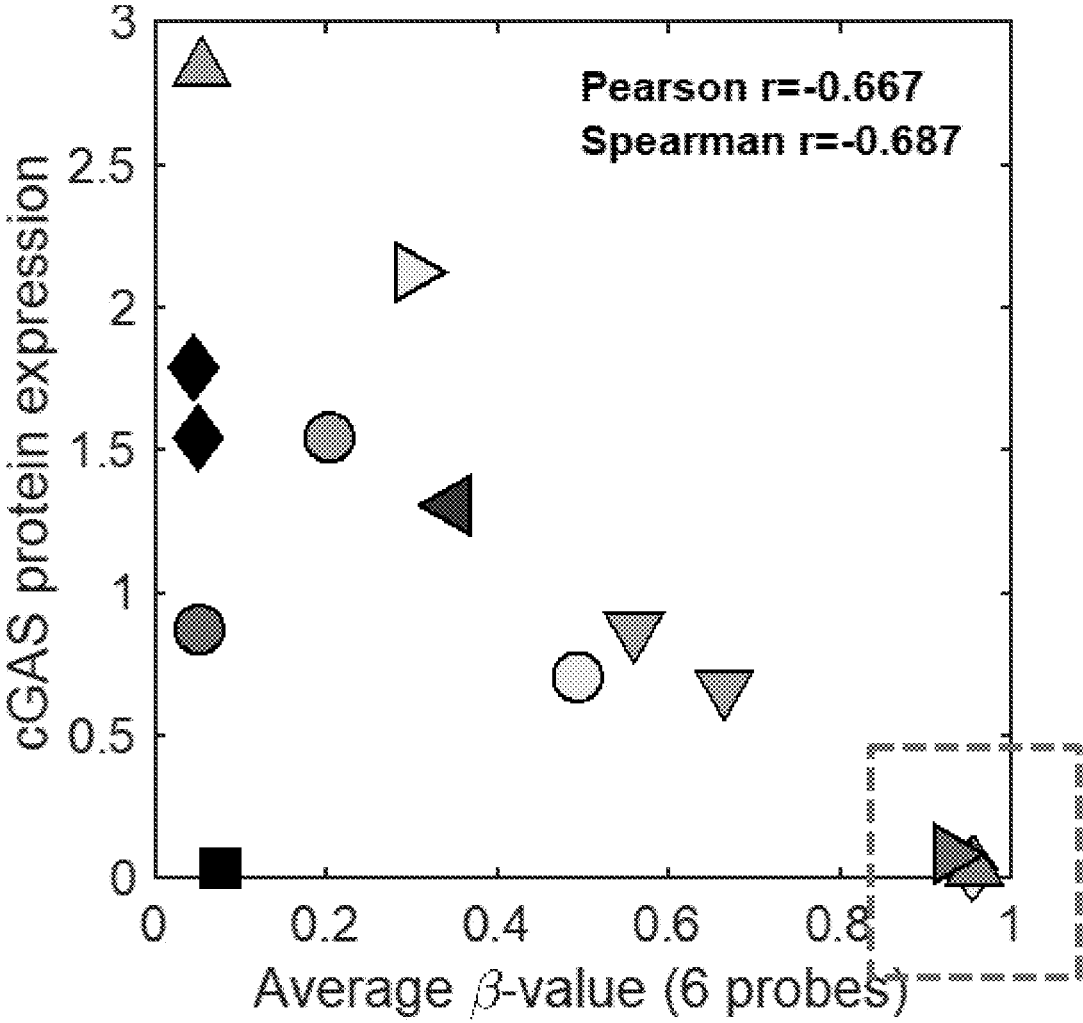
FIG. 35B shows the correlation between the average methylation for the 6 first probes and the protein expression of cGAS. It is clear that in most of the cell lines, the expression of cGAS is epigenetically regulated by methylation. A clear exception is 888-MEL that shows low methylation and also low protein expression of cGAS.
Figure 36A:
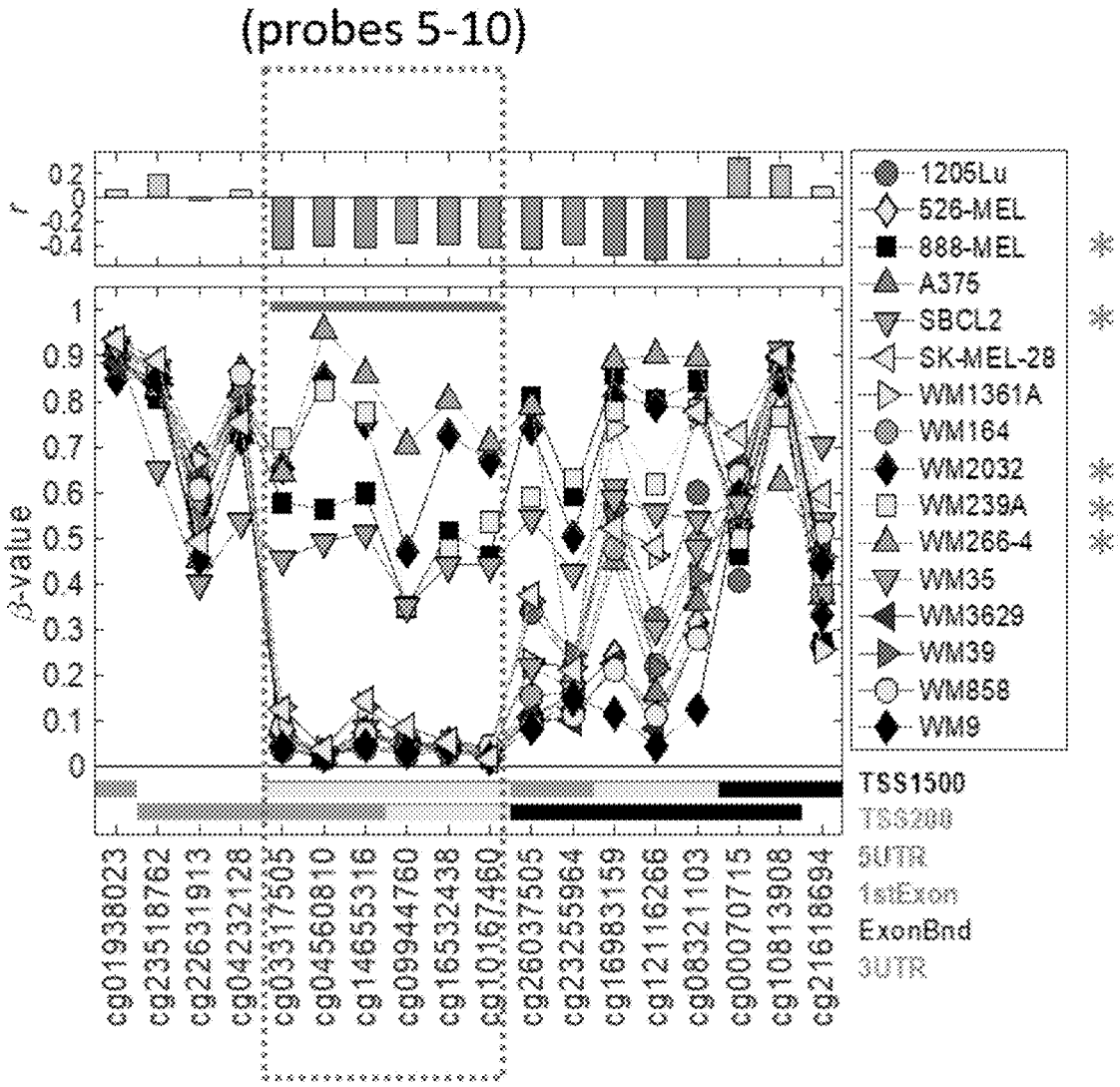
FIGS. 36A and 36B shows STING is represented by 18 probes on the EPIC chip. Probes 5-15 show a negative correlation with STING protein expression. In probes 5-10, WM266-4, WM239A, WM2032, 888-MEL and SBCL2 show high degree of methylation.
Figure 36B:
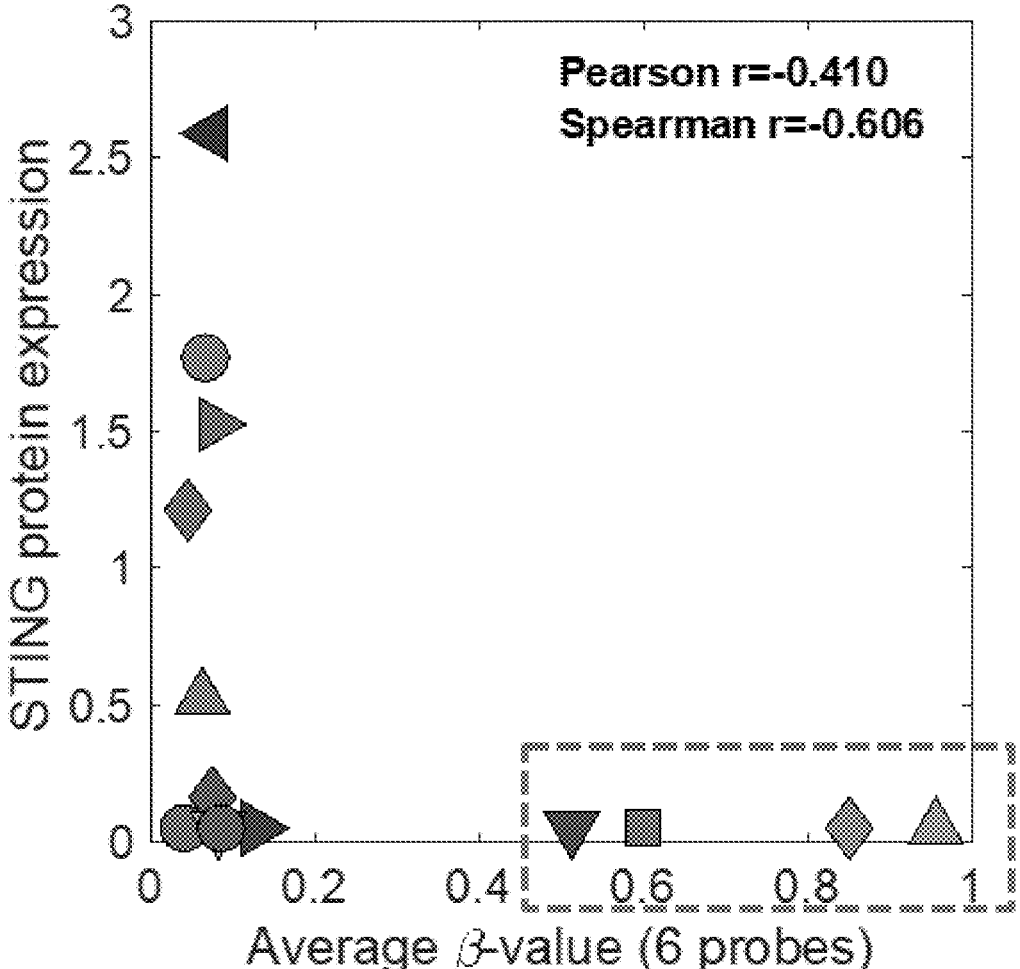
Figure 37A:
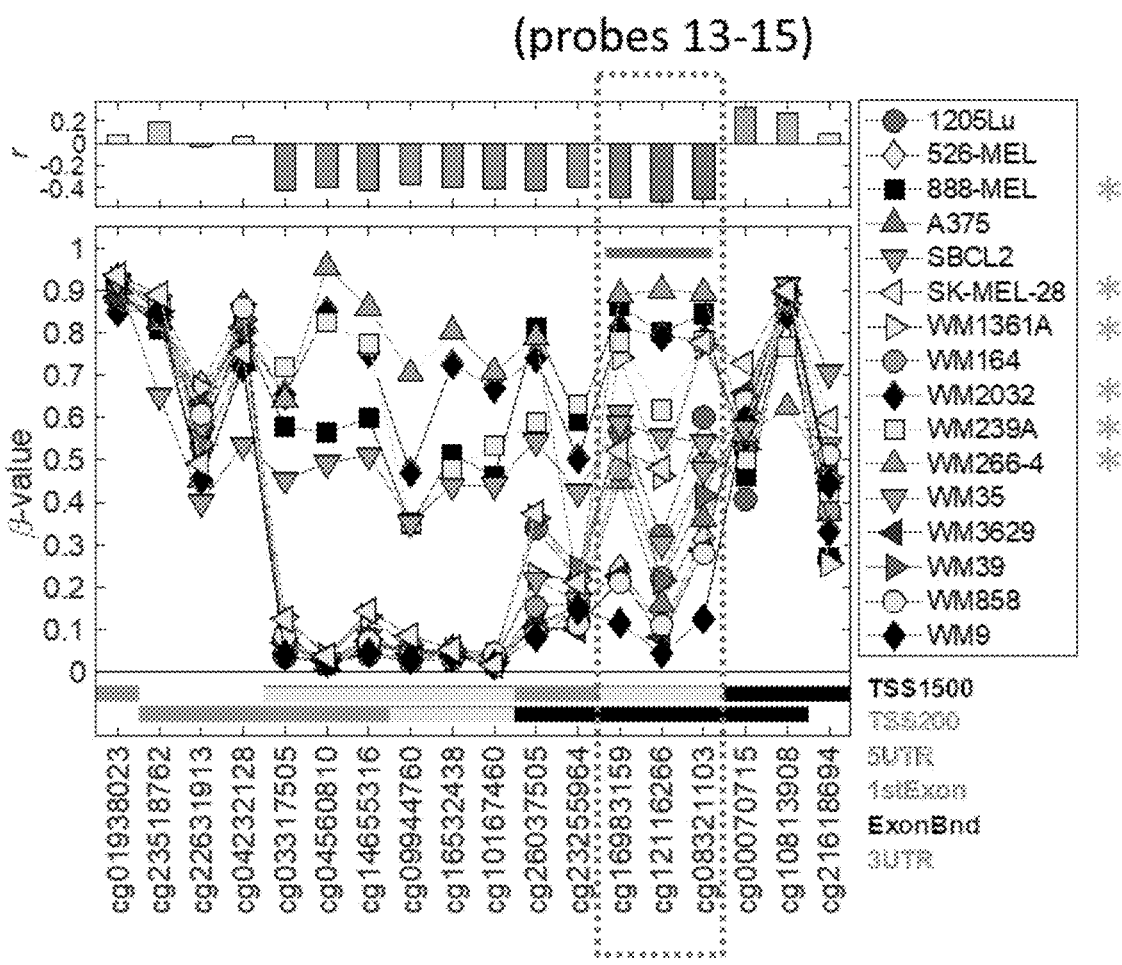
FIGS. 37A to 37C show a detailed study of probes 13-15 demonstrating that the expression of STING can be regulated by several CpG sites. Treating 526-MEL and WM858 would not respond to 5AZAtreatment.
Figure 37B:
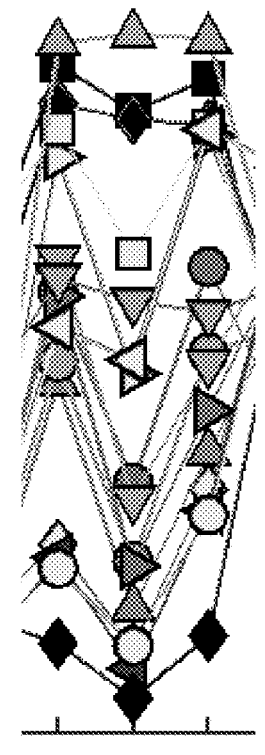
Figure 37C:
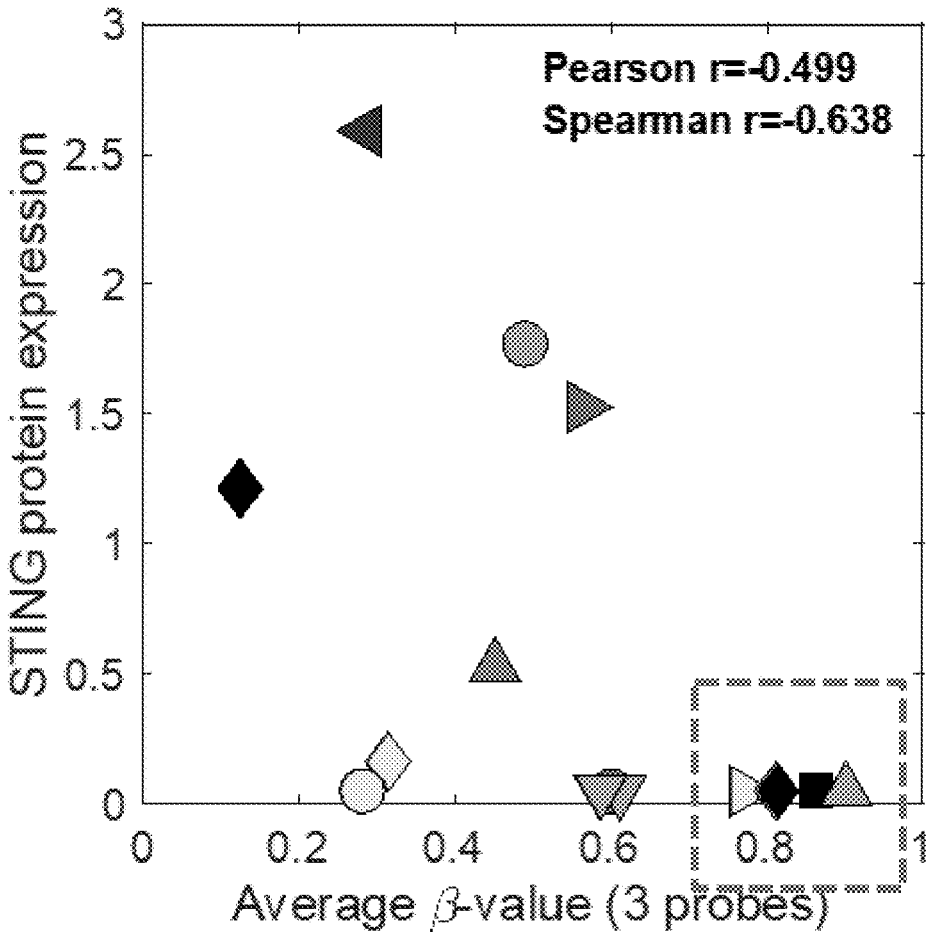
Figure 38:
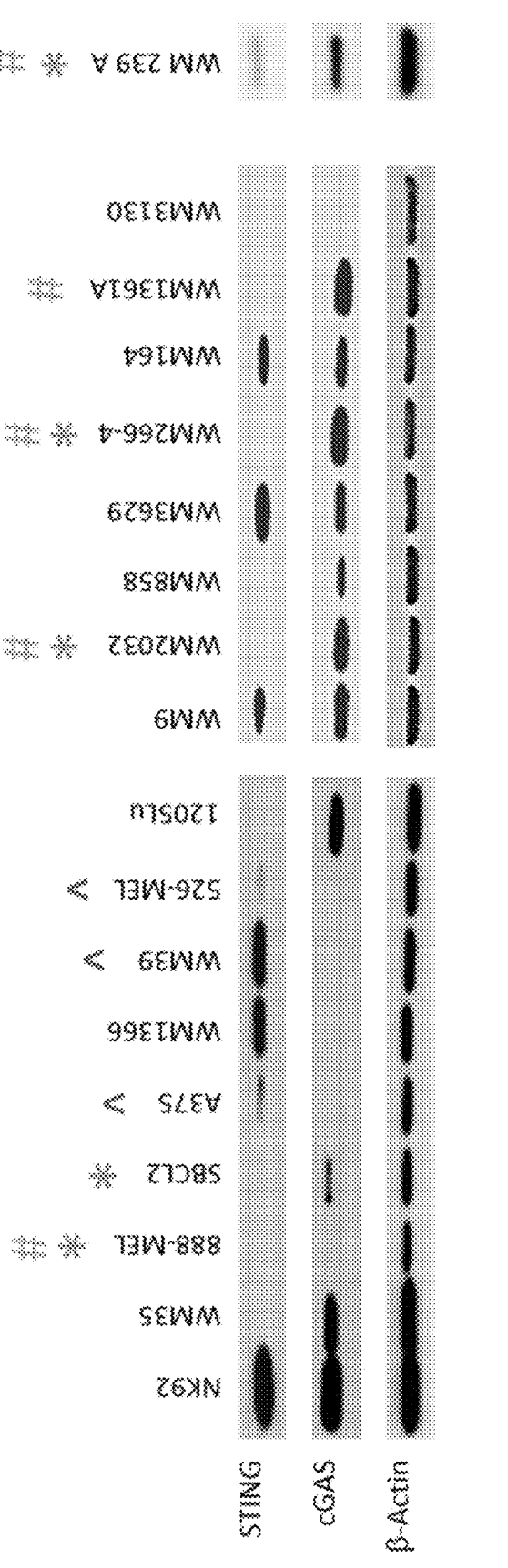
FIG. 38 shows suppression of STING and cGAS expression in human melanoma cell lines is associated with high levels of DNA methylation in STING and cGAS gene promoter regions.
Figure 39:
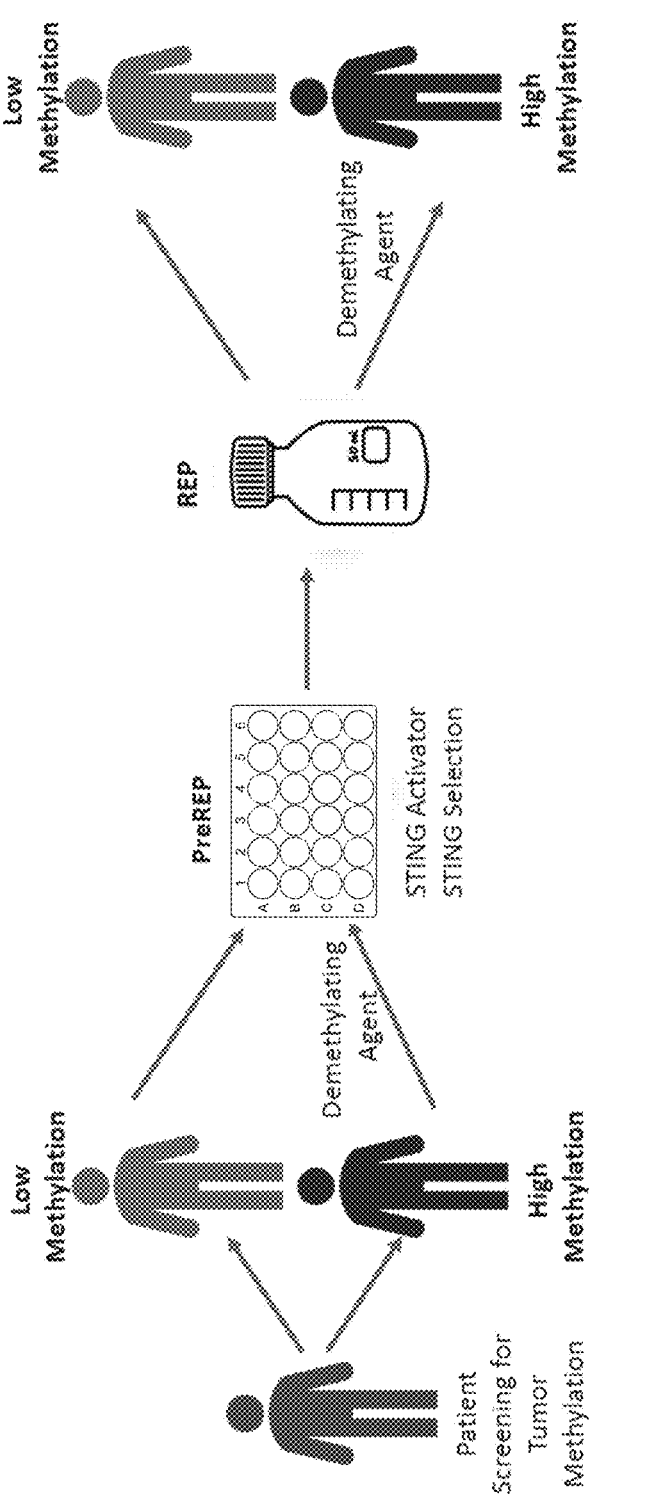
FIG. 39 illustrates an embodiment of a disclosed method for producing TILs.
Figure 40:
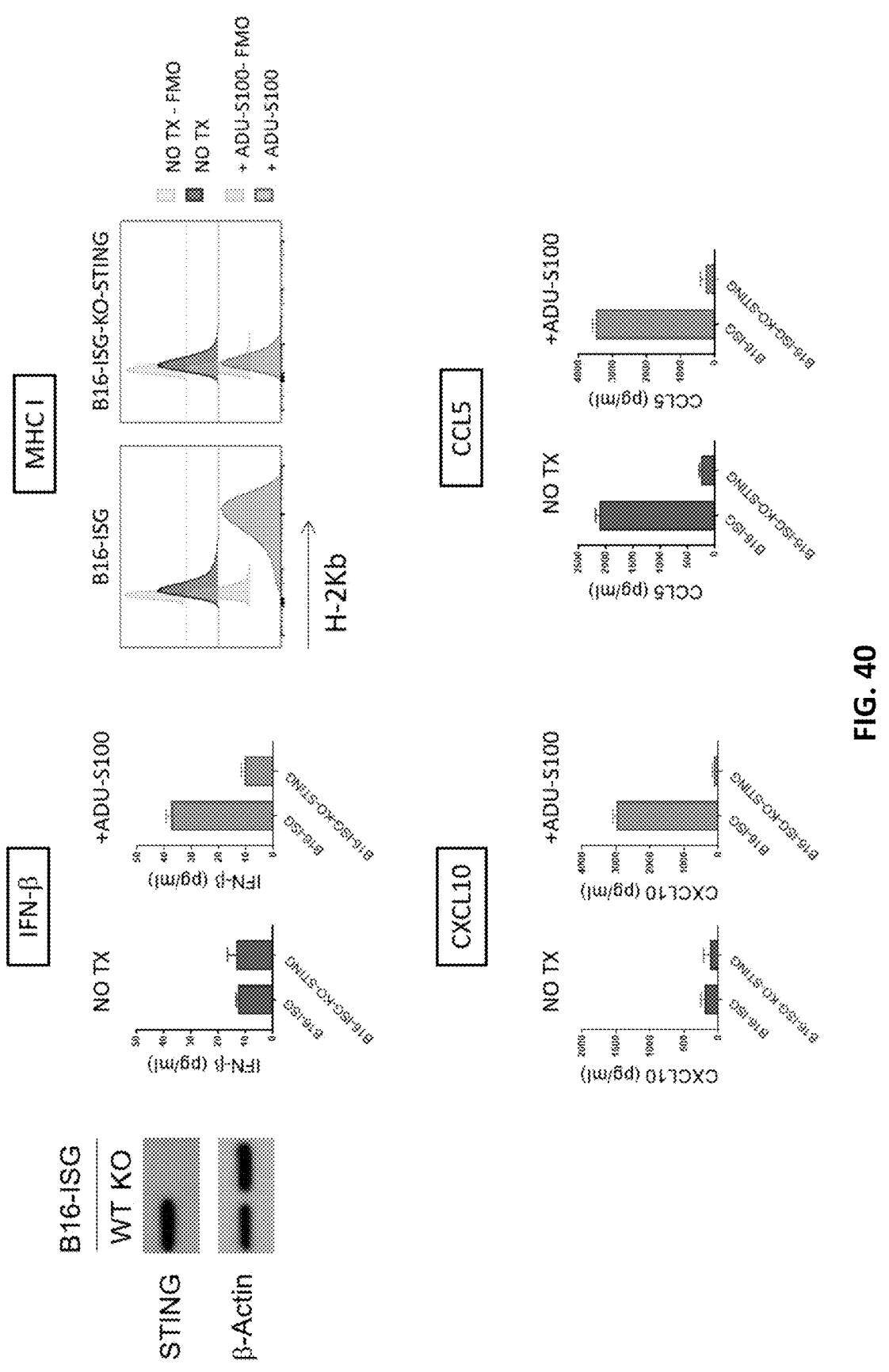
FIG. 40 shows activation of STING in tumor cells upregulates MHC-I expression and induces T cell homing chemokines.
Figure 41A:
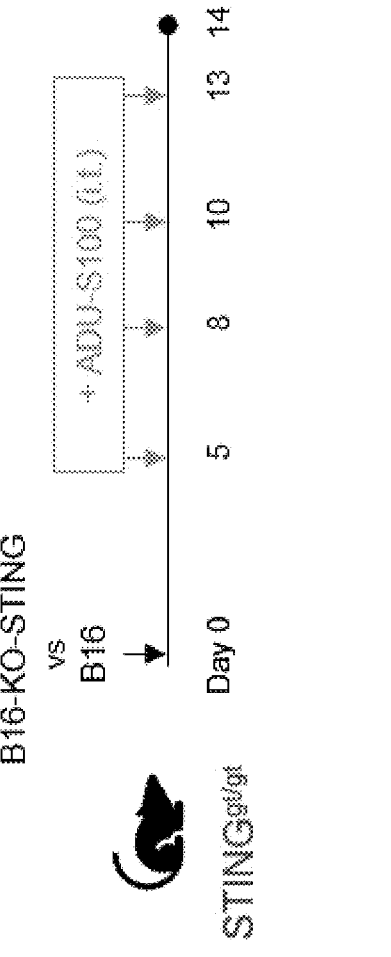
FIGS. 41A and 41B show activation of STING in tumor cells delays their growth in STING$^{gt/gt}$ mice.
Figure 41B:
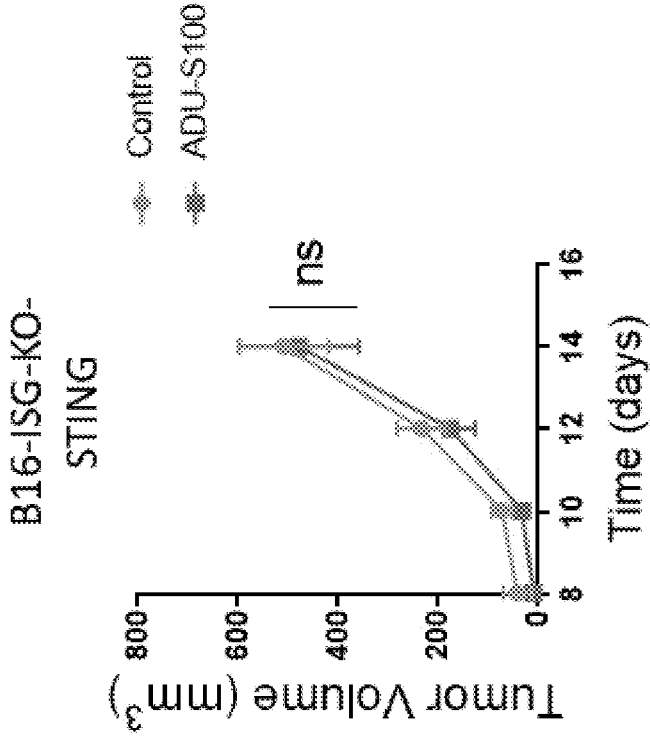
Figure 41B:
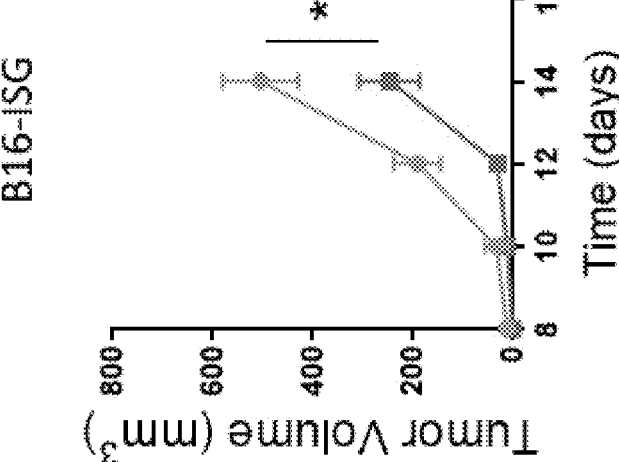
Figure 42:
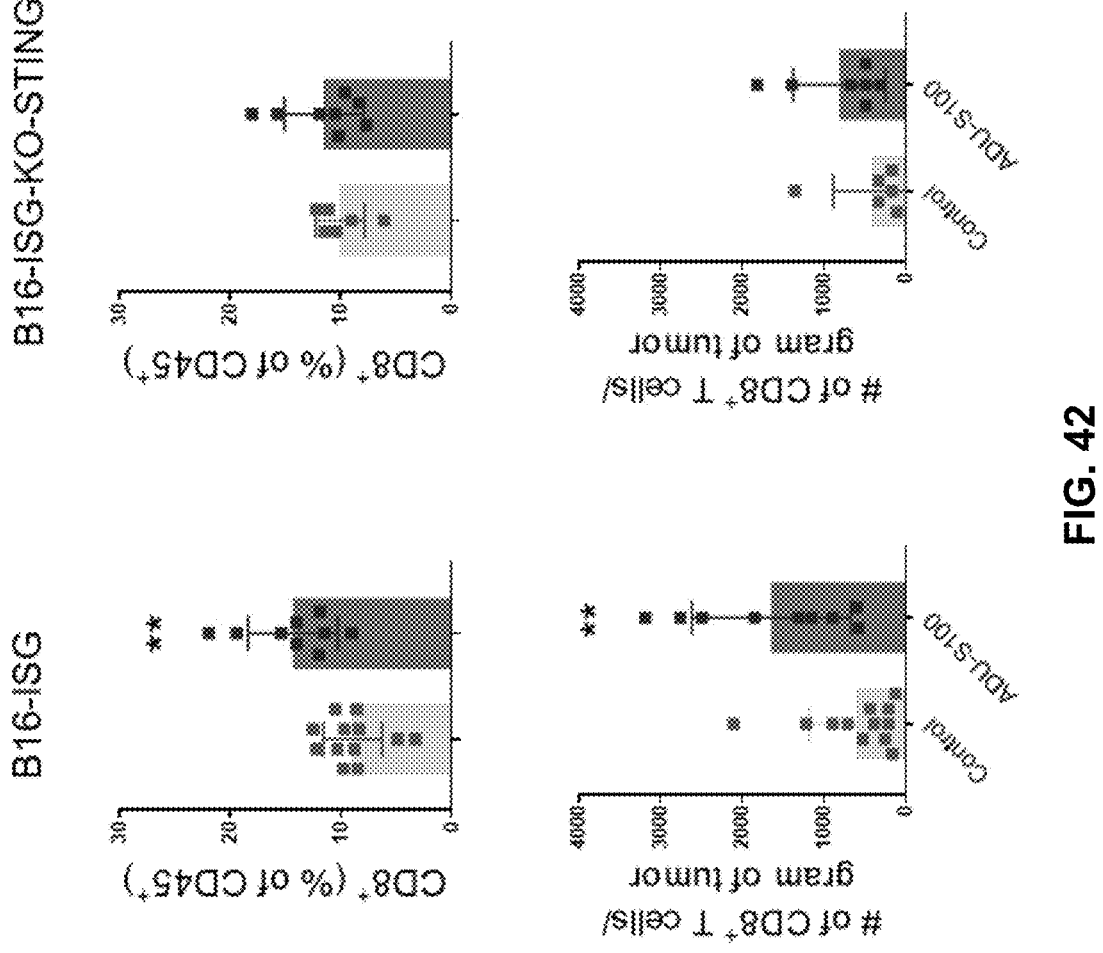
FIG. 42 shows Activation of STING in tumor cells is important for the recruitment of CD8$^+$ T cells in STING$^{gt/gt}$ mice.
Figure 43:
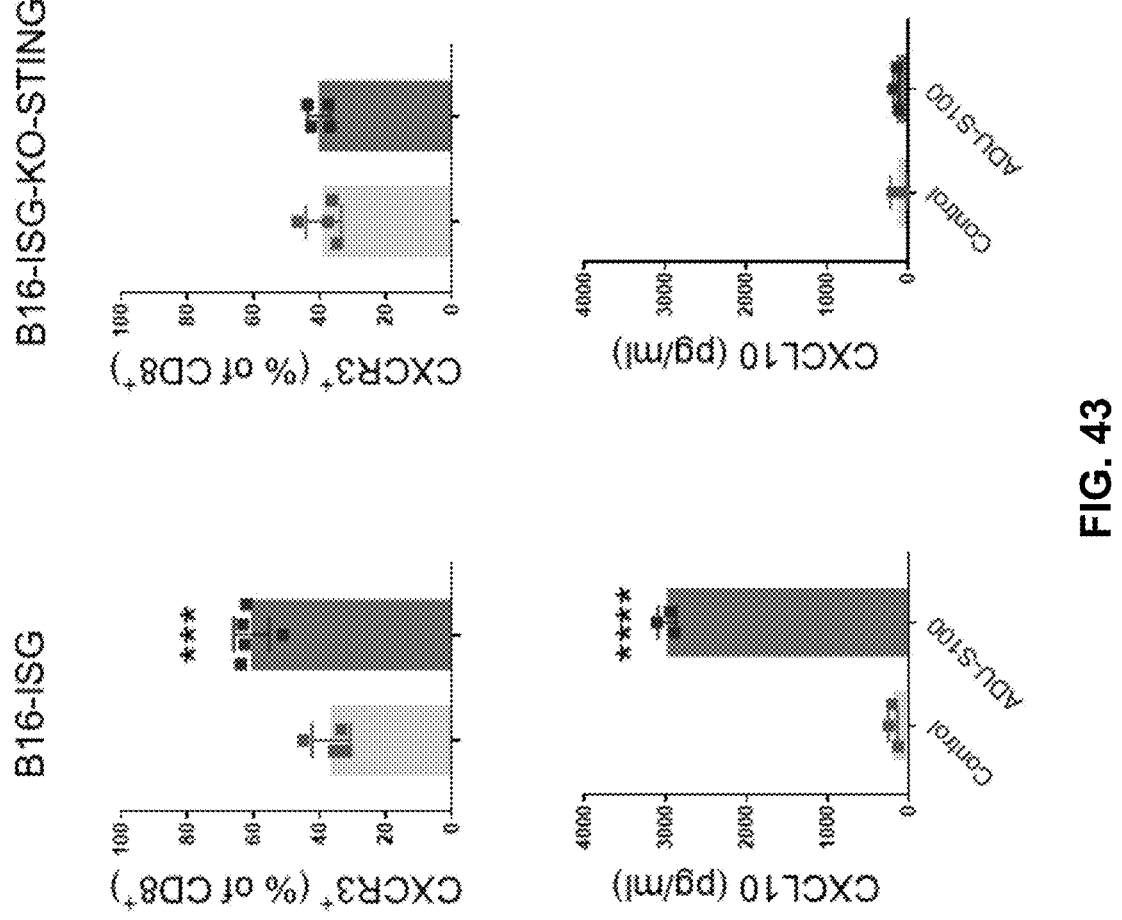
FIG. 43 shows activation of STING in tumor cells is important for the recruitment of CXCR3$^+$ CD8$^+$ T cells in STING$^{gt/gt}$ mice.
Figure 44A:
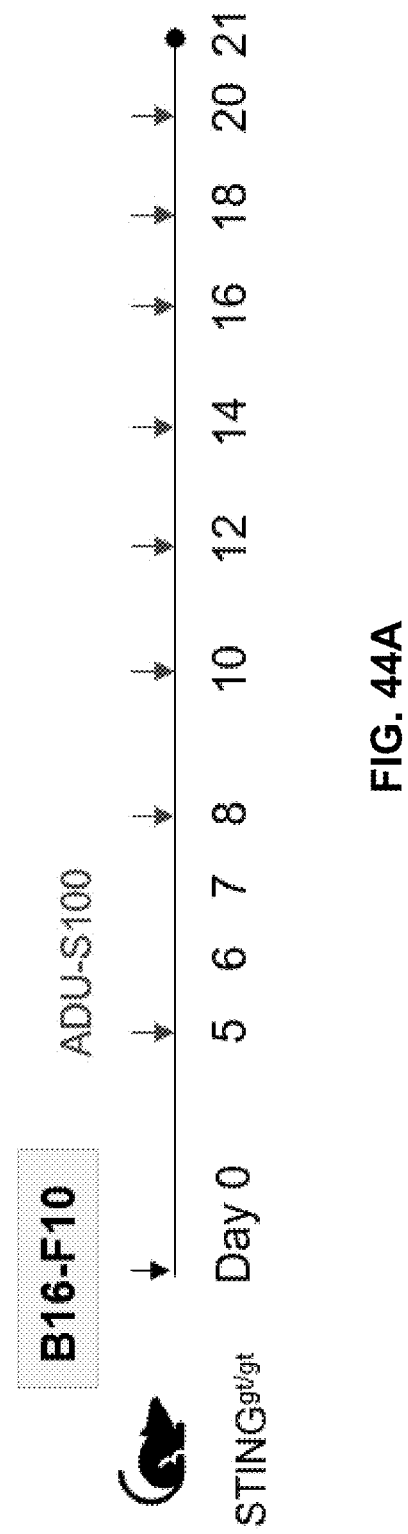
FIGS. 44A and 44B show agonist therapy becomes less effective in controlling B16 tumors at the late stage in STING$^{gt/gt}$ mice.
Figure 44B:
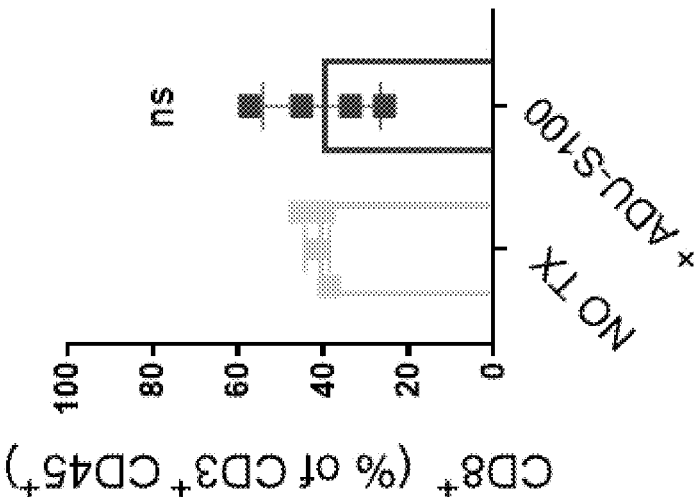
Figure 44B:
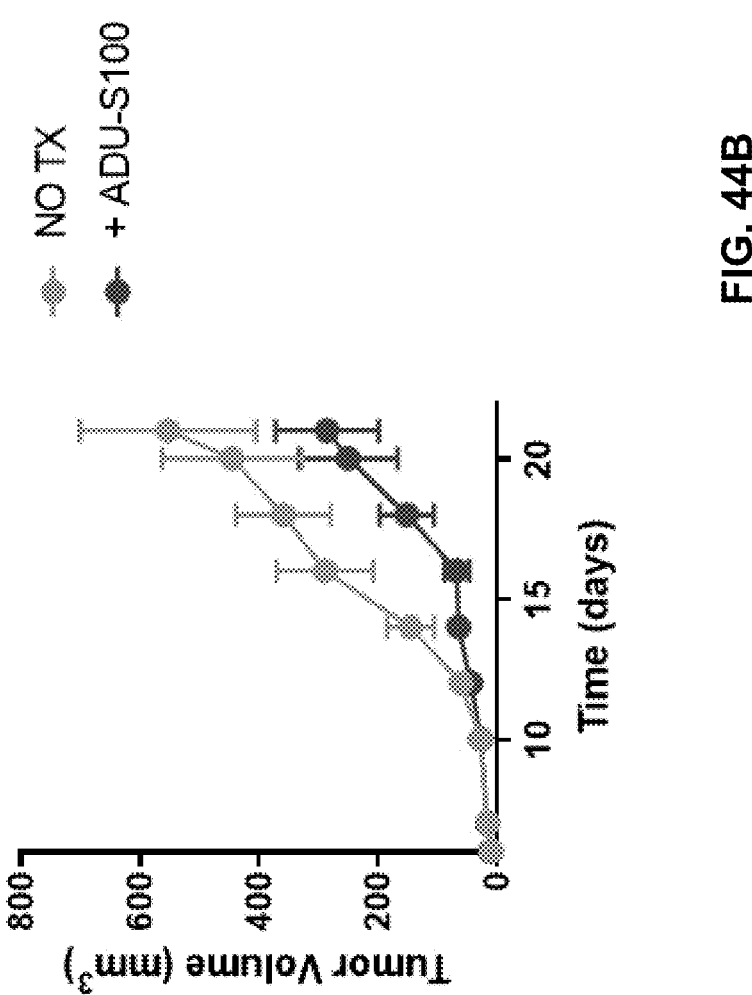
Figures 45A, 45B:
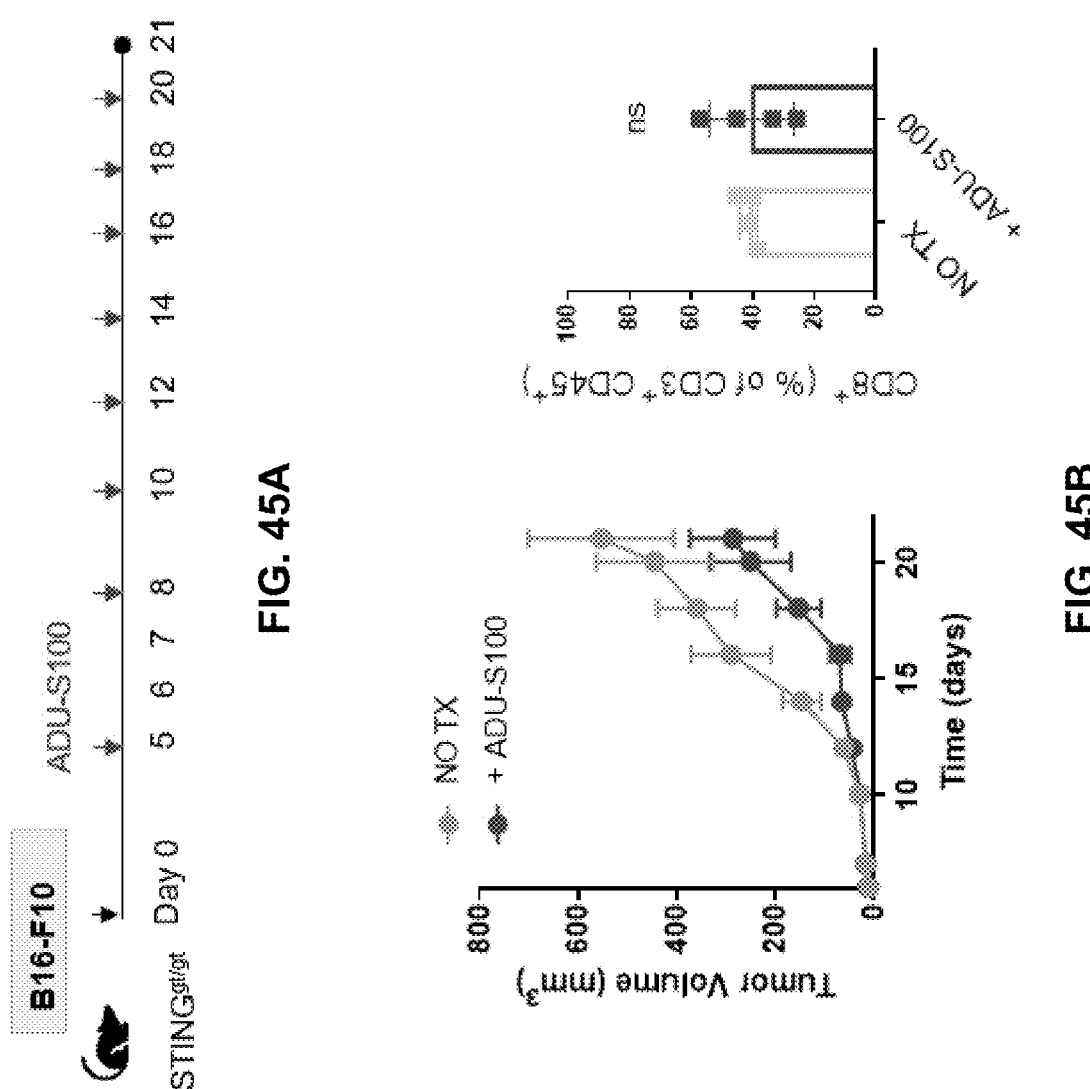
FIGS. 45A to 45D show agonist therapy becomes less effective in controlling tumors at the late stage in STING$^{gt/gt}$ mice.
Figures 45C, 45D:
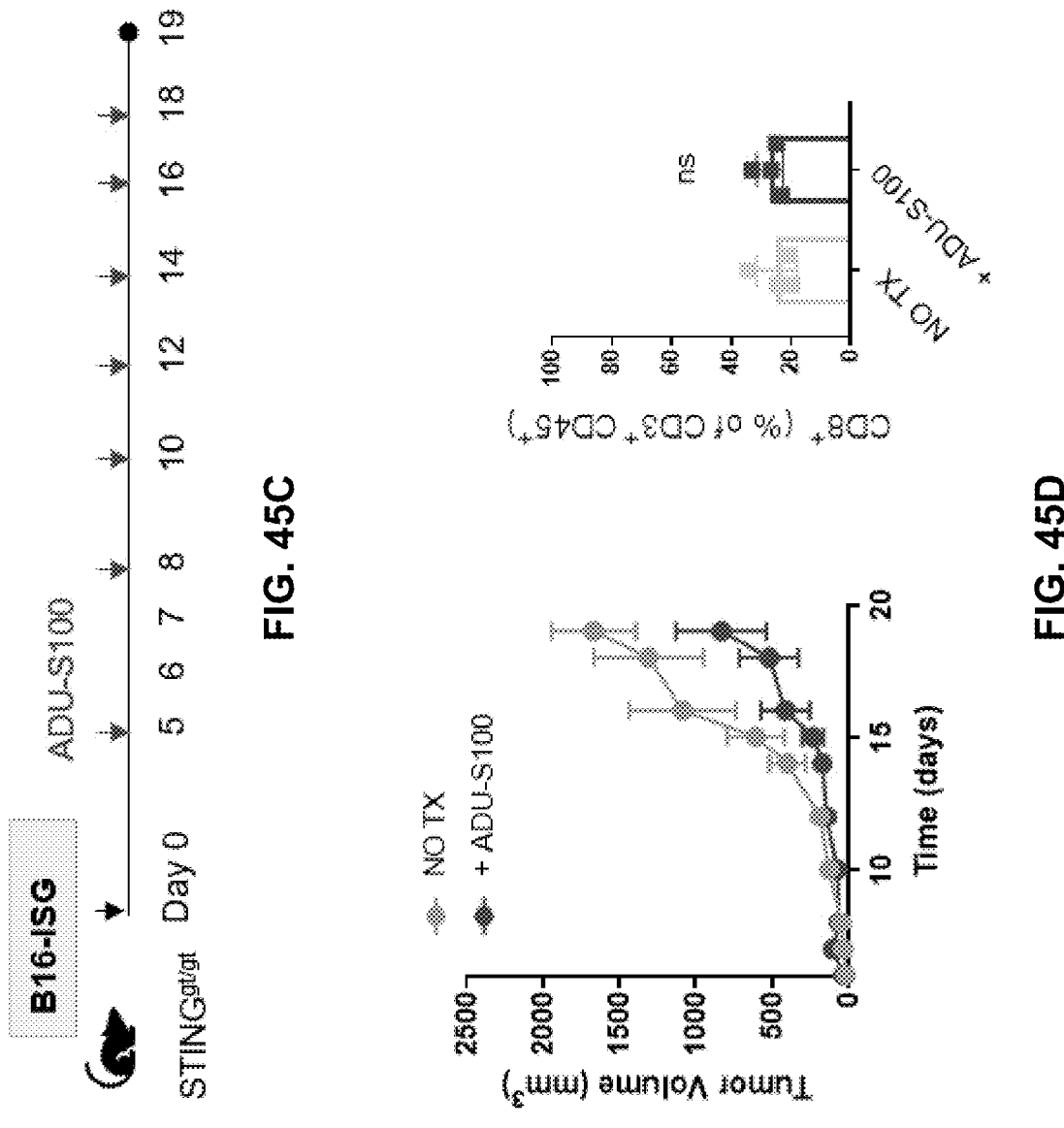
Figure 46A:
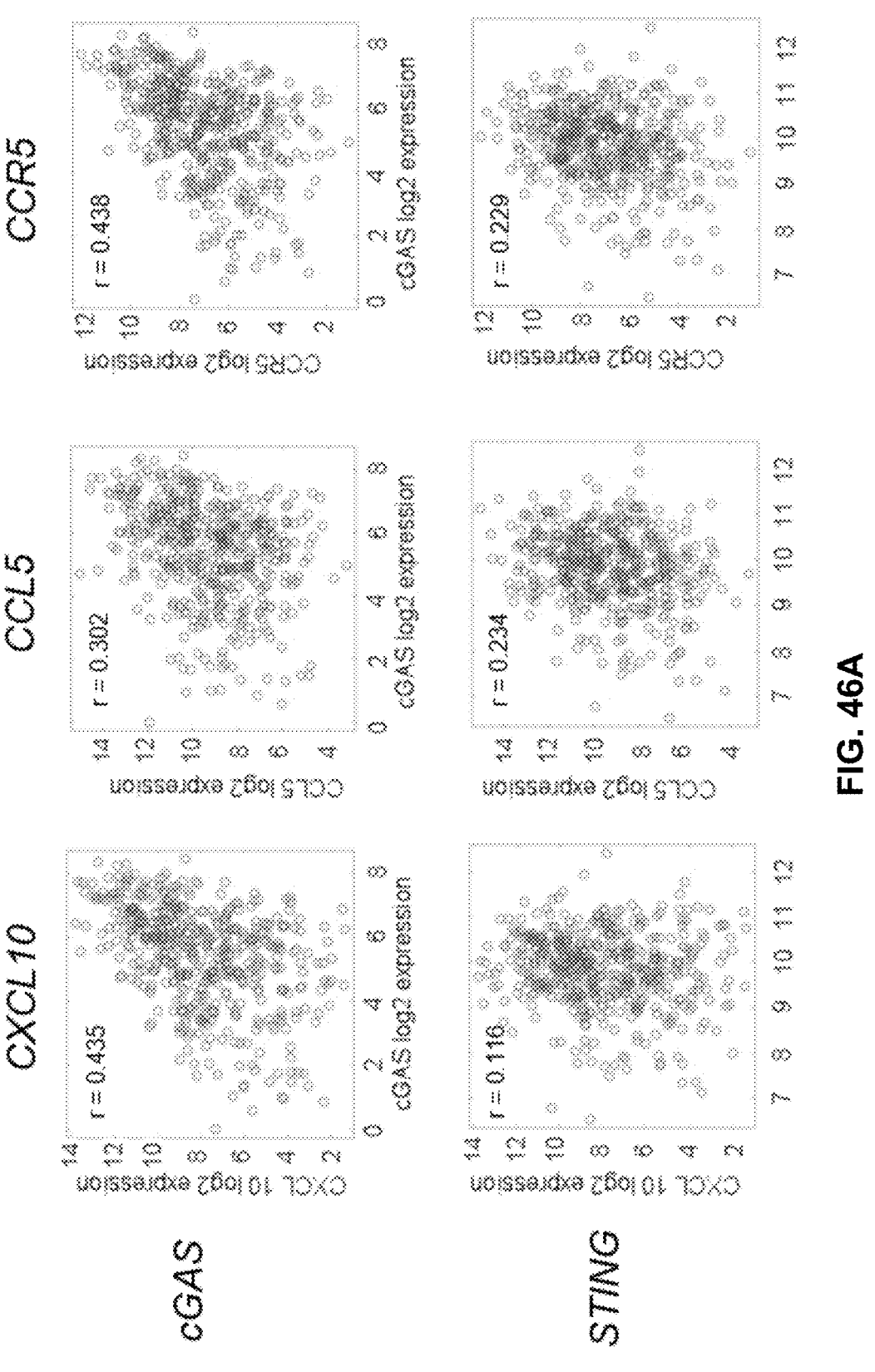
FIGS. 46A and 46B show cGAS, but not STING expression in human melanomas correlates with CD8 T cell infiltration.
Figure 46B:
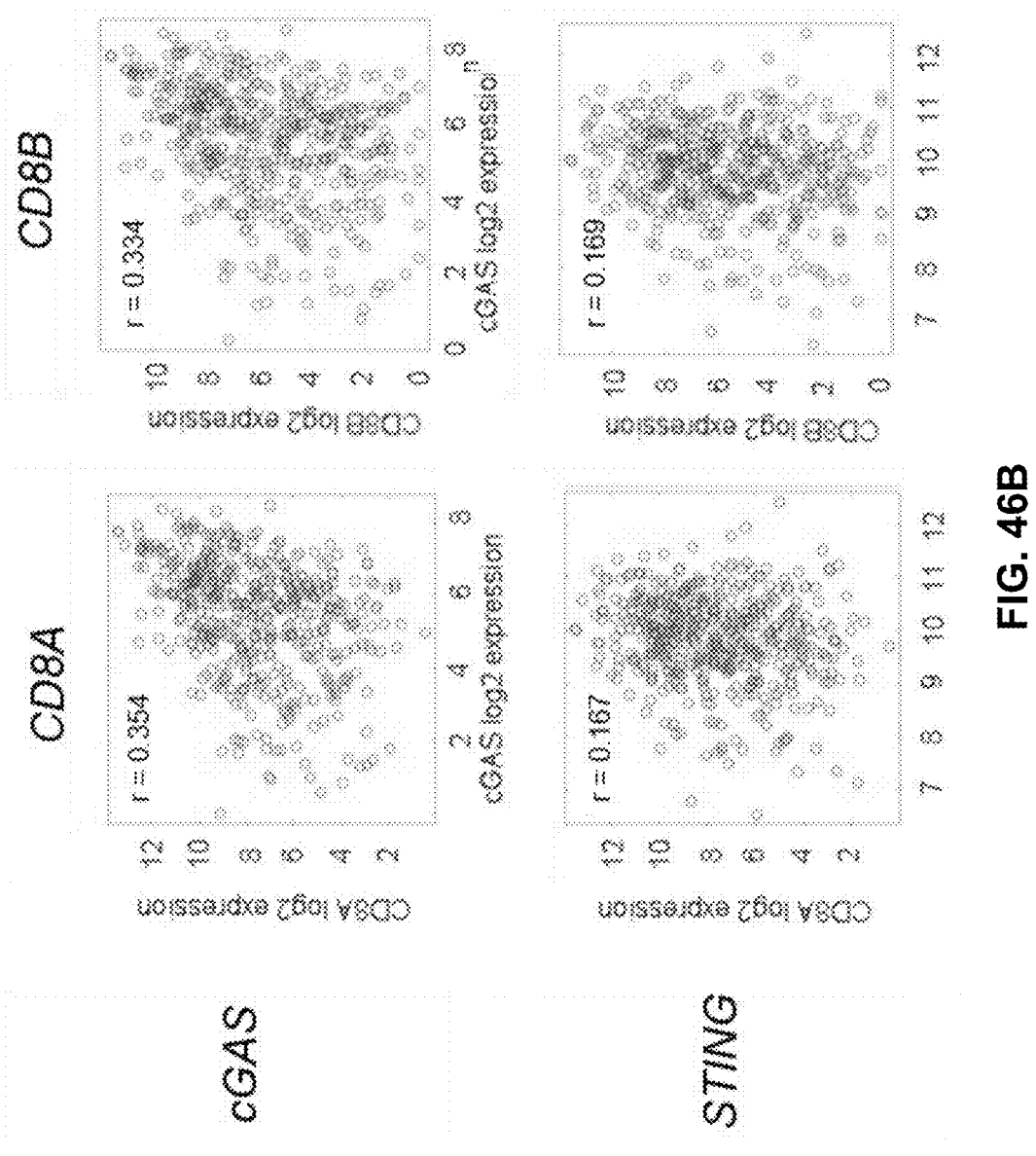
Figure 47A:
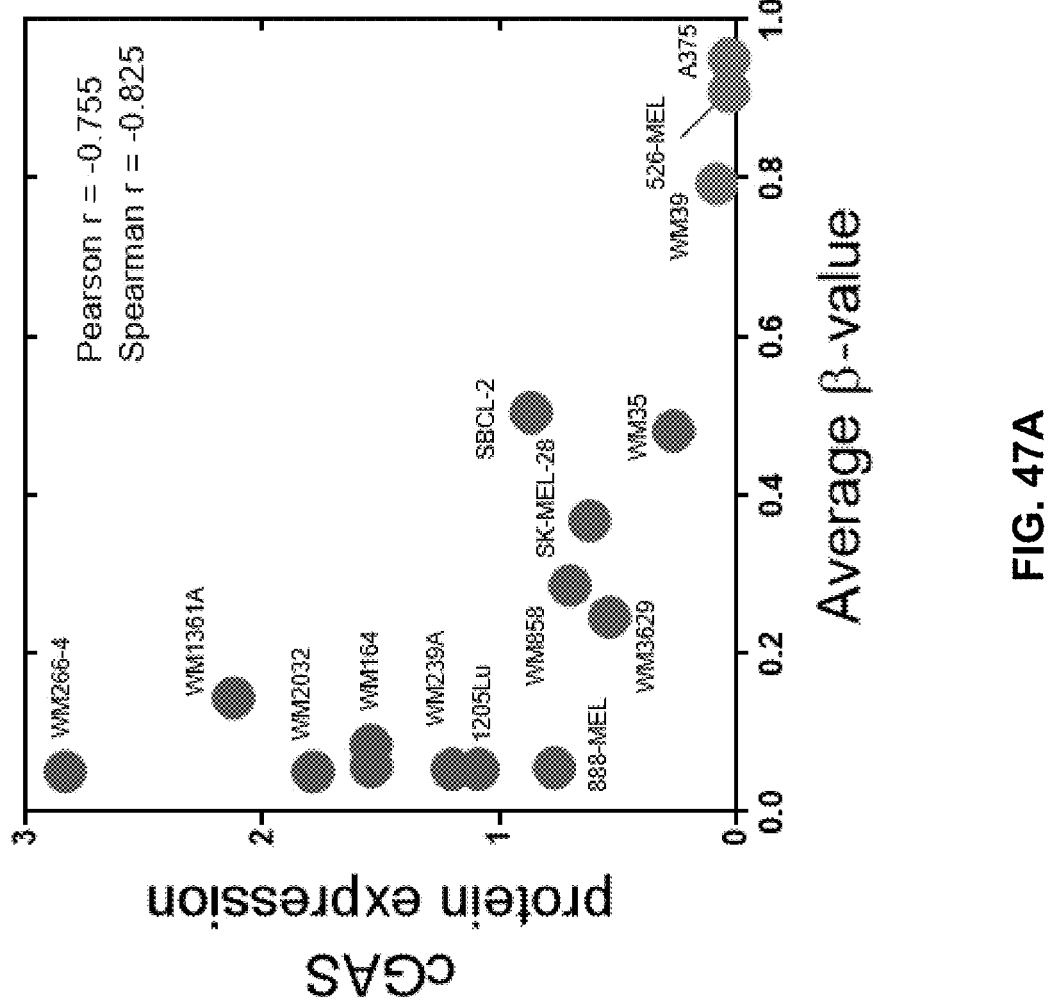
FIGS. 47A and 47B show DNA hypermethylation silences cGAS expression in human melanoma cell lines.
Figure 47B:
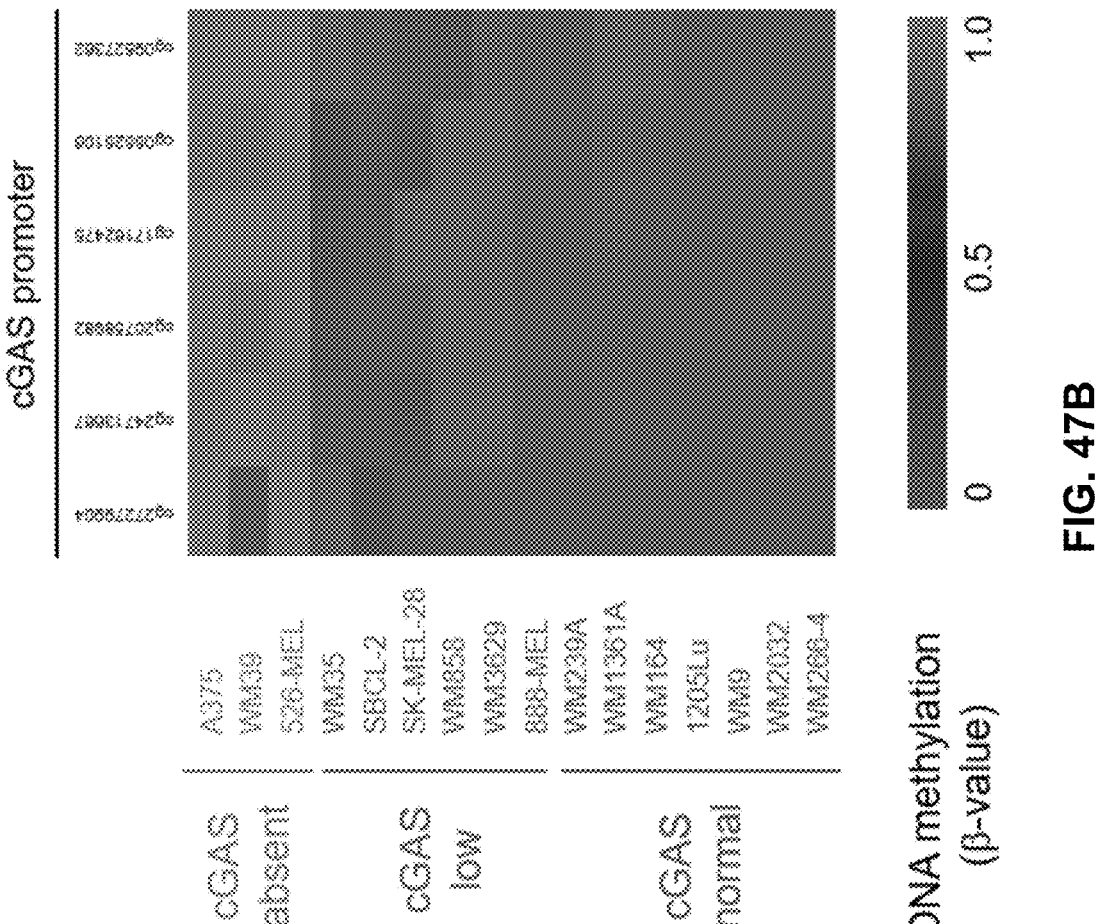
Figure 48A:
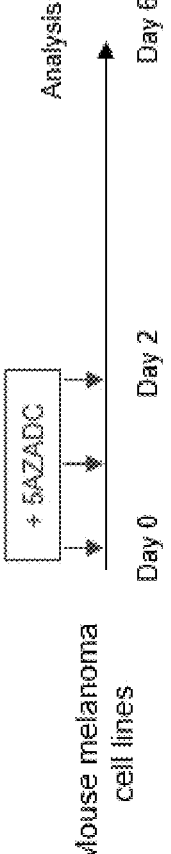
FIGS. 48A and 48B show DNA demethylation can restore cGAS and enhance STING activation in multiple murine melanoma cell lines.
Figure 48A:
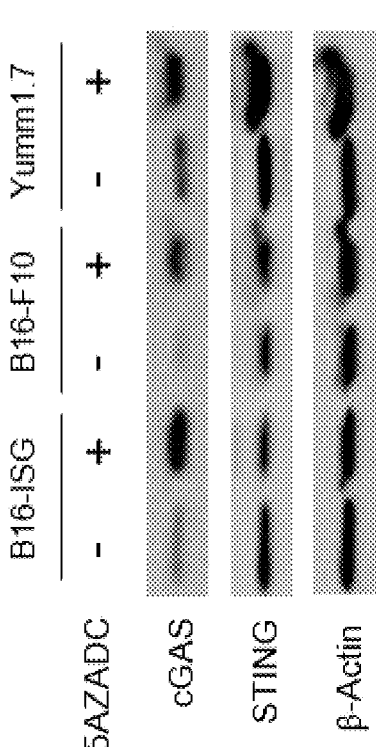
Figure 48B:
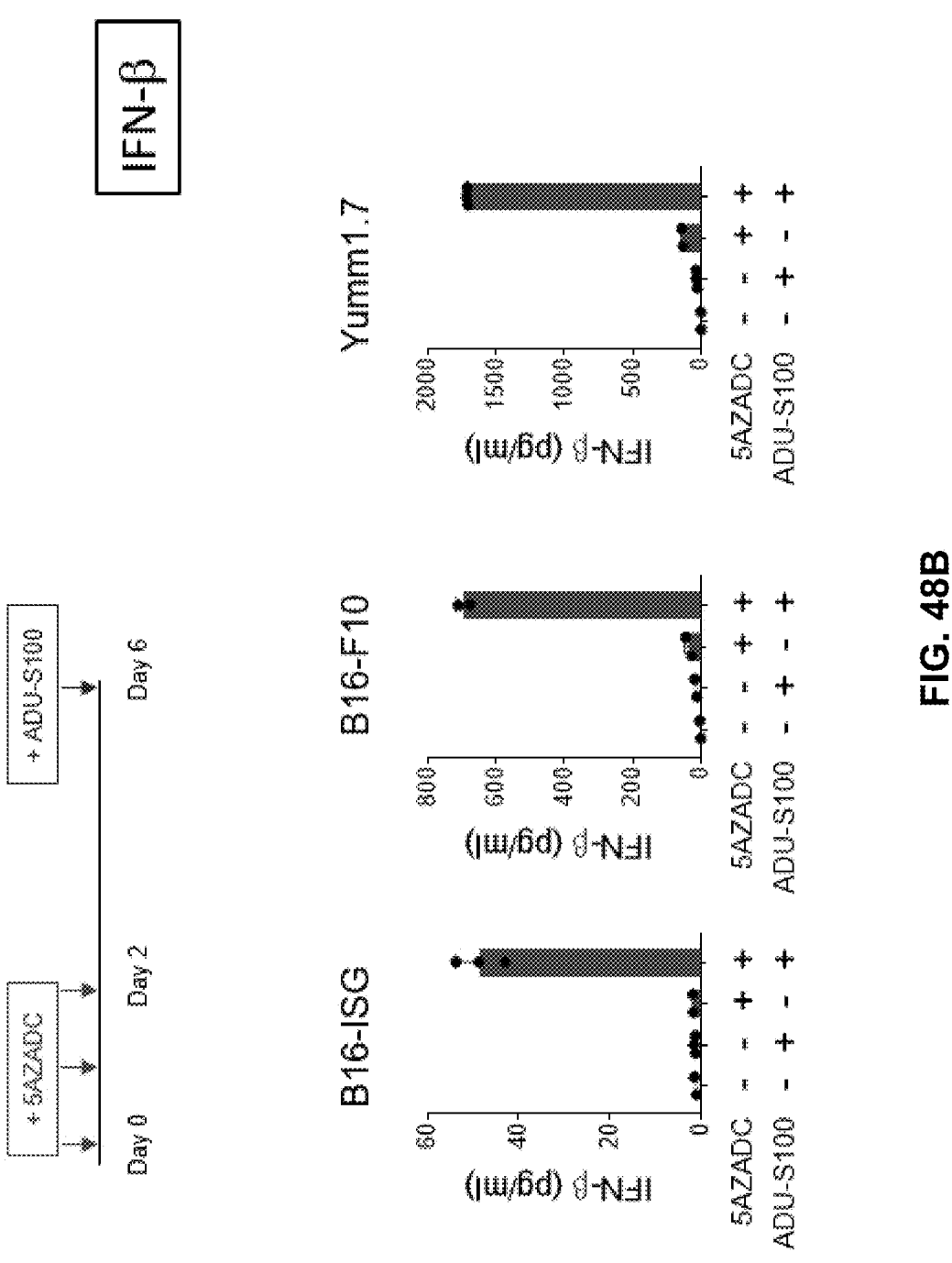
Figure 49A:
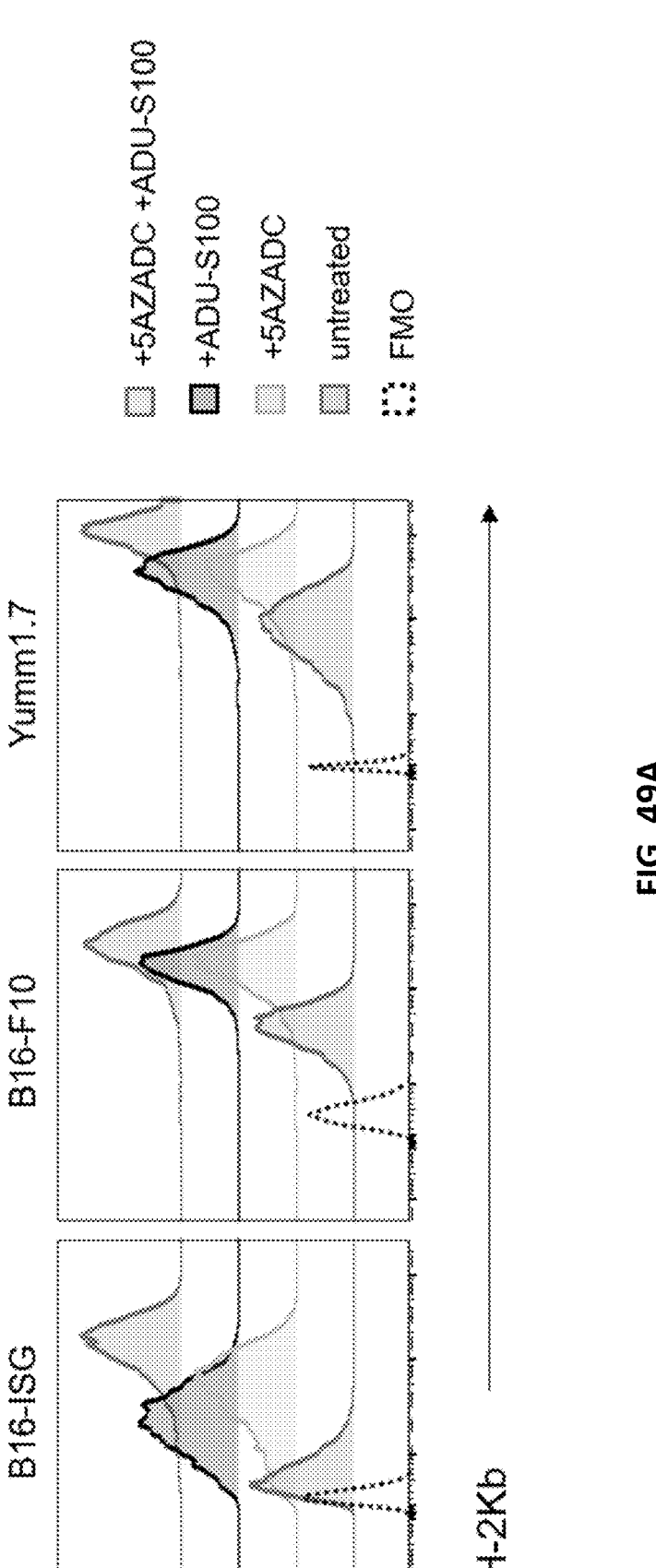
FIGS. 49A and 49B show DNA demethylation-mediated cGAS reconstitution enhances STING agonist-induced MHC I upregulation.
Figure 49B:
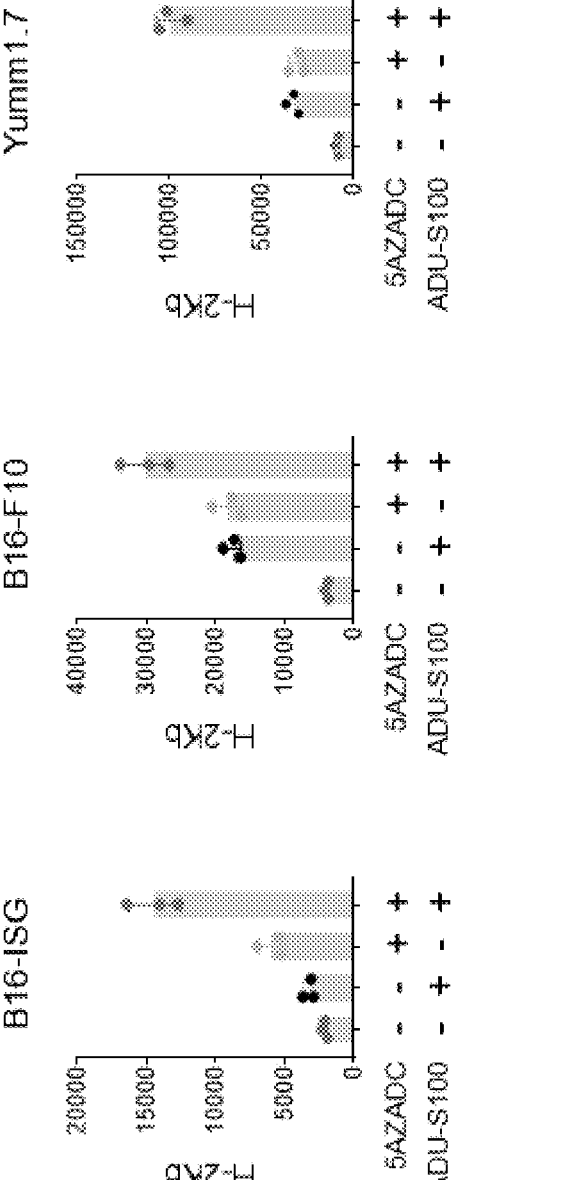
Figures 50A, 50B, 50C:
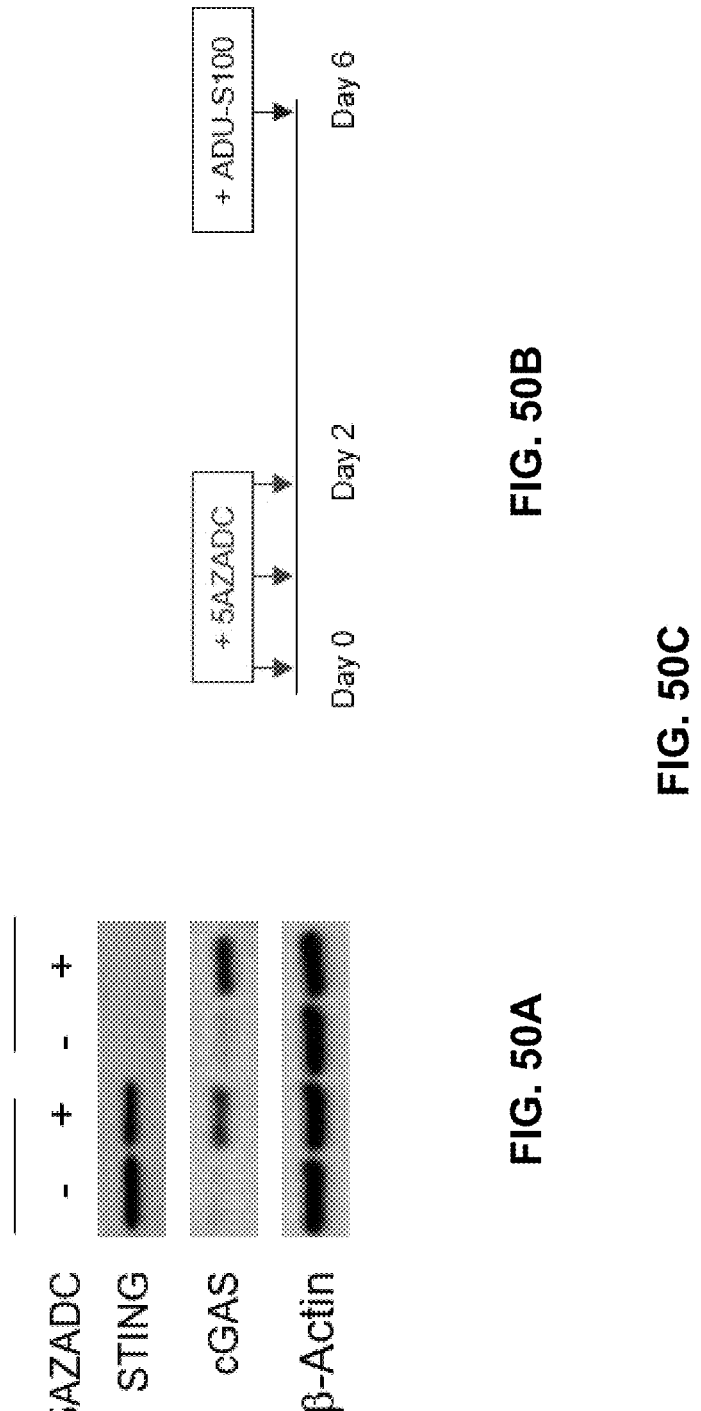
FIGS. 50A to 50E show DNA demethylation-induced increased IFN-β production in response to agonist stimulation in B16 cells is STING mediated.
Figures 50D, 50E:
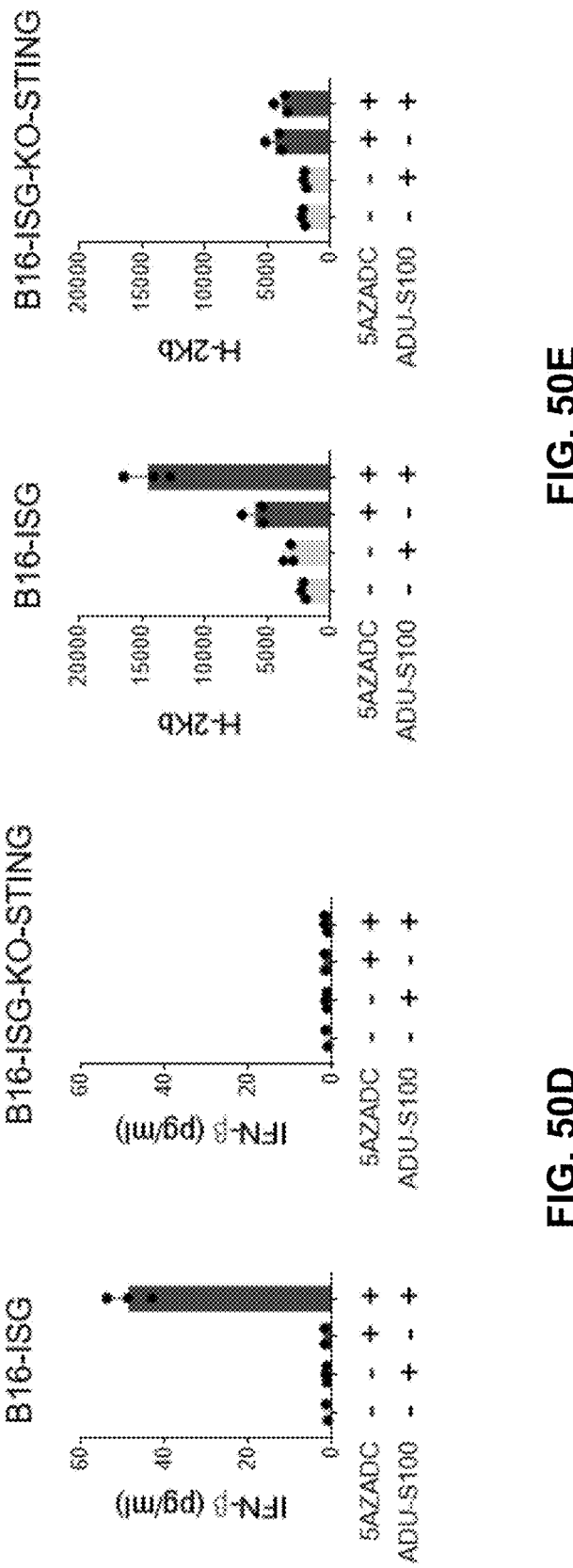
Figures 51A, 51B, 51C:
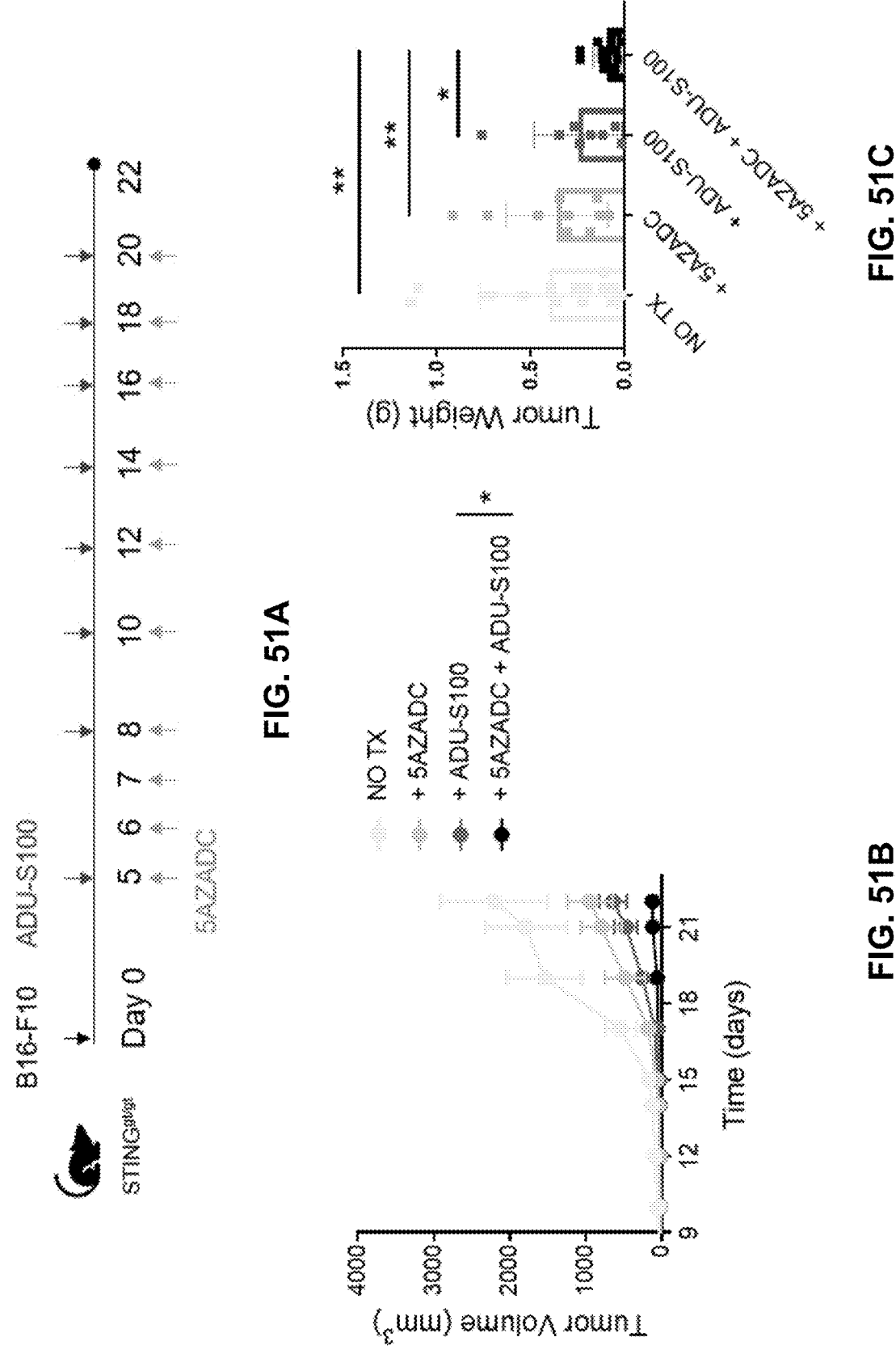
FIGS. 51A to 51C show demethylation improves B16-F10 tumor response to STING agonist therapy in STING$^{gt/gt}$ mice.
Figures 52A, 52B, 52C:
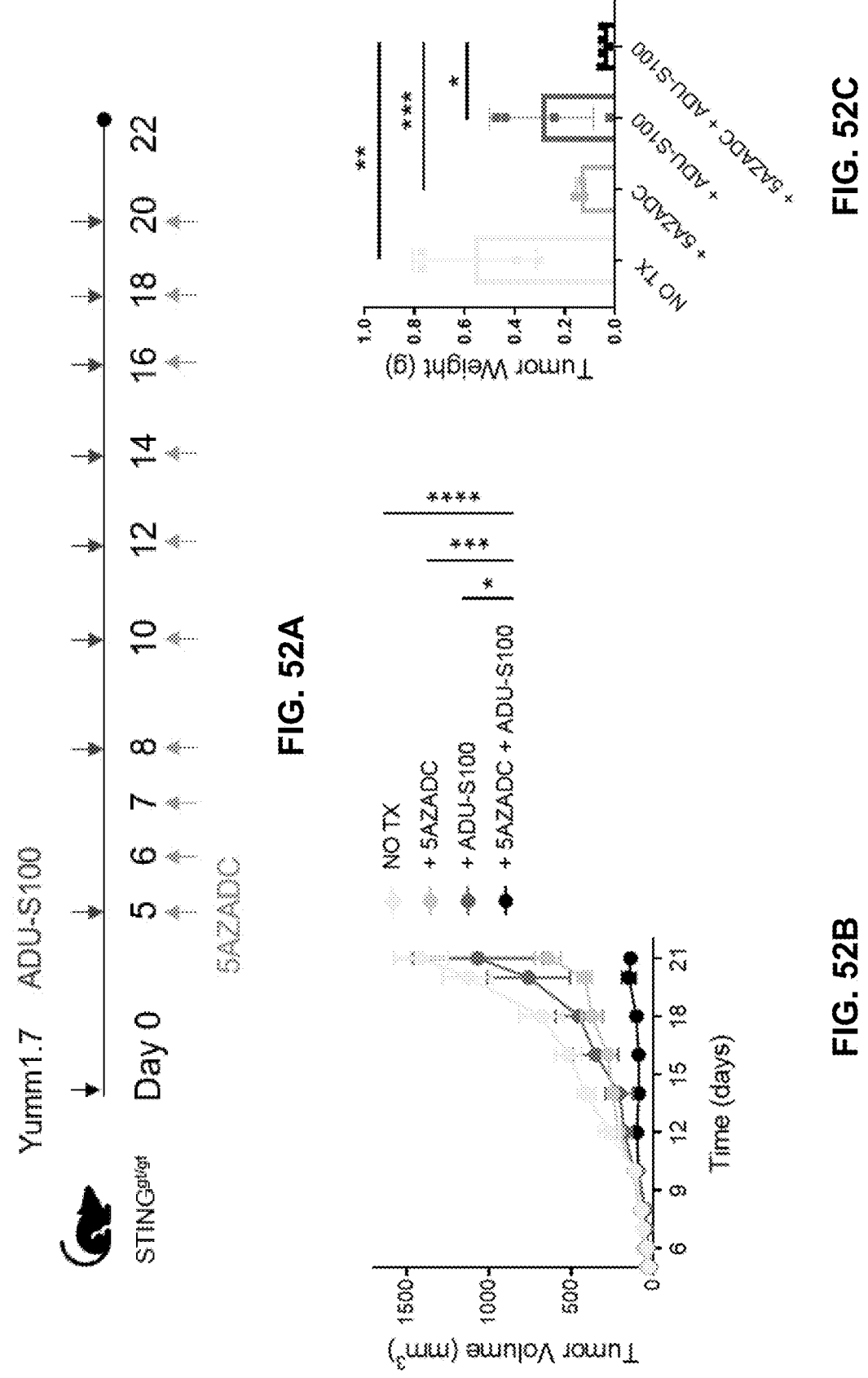
FIGS. 52A to 52C show eemethylation improves Yumm1.7 tumor response to STING agonist therapy in STING$^{gt/gt}$ mice.
Figure 53A:
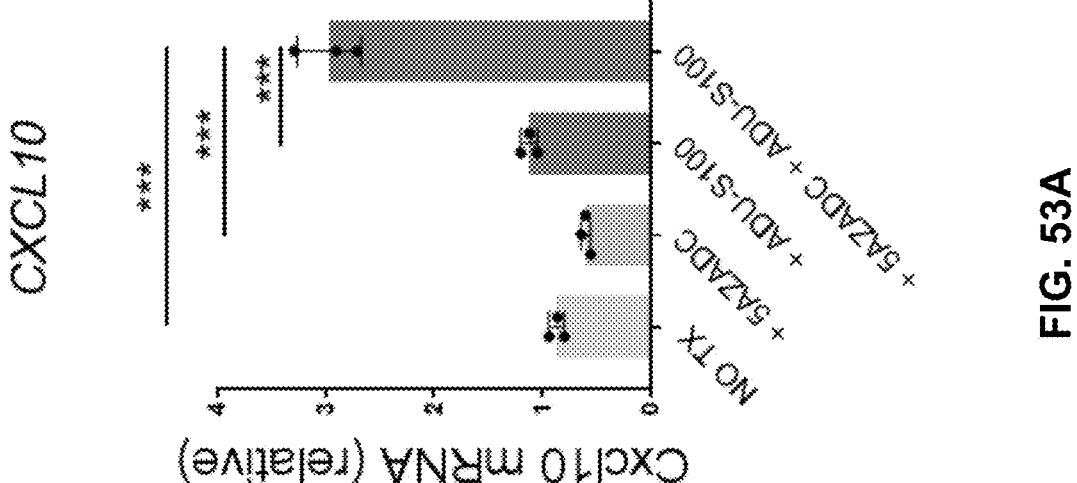
FIGS. 53A and 53B show enhanced CXCL10 induction in B16 tumors in response to combination therapy promotes tumor infiltration of CXCR3$^+$CD8$^+$ T cells in STING$^{gt/gt}$ mice.
Figure 53B:
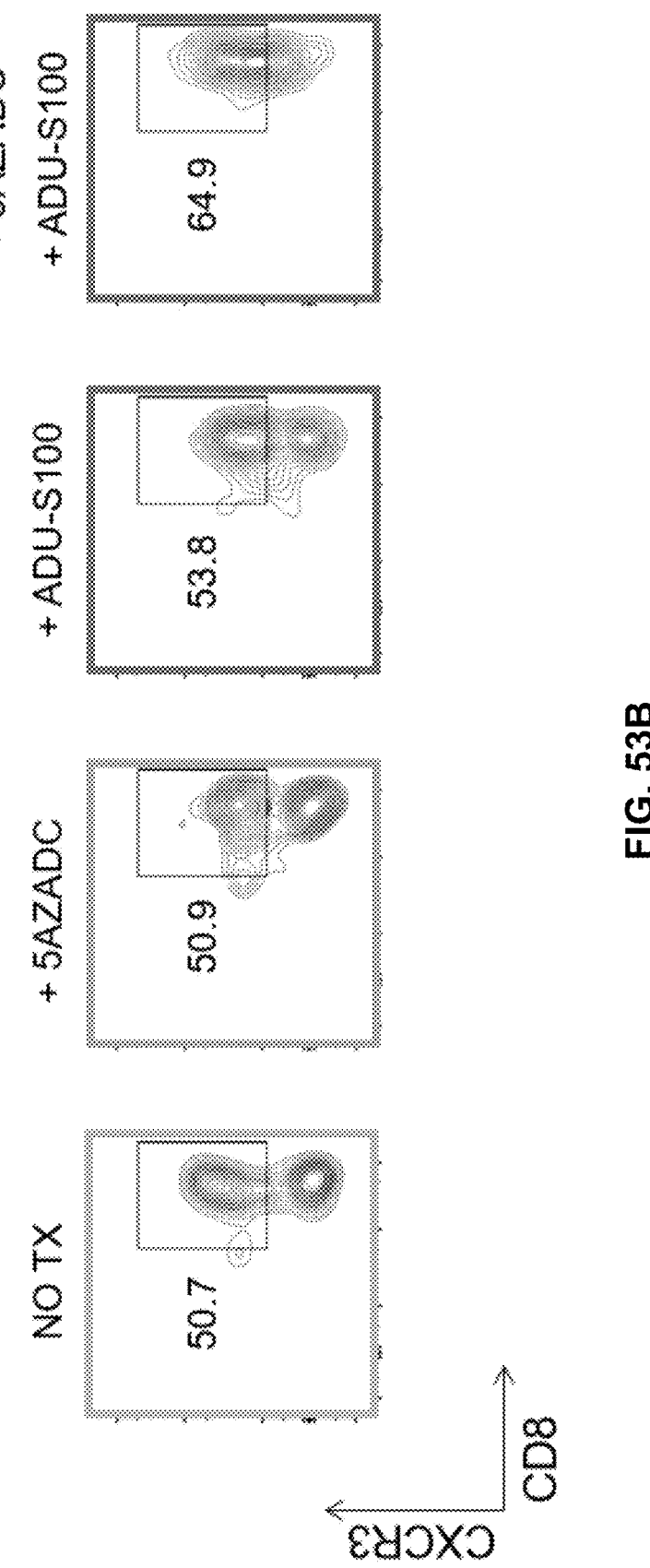
Figure 54:
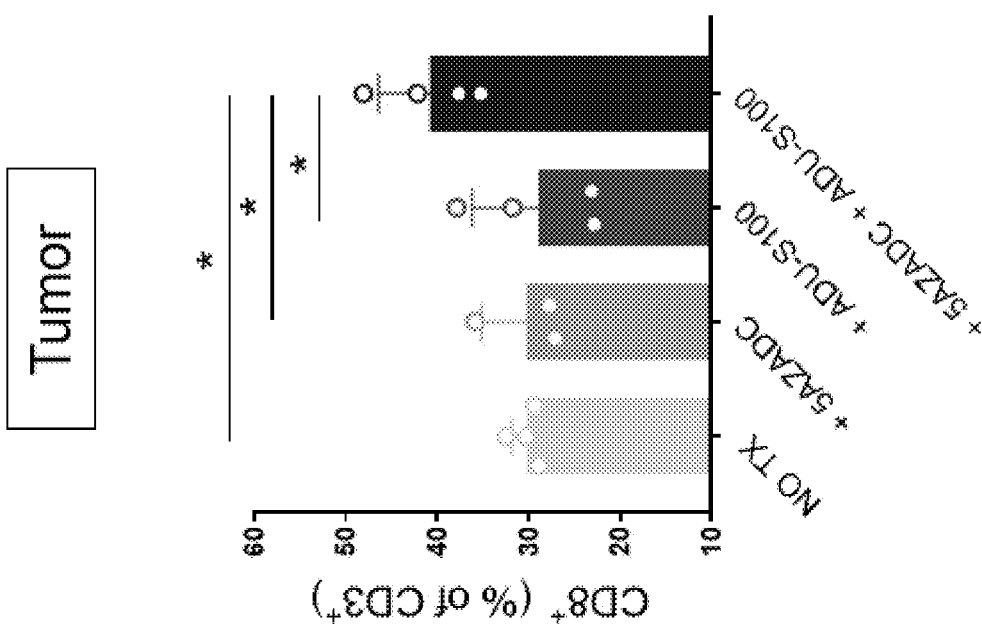
FIG. 54 shows combination therapy induces CD8$^+$ T cell enrichment in spleens and tumors in STING$^{gt/gt}$ mice.
Figure 54:
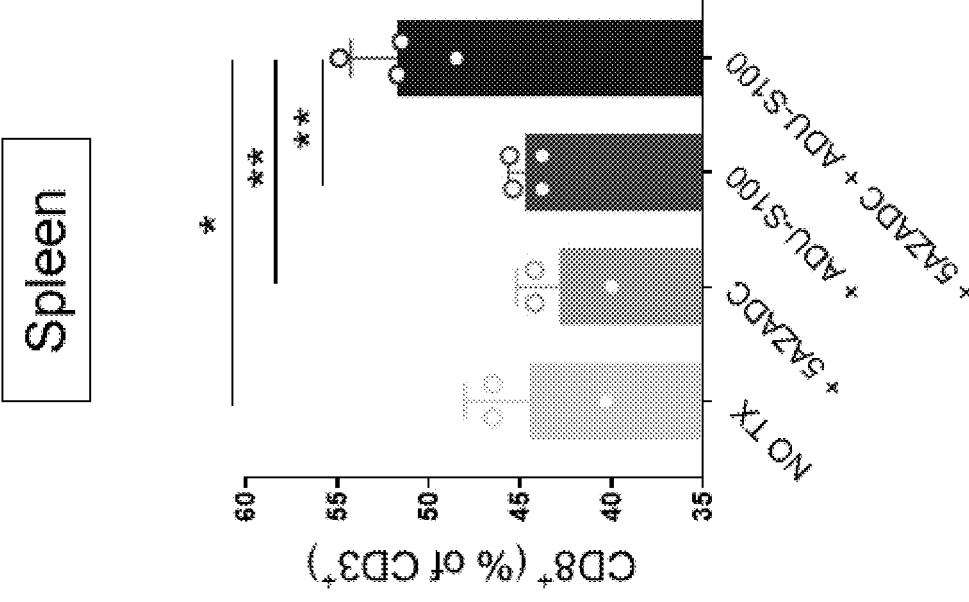
Figure 55A:
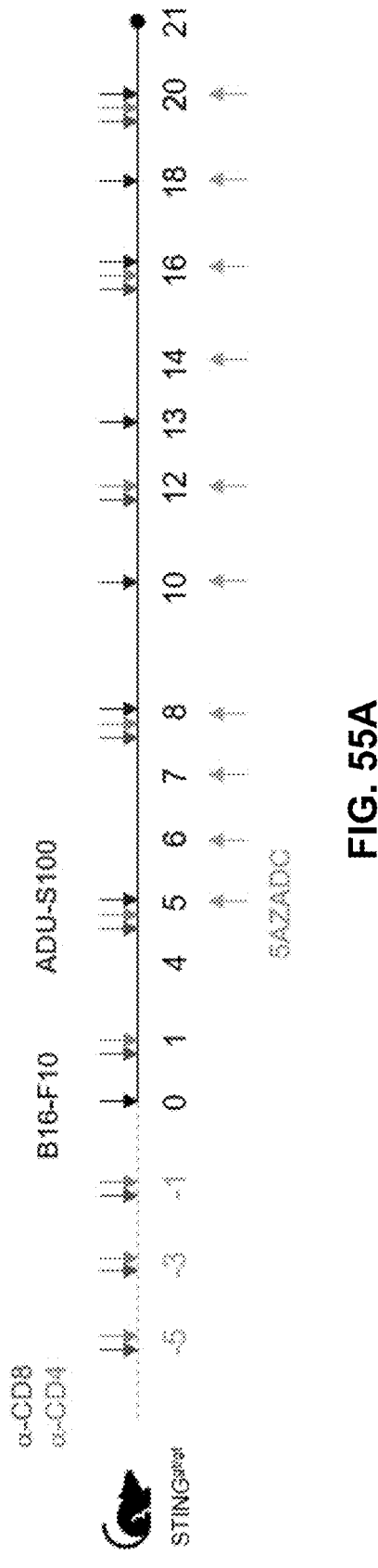
FIGS. 55A and 55B show depletion of CD8 T cells abrogates B16-F10 response to combination therapy in STING$^{gt/gt}$ mice.
Figure 55B:
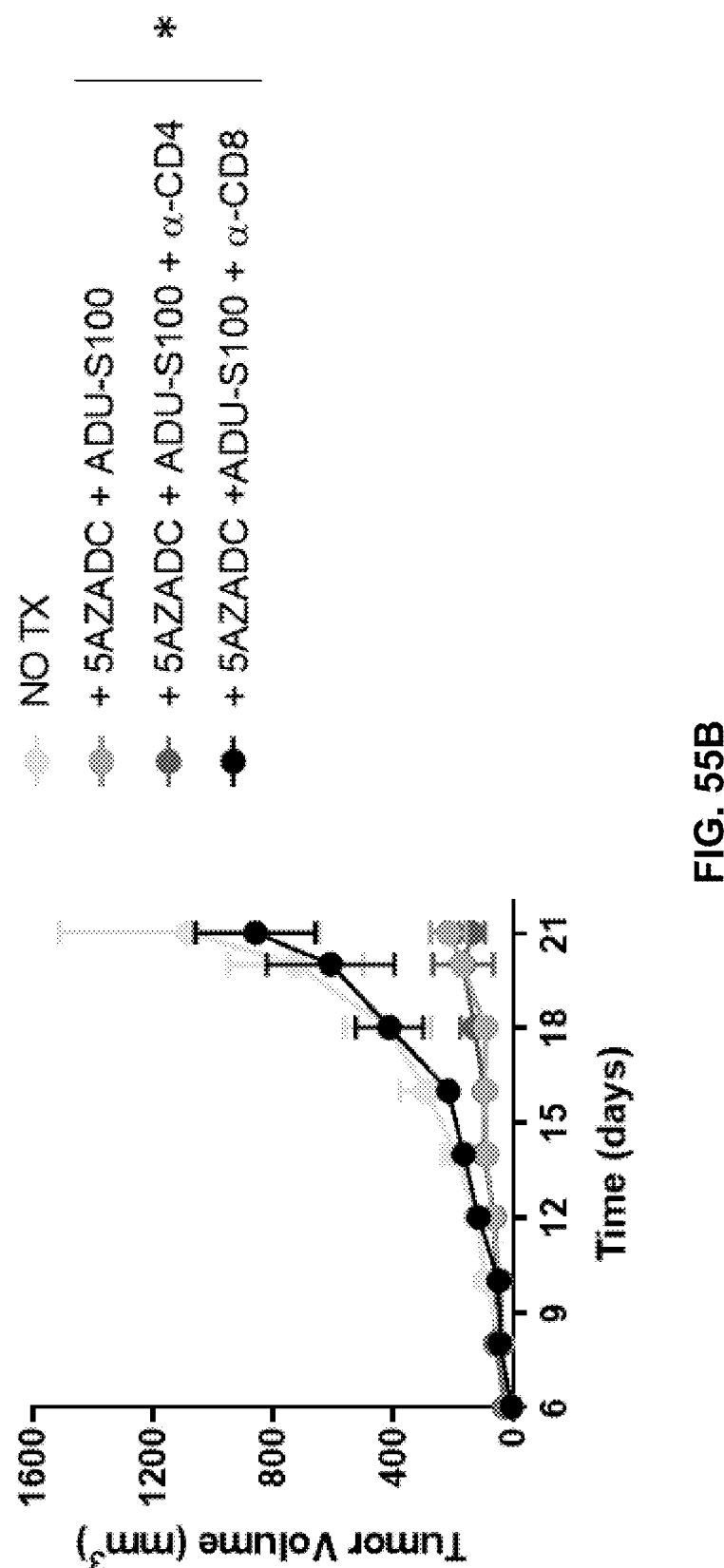
Figure 56:
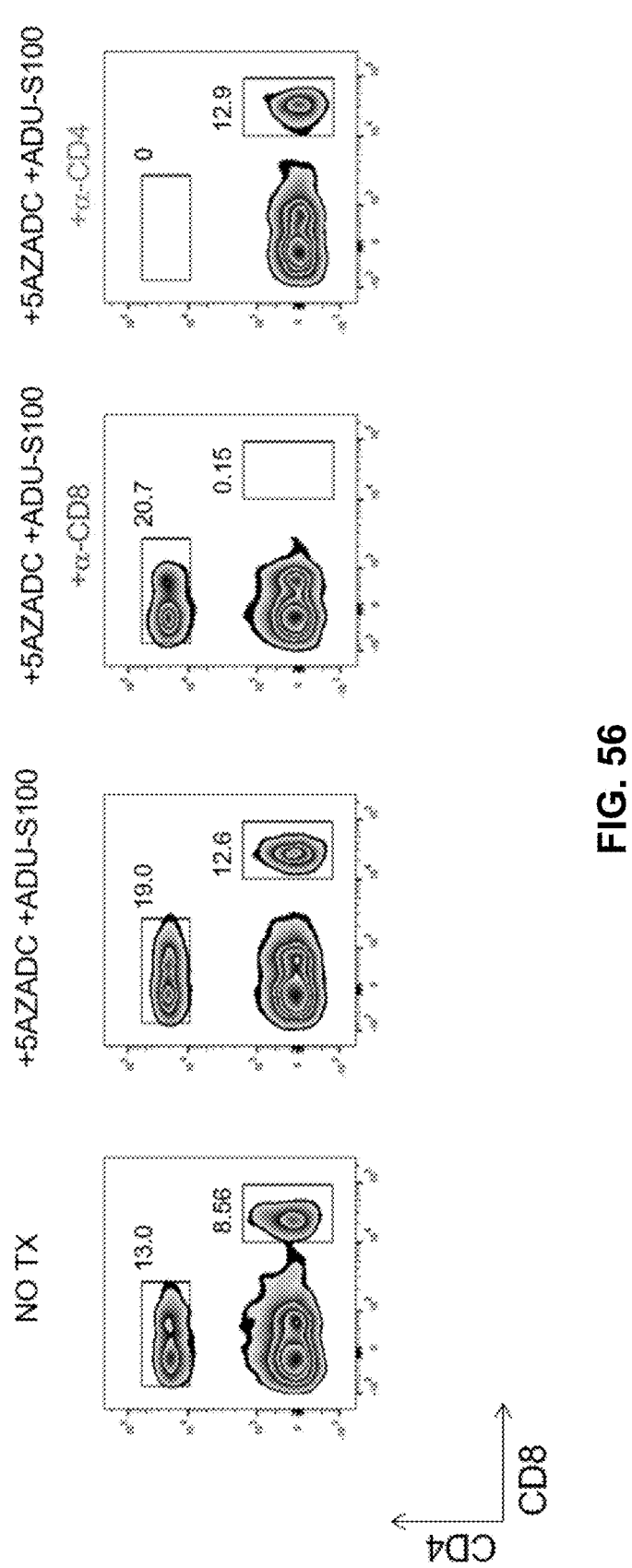
FIG. 56 shows verifying in vivo depletions.
Figure 57:
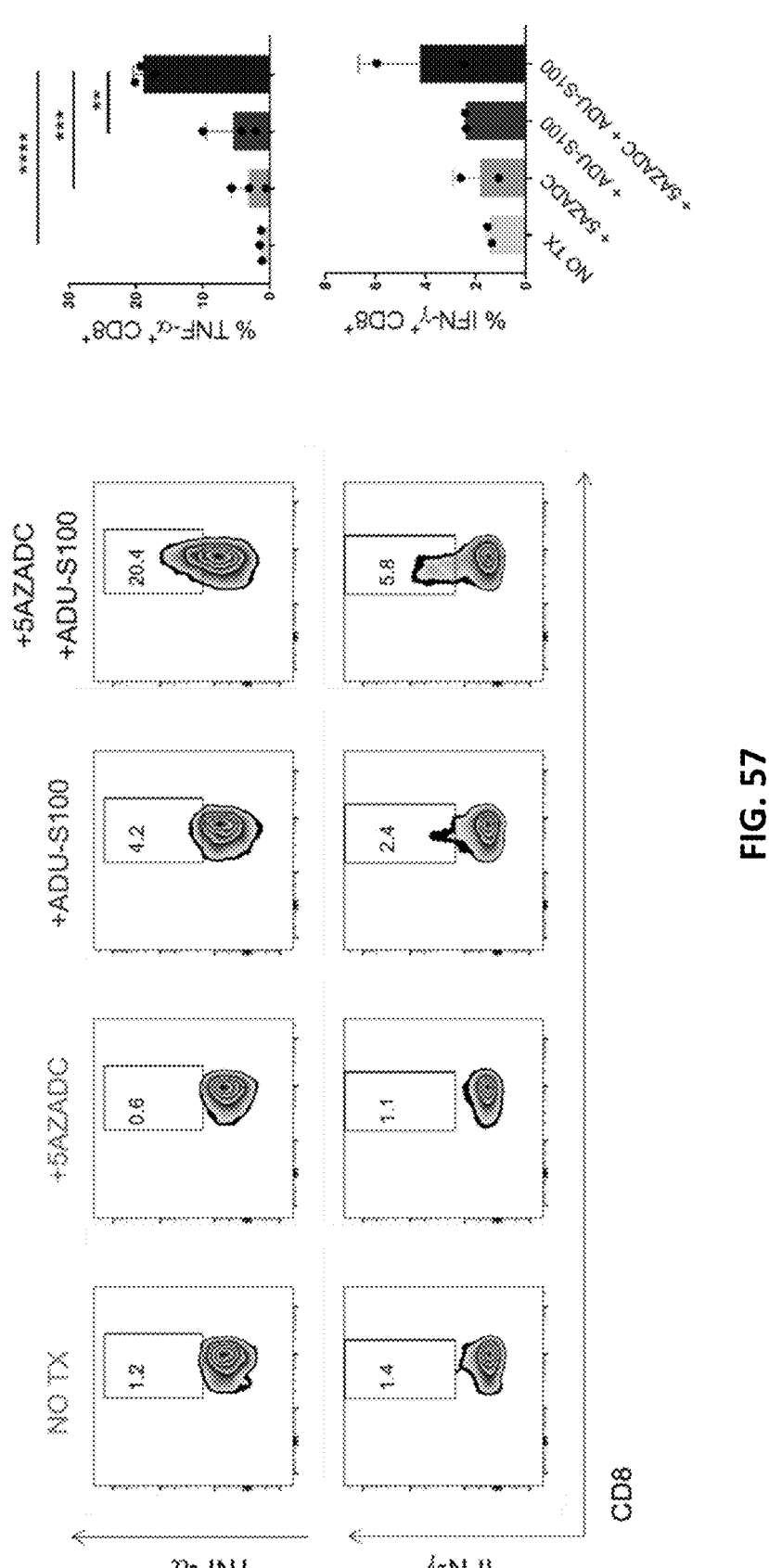
FIG. 57 shows combination therapy promotes activation and effector function of CD8$^+$ T cells.
Figure 58:
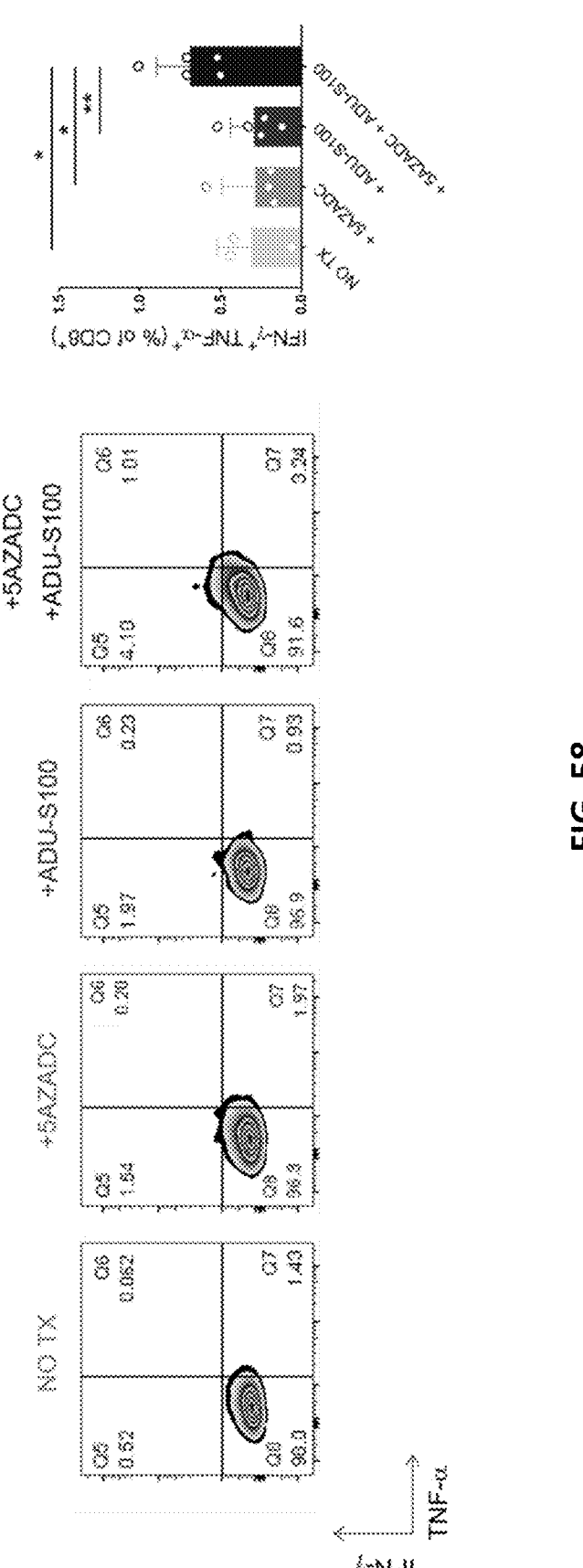
FIG. 58 shows combination therapy promotes activation and effector function of CD8$^+$ T cells.
Figure 59:
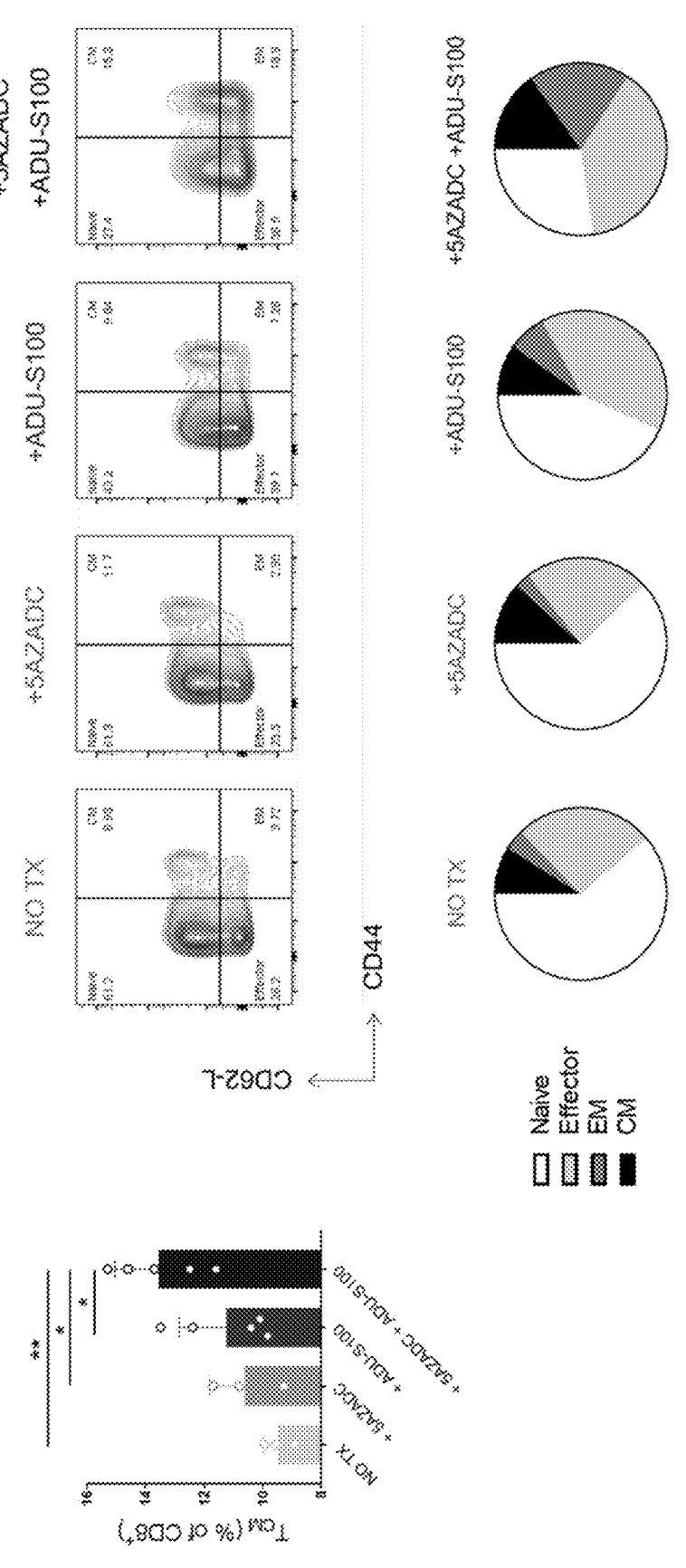
FIG. 59 shows combination therapy induces splenic CD8$^+$ T cell effector/memory differentiation.
Figure 60:
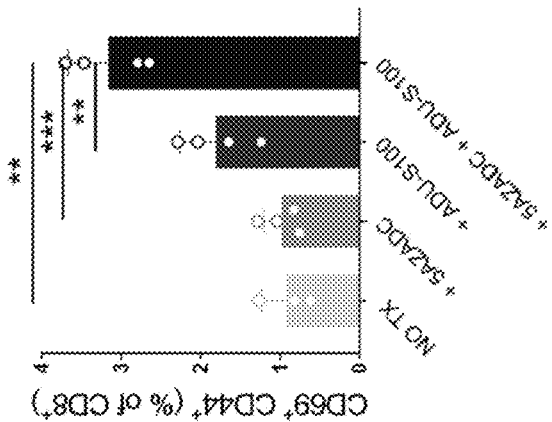
FIG. 60 shows combination therapy promotes expression of the activation markers in splenic CD8$^+$ T cells.
Figure 60:
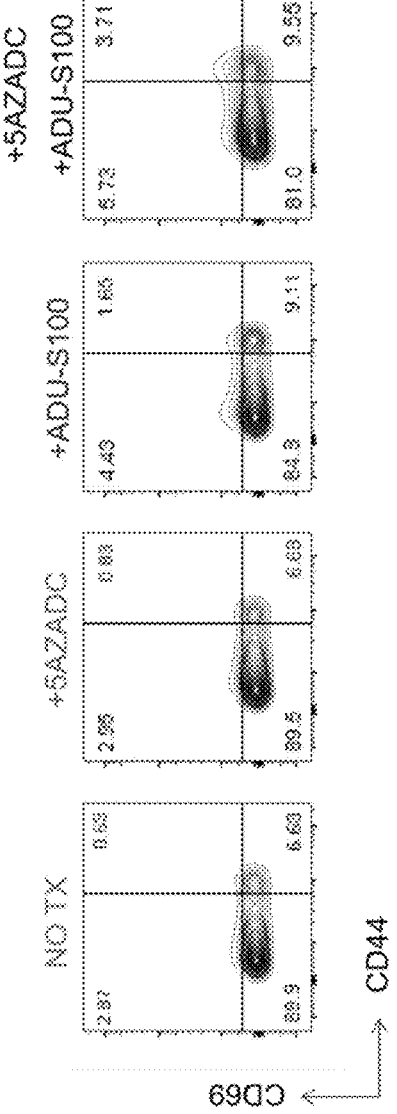
Figure 61:
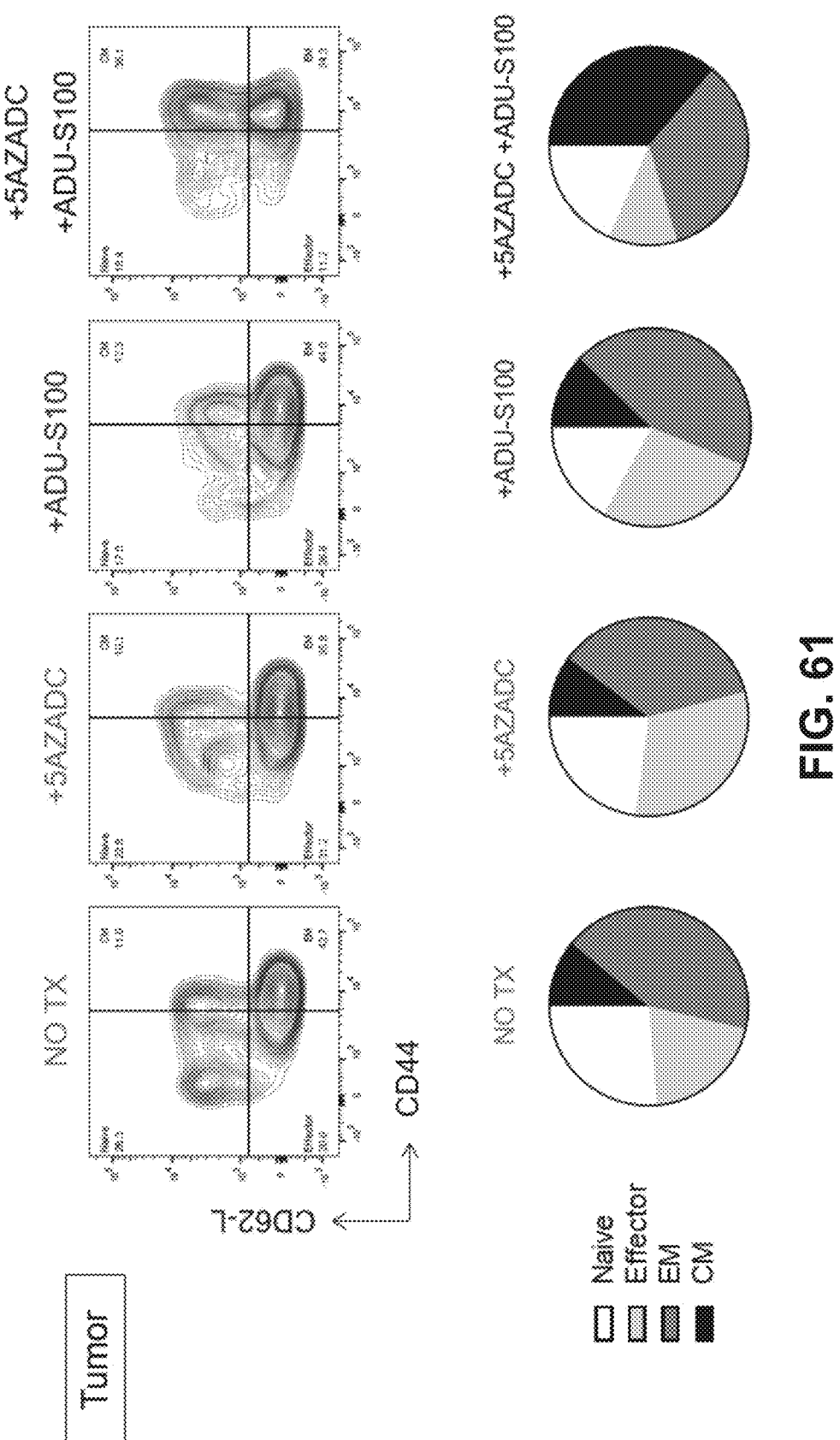
FIG. 61 shows CD8$^+$ TILs in combination therapy-treated mice indicate memory phenotype.
Figure 62:
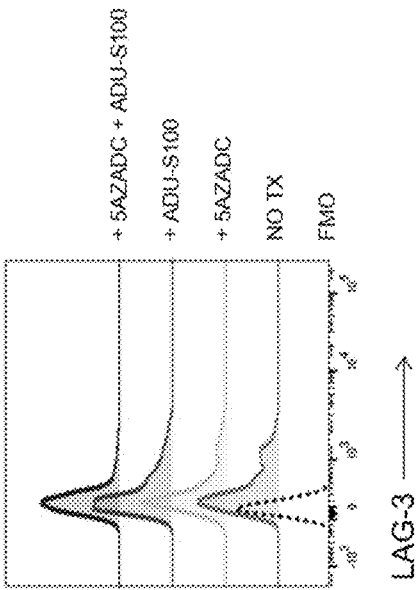
FIG. 62 shows CD8$^+$ TILs in combination therapy-treated mice indicate less exhausted phenotype.
Figure 62:
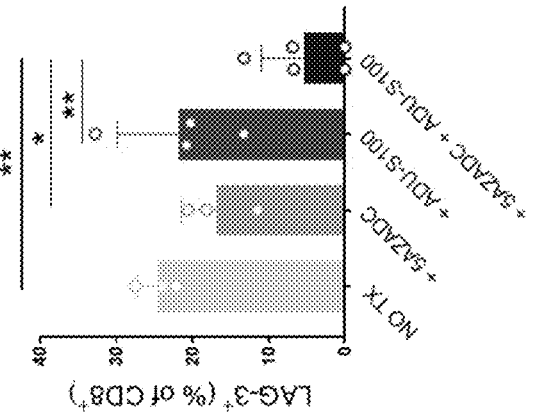
Figure 62:
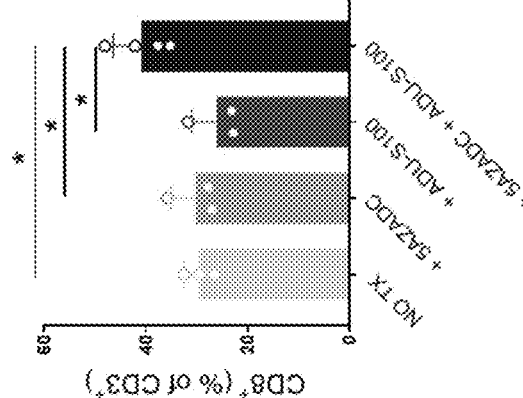
Figure 63A:
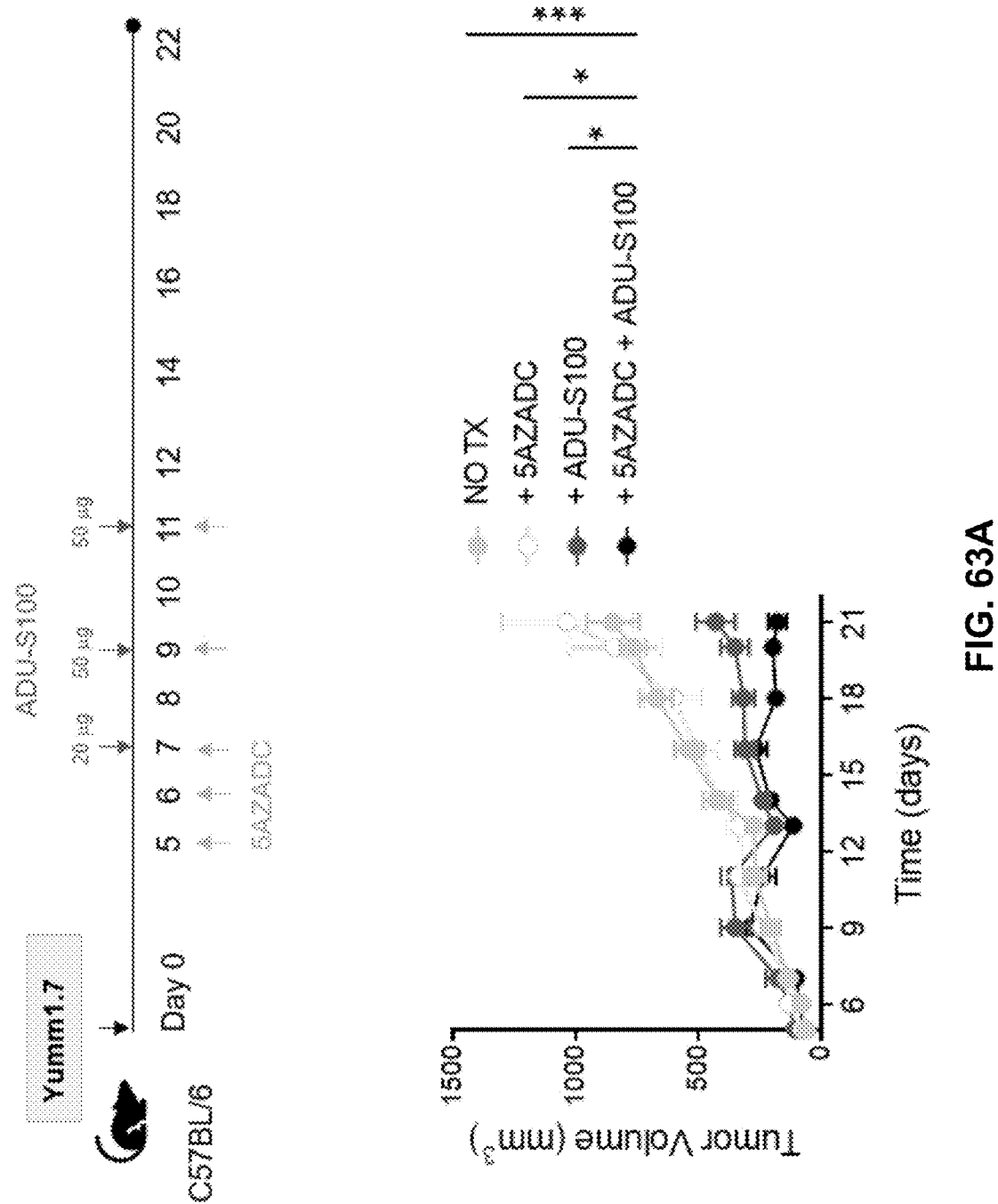
FIGS. 63A to 63C show combination therapy in WT (C57BL/6) mice (FIG. 63A), STING$^{gt/gt}$ mice (FIG. 63B), and C57BL/6 mice (FIG. 63C).
Figure 63B:
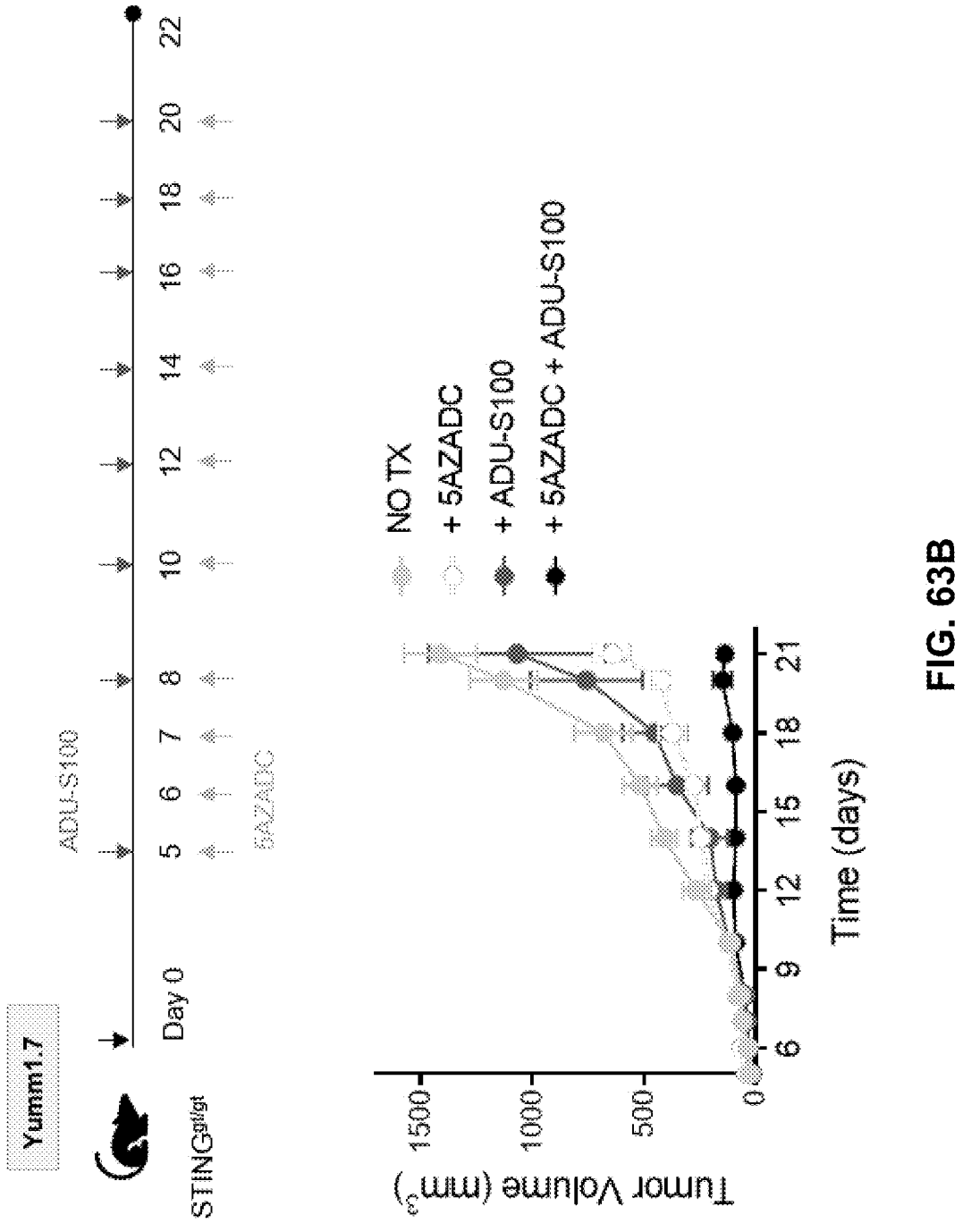
Figure 63C:
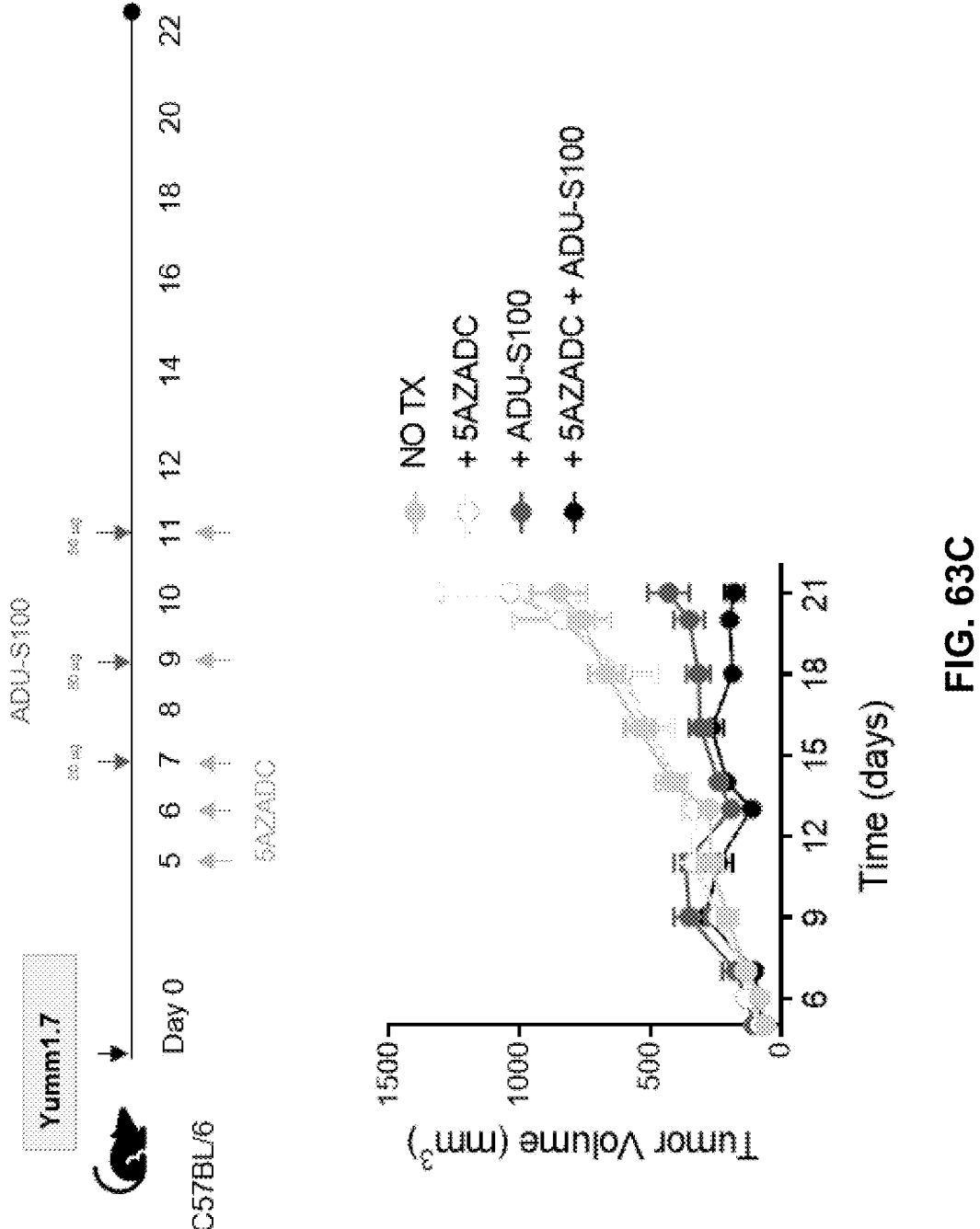
Figure 64A:
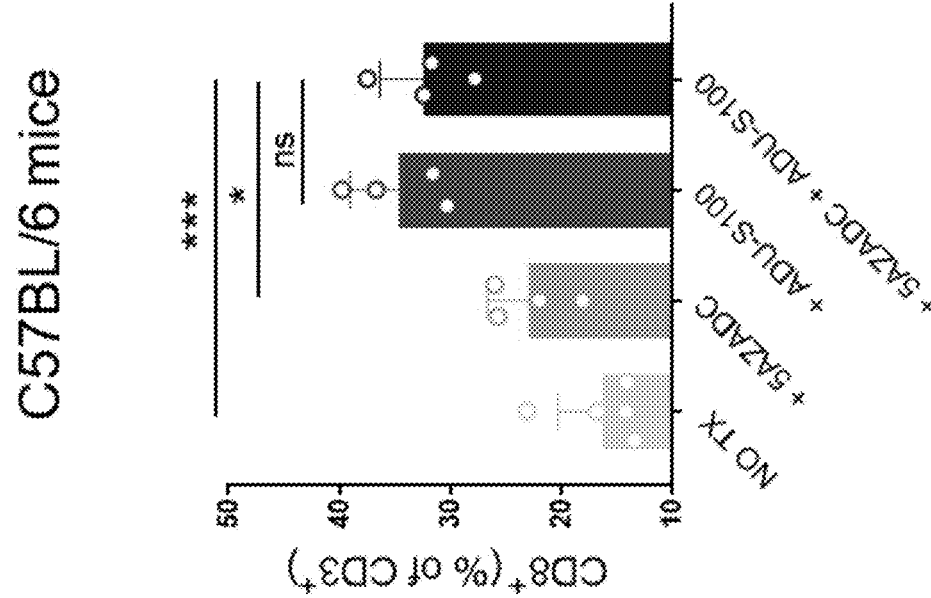
FIGS. 64A and 64B show % CD8$^+$ T cells in STING$^{gt/gt}$ mice and C57BL/6 mice after combination therapy.
Figure 64A:
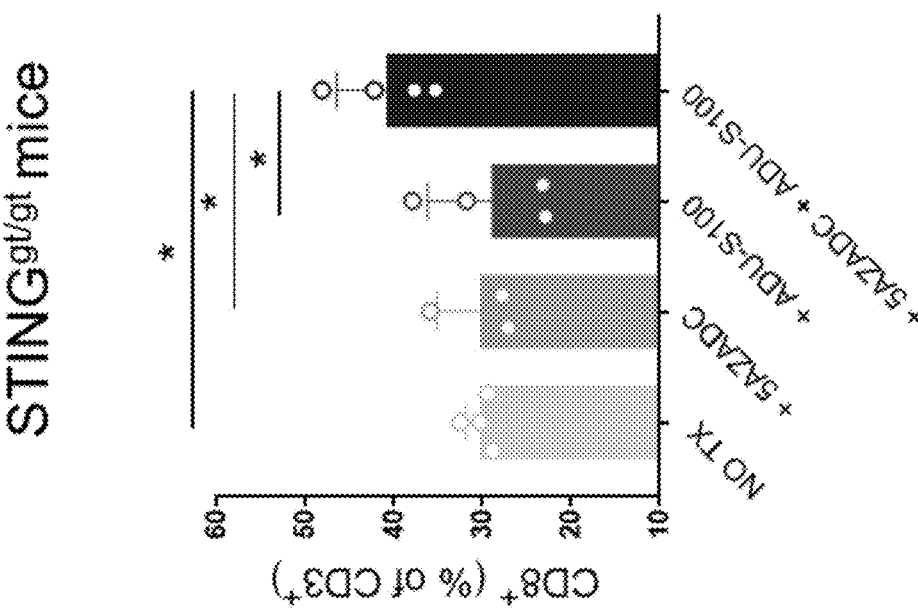
Figure 64B:
Figure 64B:
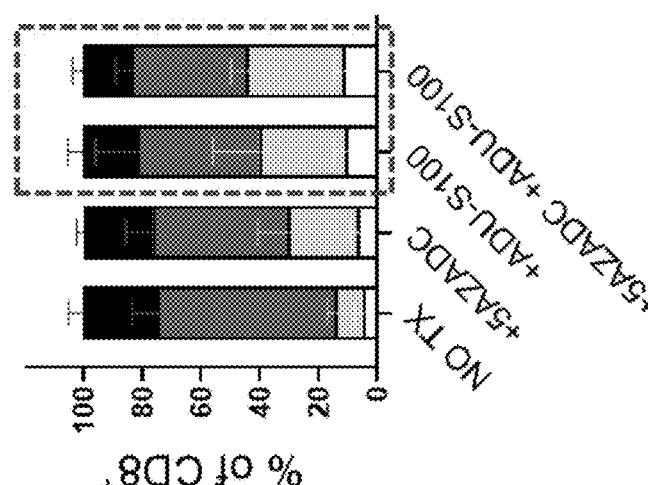
Figure 64B:
Figure 64B:
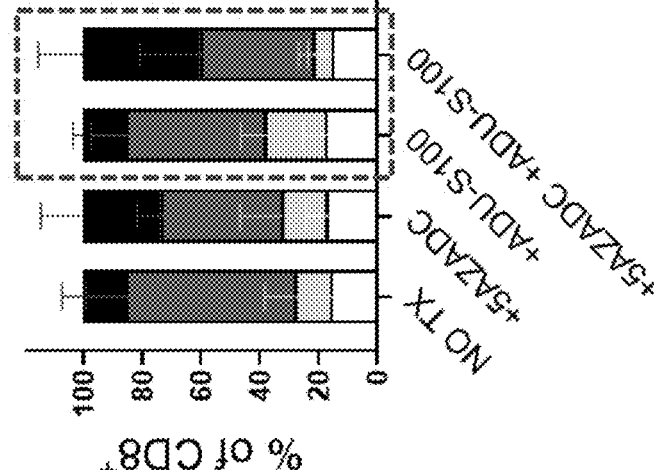
Figure 65:
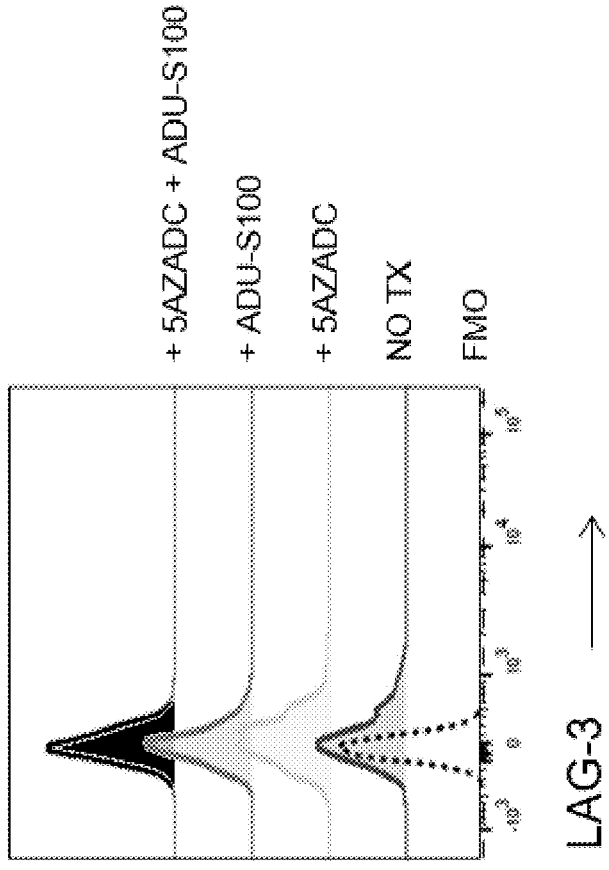
FIG. 65 shows CD8$^+$ TILs in combination therapy-treated C57BL/6 mice indicate less exhausted phenotype.
Figure 65:
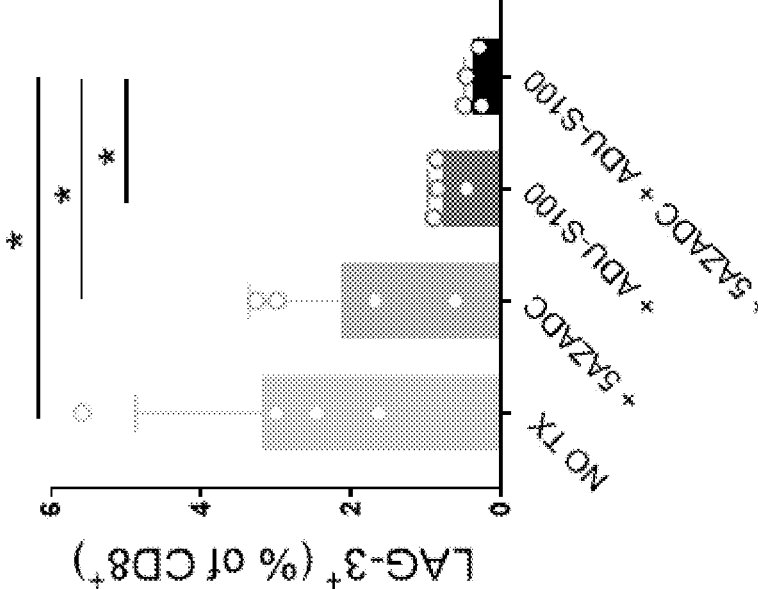
Figure 66:
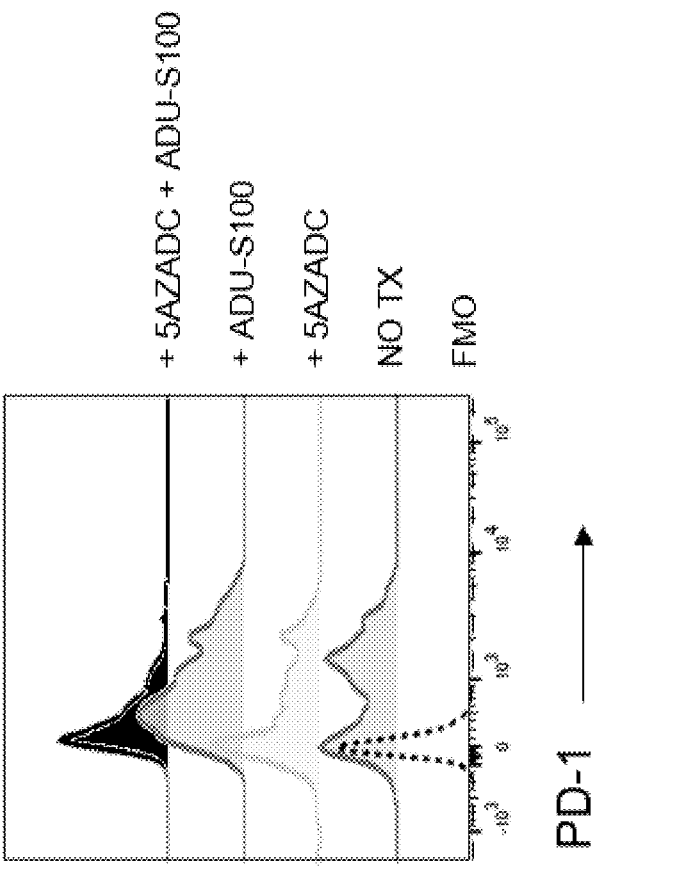
FIG. 66 shows CD8$^+$ TILs in combination therapy-treated C57BL/6 mice indicate less exhausted phenotype.
Figure 67A:
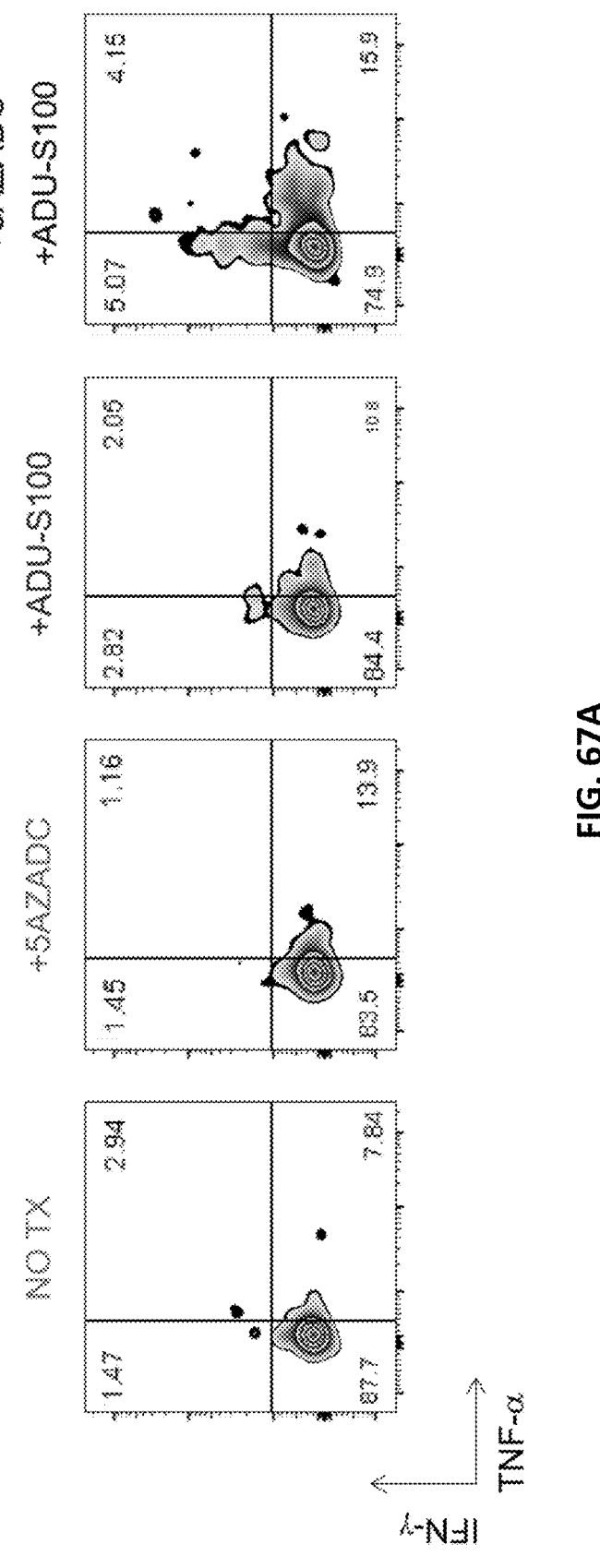
FIGS. 67A and 67B show combination therapy promotes activation and effector function of CD8$^+$ T cells.
Figure 67B:
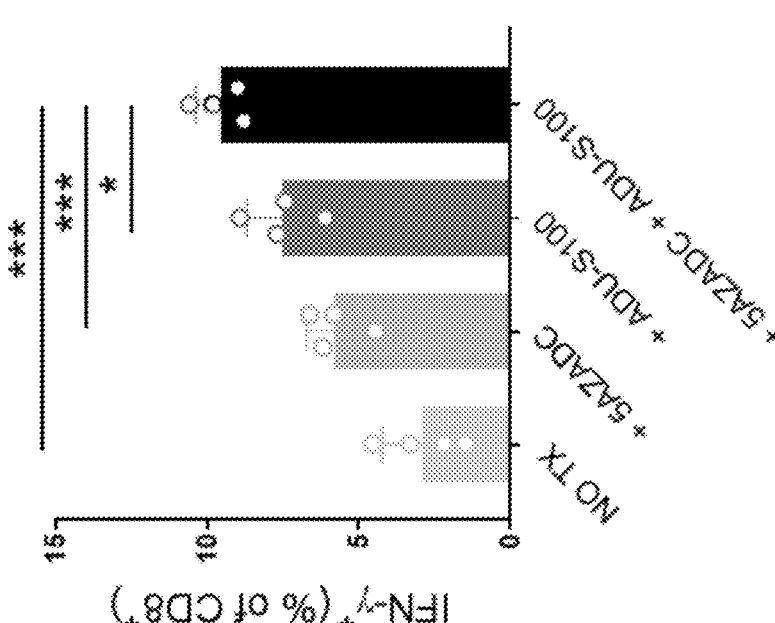
Figure 67B:
Figure 67B:
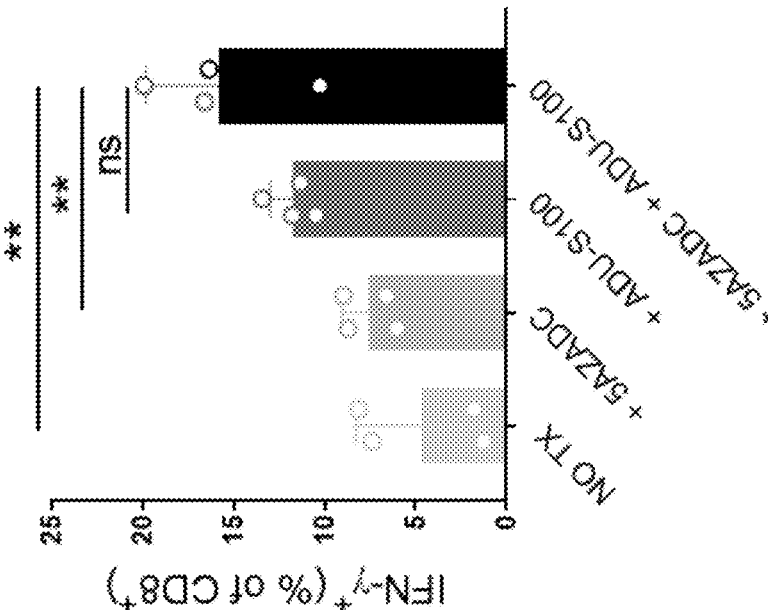
Figure 68:
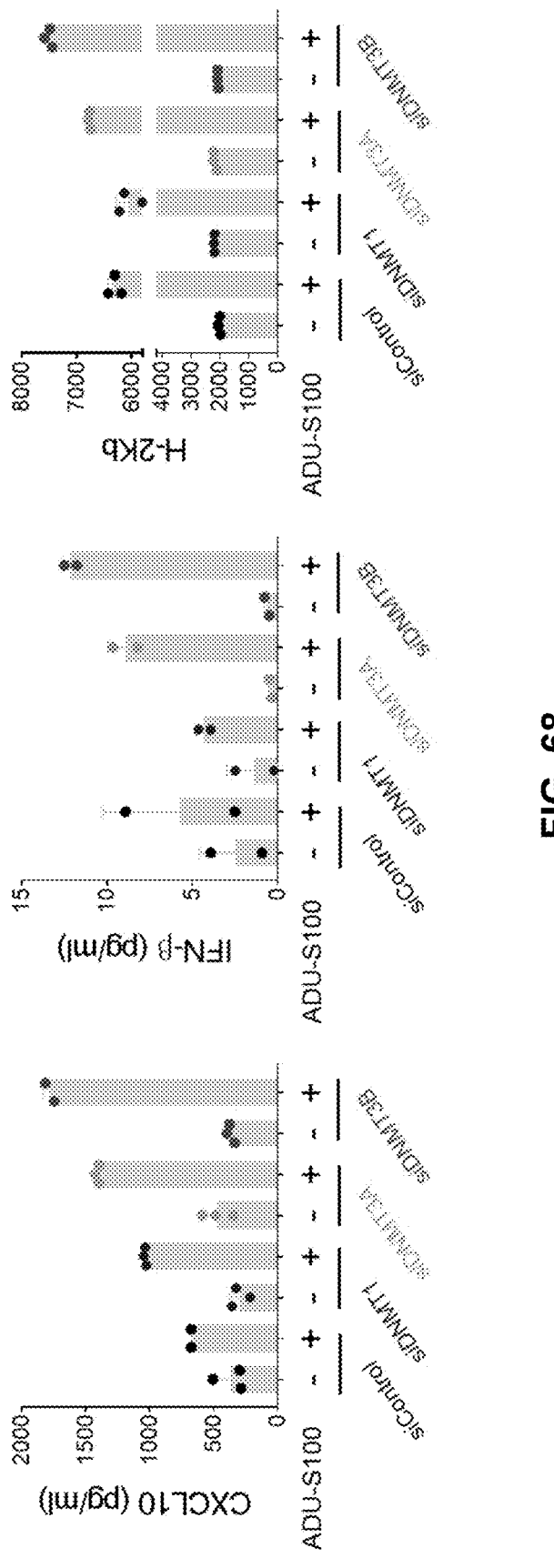
FIG. 68 shows effects of siRNA siDNMT1, siDNMT3A, and siDNMT3B CXCL10, IFN-β, and H-2Kb.
Figure 69:
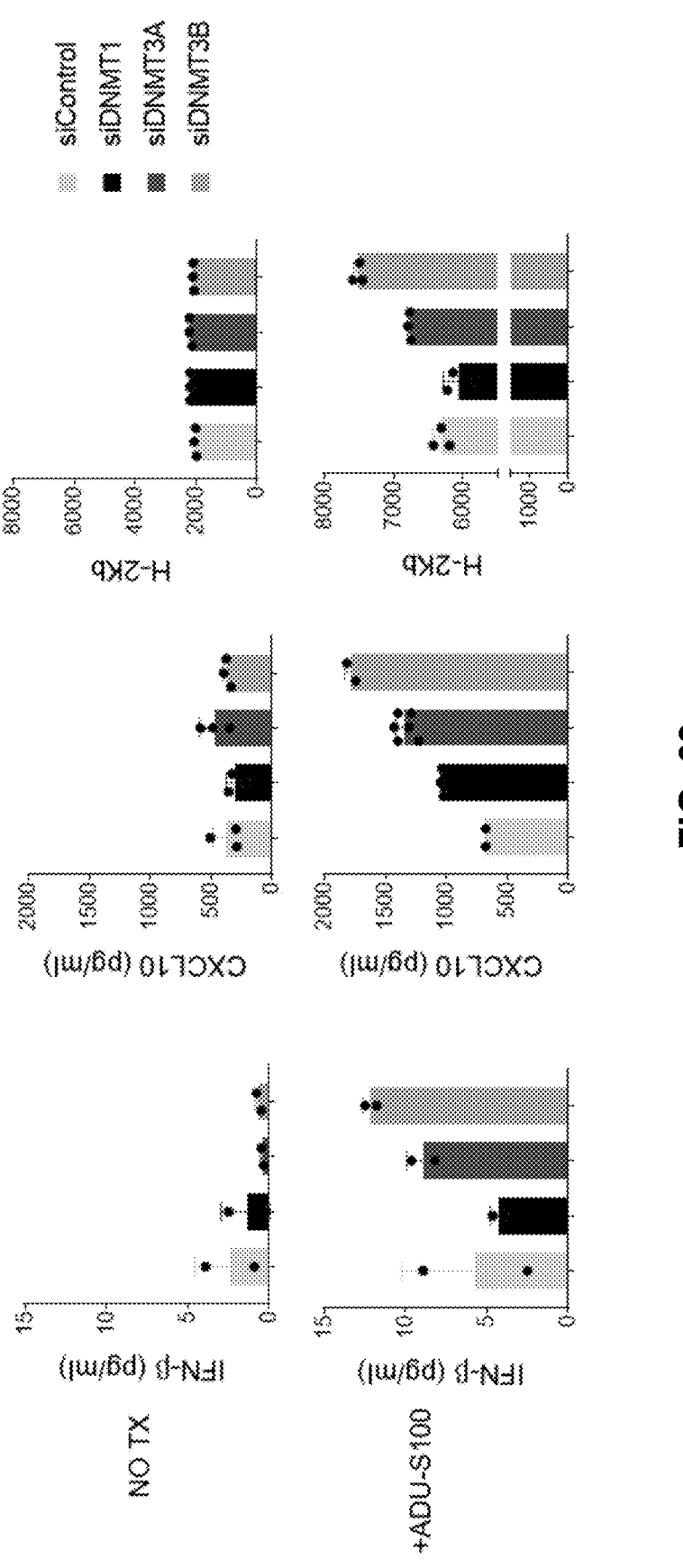
FIG. 69 shows effects of siRNA siDNMT1, siDNMT3A, and siDNMT3B CXCL10, IFN-β, and H-2Kb with and without ADU-S100.
Figure 70:
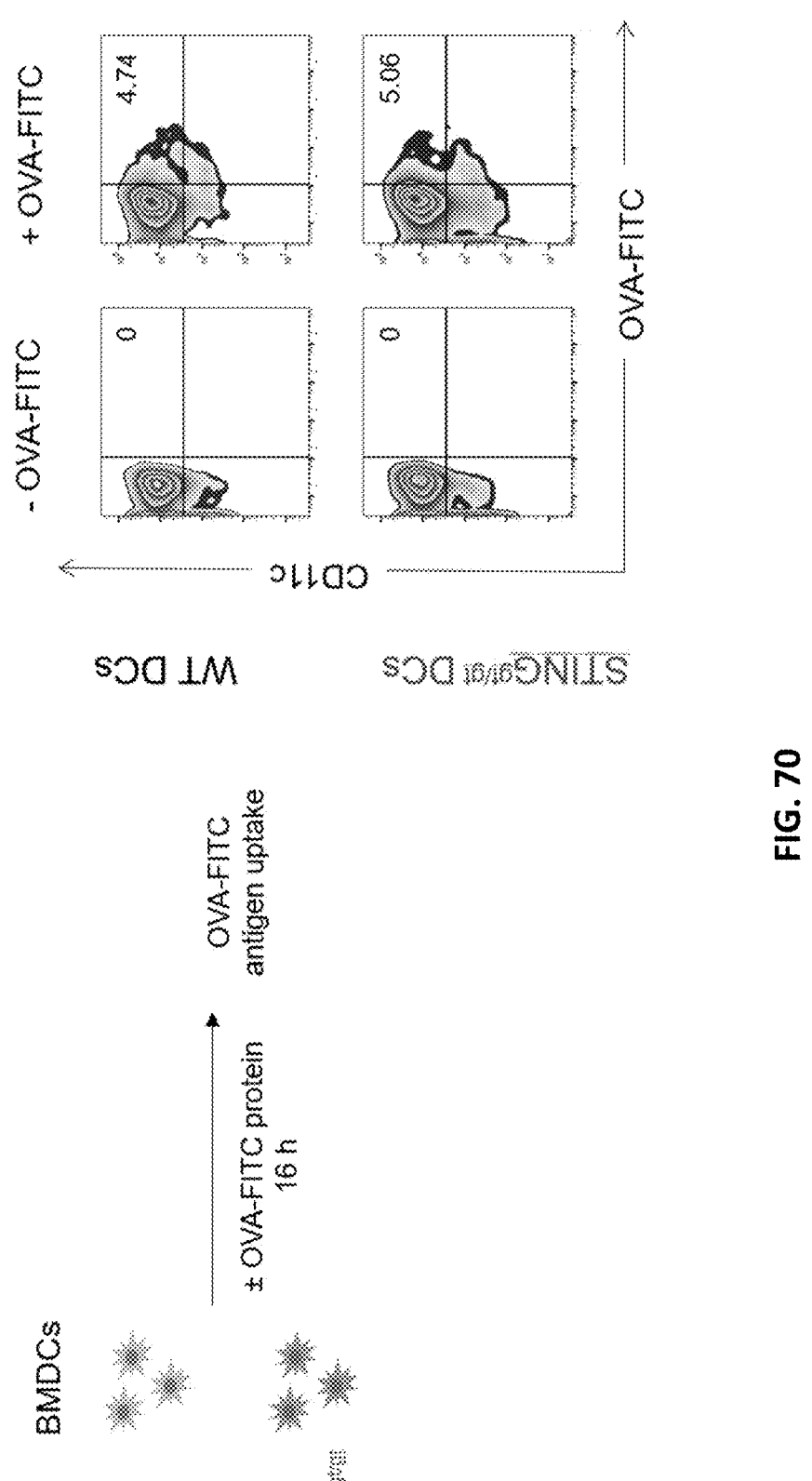
FIG. 70 shows antigen processing remains intact in STING$^{gt/gt}$ DCs.
Figure 71:
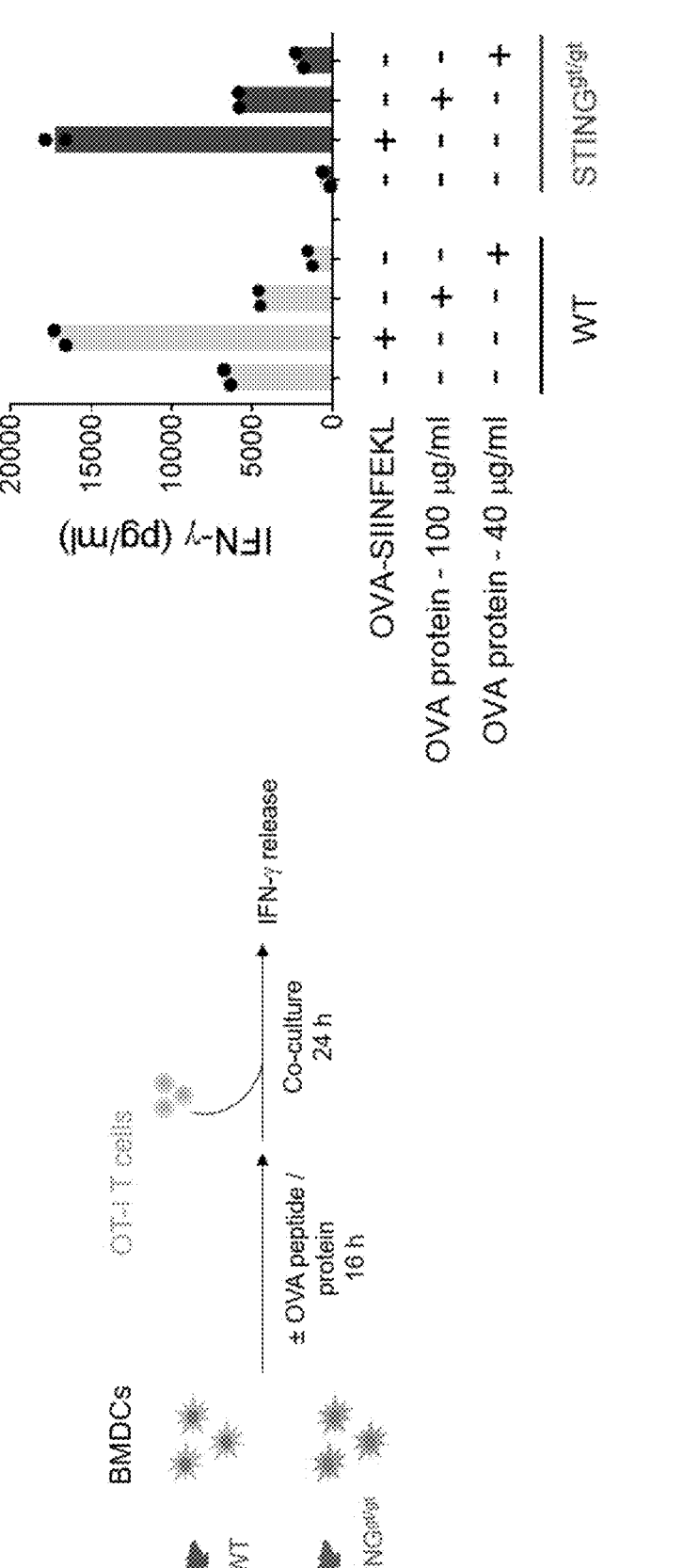
FIG. 71 shows STING$^{gt/gt}$ DCs display comparable antigen presentation and processing capacity to WT DCs.
Figures 72A, 72B:
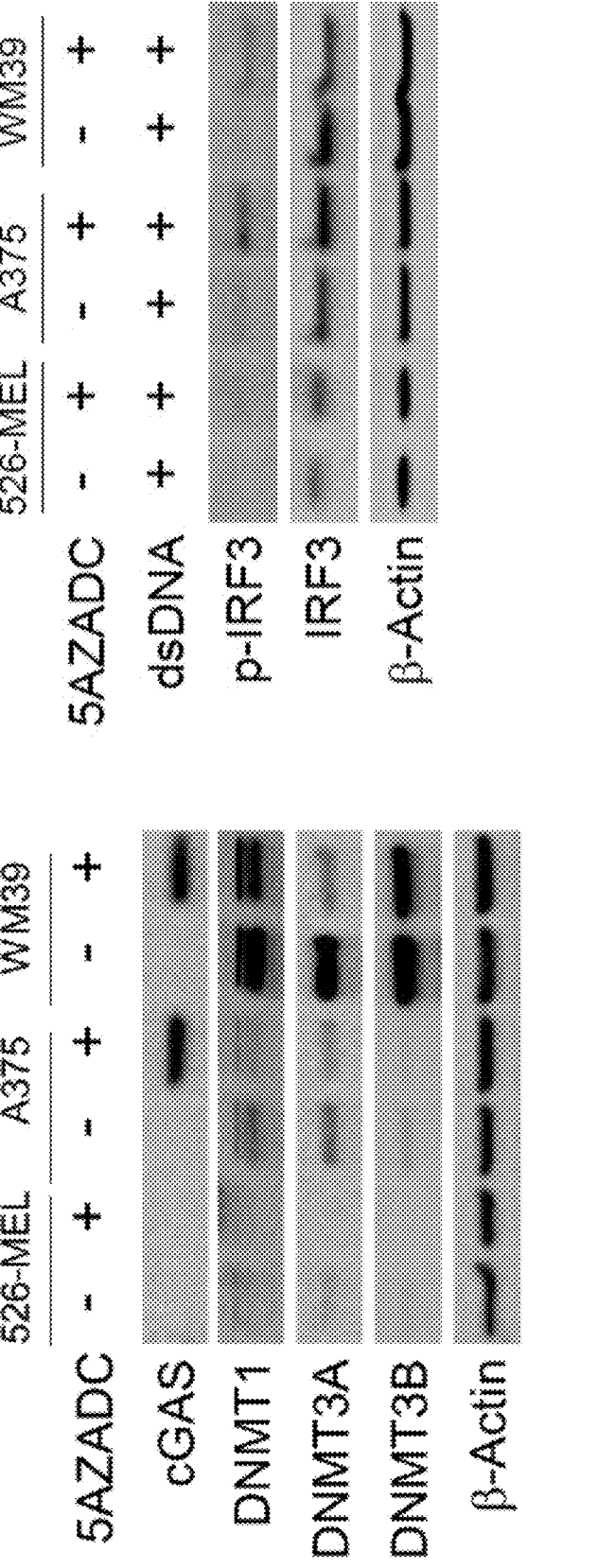
FIG. 72A shows immunoblot analysis of cGAS, DNMT1, DNMT3A and DNMT3B expression in cGAS-negative human melanoma cell lines with or without 5AZADC treatment.
FIGS. 72B to 72D show immunoblot analysis of p-IRF3 and total IRF3 (FIG. 72B) and induction of IFN-β (FIG. 72C) and CXCL10 (FIG. 72D) in indicated cell lines after stimulation with dsDNA measured using ELISA.
Figure 72C:
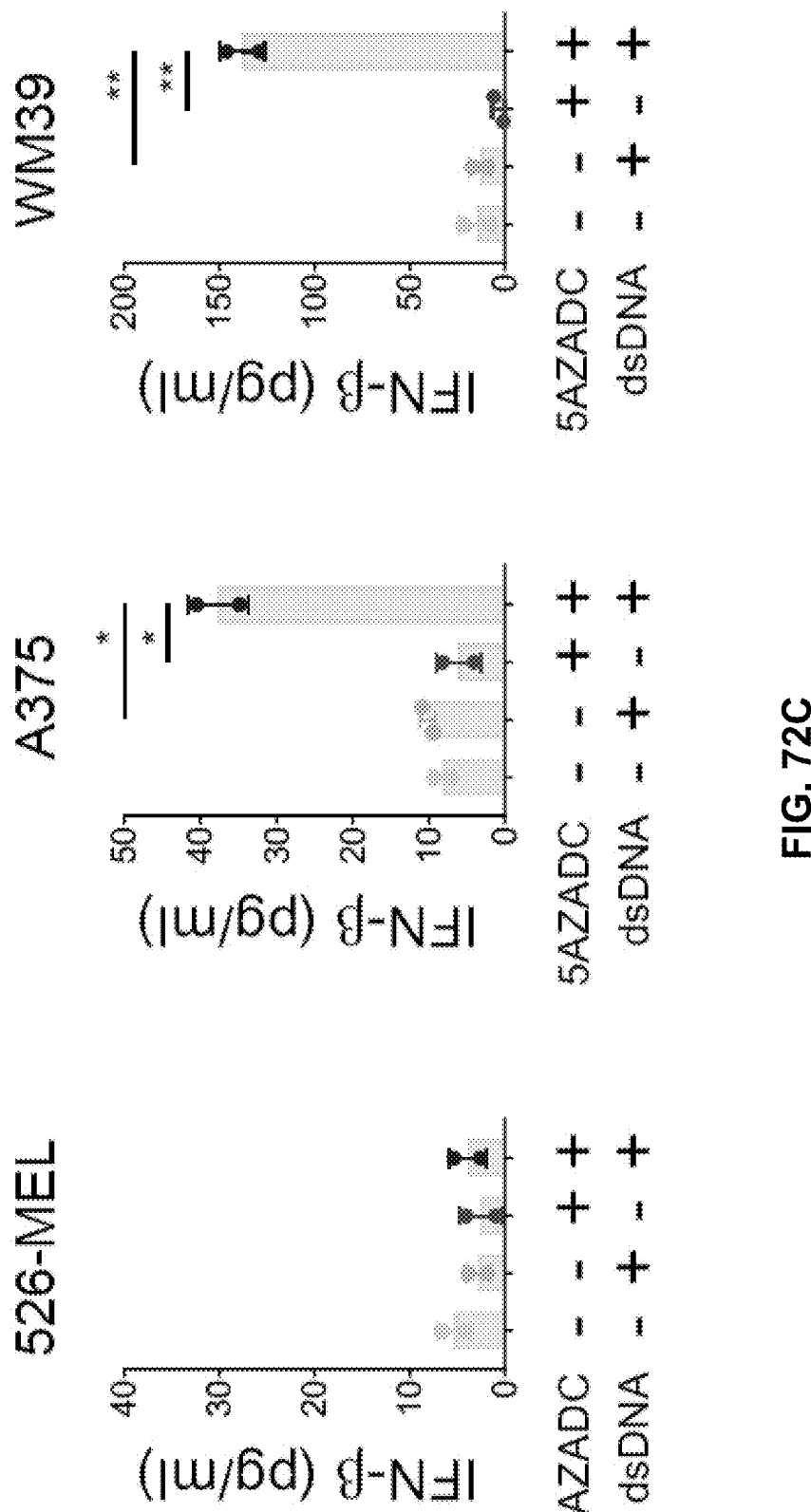
Figure 72D:
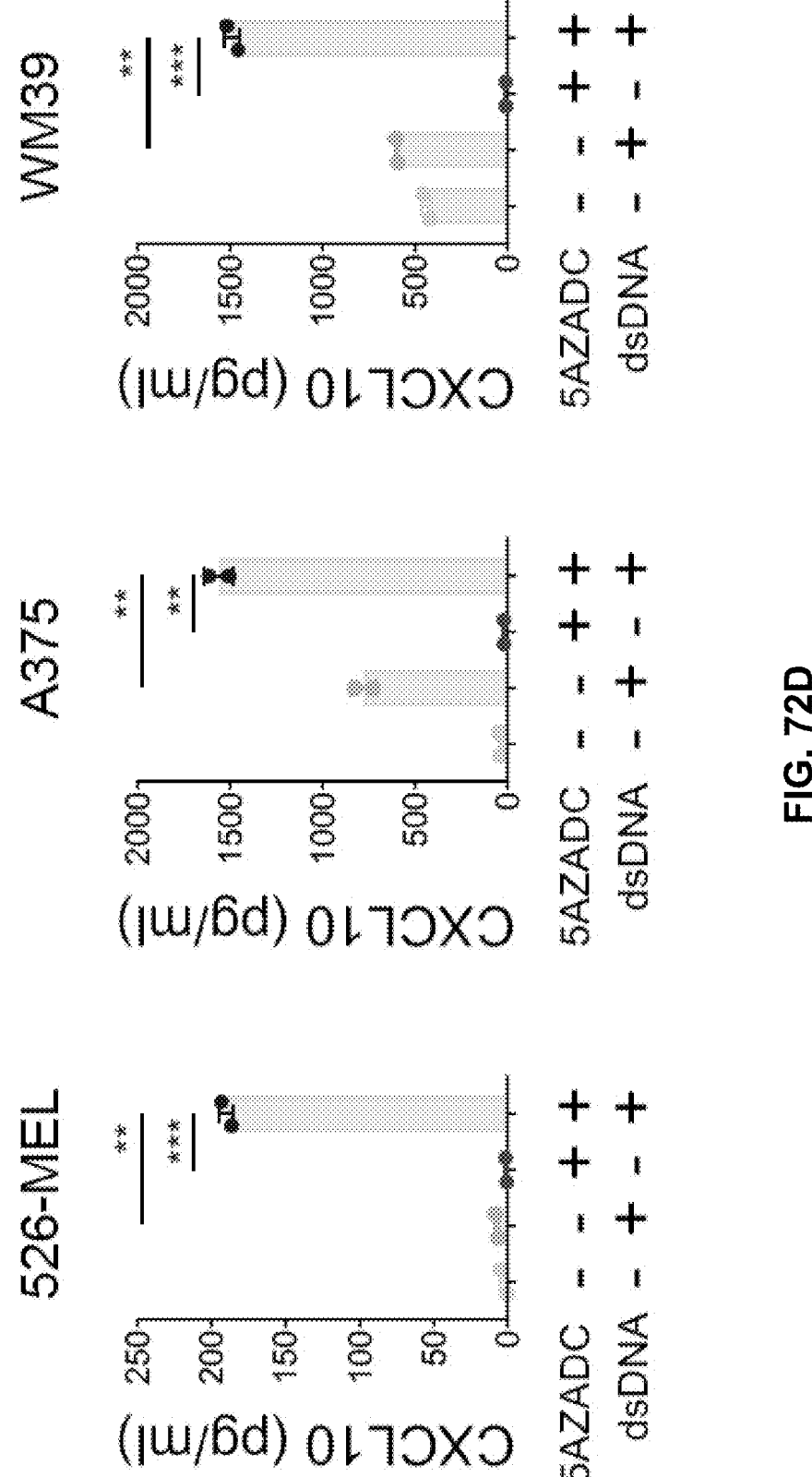
Figure 73A:
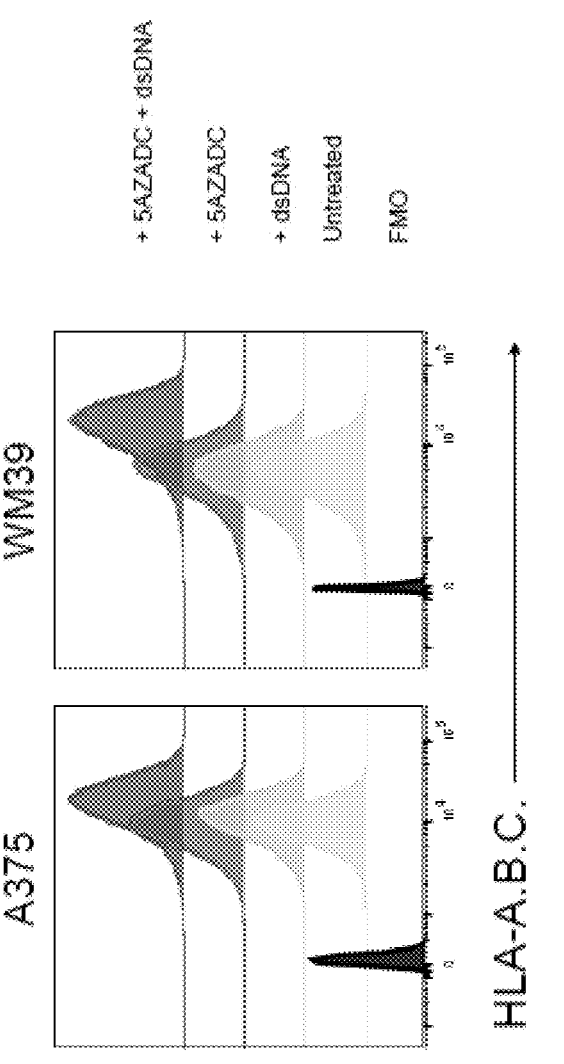
FIGS. 73A and 73B show representative histograms (FIG. 73A) and mean fluorescence intensity (MFI) of HLA-A.B.C expression on indicated melanoma cell lines (FIG. 73B).
Figure 73B:
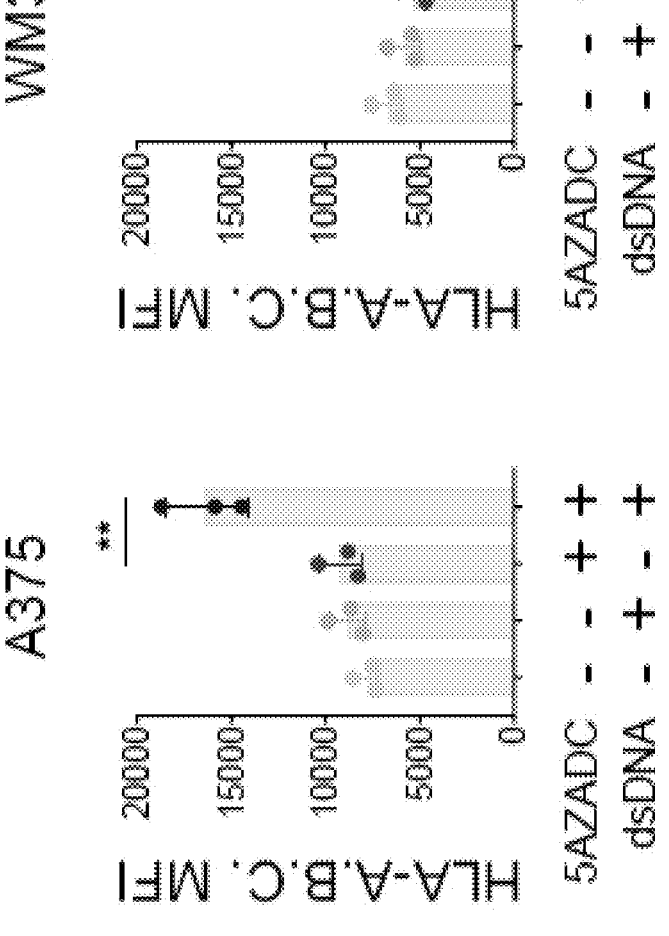
Figure 73C:
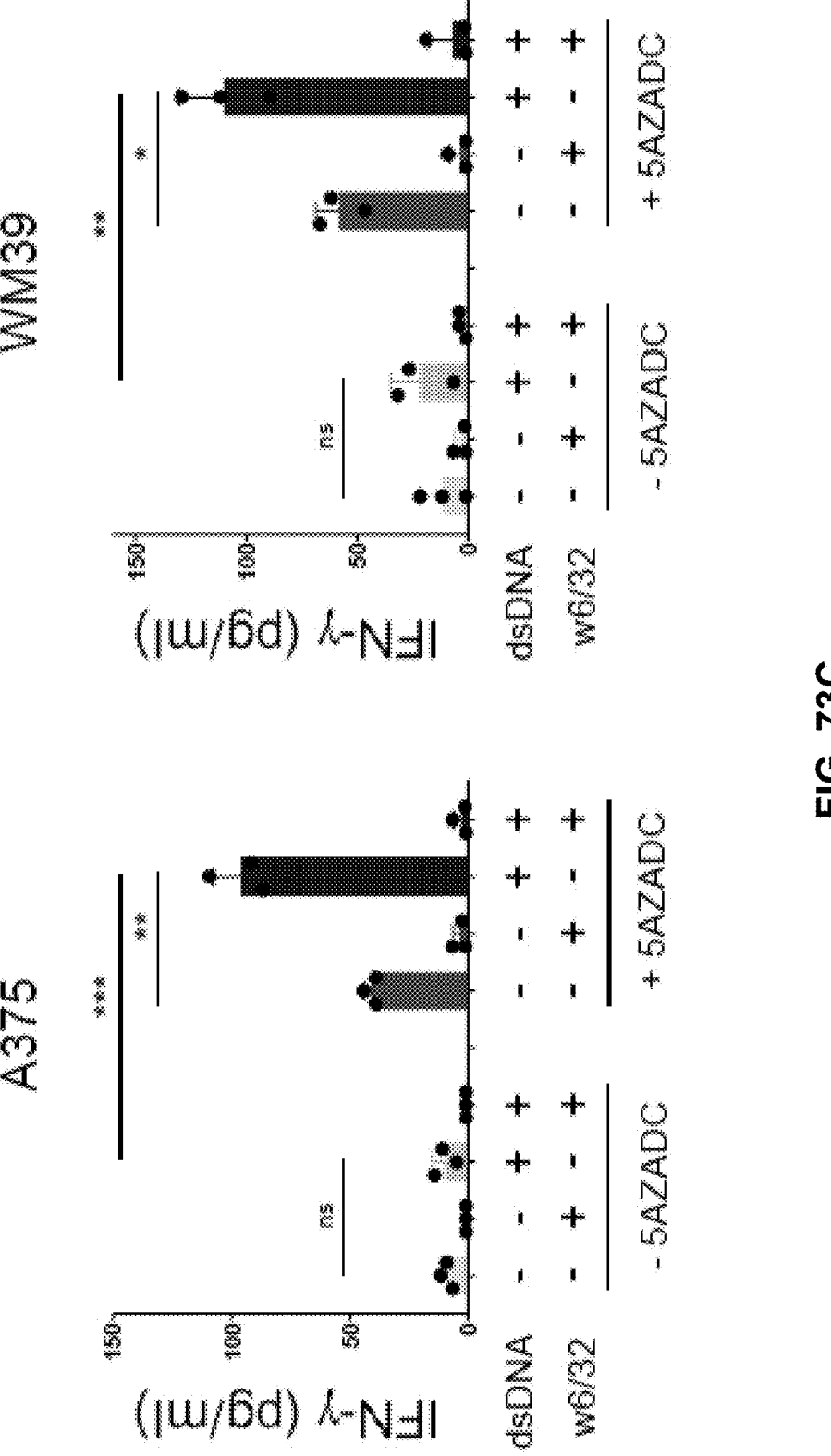
FIGS. 73C and 73D show HLA-matched human melanoma TIL samples were cocultured with A375 and WM39 cells (FIG. 73C) with or without 5AZADC pretreatment in the presence or absence of dsDNA. Co-culture supernatants were collected after 24 h and IFN-g levels were measured using ELISA. Specific lysis of MART-1—pulsed WM39 (±5AZADC and/or ±dsDNA) targets by HLA-matched TIL 123 at the indicated effector/target (E/T) ratios (FIG. 73D).
Figure 73D:
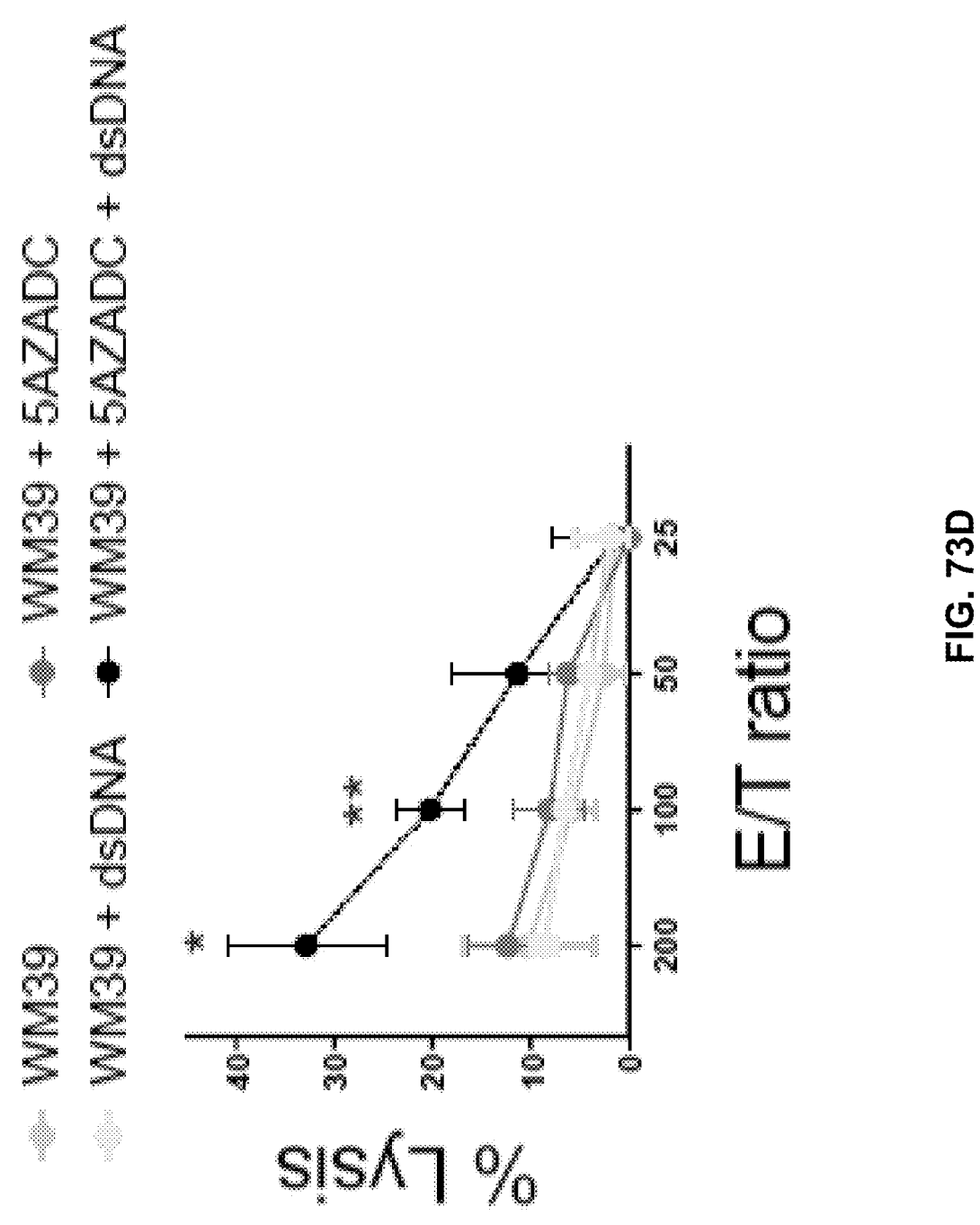
Figure 74A:
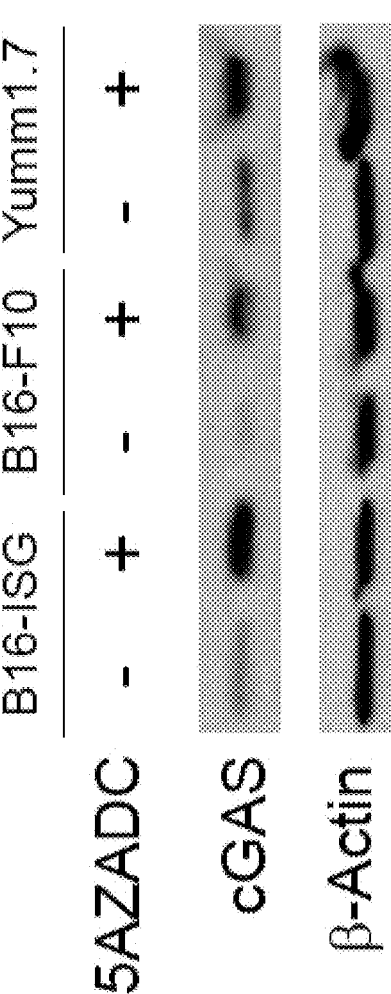
FIG. 74A shows immunoblot analysis of cGAS expression in murine melanoma cell lines with or without 5AZADC treatment.
Figure 74B:
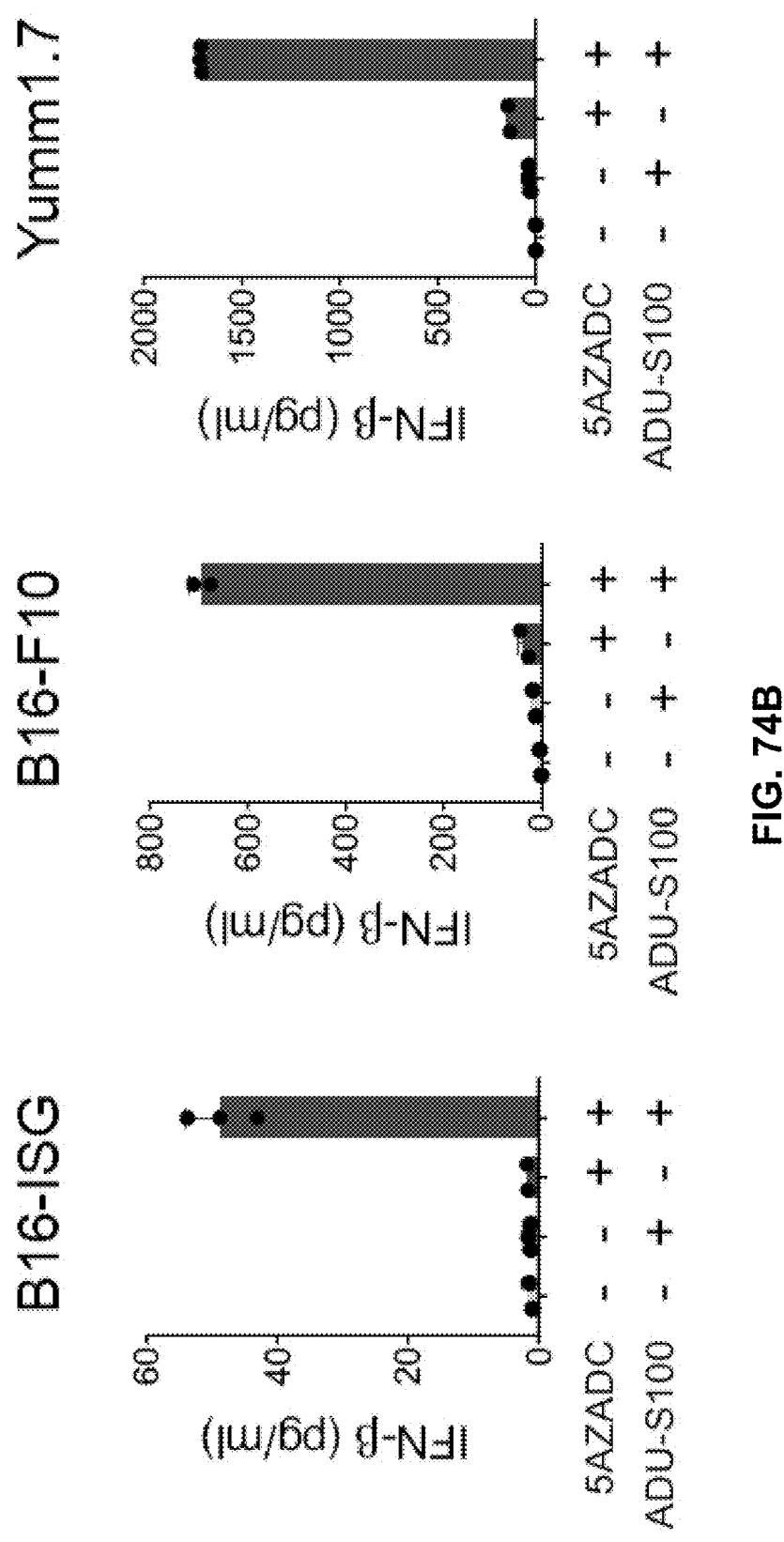
FIG. 74B shows induction of IFN-β in indicated cell lines after stimulation with ADU-S100.
Figure 74C:
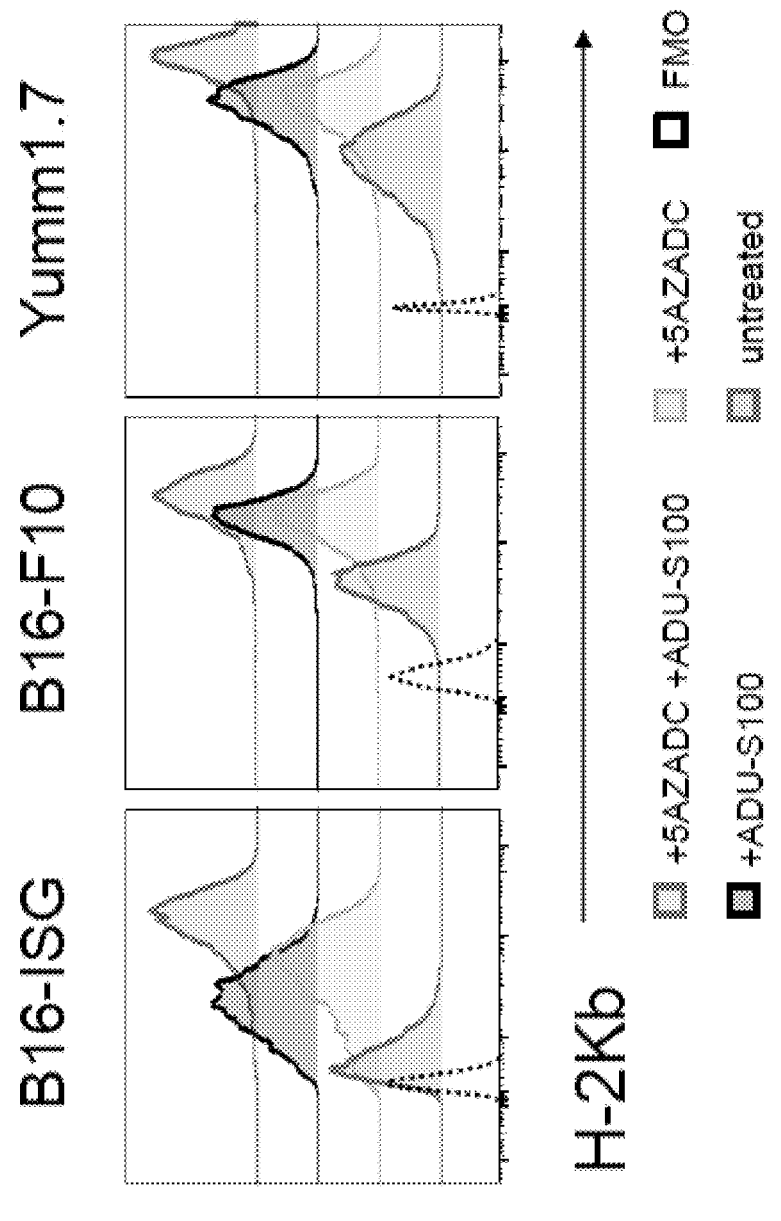
FIGS. 74C and 74D show representative histograms (FIG. 74C) and mean fluorescence intensity (MFI) of H-2Kb expression on indicated cell lines (FIG. 74D).
Figure 74D:
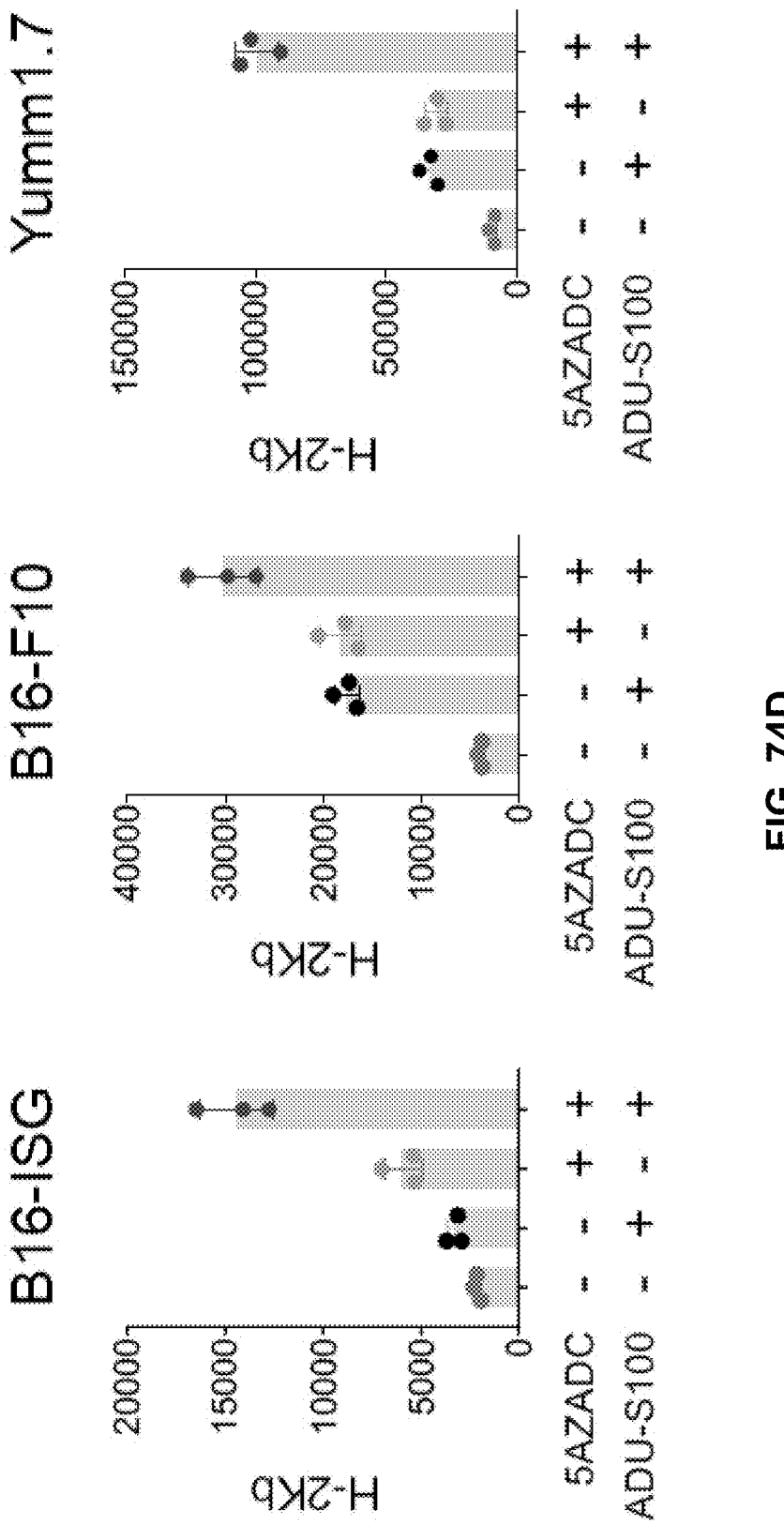
Figure 75A:
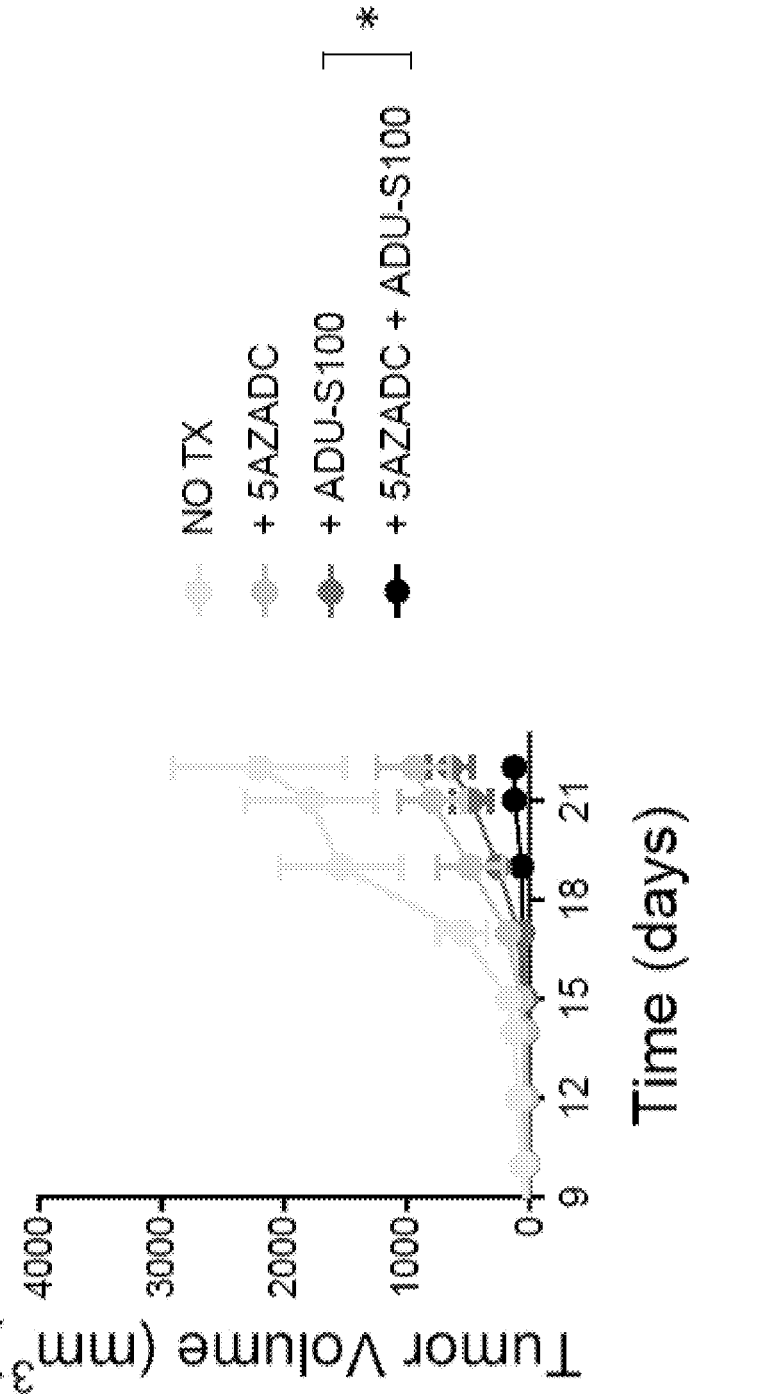
FIG. 75A shows tumor growth curves of STING$^{gt/gt}$ mice bearing B16-F10 tumors treated with intratumoral injection of 5AZADC and/or ADU-S100.
Figure 75C:
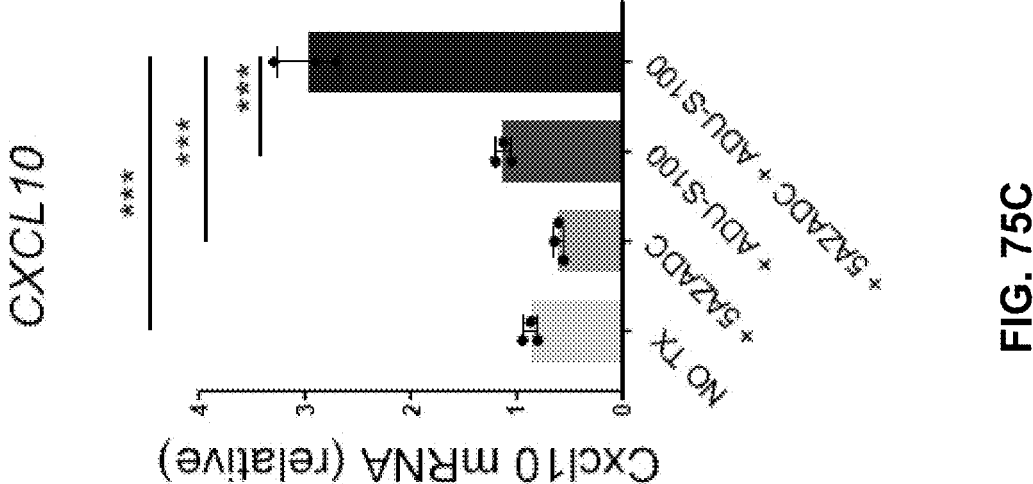
FIGS. 75B and 75B show quantitative reverse transcription PCR analysis of IFN-β (FIG. 75B) and CXCL10 (FIG. 75C) gene expression in tumor lesions from STING$^{gt/gt}$ mice bearing B16-F10 tumors 24 hr post treatment with 5AZADC and/or ADU-S100.
FIG. 75D shows frequency of CXCR3+ CD8+ T cells in B16-F10 tumors treated with intratumoral injection of 5AZADC and/or ADU-S100.
FIG. 75E shows tumor growth curves of intact, CD4-depleted or CD8-depleted STING$^{gt/gt}$ mice bearing B16-F10 tumors treated with intratumoral injection of 5AZADC and/or ADU-S100.
Figure 75B:
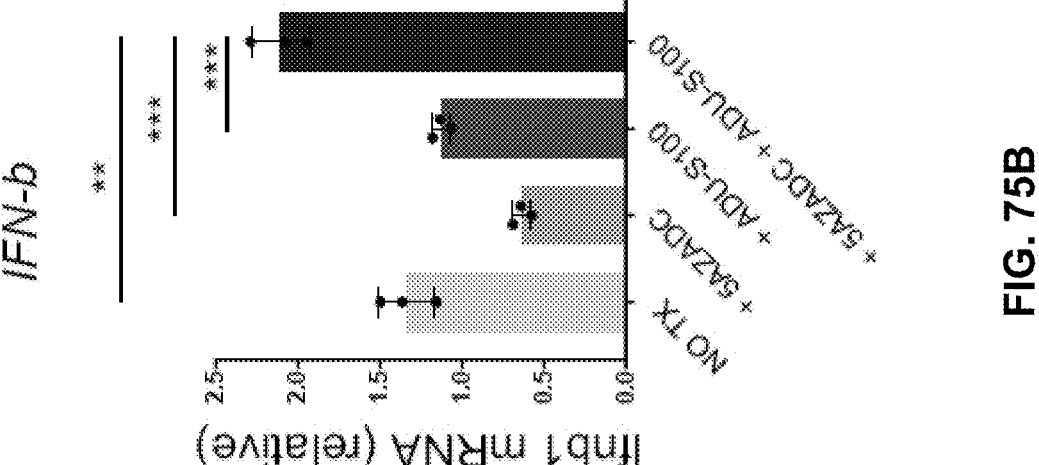
Figure 75D:
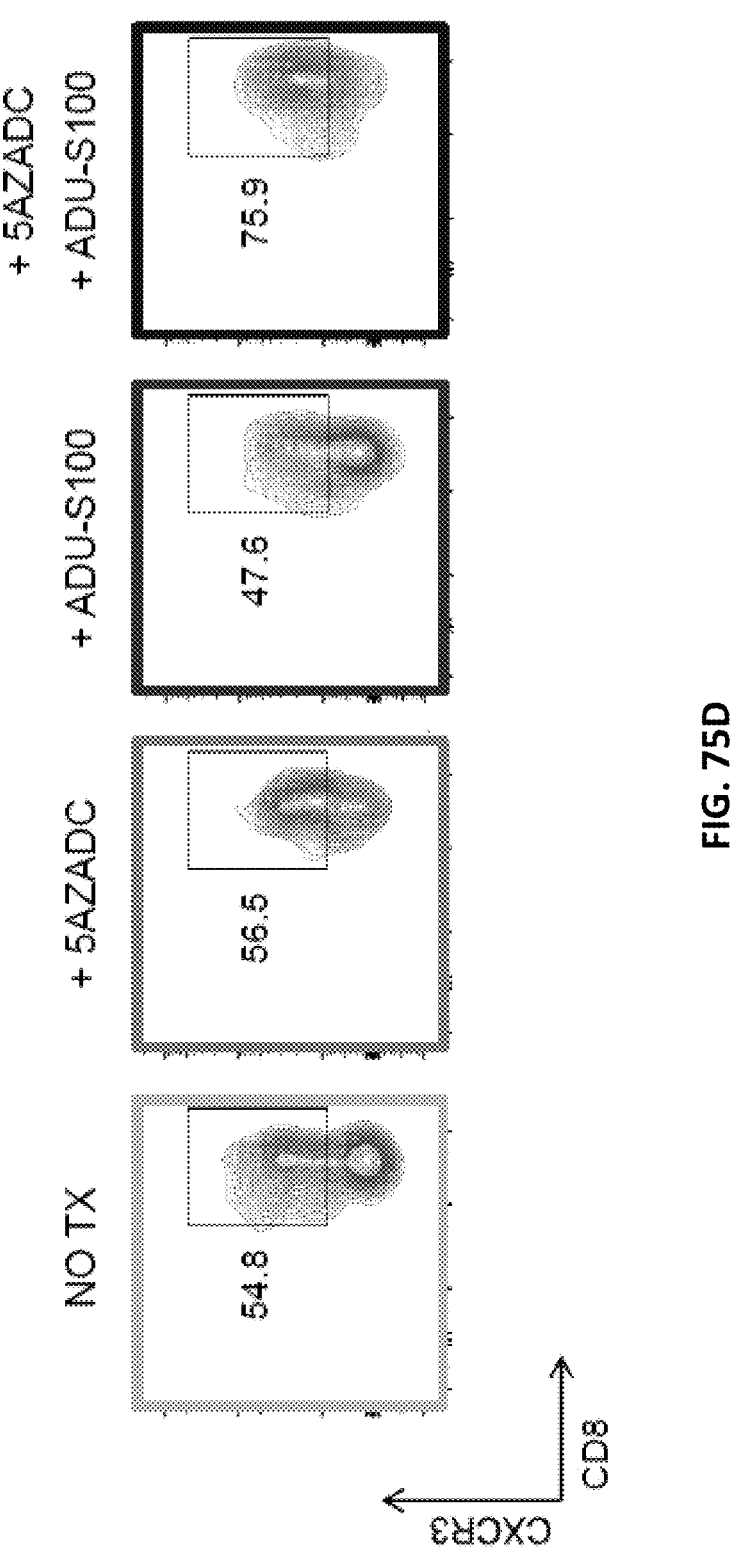
Figure 75E:
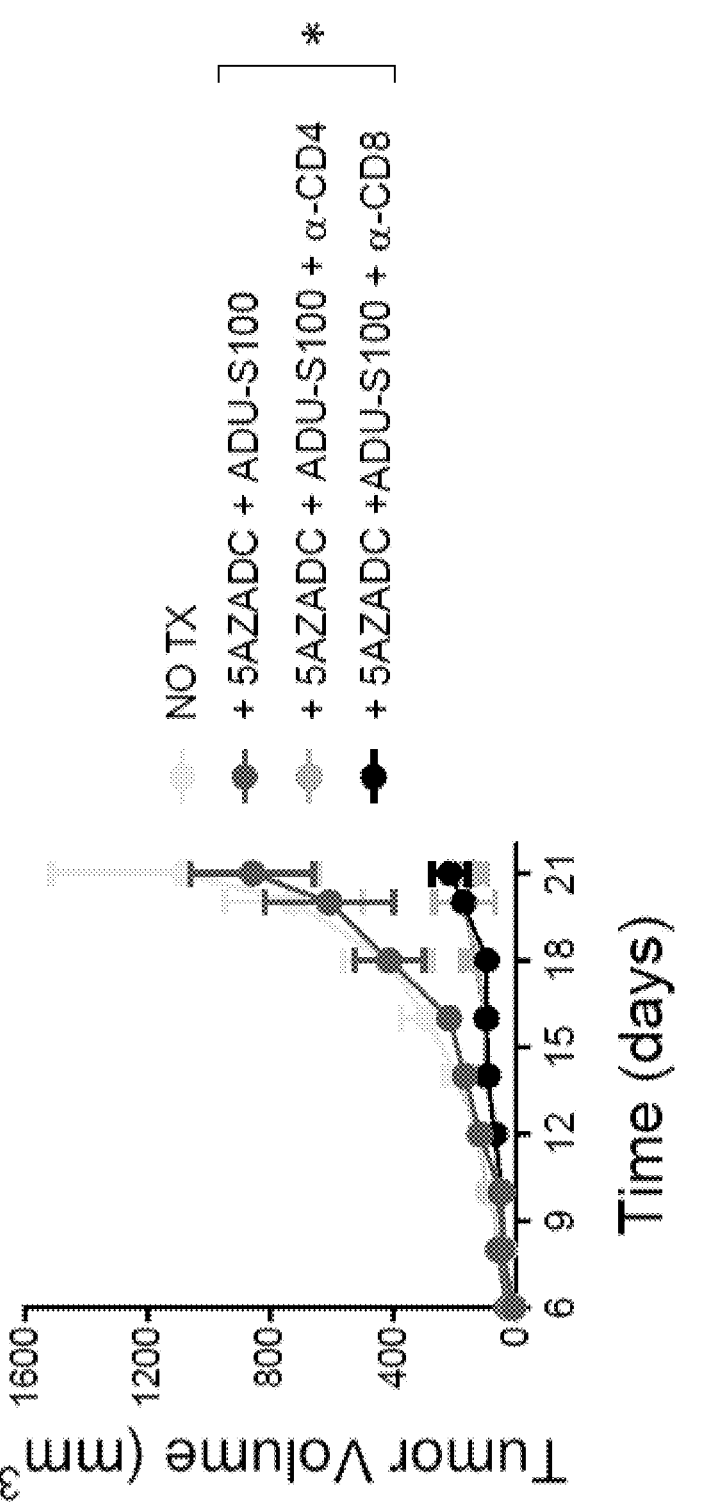
Figure 76:
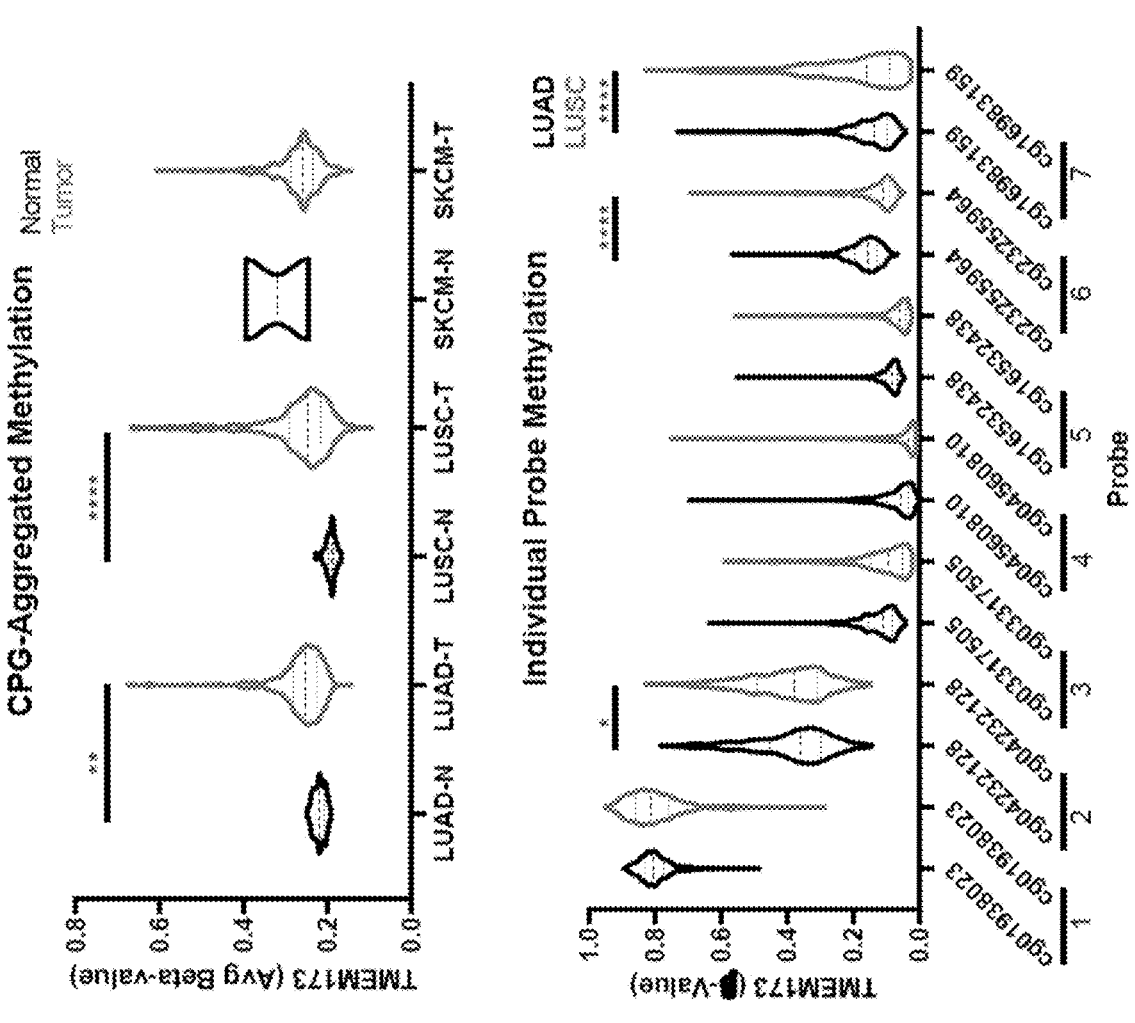
FIG. 76 shows sting methylation with 7 probes.
Figure 77:
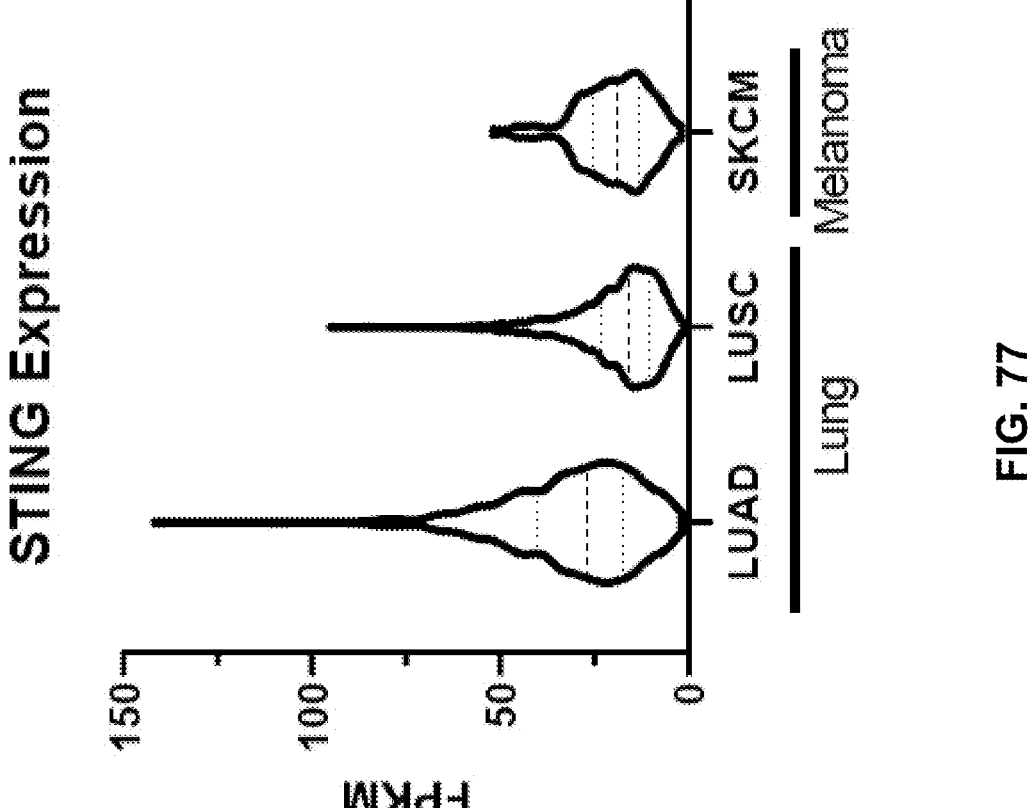
FIG. 77 shows STING expression in lung adenocarcinoma (LUAD), lung squamous cell carcinoma (LUSC), and skin cutaneous melanoma (SKCM).

[51]Cr release cytotoxicity assays were next performed using WM39, MART-1 pulsed WM39, WM3629, and 526-MEL as target cells and TIL 195 as effector cells in the presence or absence of 2'3'-cGAMP, to determine cytolytic activity of TIL against melanoma cells stimulated with the agonist. Similar to the finding of increased TIL production of IFN-γ, STING activation in both WM39 and MART-1 pulsed WM39 cells resulted in marked increases in their lysis by TIL 195 (>2-fold, p<0.05) (FIGS. 17A and 17B). Blocking MHC class I in WM39 targets effectively inhibited specific TIL lysis in agonist treated groups (FIG. 17C), indicating that the enhanced cytotoxic activity in response to activation of STING signaling was driven by MHC class I restricted TIL. To further confirm that this effect was mediated by cytolytic activity of TIL per se and not by the STING agonist, two control groups in which WM39 target cells were incubated with or without 2'3'-cGAMP in the absence of TIL were included. No significant difference of cytotoxicity in these two groups was found, which argued that stimulation with the STING agonist alone did not result in any major cytotoxicity. Increased (p<0.05) cytotoxicity in 2'3'-cGAMP-treated WM3629 cells was observed compared to the controls (FIG. 17D). However, 2'3'-cGAMP stimulation of 526-MEL targets, which were defective in STING signaling, did not alter their specific lysis by TIL 195. To better compare the cytolytic activity of TIL against different agonist-treated and untreated melanoma targets, we calculated lytic units (FIG. 17E). There was more than a 10-fold increase in lytic potential of TIL 195 against 2'3'-cGAMP-treated WM39 and MART-1-pulsed WM39 cells compared to their controls. Similarly, activation of STING in WM3629 cells resulted in in greater lysis by TIL 195. In contrast, 2'3'-cGAMP-treated 526-MEL cells did not induce any increase in lysis by TIL 195.
STING Activation in Human Melanoma Cell Lines Induces Up-Regulation of MHC Class I Following the observation of enhanced antigenicity of human melanoma cell lines triggered by agonist-induced activation of STING signaling, the expression of MHC class I on 2'3'-cGAMP-stimulated melanoma cells was next examined. Surface expression of MHC class I in all four cell lines with functional STING signaling (WM9, WM3629, A375 and WM39) was significantly increased (p<0.01, fold change >1.6) following the stimulation with the STING agonist (FIGS. 18A and 18B). In contrast, there were no significant changes in the expression of MHC class I in 1205Lu, WM266-4, WM2032 and 526-MEL cell lines with an impaired STING signaling following their exposure to the agonist. Together, these results indicated that activation of STING signaling could induce up-regulation of MHC class I in a subset of melanoma cell lines, leading to more effective immune recognition and antigen presentation to TIL.
Knockdown of STING Blocks Agonist-Induced Upregulation of MHC Class I in Melanoma Cells STING expression in WM39 cells was next stably knocked down with lentivirus-based short hairpin RNA targeting STING (sh-STING). We used WM39 cells expressing a non-targeting hairpin as control cells (sh-control). Immunoblot analysis indicated complete deletion of STING in WM39 cells transduced with sh-STING (FIG. 19A). Knockdown of STING blocked phosphorylation of IRF3 and agonist-induced induction of CXCL10 and IFN-β in WM39 cells in response to stimulation with 2'3'-cGAMP (FIG. 19B-19D). Unlike WM39 and sh-control for which stimulation with the agonist resulted in more than 2.5-fold higher surface expression of MHC class I (p<0.01), stimulation with the agonist did not cause any increase in MHC class I for sh-STING cells (FIGS. 19E and 19F) demonstrating that the upregulation of MHC class I in response to stimulation with the agonist occurs through activation of STING signaling.
STING is Essential for Agonist-Induced Enhanced Antigenicity in Melanoma Cells To further confirm the role of STING signaling in enhancing antigenicity of melanoma, sh-STING, sh-control and non-transfected WM39 cells were used in co-cultures with TIL 195 in the presence and absence of 2'3'-cGAMP. In contrast to WM39/TIL 195 and sh-control/TIL 195 co-cultures for which stimulation with the agonist resulted in more than 25-fold higher IFN-γ release (P<0.05), no increase in IFN-γ induction was observed in sh-STING/TIL 195 co-cultures in the presence of the agonist (FIG. 7A). [51]Cr cytotoxicity assays were also performed using sh-STING, sh-control and WM39 as target cells and TIL 195 as effector cells at different effector to target ratios with or without 2'3'-cGAMP. While there was increased cytolytic activity with TIL 195 against both WM39 and sh-control in the presence of the agonist, inhibition of STING signaling in sh-STING led to complete blockade of this response (FIG. 7B), as reflected by the corresponding lytic units (FIG. 7C).

DISCUSSION

Immunotherapies including adoptive cell transfer of tumor infiltrating lymphocytes and immune checkpoint inhibitor antibodies have shown efficacy in patients with metastatic melanoma (Rosenberg S A, et al. Science. 2015 348:62-8; Pilon-Thomas S, et al. J Immunother. 2012 35:615-20; Postow M A, et al. N Engl J Med. 2015 372:2006-17). However, there remains a notable subset of melanoma patients treated with immune-based therapies that does not achieve clinical benefit (26-28). Therefore, understanding the mechanisms underlying both successful and failed immune responses has important implications for improving immunotherapeutic approaches.

As TIL-based immunotherapies have been developed on the basis of expanding tumor-reactive T cells from the tumor microenvironment, it is evident that a spontaneous adaptive immunity exists within tumors, although in a dysfunctional state (Topalian S, et al. J Immunol. 1989 142:3714-25; Robbins P F, et al. Nat Med. 2013 19:747-52). Moreover, a pre-existing CD8+ T cell infiltrate within tumors has been strongly associated with clinical response to checkpoint blockade immunotherapies in melanoma patients (Tumeh P C, et al. Nature. 2014 515:568-71), indicating the prognostic significance of endogenous T cell responses. These observations have led to an important question regarding how the innate immune system could detect cancer and initiate a spontaneous adaptive T cell response against tumor antigens without the presence of infectious pathogens (Corrales L, et al. J Immunol. 2013 190:5216-25).

Studies using different gene-targeted mouse models deficient in specific innate immune pathways have identified STING pathway to be the major innate immune sensing mechanism for the detection of immunogenic tumors and initiation of a spontaneous T cell response (Woo S-R, et al. Immunity. 2014 41:830-42). Based on this finding, multiple studies have been conducted to evaluate whether direct activation of STING signaling using pharmacologic STING agonists could be used in facilitating antitumor immune responses in mouse models (Corrales L, et al. Cell reports. 2015 11:1018-30; Conlon J, et al. The Journal of Immunology. 2013 190:5216-25; Fu J, et al. Sci Transl Med. 2015 7:283ra52). While they all found enhanced therapeutic activity by intratumoral administration of STING agonists, mechanistic details regarding how direct activation of STING signaling could potentiate antitumor immunity remain largely unknown. In fact, it is currently unclear how STING agonists could impact cell types other than APCs in a tumor microenvironment, in particular tumor cells.

Although evidence suggests STING signaling is frequently impaired in human melanoma cells (Xia T, et al. Cancer research. 2016 76:6747-59), there remains a subset of melanomas with STING expression for which the functional significance of STING activation has not been well explored. In this study, it is shown that many melanoma cell lines have lost the expression of STING and are therefore defective in responding to stimulation with the STING agonist 2'3'-cGAMP. Also shown is impaired functional responses to stimulation with the STING agonist in some melanoma cells that expressed STING, suggesting that STING signaling can be inhibited not only by suppression of STING/cGAS expression but also through other molecular mechanisms that remain to be determined (Xia T, et al. Cancer research. 2016 76:6747-59; Chen Q, et al. Nat Immunol. 2016 17:1142-9). Interestingly, stimulation with the 2'3'-cGAMP agonist can induce potent STING activation in a subset of human melanoma cell lines leading to downstream production of IFN-β and CXCL10. Such agonist-induced activation of the STING pathway can increase antigenicity of melanoma cells through the augmentation of MHC class I expression and result in better tumor-antigen recognition by immune T cells.

Down-regulation of MHC class I is one of the major mechanisms used by tumor cells to evade host immune recognition (Seliger B, et al. Immunol Today. 2000 21:455-64; Hicklin D J, et al. J Clin Invest. 1998 101:2720-9). Loss or down-regulation of MHC class I was associated with significantly lower levels of tumor infiltrating lymphocytes and poor clinical outcomes in patients with metastatic melanoma. Such correlations were found in melanoma cell lines derived from both recurrent metastases in patients who had initially experienced clinical responses to TIL-based therapies (Restifo N P, et al. J Natl Cancer Inst. 1996 88:100-8; Garrido F, et al. Curr Opin Immunol. 2016 39:44-51; Chang C-C, et al. J Immunol. 2005 174:1462-71) or from previously untreated melanoma patients that showed resistance to anti-CTLA-4 therapy later (Rodig S J, et al. Sci Transl Med. 2018 10:eaar3342). In contrast, tumor regression was correlated with positive tumor MHC class I expression, highlighting the functional significance of antigen presentation by tumor cells in the initiation of successful anti-tumor responses (Carretero R, et al. Int J Cancer. 2012 131:387-95).

Although the molecular mechanism(s) underlying STING agonist-induced up-regulation of MHC class I remains undefined, it depends on activation of STING signaling, as up-regulation of MHC class I was not observed in melanoma cell lines with defective STING signaling following their stimulation with 2'3'-cGAMP. Also, findings suggest that STING agonist-mediated up-regulation of MHC class I occurs through type I IFN dependent mechanisms, as this effect was found in tumor cells stimulated with the agonist in the absence of TIL and IFN-γ. Taken together, data support the concept that agonist-induced intact activation of STING signaling in melanomas could be considered as a therapeutic intervention to restore MHC class I surface expression and subsequently to enhance tumor antigen recognition and tumor cell destruction by immune T cells.

Activation of STING signaling in melanoma cell lines results in downstream induction of IFN-β. STING-mediated IFN-β induction in dendritic cells has been found to be essential for their activation and the cross-priming of cytotoxic T cells (Woo S-R, et al. Immunity. 2014 41:830-42). Similarly, recent work has shown that initiation of a robust adaptive immune response to radiation therapy requires STING-mediated IFN-β induction in dendritic cells (Deng L, et al. Immunity. 2014 41:843-52).

Although the contribution of IFN-β produced by tumor cells in response to STING agonists in modulating interactions between tumor cells and the immune system and subsequent initiation of tumor-specific T-cell responses had not been previously explored, there was evidence that agonist-mediated induction of IFN-β in melanoma cell lines when co-cultured with their HLA-matched TIL strongly correlates with increased TIL production of IFN-γ and T lymphocyte-mediated cytotoxicity. In addition, IFN-β induction in tumor cells has been previously reported to initiate a series of orchestrated events involving autocrine and paracrine signals resulting in inducing multiple effects on both tumor cells and antigen presenting cells, including regulation of antigen processing, peptide transfer, peptide-loading complex, MHC class I expression, or downstream induction of other cytokines and/or chemokines such as CXCL10 (Diamond M S, et al. J Exp Med. 2011 208:1989-2003; Sistigu A, et al. Nat Med. 2014 20:1301-9). Therefore, it may be of benefit to determine the functional contribution of IFN-β induced by tumor cells in response to the STING agonist in initiation of the antitumor immunity.

As one of the major characteristic chemokines of type I IFN immune response and STING signaling (Barber G N. Trends Immunol. 2014 35:88-93; Zitvogel L, et al. Nat Rev Immunol. 2015 15:405-14), there was downstream induction of CXCL10 in melanoma cell lines with intact STING signaling following their stimulation with 2'3'-cGAMP. Along with CXCL9, another CXCR3-binding chemokine, CXCL10 has been identified as the dominant mediator for the recruitment of CXCR3+ tumor-specific T lymphocytes into the tumors and its intratumoral expression correlated with favorable clinical outcomes in patients with melanoma and colorectal cancer (Mlecnik B, et al. Gastroenterology. 2010 138:1429-40; Wolchok J D, et al. N Engl J Med. 2017 377:1345-56; Mikucki M, et al. Nat Commun. 2015 6:7458). It is also one of the chemokines in our earlier reported 12-chemokine gene signature classifier predicting the presence of the tumor-localized, tertiary lymphoid structures, which are found to positively correlate with overall survival in certain patients with metastatic melanoma (Messina J L, et al. Sci Rep. 2012 2:765). In addition, CXCL10 has been shown to promote the generation and function of effector T cells (Dufour J H, et al. J Immunol. 2002 168:3195-204). Given the important role of CXCL10 in mediating T cell recruitment and its positive prognostic value, it seems likely that STING-agonist mediated induction of CXCL10 by tumor cells could further facilitate recruitment of effector T cells into the tumor microenvironment. This can have at least three important implications. First, it could be used to recruit higher numbers of T cells into the tumors that lack T cell infiltration and therefore increase the likelihood of patients responding to current immune checkpoint antibody therapies. Second, a same strategy could be used in TIL-based therapies prior to tumor resection and TIL expansion to attract higher numbers of tumor-specific T cells into the tumors with the aim of increasing the probability of successful expansion of tumor-reactive TIL ex vivo. A third implication would also be in adoptive T cell therapy where STING agonist-mediated CXCL10 induction in tumor cells could be used to improve TIL trafficking into the tumor sites.

In summary, disclosed herein is the functional significance of the STING signaling activation in human melanoma cell lines in response to stimulation with a STING agonist. The disclosed data support that intact activation of STING signaling in melanomas can promote antitumor immunity by regulating tumor cell-intrinsic factors that improve tumor-antigen presentation and recognition by immune T cells, as well as their trafficking.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for producing enhanced tumor infiltrating lymphocytes (TILs), comprising
   a) culturing tumor cells from a subject in the presence of
      i) a demethylating agent in an amount effective to demethylate STING proteins in the tumor cells and ii) a STING agonist in an amount effective to demethylate STING proteins in the tumor cells; and
   b) co-culturing TILs with these treated tumor cells and further expanding the TILs after their exposure.

2. The method of claim 1, wherein the TILs are HLA matched to a subject.

3. The method of claim 1, wherein the demethylating agent comprises 5-aza-2'-deoxycytidine.

4. The method of claim 3, wherein the STING agonist comprises 2'3'-cyclic-GMP-AMP (2'3'-cGAMP).

5. The method of claim 1, further comprising assaying a biopsy sample from the subject for STING expression, cGAS expression, or a combination thereof.

6. The method of claim 1, further comprising assaying a biopsy sample from the subject for DNA methylation within the regulatory regions of STING and/or cGAS genes.

7. The method of claim 1, wherein the tumor cells comprise melanoma, ovarian cancer, breast cancer, or colorectal tumor cells.

8. A method for producing enhanced tumor infiltrating lymphocytes (TILs), comprising
   a) treating a subject with an effective amount of a demethylating agent to increase STING expression in tumor cells of the subject;
   b) isolating tumor cells from the subject;
   c) culturing the tumor cells in the presence of a STING agonist in an amount effective to increase the antigenicity of the tumor cells; and
   d) co-culturing TILs with these treated tumor cells and further expanding the TILs after their exposure.

9. The method of claim 8, wherein step c) further comprises culturing the tumor cells in the presence of a demethylating agent in an amount effective to demethylate STING proteins in the tumor cells.

10. The method of claim 8, further comprising detecting in a biopsy sample from the subject reduced STING expression, reduced cGAS expression, or a combination thereof prior to step a).

11. The method of claim 8, further comprising detecting in a biopsy sample from the subject DNA methylation within regulatory regions of STING and/or cGAS genes prior to step a).

12. The method of claim 8, wherein the TILs are HLA matched to a subject.

13. The method of claim 8, wherein the demethylating agent comprises 5-aza-2'-deoxycytidine.

14. The method of claim 13, wherein the STING agonist comprises 2'3'-cyclic-GMP-AMP (2'3'-cGAMP).

15. The method of claim 8, further comprising assaying a biopsy sample from the subject for STING expression, cGAS expression, or a combination thereof.

16. The method of claim 8, further comprising assaying a biopsy sample from the subject for DNA methylation within the regulatory regions of STING and/or cGAS genes.

17. The method of claim 8, wherein the tumor cells comprise melanoma, ovarian cancer, breast cancer, or colorectal tumor cells.

* * * * *